United States Patent
Lee et al.

(10) Patent No.: US 12,258,580 B2
(45) Date of Patent: Mar. 25, 2025

(54) PROCESS FOR GENERATING THERAPEUTIC COMPOSITIONS OF ENGINEERED CELLS

(71) Applicant: Juno Therapeutics, Inc., Seattle, WA (US)

(72) Inventors: Sarah Y. Lee, Mercer Island, WA (US); Pascal Beauchesne, Seattle, WA (US); Mark L. Bonyhadi, Sammamish, WA (US); Ryan L. Crisman, Seattle, WA (US); Ryan P. Larson, Seattle, WA (US); Mary Mallaney, Seattle, WA (US); Christopher Glen Ramsborg, Seattle, WA (US); Clinton Weber, Seattle, WA (US); John Matthew Wesner, Seattle, WA (US); Nathan Yee, Seattle, CA (US)

(73) Assignee: Juno Therapeutics, Inc., Seattle, WA (US)

( * ) Notice: Subject to any disclaimer, the term of this patent is extended or adjusted under 35 U.S.C. 154(b) by 757 days.

(21) Appl. No.: 16/760,240

(22) PCT Filed: Oct. 31, 2018

(86) PCT No.: PCT/US2018/058590
§ 371 (c)(1),
(2) Date: Apr. 29, 2020

(87) PCT Pub. No.: WO2019/089855
PCT Pub. Date: May 9, 2019

(65) Prior Publication Data
US 2020/0354677 A1    Nov. 12, 2020

Related U.S. Application Data

(60) Provisional application No. 62/721,603, filed on Aug. 22, 2018, provisional application No. 62/596,771, filed on Dec. 8, 2017, provisional application No. 62/580,409, filed on Nov. 1, 2017.

(51) Int. Cl.
*C12N 5/0783* (2010.01)
*A61K 39/00* (2006.01)

(52) U.S. Cl.
CPC ........ *C12N 5/0636* (2013.01); *A61K 39/4611* (2023.05); *A61K 39/4631* (2023.05); *A61K 39/464412* (2023.05); *A61K 2239/48* (2023.05); *C12N 2501/2302* (2013.01); *C12N 2501/2307* (2013.01); *C12N 2501/2315* (2013.01); *C12N 2501/999* (2013.01); *C12N 2510/00* (2013.01)

(58) Field of Classification Search
CPC .......... C12N 5/0636; C12N 2501/2302; C12N 2501/2307; C12N 2501/2315; C12N 2501/999; C12N 2510/00; A61K 2039/5156; A61K 2039/5158; A61K 39/0011; A61K 35/17; C07K 2319/03; C07K 14/7051; A61P 35/00
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 4,795,698 A | 1/1989 | Owen |
| 5,087,616 A | 2/1992 | Myers |
| 5,168,062 A | 12/1992 | Stinski |
| 5,200,084 A | 4/1993 | Liberti |
| 5,219,740 A | 6/1993 | Miller |
| 5,385,839 A | 1/1995 | Stinski |
| 5,773,224 A | 6/1998 | Grandics et al. |
| 5,994,136 A | 11/1999 | Naldini et al. |
| 6,013,516 A | 1/2000 | Verma et al. |
| 6,040,177 A | 3/2000 | Riddell et al. |
| 6,123,655 A | 9/2000 | Fell |
| 6,207,453 B1 | 3/2001 | Maass |
| 6,410,319 B1 | 6/2002 | Raubitschek |
| 6,451,995 B1 | 9/2002 | Cheung |

(Continued)

FOREIGN PATENT DOCUMENTS

| | | |
|---|---|---|
| CN | 103 305 464 | 9/2013 |
| CN | 103 503 438 | 1/2014 |

(Continued)

OTHER PUBLICATIONS

Finney et. al., (J Immunol, 172(1): 104-113, (2004) (Year: 2004).*
Levine et. al. 4:92-101, (2017) (Year: 2017).*
Chang et. al., 156:358-365, (2017) (Year: 2017).*
Kemper et. al., J Biomedical Optics, 15(3), 036009, (2010) (Year: 2010).*

(Continued)

*Primary Examiner* — Meera Natarajan
*Assistant Examiner* — Francesca Edgingtongiordano
(74) *Attorney, Agent, or Firm* — MORRISON & FOERSTER LLP

(57) ABSTRACT

The present disclosure provides methods for genetically engineering T cells, such as CD4+ T cells, for use in cell therapy. In some aspects, the provided methods include one or more steps for incubating the cells under stimulating conditions, introducing a recombinant polypeptide to the cells through transduction or transfection, and cultivating the cells under conditions that promote proliferation and/or expansion. In some aspects, the incubation and/or the cultivation is performed in the presence of recombinant IL-2. In some aspects, the provided methods are an efficient, reliable means to produce genetically engineered T cells with a high degree of success.

41 Claims, 6 Drawing Sheets

Specification includes a Sequence Listing.

(56) References Cited

U.S. PATENT DOCUMENTS

| | | |
|---|---|---|
| 6,733,433 B1 | 5/2004 | Fell |
| 7,070,995 B2 | 7/2006 | Jensen |
| 7,265,209 B2 | 9/2007 | Jensen |
| 7,354,762 B2 | 4/2008 | Jensen |
| 7,362,449 B2 | 4/2008 | Dubois et al. |
| 7,446,179 B2 | 11/2008 | Jensen |
| 7,446,190 B2 | 11/2008 | Sadelain |
| 7,446,191 B2 | 11/2008 | Jensen |
| 8,008,450 B2 | 8/2011 | Williams et al. |
| 8,153,765 B2 | 4/2012 | Park et al. |
| 8,324,353 B2 | 12/2012 | Jensen |
| 8,339,645 B2 | 12/2012 | Nakawaki |
| 8,389,282 B2 | 3/2013 | Sadelain et al. |
| 8,479,118 B2 | 7/2013 | Lyndersay et al. |
| 8,603,477 B2 | 12/2013 | Afar et al. |
| 8,802,374 B2 | 8/2014 | Jensen |
| 8,822,647 B2 | 9/2014 | Jensen |
| 8,911,993 B2 | 12/2014 | June et al. |
| 9,684,281 B2 | 6/2017 | Mathuis et al. |
| 9,904,248 B2 | 2/2018 | Mathuis et al. |
| 10,131,882 B2 | 11/2018 | Matthew et al. |
| 10,428,351 B2 | 10/2019 | Crisman et al. |
| 11,400,115 B2 | 8/2022 | Ramsbourg et al. |
| 11,413,310 B2 | 8/2022 | Albertson et al. |
| 11,466,253 B2 | 10/2022 | Germeroth et al. |
| 11,851,678 B2 | 12/2023 | Mujacic et al. |
| 11,944,647 B2 | 4/2024 | Albertson et al. |
| 2002/0131960 A1 | 9/2002 | Sadelain |
| 2007/0116690 A1 | 5/2007 | Yang et al. |
| 2008/0085532 A1 | 4/2008 | Gorlach et al. |
| 2008/0171951 A1 | 7/2008 | Fell |
| 2010/0260748 A1 | 10/2010 | Elkins et al. |
| 2011/0003380 A1 | 1/2011 | Miltenyi |
| 2011/0070581 A1 | 3/2011 | Gupta |
| 2011/0293667 A1 | 12/2011 | Baksh et al. |
| 2012/0189622 A1 | 7/2012 | Tesar et al. |
| 2013/0029418 A1 | 1/2013 | Angel et al. |
| 2013/0149337 A1 | 6/2013 | Cooper et al. |
| 2013/0287748 A1 | 10/2013 | June |
| 2014/0255993 A1 | 9/2014 | Follstad et al. |
| 2014/0271635 A1 | 9/2014 | Brogdon et al. |
| 2014/0314795 A1 | 10/2014 | Riddell et al. |
| 2015/0202286 A1 | 7/2015 | June et al. |
| 2015/0283178 A1 | 10/2015 | June et al. |
| 2016/0046724 A1 | 2/2016 | Brogdon et al. |
| 2016/0122782 A1 | 5/2016 | Crisman et al. |
| 2016/0152723 A1 | 6/2016 | Chen et al. |
| 2016/0206656 A1 | 7/2016 | Gilbert et al. |
| 2016/0362472 A1 | 12/2016 | Bitter et al. |
| 2017/0037369 A1 | 2/2017 | Ramsborg et al. |
| 2017/0051252 A1 | 2/2017 | Morgan et al. |
| 2017/0209492 A1 | 7/2017 | June et al. |
| 2018/0296602 A1 | 10/2018 | Riddell et al. |
| 2020/0016199 A1 | 1/2020 | Turtle et al. |
| 2020/0147136 A1 | 5/2020 | Albertson et al. |
| 2020/0239910 A1 | 7/2020 | Bonyhadi |
| 2020/0384025 A1 | 12/2020 | Mujacic et al. |
| 2021/0017249 A1 | 1/2021 | Sather et al. |
| 2021/0163893 A1 | 2/2021 | Westoby et al. |
| 2021/0207080 A1 | 7/2021 | Beauchesne et al. |
| 2022/0008465 A1 | 1/2022 | Trede et al. |
| 2022/0031746 A1 | 2/2022 | Gillenwater et al. |
| 2022/0088070 A1 | 3/2022 | Albertson et al. |
| 2023/0071910 A1 | 3/2023 | Farazi |
| 2023/0090117 A1 | 3/2023 | Haig et al. |
| 2023/0090176 A1 | 3/2023 | Ramsborg et al. |
| 2023/0149458 A1 | 5/2023 | Albertson et al. |
| 2023/0190814 A1 | 6/2023 | Ramsborg et al. |
| 2024/0076617 A1 | 3/2024 | Mujacic et al. |
| 2024/0115612 A1 | 4/2024 | Albertson et al. |

FOREIGN PATENT DOCUMENTS

| | | | |
|---|---|---|---|
| CN | 104 450 614 A | 3/2015 | |
| CN | 106 635 955 A | 5/2017 | |
| CN | 106 754 670 A | 5/2017 | |
| CN | 106 801 032 | 6/2017 | |
| CN | 106 834 218 | 6/2017 | |
| EP | 0452342 | 10/1991 | |
| EP | 1631788 | 3/2006 | |
| EP | 2537416 | 12/2012 | |
| EP | 3372670 | 9/2018 | |
| JP | 2006-525013 | 11/2006 | |
| WO | WO 1996/013593 | 5/1996 | |
| WO | WO 1996/018105 | 6/1996 | |
| WO | WO 1998/040510 | 9/1998 | |
| WO | WO 1999/018129 | 4/1999 | |
| WO | WO 1999/025817 | 5/1999 | |
| WO | WO 1999/060120 | 11/1999 | |
| WO | WO 2000/014257 | 3/2000 | |
| WO | WO 2000/038762 | 7/2000 | |
| WO | WO 2000/043551 | 7/2000 | |
| WO | WO 2003/020763 | 3/2003 | |
| WO | WO 2004/029221 | 4/2004 | |
| WO | WO 2004/033685 | 4/2004 | |
| WO | WO 2004/096975 | 11/2004 | |
| WO | WO 2006/000830 | 1/2006 | |
| WO | WO 2006/099875 | 9/2006 | |
| WO | WO 2007/117602 | 10/2007 | |
| WO | WO 2008/035631 | 3/2008 | |
| WO | WO 2009/003493 | 1/2009 | |
| WO | WO 2009/072003 | 6/2009 | |
| WO | WO 2009/072006 | 6/2009 | |
| WO | WO 2009/076524 | 6/2009 | |
| WO | WO 2009/090929 | 7/2009 | |
| WO | WO 2011/044186 | 4/2011 | |
| WO | WO 2012/062904 | 5/2012 | |
| WO | WO 2012/081650 | 6/2012 | |
| WO | WO 2012/092612 | 7/2012 | |
| WO | WO 2012/129514 | 9/2012 | |
| WO | WO 2013/011011 | 1/2013 | |
| WO | WO 2013/038272 | 3/2013 | |
| WO | WO 2013/062365 | 5/2013 | |
| WO | WO 2013/071154 | 5/2013 | |
| WO | WO 2013/123061 | 8/2013 | |
| WO | WO 2013/124474 | 8/2013 | |
| WO | WO 2013/126726 | 8/2013 | |
| WO | WO 2013/166321 | 11/2013 | |
| WO | WO 2014/011984 | 1/2014 | |
| WO | WO 2014/011996 | 1/2014 | |
| WO | WO 2014/031687 | 2/2014 | |
| WO | WO- 2014/055668 | 4/2014 | |
| WO | WO 2014/210064 | 12/2014 | |
| WO | WO 2015/095895 | 6/2015 | |
| WO | WO 2015/157252 | 10/2015 | |
| WO | WO 2015/157384 | 10/2015 | |
| WO | WO 2015/158868 | 10/2015 | |
| WO | WO 2015/164675 | 10/2015 | |
| WO | WO 2015/164745 | 10/2015 | |
| WO | WO 2015/181253 | 12/2015 | |
| WO | WO 2016/019300 | 2/2016 | |
| WO | WO 2016/028896 | 2/2016 | |
| WO | WO 2016/033570 | 3/2016 | |
| WO | WO 2016/073602 | 5/2016 | |
| WO | WO 2016/090190 | 6/2016 | |
| WO | WO 2016/090312 | 6/2016 | |
| WO | WO 2016/090320 | 6/2016 | |
| WO | WO 2016/090327 | 6/2016 | |
| WO | WO 2016/090329 | 6/2016 | |
| WO | WO 2016/090369 | 6/2016 | |
| WO | WO-2016090369 A1 * | 6/2016 | ............. A61K 35/17 |
| WO | WO 2016/164580 | 10/2016 | |
| WO | WO 2016/164731 | 10/2016 | |
| WO | WO 2016/172606 | 10/2016 | |
| WO | WO 2016/191755 | 12/2016 | |
| WO | WO 2016/191756 | 12/2016 | |
| WO | WO 2017/035362 | 12/2016 | |
| WO | WO 2017/015427 | 1/2017 | |
| WO | WO 2017/015490 | 1/2017 | |
| WO | WO 2017/019848 | 2/2017 | |
| WO | WO 2017/023803 | 2/2017 | |
| WO | WO 2017/027291 | 2/2017 | |
| WO | WO 2017/049166 | 3/2017 | |
| WO | WO 2017/053889 | 3/2017 | |

(56) References Cited

FOREIGN PATENT DOCUMENTS

| WO | WO 2017/058850 |    | 4/2017 |          |
|----|----------------|----|--------|----------|
| WO | WO 2017/068421 |    | 4/2017 |          |
| WO | WO 2017/096329 |    | 6/2017 |          |
| WO | WO 2017/156479 |    | 9/2017 |          |
| WO | WO 2017/157505 |    | 9/2017 |          |
| WO | WO 2017/161353 |    | 9/2017 |          |
| WO | WO-2017156479  | A1 * 9/2017 | ............ C07K 14/47 |
| WO | WO 2017/177137 |    | 10/2017 |         |
| WO | WO 2017/214207 |    | 12/2017 |         |
| WO | WO 2018/106732 |    | 6/2018 |          |
| WO | WO 2018/157171 |    | 8/2018 |          |
| WO | WO 2018/162352 |    | 9/2018 |          |
| WO | WO 2018/191723 |    | 10/2018 |         |
| WO | WO 2018/223101 |    | 12/2018 |         |
| WO | WO 2019/109053 |    | 6/2019 |          |
| WO | WO 2019/113556 |    | 6/2019 |          |
| WO | WO 2019/113557 |    | 6/2019 |          |
| WO | WO 2019/213184 |    | 11/2019 |         |
| WO | WO 2020/033927 |    | 2/2020 |          |
| WO | WO 2020/102770 |    | 5/2020 |          |
| WO | WO 2020/113188 |    | 6/2020 |          |
| WO | WO 2020/113194 |    | 6/2020 |          |
| WO | WO 2021/151008 |    | 7/2021 |          |

OTHER PUBLICATIONS

Marthandan et. al. Immunity & Ageing, 10(7): 1-16, (2013) (Year: 2013).*
Bondanza (Blood, 117(24):6469-6478, (2011) (Year: 2011).*
Al-Shanti and Aldahoudi (Immunological Investigations, 36:85-104, (2007)) (Year: 2007).*
Akronbiotech 1-9 (2023) (Year: 2023).*
Marenghi et. al. GE 1-2 (2014) (Year: 2014).*
U.S. Appl. No. 16/769,971, filed Jun. 4, 2020, by Majacic et al.
U.S. Appl. No. 16/770,052, filed Jun. 4, 2020, by Pascal et al.
Abramson et al., "Updated safety and long term clinical outcomes in Transcend NHL 001, pivotal trial of lisocabtagene maraleucel (JCAR017) in R/R aggressive NHL," J Clin Oncol (2018) 36(15_suppl):7505-7505.
Abramson et al., "High durable CR rates in Relapsed/Refractory (R/R) Aggressive B-NHL Treated with the CD19-Directed CAR T Cell Product JCAR017 (Transcend NHL 001): Defined Composition Allows for Dose-Finding and Definition of Pivotal Cohort," Blood (2017).
Abramson et al., "Transcend NHL 001: Ininunotherapy with the CD19-Directed CAR T-Cell Product JCARO17 Results in High Complete Response Rates in Relapsed or Refractory B-Cell Non-Hodgkin Lymphoma," Blood (2016) 128(22):4192.
Aksoy et al., "Human primary T cells: A practical guide," dated Jun. 19, 2018. Retrieved from https://peerj.com/preprints/26993.html.
Al-Lazikani et al., "Standard conformations for the canonical structures of immunoglobulins," J Mol Biol (1997) 273(4):927-948.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Anonymous, "Scientists helping scietiests™ | WWW Optimization of Human T Cell Expansion Protocol: Effects of Early Cell Dilution," (2018).
Benson et al., "CS1-Directed monoclonal antibody therapy for multiple myeloma," J Clin Oncol (2012) 30(16):2012-2015.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.

Brown et al., "Structure-Based Mutagenesis of the Human Immunodeficiency Virus Type 1 DNA Attachment Site: Effects on Integration and cDNA Synthesis," J Viral (1999) 73(11):9011-9020.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Cavaletti et al., "Chemotherapy-induced peripheral neurotoxicity," Nat Rev Neurol (2010) 6(12):657-666.
Cavalieri et al., "Human T lymphocytes transduced by lentiviral vectors in the absence of TCR activation maintain an intact immune competence," Blood (2003) 102(2): 497-505.
Chang et al., "Identification and selective expansion of functionally superior T cells expressing chimeric antigen receptors," J Transl Med (2015) 13(1):161.
Chervin et al., "Engineering higher affinity T cell receptors using a T cell display system," J Immunol Methods. (2008) 339(2): 175-84.
Cheson , "Staging and response assessment in lymphomas: the new Lugano classification," Chin Clin Oncol (2015) 4(1):5.
Cheson et al., "Recommendations for initial evaluation, staging, and response assessment of Hodgkin and non-Hodgkin lymphoma: the Lugano classification," J Clin Oncol (2014) 32(27):3059-3068.
Chicaybam et al., "An efficient low cost method for gene transfer to T lymphocytes," PLoS One (2013) 8(3): e60298.
Chothia et al.,. "The outline structure of the T-cell alpha beta receptor," EMBO J. (1988) 7(12): 3745-55.
Chu et al., "CS1-specific chimeric antigen receptor (CAR)-engineered natural killer cells enhance in vitro and in vivo antitumor activity against human multiple myeloma," Leukemia (2014) 28(4):917-927.
Clackson et al., "Making antibody fragments using phage display libraries," Nature (1991) 352(6336):624-628.
Cooper et al., "T-cell clones can be rendered specific for CD19: toward the selective augmentation of the graft-versus-B-lineage leukemia effect," Blood. (2003) 101:1637-1644.
Coustan-Smith et al., "Immunological detection of minimal residual disease in children with acute lymphoblastic leukaemia," Lancet (1998) 351(9102):P550-554.
Davila et al., "CD19 CAR-targeted T cells induce long-term remission and B Cell Aplasia in an immunocompetent mouse model of B cell acute lymphoblastic leukemia," PLoS One (2013) 8(4): e61338.
Davila et al., "Efficacy and toxicity management of 19-28z CAR T cell therapy in B cell acute lymphoblastic leukemia," Science Translational Medicine (2014) 6(224):224ra25.
De Felipe et al., "Targeting of proteins derived from self-processing polyproteins containing multiple signal sequences," Trafic (2004) 5(8):616-626.
De Felipe, "Skipping the co-expression problem: the new 2A "Chysel" technology," Genetics Vaccines and Therapy (2004) 2:13.
Dull, T. et al. (Nov. 1998) "A Third-Generation Lentivirus Vector with a Conditional Packaging System," J. Viral. 72:8463-8471.
Eisenhauer et al., "New response evaluation criteria in solid tumours: Revised RECIST guideline (version 1.1)," EJC (2009) 45(2):P228-247.
Engelman et al., "Multiple effects of mutations in human immunodeficiency virus type 1 integrase on viral replication," J Viral (1995) 69(5):2729-2736.
Entschladen et al., "Differential requirement of protein tyrosine kinases and protein kinase C in the regulation of T cell locomotion in three-dimensional collagen matrices," J Immunol. (1997) 159(7): 3203-3210.
Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.
Foon et al., "Immunologic classification of leukemia and lymphoma," Blood (1986) 68(1):1-31.
Fraietta et al., "Biomarkers of Response to Anti-CD19 Chimeric Antigen Receptor (CAR) T-Cell Therapy in Patients with Chronic Lymphocytic Leukemia," Blood (2016) 128(22):57.

(56) References Cited

OTHER PUBLICATIONS

Friedl et al., "T lymphocyte locomotion in a three-dimensional collagen matrix: Expression and function of cell adhesion molecules," J Immunol. (1995) 154: 4973-4985.
Gardner et al., "Intent to treat leukemia remission by CD19CAR T cells of defined formulation and dose in children and young adults," Blood (2017) 129(25):3322-3331.
Garfall et al., "Posterior Reversible Encephalopathy Syndrome (PRES) after infusion of anti-Bcma CAR T cells (CART_BCMA) for multiple myeloma: Successful Treatment with Cyclophophamide," Blood (2016) 128(22):5702.
Gargett et al., "Different cytokine and stimulation conditions influence the expansion and immune phenotype of third-generation chimeric antigen receptor T cells specific for tumor antigen GD2," Cytotherapy (2015) 17(4):487-495.
Ghobadi et al., "Chimeric antigen receptor T cell therapy for non-Hodgkin lymphoma," Curr Res Transl Med (2018) 66(2):43-49.
Grupp et al., "Chimeric Antigen Receptor-Modified T Cells for Acute Lymphoid Leukemia," N Engl J Med (2013) 368:1509-1518.
Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood (2008) 111(12):5446-5456.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Honegger et al., "Yet another numbering scheme for immunoglobulin variable domains: an automatic modeling and analysis tool," J Mol Biol (2001) 309(3):657-670.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese).
Imamoto et al., "Advantages of AlaGln as an additive to cell culture medium: use with anti-CD20 chimeric antibody-producing Potelligent™ CHO cell lines," Cytotechnology (2013) 65:135-143.
Janeway et al., Immunobiology: The Immune System in Health and Disease, 3rd ED., Current Biology Publications (1997), p. 4:33.
Johnson et al., "Imaging for Staging and Response Assessment in Lymphoma," Radiology (2015) 276(2):323-338.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kindt et al., "Antigens and Antibodies," in Chapter 4 of Kuby Immunology, 6th ed., W.H. Freeman and Co., N.Y, (2007) pp. 91, 14 pages.
Klebanoff et al., "Sorting through subsets: which T-cell populations mediate highly effective adoptive immunotherapy?," J Immunother. (2012) 35(9): 651-660.
Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kurucz et al., "A bacterially expressed single-chain Fv construct from the 2B4 T-cell receptor," Proc Natl Acad Sci U S A. (1993) 90(9): 3830-3834.
Lada et al., "Quantitation of integrated HIV provirus by pulsed-field gel electrophoresis and droplet digital PCR," J Clin Microbiol (2018) 56(12):e01158.
Lee et al., "T cells expressing CD19 chimeric antigen receptors for acute lymphoblastic leukaemia in children and young adults: a phase 1 dose-escalation trial." The Lancet (2015) 385(9967) : 517-528.
Lefranc et al., "IMGT unique numbering for immunoglobulin and T cell receptor variable domains and Ig superfamily V-like domains," Dev Comp Immunol (2003) 27(1):55-77.
Li et al., "Comparison of anti-CD3 and anti-CD28-coated beads with soluble anti-CD3 for expanding human T cells: Differing impact on CD8 T cell phenotype and responsiveness to restimulation," J Transl Med (2010) 8(1):104.
Li et al., "Comparison of inlet geomery in microfluidic cell affinity chromatography," Analytical chemistry (2011) 83(3):774-781.
Li et al., "Negative enrichment of target cells by microfluidic affinity chromatography," Analytical Chemistry (2011) 83(20):7863-7869.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (2016) 34(4):430-434.
Lu et al., "A Rapid Cell Expansion Process for Production of Engineered Autologous CAR-T Cell Therapies," Human Gene Therapy Methods (2016) 27(6):209-218.
MacCallum et al., "Antibody-antigen interactions: contact analysis and binding site topography," J Mol Biol (1996) 262(5):732-745.
Manuri et al., "piggyBac transposon/transposase system to generate CD19-specific T cells for the treatment of B-lineage malignancies," Hum Gene Ther (2010) 21(4): 427-437.
Maude et al., "Tisagenlecleucel in Children and Young Adults with B-Cell Lymphoblastic Leukemia," New Engl J Med (2018) 378(5):439-448.
Martin et al., "Modeling antibody hypervariable loops: a combined algorithm," PNAS (1989) 86(23):9268-9272.
McWilliams et al., "Mutations in the 5' end of the human immunodeficiency virus type 1 polypurine tract affect RNase H cleavage specificity and virus titer," J Viral (2003) 77(20):11150-11157.
Miller et al., "Improved retroviral vectors for gene transfer and expression," BioTechniques (1989) 7:980-990.
Miller et al., "Retrovirus packaging cells," Human Gene Therapy (1990) 1:5-14.
Miyoshi et al. "Development of a self-inactivating lentivirus vector," J Viral (1998) 72(10):8150-8157.
Naldini et al., "In vivo gene delivery and stable transduction of nondividing cells by a lentiviral vector," Science. Apr. 12, 1996;272(5259):263-7.
Naldini et al., "Lentiviruses as gene transfer agents for delivery to non-dividing cells", Curr Opin Biotechnol., Oct. 9, 1998; 5:457-63.
Neeson et al., "Ex vivo culture of chimeric antigen receptor T cells generates functional CD8+ T cells with effector and central memory-like phenotype," Gene Therapy (2010) 17(9):1105-1116.
Okamoto et al., "A promising vector for TCR gene therapy: differential effect of siRNA, 2A peptide, and disulfide bond on the introduced TCR expression," Mol Ther Nucl Acids (2012) 1(12):1-11.
Park et al., "Treating cancer with genetically engineered T cells," Trends Biotechnol. (2011) 29(11): 550-557.
Philpott et al., "Use of Nonintegrating Lentiviral Vectors for Gene Therapy," Human Gene Therapy (2007) 18:483.

(56) References Cited

OTHER PUBLICATIONS

Portolano et al., "Lack of promiscuity in autoantigen-specific H and L chain combinations as revealed by human H and L chain "roulette"," J Immunol (1993) 150(3):880-887.
Powell et al., "Sequence and structural determinants required for priming of plus-strand DNA synthesis by the human immunodeficiency virus type 1 polypurine tract," J Viral (1996) 70(8):5288-5296.
Pullagurla et al., "Parallel affinity-based isolation of leukocyte subsets using microfluidics: application for stroke diagnosis," Analytical chemistry (2014) 86(8):4058-4065.
Ramsborg et al., "JCAR017 Is a Defined Composition CAR T Cell Product with Product and Process Controls That Deliver Precise Doses of CD4 and CD8 Car T Cell to Patients with NHL", Blood (Dec. 7, 2017) 130(Issue Supplement 1): 4471.
Ramsborg et al., "JCAR017 Is a Defined Composition CAR T Cell Product with Product and Process Controls That Deliver Precise Doses of CD4 and CD8 Car T Cell to Patients with NHL", Poster 4471 Presentation at 2017 American Society of Hematology, Dec. 9-12, 2017.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Schlueter et al., "Specificity and Binding Properties of a Single-chain T Cell Receptor," J Mol Biol (1996) 859-869.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74.
Singh et al., "ProPred: prediction of HLA-DR binding sites," Bioinformatics. (2001) 17(12): 1236-1237.
Singh et al., "Early memory phenotypes drive T cell proliferation in patients with pediatric malignancies," Sci Transl Med (2016) 8(320):320ra3.
Soman et al., "MTS dye based colorimetric CTLL-2 cell proliferation assay for product release and stability monitoring of interleukin-15: assay qualification, standardization and statistical analysis," J Immunol Methods (2009) 348(1-2):83-94.
Soo Hoo et al., "Characterization of a single-chain T-cell receptor expressed in Escherichia coli," Proc Natl Acad Sci U S A. (1992) 89(10): 4759-4763.
Stemberger et al., "Novel Serial Positive Enrichment Technology Enables Clinical Multiparameter Cell Sorting," PLoS One (2012) 7(4): e35798.
Tai et al., "Antibody-Based Therapies in Multiple Myeloma," Bone Marrow Research (2010) vol. 2011. Article ID 924058.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Anti-CD19 Chimeric Antigen Receptor-Modified T Cell Therapy for B Cell Non- Hodgkin Lyphoma and Chronic Lyphocytic Leukemia: Fludarabine and Cyclophosphamide Lyphodepletion Imprives In Vivo Expansion and Persistence of CAR-T Cells and Clinical Outcomes," Blood (2015) 126:184.
Turtle et al., "CD19 CAR-T cells of defined CD4+:CD8+ composition in adult B cell ALL patients," J. Clin. Invest. (2016) 126(6):2123-38.
Turtle et al., "Engineered T cells for anti-cancer therapy," Curr. Opin. Immunol. (2012) 24(5): 633-39.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.
Van Tendeloo et al., "High-level transgene expression in primary human T lymphocytes and adult bone marrow CD34+ cells via electroporation-mediated gene delivery," Gene Therapy (2000) 7(16): 1431-1437).
Verhoeyen et al., "Lentiviral vector gene transfer into human T cells," Methods Mol Biol. (2009) 506: 97-114.
Vormittag et al., "A guide to manufacturing CAR T cell therapies," Curr Opin in Biotechnology (2018) 53:164-181.
Wadhwa et al., "Receptor mediated glycotargeting," J. Drug Targeting (1995) 3: 111.
Wadhwa et al., "Strategies for detection, measurement and characterization of unwanted antibodies induced by therapeutic biologicals," J Immunol Methods (2003) 278(1-2):1-17.
Wang et al., "Clinical manufacturing of CAR T cells: foundation of a promising therapy," Molecular Therapy—Oncolytics (2016) 3:16015.
Wang et al., "Phenotypic and functional attributes of lentivirus-modified CD19-specific human CD8+ central memory T cells manufactured at clinical scale," J Immunother. (2012) 35(9):689-701.
Wang et al., "Open-tubular capillary cell affinity chromatography: single and tandem blood cell separation," Anal Chem (2008) 80(6):2118-2124.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of Escherichia coli. Influence of folding catalysts," J Mol Biol. (1994) 242(5): 655-669.
Xu et al., "Closely related T-memory stem cells correlate with in vivo expansion of CAR.CD19-T cells and are preserved by IL-7 and IL-15," Blood (2014) 123(24):3750-3759.
Xu et al., "Cytokine release syndrome in cancer immunotherapy with chimeric antigen receptor engineered T cells," Cancer Letters (2014) 343(2):172-178.
Xu et al., "Multiparameter comparative analysis reveals differential impacts of various cytokines on CART cell phenotype and function ex vivo and in vivo," Oncotarget (2016) 7(50):82354-82368.
Yarilin, "Immunology principles," M. Medicine (1999) 184-195, 339-347 (English Translation included).
Zhao et al., "Development of the First World Health Organization Lentiviral Vector Standard: Toward the production control and standardization of lentivirus-based gene therapy products," Human Gene Therapy Methods (2017) 28(4):205-214.
Zufferey et al. "Self-Inactivating Lentivirus Vector for Safe and Efficient In Vivo Gene Delivery," J. Viral (1998) 72(12):9873-9880.
Zufferey et al., "Multiply attenuated lentiviral vector achieves efficient gene delivery in vivo," Nat Biotechnol. Sep. 1997;15(9):871-875.
U.S. Appl. No. 17/794,245, filed Jan. 22, 2021, by Germeroth et al.
U.S. Appl. No. 17/850,875, filed Jun. 27, 2022, by Ramsborg et al.
U.S. Appl. No. 17/846,868, filed Jun. 22, 2022, by Albertson et al.
Applikon Biotechnology/BioPharma-Reporter (2016) How automation has changed the way we count cells BioPharma-Reporter.com; 1-4 (Year: 2016).
Casati et al., "Clinical-scale selection and viral transduction of human naïve and central memory CD8+ T cells for adoptive cell therapy of cancer patients," Cancer Immunology (2013) 62(10): 1563-1573.
Church et al., "Tumor-specific CD4+ T cells maintain effector and memory tumor-specific CD8+ T cells," Eur J Immunol (2014) 44: 69-79.
Eaker et al., "Concise review: guidance in developing commercializable autologous/patient-specific cell therapy manufacturing," Stem Cells Transl Med. (2013) 2(11): 871-83.
Fraietta et al., "Determinants of response and resistance to CD19 chimeric antigen receptor (CAR) T cell therapy of chronic lymphocytic leukemia," Nat Med. (May 2018) 24(5):563-571. Epub Apr. 30, 2018.

(56) References Cited

OTHER PUBLICATIONS

Franke et al., "Antibodies against CD20 or B-cell receptor induce similar transcription patterns in human lymphoma cell lines," PLoS One.(2011) 6(2): e16596.
Frayer et al., "Mean Body Weight, Height, Waist Circumference, and Body Mass Index Among Adults: United States, 1999-2000 Through 2015-2016," Natl Health Stat Report. (2018) (122):1-16.
Gearing et al., "The international standard for human interleukin-2. Calibration by international collaborative study," J Immunological Methods (1988) 114(1-2):3-9.
Gunzer et al,, "Two-step negative enrichment of CD4+ and CD8+ T cells from murine spleen via nylon wool adherence and an optimized antibody cocktail," J Immunol Methods. (2001) 258(1-2): 55-63.
Hudecek et al., "The nonsignaling extracellular spacer domain of chimeric antigen receptors is decisive for in vivo antitumor activity," Cancer Immunol Res (2015) 3(2):125-135.
Hunziker et al., "Exhaustion of cytotoxic T cells during adoptive immunotherapy of virus carrier mice can be prevented by B cells or CD4+ T cells," Eur J Immunol (2002) 32(2):374-382.
Janas et al., "Perfusion's role in maintenance of high-density T-cell cultures," BioProcesses International. (2015) pp. 1-12.
Kahn et al., "Optimization of retroviral vector-mediated gene transfer into endothelial cells in vitro," Circ Res. (1992) 71(6):1508-17.
Klaver et al., "T Cell Maturation Stage Prior to and During GMP Processing Informs on CAR T Cell Expansion in Patients," Front Immunol. (2016) 7:648.
Larson et al., "Defined cell composition and precise control over JCAR017 dose enables identification of relationships between chimeric antigen receptor T cell product attributes, pharmacokinetics, and clinical endpoints in NHL", Cancer Res (Jul. 1, 2018) 78(13 Supplement): 960.
Larson et al., "Defined cell composition and precise control over JCAR017 dose enables identification of relationships between chimeric antigen receptor T cell product attributes, pharmacokinetics, and clinical endpoints in NHL", Oral Presentation 960 at 2018 AACR Annual Meeting, Apr. 14-18, 2018.
Law et al., "What does it take to bind CAR?," Mol Ther. (2005) 12(4):599-609.
Li et al., "Directed evolution of human T-cell receptors with picomolar affinities by phage display," Nature Biotechnology (2005) 23:349-354.
Li et al., "Multiparameter cell affinity chromatography: Separation and analysis in a single microfluidic channel," Anal Chem (2012) 84(19):8140-8148.
Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.
Moeller et al., "Adoptive transfer of gene-engineered CD4+ helper T cells induces potent primary and secondary tumor rejection," Blood (2005) 106(9):2995-3003.
Nascimbeni et al., "Peripheral CD4+CD8+ T cells are differentiated effector memory cells with antiviral functions," Blood (2004) 104(2):478-86.
Skea et al., "The selective expansion of functional T cell subsets," J Hematother Stem Cell Res. (1999) 8(5): 525-38.
Sun et al., "Early transduction produces highly functional chimeric antigen receptor-modified virus-specific T-cells with central memory markers: a Production Assistant for Cell Therapy (PACT) translational application," J Immunother Cancer. (2015) 3:5.
Turtle et al., "Durable Molecular Remissions in Chronic Lymphocytic Leukemia Treated With CD19-Specific Chimeric Antigen Receptor-Modified T Cells After Failure of Ibrutinib," J Clin Oncol. (2017) 35(26): 3010-3020.
U.S. Appl. No. 18/166,447, filed Feb. 8, 2023, by Ramsborg et al.
Berthois et al., "Phenol red in tissue culture media is a weak estrogen: implications concerning the study of estrogen-responsive cells in culture," Proc Natl Acad Sci U S A. (1986);83(8):2496-500.

Carpenter et al., "B-cell maturation antigen is a promising target for adoptive T-cell therapy of multiple myeloma," Clin Cancer Res. (2013) 19:2048-2060.
Cheadle et al., "Chimeric antigen receptors for T-cell based therapy," Methods Mol Biol (2012) 907:645-666.
Cho et al., "Human mammalian cell sorting using a highly integrated micro-fabricated fluorescence-activated cell sorter (µFACS)," Lab on a Chip (2010) 10:1567-1573.
Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175(9):5799-5808.
Darling et al., "Kinetic exclusion assay technology: characterization of molecular interactions," Assay Drug Dev Technol. (2004) 2:647-657.
Dimopoulos et al., "Current treatment landscape for relapsed and/or refractory multiple myeloma," Nat Rev Clin Oncol. (2015) 12:42-54.
Ex-Cell 302. Material Safety Data Sheet. SAFC Bioscience. p. 1-2. (Year: 2006).
Fan et al., "Durable remissions with BCMA-specific chimeric antigen receptor (CAR)-modified T cells in patients with refractory/relapsed multiple myeloma," Journal of Clinical Oncology (2017) 35(18_suppl): LBA3001-LBA3001.
Frecha et al., "Advances in the field of lentivector-based transduction of T and B lymphocytes for gene therapy," Mol Ther (2010) 18(10):1748-1757.
Garfall et al., "Immunotherapy with chimeric antigen receptors for multiple myeloma," Discov Med (2014) 17(91):37-46.
Gattinoni et al., "T memory stem cells in health and disease," Nat Med (2017), 23: 18-27.
GlutaMAX-1. Gibco. p. 1 (Year: 2010).
Godin et al., "Microfluidics and photonics for Bio-System-on-a-Chip: A review of advancements in technology towards a microfluidic flow cytometry chip," J Biophotonics (2008) 1(5):355-376.
Hackett et al., "A transposon and transposase system for human application," Molecular Therapy: The Journal of the American Society of Gene Therapy (2010) 18:674-683.
Howarth et al., "A monovalent streptavidin with a single femtomolar biotin binding site," Nature Methods (2006) 3:267-273.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese) English Tranlsation provided.
Irving et al., "Engineering Chimeric Antigen Receptor T-Cells for Racing in Solid Tumors: Don't Forget the Fuel," Front Immunol. (Apr. 3, 2017) 8:267.
Jeon et al. Development of a serum-free medium for in vitro expansion of human cytotoxic T lymphocytes using a statistical design. BMC Biotechnology 2010, 10:70. p. 1-9 (Year: 2010).
Jethwa et al., "Use of gene-modified regulatory T-cells to control autoimmune and alloimmune pathology: is now the right time?," Clin Immunol. (2014) 150(1):51-63.
Karnieli et al. A consensus introduction to serum replacements and serum-free media for cellular therapies. Cytotherapy, 2017; 19: 155-169 (Year: 2017).
Katz et al., "Therapeutic targeting of CD19 in hematological malignancies: past, present, future and beyond." Leuk Lymphoma. (2014) 55(5):999-1006.
Klebanoff et al., "IL-15 enhances the in vivo antitumor activity of tumor-reactive CD8+ T cells," Proc Natl Acad Sci USA (2004) 101: 1969-74.
Lee et al., "Current concepts in the diagnosis and management of cytokine release syndrome," Blood (2014) 124(2):188-195.
Life Technologies Corporation (2013) OpTmizerTMCTSTMT-cell Expansion SFM Technical information; pp. 1-2 (Year: 2013).
Lim et al., "Engineered streptavidin monomer and dimer with improved stability and function," Biochemistry (2010) 50:8682-8691.
Lupton et al., "Dominant positive and negative selection using a hygromycin phosphotransferase-Thymidine kinase dusion gene," Molecular and cellular biology (1991) 11(6):3374-3378.

(56) References Cited

OTHER PUBLICATIONS

Mak et al., "Glutathione Primes T Cell Metabolism for Inflammation," Immunity. (2017) 46(4):675-689.
Makita et al., "Clinical development of anti-CD19 chimeric antigen receptor T-cell therapy for B-cell non-Hodgkin lymphoma," Cancer Sci. Jun, 2017; 108(6):1109-1118.
Mei et al., "Rationale of anti-CD19 immunotherapy: an option to target autoreactive plasma cells in autoimmunity," Arthritis Res Ther. (2012) 14 Suppl 5(Suppl 5):S1.
Navarro et al., "Estrogen Stimulation Differentially Impacts Human Male and Female Antigen-Specific T Cell Anti-Tumor Function and Polyfunctionality," Gender and the Genome. (2017) 1:4, 167-179.
Okern et al.,, "CTS™ immune cell SR for serum free culture and expansion of human T cells," J Immunother Cancer. (2015); 3(Suppl 2): P1.
Riddell et al., "The Fred Hutchinson Cancer Research Center and the University of Washington School of Medicine, Department of Medicine, Division of Oncology Oct. 7, 1991," Human Gene Therapy (1992) 3:319-338.
RPMI-1640 medium. Sigma-Aldrich. p. 1-2 (Year: 2007).
Siddiqi et al., "Rapid MRD-Negative Responses in Patients with Relapsed/Refractory CLL Treated with Liso-Cel, a CD19-Directed CAR T-Cell Product: Preliminary Results from Transcend CLL 004, a Phase 1/2 Study Including Patients with High-Risk Disease Previously Treated with Ibrutinib," Blood (2018) 132 (Suppl. 1):300.
Smith et al., "Ex vivo expansion of human T cells for adoptive immunotherapy using the novel xeno-free CTS immune cell serum replacement," Clin Transl Immunol (2015) 4:e31.
Sun et al., "Defective CD8 T cell memory following acute infection without CD4 T cell help," Science (2003) 300: 339-42.
Tai et al., "Targeting B-cell maturation antigen in multiple myeloma," Immunotherapy (2015) 7:1187-1199.
Technical Bulletin. Animal-Component Free Recombinant Human Insulin is Suitable for Use in Serum-Free Media. SAFC Bioscience. p. 1-4 (Year: 2006).
Tran et al., "Minimally cultured tumor-infiltrating lymphocytes display optimal characteristics for adoptive cell therapy," J Immunother (2008) 31: 742-51.
Turtle et al. "Addition of fludarabine to cyclophosphamide lymphodepletion improves in vivo expansion of CD19 chimeric antigen receptor-modified T cells and clinical outcome in adults with B cell acute lymphoblastic leukemia." Blood 126.23 (2015): 3773.
Vairy et al., "CTL019 (tisagenlecleucel): CAR-T therapy for relapsed and refractory B-cell acute lymphoblastic leukemia," Drug Des Devel Ther. (2018) 12:3885-3898.
Venkateshaiah et al., "GPRC5D Is a Cell Surface Plasma Cell Marker Whose Expression Is High In Myeloma Cells and Reduced Following Coculture With Osteoclasts," Blood (2013) 122 (21): 3099.
Wu et al., "Engineering soluble monomeric streptavidin with reversible biotin binding capability," J Biol Chem (2005) 280(24):23225-23231.
Zhang et al., "A novel approach to make homogeneous protease-stable monovalent streptavidin," Biochem Biophys Res Commun (2015) 463(4):1059-1063.
Dupont et al., "Comparative dose-responses of recombinant human IL-2 and IL-7 on STAT5 phosphorylation in CD4+FOXP3-cells versus regulatory T cells: a whole blood perspective," Cytokine. (2014) 69(1):146-9.
Qian et al., "Advances in the Development of Interleukin-2 and its Analogues," Chinese Journal of Pharmaceuticals. (2020) 947-955. (Article in Chinese; English abstract provided).
Abramson et al., "High durable CR rates and preliminary safety profile for JCAR017 in R/R aggressive b-NHL (Transcend NHL 001 Study): A defined composition CD19-directed CAR T-cell product with potential for outpatient administration," Journal of Clinical Oncology. (2018) 36:5_suppl. 120-120, 4 pages.
Chen et al. "Anti-CD19 Chimeric Antigen Receptor T Cells Improve Responses to Chemotherapy-Refractory Mantle Cell Lymphoma: A Case Report," Blood (2016) 128(22): 5393, 2 pages.
Dong, Modern Biology, Beijing Institute of Technology Press, 1st edition, p. 328, Jul. 31, 2016 (Article in Chinese; English translation provided).
Hinrichs et al., "Human effector CD8+ T cells derived from naive rather than memory subsets possess superior traits for adoptive immunotherapy," Blood. (2011) 117(3):808-14.
Hou et al., "Tutorial on Animal Cell Culture Techniques," Gansu Science and Technology Press (2009) 520, Chapter 9, p. 105. (Article in Chinese; English translation provided).
Janssen Pharmaceutical K.K., "Submission of application for additional indication of "Imbruvica (R)" for untreated chronic lymphocytic leukemia (including small lymphocytic lymphoma)," [online] Published Nov. 21, 2017, 3 pages. (English translation provided) <https://www.janssen.com/japan/press-release/20171121>.
Juno Therapeutics, "Juno Advances CAR T-cell CAR017 and Halts CAR015 in Non-Hodgkin Lymphoma," Cancer Biology, retrieved on Nov. 7, 2023, 7 pages. https://blogs.shu.edu/cancer/2017/03/08/juno-advances-car-t-cell-car017-and-halts-car015-in-non-hodgkin-lymphoma/.
Kaartinen et al., "Low interleukin-2 concentration favors generation of early memory T cells over effector phenotypes during chimeric antigen receptor T-cell expansion," Cytotherapy (2017) 19(6):689-702.
Poltorak et al., "Expamers: a new technology to control T cell activation," Sci Rep. (2020) 10(1):17832, 15 pages.
Qasim et al., "612. Acute Lymphoblastic Leukemia: Clinical Studies: Poster I. Preliminary Results of UCART19, an Allogeneic Anti-CD19 CAR T-Cell Product in a First-in-Human Trial (PALL) in Pediatric Patients with CD19+ Relapsed/Refractory B-Cell Acute Lymphoblastic Leukemia," Blood (2017) 130(Supplement 1):1271, 3 pages.
Qasim et al., "Preliminary Results of UCART19, an Allogeneic Anti-CD19 CAR T-Cell Product in a First-in-Human Trial (PALL) in Pediatric Patients with CD19+ Relapsed/Refractory B-Cell Acute Lymphoblastic Leukemia," Poster, Atlanta Dec. 9-12, 2017, 1 page.
Ramos et al., "In Vivo Fate and Activity of Second- versus Third-Generation CD19-Specific CAR-T Cells in B Cell Non-Hodgkin's Lymphomas," Mol Ther (2018) 26(12):2727-2737.
RPMI 1640. catalog #32404, downloaded from https://www.thermofisher.com/us/en/home/technical-resources/media-formulation.192.html. p. 1-2 (Year: 2023).
Supplementary Materials for Turtle et al., "Immunotherapy of Non-Hodgkin's Lymphoma with a Defined Ratio of CDS+ and CD4+ CD19-specific Chimeric Antigen Receptor-modified T cells," Science Translational Medicine (2016) vol. 8 (155) 355ra116, 16 pages.
WHO unit chart. PeproTech. downloaded from https://www.peprotech.com/en/who-unit-chart. p. 1-2 (Year: 2023).
Amos et al., "The role of caspase 3 and BclxL in the action of interleukin 7 (IL-7): a survival factor in activated human T cells," Cytokine. (1998) 10(9):662-8.
Hirakawa et al., "IL-2, IL-7, IL-15 and IL-6 Induce Differential Activation of Naive and Memory T Cell Subsets," Blood (2015) 126(23):3425, 4 pages.
Jiang Bo, Fundamentals and Clinics of Apoptosis, People's Military Medical Press, p. 141, Jul. 1999 (Reference in Chinese; English translation provided).
Saligrama et al., "IL-15 maintains T-cell survival via S-nitrosylation-mediated inhibition of caspase-3," Cell Death Differ. (2014) 21(6):904-14.
Weigmann, "Cell Isolation of Spleen Mononuclear Cells," Bio-Protocol (2013) 3(9):4 pages.
U.S. Appl. No. 18/882,479, filed Sep. 11, 2024, by Albertson et al.
U.S. Appl. No. 18/893,872, filed Sep. 23, 2024, by Albertson et al.
Anastasov et al., "Optimized Lentiviral Transduction Protocols by Use of a Poloxamer Enhancer, Spinoculation, and scFv-Antibody Fusions to VSV-G," Methods Mol Biol (2016) 1448:49-61.
Avdic et al., "Human Cytomegalovirus-Encoded Human Interleukin-10 (IL-10) Homolog Amplifies Its Immunomodulatory Potential by Upregulating Human IL-10 in Monocytes," J Virol. (2016) 90(8): 3819-3827.
Boyman et al., "The role of interleukin-2 in memory CD8 cell differentiation," Adv Exp Med Biol (2010) 684:28-41.

(56) References Cited

OTHER PUBLICATIONS

Davis et al., "Assessment of a positive selection technique using an avidin col. to isolate human peripheral blood T cell subsets," J Immunol Methods. (1994) 175(2):247-57.
Fernandes et al., "Kinetics of class II MHC expression on cytotoxic T cells generated by skin allograft," Tissue Antigens. (1990) 36(3):93-9.
Krug et al., "A GMP-compliant protocol to expand and transfect cancer patient T cells with mRNA encoding a tumor-specific chimeric antigen receptor," Cancer Immunol Immunother (2014) 63(10):999-1008.
Litvinova et al., "The influence of immunoregulatory cytokines IL-2, IL-7, and IL-15 upon activation, proliferation, and apoptosis of immune memory T-cells in vitro," Cell and Tissue Biology (2013) 7(6):539-544.
Mackensen et al., "Anti-CD19 CAR T cell therapy for refractory systemic lupus erythematosus," Nat Med (2022) 28(10):2124-2132 and Supplementary Materials.
Medvec et al., "Improved Expansion and In Vivo Function of Patient T Cells by a Serum-free Medium," Mol Ther Methods Clin Dev. (2017) 8:65-74.
Mougiakakos et al., "CD19-Targeted CAR T Cells in Refractory Systemic Lupus Erythematosus," N Engl J Med (2021) 385(6):567-569 and Supplementary Appendix.
Salmon, "Arming T cells against B cells in systemic lupus erythematosus," Nat Med (2022) 28(10):2009-2010.
Sommermeyer et al., "Chimeric antigen receptor-modified T cells derived from defined CD8+ and CD4+ subsets confer superior antitumor reactivity in vivo," Leukemia (2016) 30: 492-500, 20 pages.

\* cited by examiner

PROCESS FOR GENERATING THERAPEUTIC COMPOSITIONS OF ENGINEERED CELLS

CROSS-REFERENCE TO RELATED APPLICATIONS

This application is a National Stage application under 35 U.S.C. § 371 of International Application No. PCT/US2018/058590, filed on Oct. 31, 2018, which claims priority from U.S. provisional application No. 62/580,409, filed Nov. 1, 2017, entitled "PROCESS FOR GENERATING THERAPEUTIC COMPOSITIONS OF ENGINEERED CELLS," U.S. provisional application No. 62/596,771, filed Dec. 8, 2017, entitled "PROCESS FOR GENERATING THERAPEUTIC COMPOSITIONS OF ENGINEERED CELLS," and U.S. provisional application No. 62/721,603, filed Aug. 22, 2018, entitled "PROCESS FOR GENERATING THERAPEUTIC COMPOSITIONS OF ENGINEERED CELLS," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042013200SeqList.txt, created Apr. 27, 2020 which is 36,268 bytes in size. The information in the electronic format of the Sequence Listing is incorporated by reference in its entirety.

FIELD

The present disclosure provides methods for genetically engineering T cells, such as CD4+ T cells and/or CD8+ T cells, for use in cell therapy. In some aspects, the provided methods include one or more steps for incubating the cells under stimulating conditions, introducing a recombinant polypeptide to the cells through transduction or transfection, and cultivating the cells under conditions that promote proliferation and/or expansion. In some aspects, the incubation and/or the cultivation is performed in the presence of recombinant IL-2. In some aspects, the provided methods are an efficient, reliable means to produce genetically engineered T cells with a high degree of success.

BACKGROUND

Various cell therapy methods are available for treating diseases and conditions. Among cell therapy methods are methods involving immune cells, such as T cells, genetically engineered with a recombinant receptor, such as a chimeric antigen receptors. Improved methods for manufacturing and/or engineering such cell therapies are needed, including to provide for a more efficient process and/or an improved cell composition product. Provided are methods, kits and articles of manufacture that meet such needs.

SUMMARY

Provided in some aspects are methods for producing a composition of engineered cells, the methods involve: (a) incubating, under stimulating conditions, an input composition containing T cells enriched for CD4+ primary human T cells, said stimulating conditions including the presence of (i) a stimulatory reagent capable of activating one or more intracellular signaling domains of one or more components of a TCR complex and/or one or more intracellular signaling domains of one or more costimulatory molecules and (ii) one or more cytokines, wherein at least one cytokine is or includes recombinant human IL-2, thereby generating a stimulated composition; and (b) introducing a recombinant receptor into the stimulated composition, thereby generating an engineered composition containing engineered T cells.

In some embodiments of the methods provided herein, the input composition includes greater than or greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or the input composition consists essentially of CD4+ primary human T cells. In some embodiments, the concentration of recombinant IL-2 is from 10 IU/mL to 200 IU/mL or from about 10 to about 200 IU/mL. In some embodiments of the methods provided herein, the one or more cytokines further includes IL-7 and/or IL-15, optionally wherein the concentration of IL-7 is from 100 IU/mL to 1000 IU/mL or from about 100 IU/mL to about 1000 IU/mL and/or the concentration of IL-15 is from 1 IU/mL to 50 IU/mL or from about 1 IU/mL to about 50 IU/mL. In some embodiments of the methods provided herein, the incubating is carried out in the presence of one or more antioxidants.

Provided in some aspects are methods for producing a composition of engineered cells, the method involve: (a) incubating an input composition containing T cells enriched for one or both of CD4+ and CD8+ primary human T cells, thereby generating a stimulated composition, wherein the incubating is carried out: (1) under one or more stimulating conditions, said stimulating conditions including the presence of (i) a stimulatory reagent capable of activating one or more intracellular signaling domains of one or more components of a TCR complex and/or one or more intracellular signaling domains of one or more costimulatory molecules and (ii) one or more cytokines; and/or (2) in the presence of one or more antioxidant; and (b) introducing a recombinant receptor into the stimulated composition, thereby generating an engineered composition containing engineered T cells.

In some embodiments of the methods provided herein, the input composition includes greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells; and/or the input composition consists essentially of CD4+ and/or CD8+ primary human T cells. In some embodiments of the methods provided herein, the one or more cytokines are selected from recombinant IL-2, recombinant IL-7 and/or recombinant IL-15. In some embodiments, the concentration of recombinant IL-2 is from 10 to 200 IU/mL or from about 10 to about 200 IU/mL; the concentration of recombinant IL-7 is from 100 IU/mL to 1000 IU/mL or from about 100 IU/mL to about 1000 IU/mL; and/or the concentration of recombinant IL-15 is from 1 IU/mL to 25 IU/mL or from about 1 IU/mL to about 25 IU/mL.

In some embodiments of the methods provided herein, the input composition includes greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or the input composition consists essentially of CD4+ primary human T cells. In some embodiments, the one or more cytokines are selected from recombinant IL-2, recombinant IL-7 and recombinant IL-15. In some embodiments, the input composition includes greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells; and/or the input composition consists essentially of CD8+ primary human T cells. In some embodiments of the methods provided herein, the one or more cytokines are selected from recombinant IL-2 and recombinant IL-15.

In some embodiments of the methods provided herein, the stimulatory reagent includes a primary agent that specifically binds to a member of a TCR complex, optionally that specifically binds to CD3. In some embodiments, the stimulatory reagent further includes a secondary agent that specifically binds to a T cell costimulatory molecule, optionally wherein the costimulatory molecule is selected from CD28, CD137 (4-1-BB), OX40, or ICOS. In some embodiments of the methods provided herein, the primary and/or secondary agents include an antibody, optionally wherein the stimulatory reagent includes incubation with an anti-CD3 antibody and an anti-CD28 antibody, or an antigen-binding fragment thereof. In some embodiments, the primary agent and/or secondary agent are present on the surface of a solid support.

In some embodiments of the methods provided herein, the solid support is or includes a bead. In some embodiments, the bead has a diameter of greater than or greater than about 3.5 µm but no more than about 9 µm or no more than about 8 µm or no more than about 7 µm or no more than about 6 µm or no more than about 5 µm. In some embodiments, the bead has a diameter of or about 4.5 µm. In some embodiments, the bead is inert. In some embodiments, the bead is or includes a polystyrene surface. In some embodiments, the bead is magnetic or superparamagnetic. In some embodiments, the ratio of beads to cells is less than 3:1 or less than about 3:1. In some embodiments, the ratio of beads to cells is from 2:1 to 0.5:1 or from about 2:1 to about 0.5:1. In some embodiments, the ratio of beads to cells is at or at about 1:1.

In some embodiments of the methods provided herein, the one or more antioxidant includes a sulfur containing antioxidant. In some embodiments, the one or more antioxidants include a glutathione precursor. In some embodiments, the one or more antioxidants include N-acetyl cysteine (NAC), optionally wherein the NAC is at a concentration of from 0.2 mg/mL to 2.0 mg/mL or from about 0.2 mg/mL to about 2.0 mg/mL.

In some embodiments of the methods provided herein, the introducing includes transducing cells of the stimulated composition with a viral vector containing a polynucleotide encoding the recombinant receptor. In some embodiments, the viral vector is a retroviral vector. In some embodiments, the viral vector is a lentiviral vector or gammaretroviral vector. In some embodiments of the methods provided herein, the introducing is carried out in the presence of a transduction adjuvant. In some embodiments, the transduction adjuvant is or comprises protamine sulfate, optionally from 1 µg/ml to 50 µg/ml or from about 1 µg/ml to about 50 µg/ml protamine sulfate; a fibronectin-derived transduction adjuvant; and/or RetroNectin. In other embodiments of the methods provided herein, the introducing includes transfecting the cells of the stimulated composition with a vector containing a polynucleotide encoding the recombinant receptor. In some embodiments, the vector is a transposon, optionally a Sleeping Beauty (SB) transposon or a Piggybac transposon.

In some embodiments of the methods provided herein, the method further includes cultivating the engineered composition under conditions to promote proliferation or expansion of the engineered cells, thereby producing an output composition containing the engineered T cells. In some embodiments, the cultivating is carried out in the presence of one or more cytokines, wherein at least one cytokine is or includes recombinant human IL-2. In some embodiments, the stimulatory reagent is removed from the engineered composition prior to the cultivating.

In some embodiments, the stimulatory agent is removed within or less than 7 days after initiation of the incubating. In some embodiments, the stimulatory reagent is removed from 3 days to 6 days or from about 3 days to about 6 days after the initiation of the incubating. In some embodiments, the stimulatory reagent is removed at or at about 4 days after the initiation of the incubating. In some embodiments, removing the beads includes exposing cells of the engineered composition to a magnetic field.

Provided in other aspects are methods for producing a composition of engineered cells, the method involving cultivating, in the presence of one or more cytokines, an engineered cell composition containing CD4+ primary human T cells that include cells engineered with a recombinant receptor, wherein at least one cytokine is or includes recombinant human IL-2; wherein the method results in the proliferation or expansion of cells in the composition to produce an output composition containing engineered CD4+ cells. In some embodiments, the proliferation or expansion results in, in about, or in at least a 2-fold, 3-fold, 4-fold, 5-fold, or greater than a 5-fold increase in the number of CD4+ T cells engineered with a recombinant receptor.

In some embodiments of any of the methods provided herein, the engineered cell composition includes greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells or CD4+ recombinant receptor-expressing cells; and/or the engineered cell composition consists essentially of CD4+ primary human T cells. In some embodiments of the methods provided herein, the concentration of recombinant IL-2 is from 50 IU/mL to 500 IU/ml or from about 50 IU/mL to about 500 IU/ml. In some embodiments of any of the methods provided herein, the one or more cytokines further includes IL-7 and/or IL-15, optionally wherein the concentration of IL-7 is from 500 IU/mL to 2000 IU/mL or from about 500 IU/mL to about 2000 IU/mL and/or the concentration of IL-15 is from 5 IU/mL to 50 IU/mL or from about 5 IU/mL to about 50 IU/mL.

In some embodiments of any of the methods provided herein, the engineered cell composition is produced by a method that involves: incubating, under stimulating conditions, an input composition containing primary T cells enriched for CD4+ primary human T cells, said stimulating conditions including the presence of (i) a stimulatory reagent capable of activating one or more intracellular signaling domains of one or more components of a TCR complex and/or one or more intracellular signaling domains of one or more costimulatory molecules and (ii) one or more cytokines, wherein at least one cytokine is or includes recombinant human IL-2, thereby generating a stimulated composition; and (b) introducing a recombinant receptor into the stimulated composition, thereby generating an engineered composition containing engineered T cells.

In some embodiments of any of the methods provided herein, the input composition includes greater than or greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or the input composition consists essentially of CD4+ primary human T cells. In some embodiments of any of the methods provided herein, the one or more cytokines further includes IL-7 and/or IL-15. In some embodiments of any of the methods provided herein, the cultivating is carried out in the presence of a surfactant. In some embodiments, at least a portion of the cultivating is performed with continual mixing and/or perfusion.

Provided in another aspect are methods for producing a composition of engineered cells, involving: cultivating, in the presence of one or more cytokines, an engineered cell composition containing one or both of CD4+ and CD8+ primary human T cells that include cells engineered with a recombinant receptor, wherein the cultivating is carried out in the presence of a surfactant and/or at least a portion of the cultivating is performed with continual mixing and/or perfusion; wherein the method results in the proliferation or expansion of cells in the composition to produce an output composition containing engineered CD4+ and/or CD8+ T cells.

In some embodiments of any of these methods described above, the engineered cell composition includes greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells or CD4+ and/or CD8+ recombinant receptor-expressing primary T cells; and/or the engineered cell composition consists essentially of CD4+ and/or CD8+ primary human T cells.

In some embodiments of any of the methods provided herein, the proliferation or expansion results in, in about, or in at least a 2-fold, 3-fold, 4-fold, 5-fold, or greater than a 5-fold increase in the number of CD4+ and/or CD8+ T cells engineered with a recombinant receptor.

In some embodiments of any of the methods provided herein, the one or more cytokines are selected from recombinant IL-2, recombinant IL-7 and/or recombinant IL-15. In some embodiments, the concentration of recombinant IL-2 is from 50 IU/mL to 500 IU/mL or from about 50 IU/mL to about 500 IU/mL; the concentration of recombinant IL-7 is from 500 IU/mL to 2000 IU/mL or from about 500 IU/mL to about 2000 IU/mL; and/or the concentration of recombinant IL-15 is from 5 IU/mL to 50 IU/mL or from about 5 IU/mL to about 50 IU/mL.

In some embodiments of any of the methods provided herein, the engineered cell composition includes greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells or CD4+ and recombinant receptor-expressing primary human T cells; and/or the engineered cell composition consists essentially of CD4+ primary human T cells.

In some embodiments of any of the methods provided herein, the proliferation or expansion results in, in about, or in at least a 2-fold, 3-fold, 4-fold, 5-fold, or greater than a 5-fold increase in the number of CD8+ T cells engineered with a recombinant receptor. In some embodiments, the one or more cytokines are selected from recombinant IL-2, recombinant IL-7 and recombinant IL-15.

In some embodiments of any of the methods provided herein, the engineered cell composition includes greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells or CD8+ and recombinant receptor-expressing primary human T cells; and/or the engineered cell composition consists essentially of CD8+ primary human T cells.

In some embodiments of any of the methods provided herein, the one or more cytokines are selected from recombinant IL-2 and recombinant IL-15. In some embodiments of any of the methods provided herein, the surfactant includes a poloxamer, optionally wherein the poloxamer is present at a concentration of from 0.5 μL/mL to 5 μL/mL or from about 0.5 μL/mL to about 5 μL/mL. In some embodiments, the poloxamer is Poloxamer 188.

In some embodiments of any of the methods provided herein, the engineered cell composition is produced by a method that involves: incubating, under stimulating conditions, an input composition containing primary T cells enriched for one or both of CD4+ and CD8+ primary human T cells, said stimulating conditions including the presence of (i) a stimulatory reagent capable of activating one or more intracellular signaling domains of one or more components of a TCR complex and/or one or more intracellular signaling domains of one or more costimulatory molecules and (ii) one or more cytokines, thereby generating a stimulated composition; and (b) introducing a recombinant receptor into the stimulated composition, thereby generating an engineered composition containing engineered T cells.

In some embodiments of any of the methods provided herein, the input composition includes greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells; and/or the input composition consists essentially of CD4+ and/or CD8+ primary human T cells. In some embodiments, the one or more cytokines are selected from recombinant IL-2, recombinant IL-7 and/or recombinant IL-15.

In some embodiments of any of the methods provided herein, the input composition includes greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or the input composition consists essentially of CD4+ primary human T cells. In some embodiments, the one or more cytokines are selected from recombinant IL-2, recombinant IL-7 and recombinant IL-15.

In some embodiments of any of the methods provided herein, the input composition includes greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells; and/or the input composition consists essentially of CD8+ primary human T cells. In some embodiments, the one or more cytokines are selected from recombinant IL-2 and recombinant IL-15.

In some embodiments of any of the methods provided herein, the stimulatory reagent includes a primary agent that specifically binds to a member of a TCR complex, optionally that specifically binds to CD3. In some embodiments, the stimulatory reagent further includes a secondary agent that specifically binds to a T cell costimulatory molecule, optionally wherein the costimulatory molecule is selected from CD28, CD137 (4-1-BB), OX40, or ICOS.

In some embodiments, the primary and/or secondary agents include an antibody, optionally wherein the stimulatory reagent includes incubation with an anti-CD3 antibody and an anti-CD28 antibody, or an antigen-binding fragment thereof. In some embodiments, the primary agent and/or secondary agent are present on the surface of a solid support. In some embodiments, the solid support is or includes a bead. In some embodiments, the bead has a diameter of greater than or greater than about 3.5 µm but no more than about 9 µm or no more than about 8 µm or no more than about 7 µm or no more than about 6 µm or no more than about 5 µm. In some embodiments, the bead includes a diameter of or about 4.5 µm. In some embodiments, the bead is inert. In some embodiments, the bead is or includes a polystyrene surface. In some embodiments, the bead is magnetic or superparamagnetic. In some embodiments, the ratio of beads to cells is less than or less than about 3:1. In some embodiments, the ratio of beads to cells is from 2:1 to 0.5:1 or from about 2:1 to about 0.5:1. In some embodiments, the ratio of beads to cells is at or at about 1:1.

In some embodiments of any of the methods provided herein, the incubating is carried out in the presence of one or more antioxidant. In some embodiments, the one or more antioxidant includes a sulfur containing antioxidant. In some embodiments, the one or more antioxidants include a glutathione precursor. In some embodiments, the one or more antioxidants include N-acetyl cysteine (NAC), optionally wherein the NAC is at a concentration of from 0.2 mg/mL to 2.0 mg/mL or from about 0.2 mg/mL to about 2.0 mg/mL.

In some embodiments of any of the methods provided herein, the introducing includes transducing cells of the stimulated composition with a viral vector containing a polynucleotide encoding the recombinant receptor. In some embodiments, the viral vector is a retroviral vector. In some embodiments, the viral vector is a lentiviral vector or gammaretroviral vector. In some embodiments of any of the methods provided herein, the introducing is carried out in the presence of a transduction adjuvant. In some embodiments, the transduction adjuvant is or comprises protamine sulfate, optionally from 1 µg/ml to 50 µg/ml or from about 1 µg/ml to about 50 µg/ml protamine sulfate; a fibronectin-derived transduction adjuvant; and/or RetroNectin. In some embodiments of any of the methods provided herein, the introducing includes transfecting the cells of the stimulated composition with a vector containing a polynucleotide encoding the recombinant receptor. In some embodiments, the vector is a transposon, optionally a Sleeping Beauty (SB) transposon or a Piggybac transposon.

In some embodiments of any of the methods provided herein, the engineered cell composition does not include a stimulatory reagent and/or the stimulatory reagent has been substantially removed from the composition prior to the cultivating, said stimulatory reagent containing a reagent capable of activating one or more intracellular signaling domains of one or more components of a TCR complex and/or one or more intracellular signaling domains of one or more costimulatory molecules.

In some embodiments of any of the methods provided herein, the cultivating is performed at least until the output composition includes a threshold number of T cells. In some embodiments, the cultivating is continued for at least one day after the threshold number of T cells is reached. In some embodiments, the threshold number is at least 2-fold, at least 3-fold, at least 4-fold, at least 5-fold or more greater than the number of the engineered cell composition prior to the cultivation. In some embodiments of any of the methods provided herein, the cultivating is performed for 2 days to 10 days inclusive, and/or the cultivating is performed for at least 10 days. In some embodiments of any of the methods provided herein, subsequent to the cultivating, collecting cells of the output composition. In some embodiments, the amount of time between initiation of the incubating and collecting cells of the output composition is from 7 days to 15 days or from about 7 days to about 15 days. In some embodiments, the amount of time between initiation of the incubating and the collecting cells of the output composition is from 9 days to 13 days or from about 9 days to about 13 days. In some embodiments, the amount of time between initiation of the incubation and collecting cells of the output composition is from 8 days to 13 days or from about 8 days to about 13 days.

In some embodiments of any of the methods provided herein, the method further involves formulating cells of the output composition for cryopreservation and/or administration to a subject, optionally in the presence of a pharmaceutically acceptable excipient. In some embodiments, the cells of the output composition are formulated in the presence of a cryoprotectant. In some embodiments, the cryoprotectant includes DMSO. In some embodiments, the cells of the output composition are formulated in a container, optionally a vial or a bag.

In some embodiments of any of the methods provided herein, the method further involves isolating the CD4+ and/or the CD8+ T cells from a biological sample prior to the incubating. In some embodiments, the isolating includes selecting cells based on surface expression of CD4 and/or CD8, optionally by positive or negative selection. In some embodiments, the isolating includes carrying out immunoaffinity-based selection. In some embodiments, the biological sample includes primary T cells obtained from a subject. In some embodiments, the subject is a human subject. In some embodiments, the biological sample is or includes a whole blood sample, a buffy coat sample, a peripheral blood mononuclear cell (PBMC) sample, an unfractionated T cell sample, a lymphocyte sample, a white blood cell sample, an apheresis product, or a leukapheresis product.

In some embodiments of any of the methods provided herein, the recombinant receptor is capable of binding to a target antigen that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen. In some embodiments, the target antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, G Protein Coupled Receptor 5D (GPCR5D), Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, tEGFR, VEGF receptors, VEGF-R2, Wilms Tumor 1 (WT-1), a pathogen-specific antigen and an antigen associated with a universal tag.

In some embodiments of any of the methods provided herein, the recombinant receptor is or includes a functional non-TCR antigen receptor or a TCR or antigen-binding fragment thereof. In some embodiments of any of the methods provided herein, the recombinant receptor is a chimeric antigen receptor (CAR). In some embodiments of any of the methods provided herein, the recombinant receptor is an anti-CD19 CAR. In some embodiments, the chimeric antigen receptor includes an extracellular domain containing an antigen-binding domain. In some embodiments, the antigen-binding domain is or includes an antibody or an antibody fragment thereof, which optionally is a single chain fragment. In some embodiments, the fragment includes antibody variable regions joined by a flexible linker. In some embodiments, the fragment includes an scFv.

In some embodiments of any of the methods provided herein, the chimeric antigen receptor further includes a spacer and/or a hinge region. In some embodiments, the chimeric antigen receptor includes an intracellular signaling region. In some embodiments, the intracellular signaling region includes an intracellular signaling domain. In some embodiments, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3) chain, or a signaling portion thereof.

In some embodiments of any of the methods provided herein, the chimeric antigen receptor further includes a transmembrane domain disposed between the extracellular domain and the intracellular signaling region. In some embodiments, the intracellular signaling region further includes a costimulatory signaling region. In some embodiments, the costimulatory signaling region includes an intracellular signaling domain of a T cell costimulatory molecule or a signaling portion thereof. In some embodiments, the costimulatory signaling region includes an intracellular signaling domain of a CD28, a 4-1BB or an ICOS or a signaling portion thereof. In some embodiments, the costimulatory signaling region is between the transmembrane domain and the intracellular signaling region.

In some embodiments of any of the methods provided herein, the output composition containing the threshold number or greater number of cells is produced among greater than or greater than about 85%, greater than or greater than about 90% or greater than or greater than about 95% of the iterations of the method. In some embodiments of any of the methods described herein, the method is performed in less than 21 days, inclusive.

Provided in other aspects are compositions that contain engineered cells produced by a method described in any of the embodiments herein. In some embodiments, the composition further includes a pharmaceutically acceptable carrier. In some embodiments, the composition includes a cryoprotectant, optionally DMSO.

Provided in another aspect are articles of manufacture that contain any of the compositions described herein, and instructions for administering the output composition to a subject. In some embodiments of the article of manufacture, the subject has a disease or condition, optionally wherein the recombinant receptor specifically recognizes or specifically bind to an antigen associated with, or expressed or present on cells of, the disease or condition. In some embodiments, the output composition is a composition of engineered CD4+ T cells. In some embodiments, the output composition is an engineered composition of CD8+ T cells.

Provided in some aspects are articles of manufacture that contain a composition of engineered CD4+ T cells produced any of the methods described herein, a composition of engineered CD8+ T cells produced by any of the methods described herein, and instructions for administering the engineered CD4+ T cells and the engineered CD8+ T cells to a subject. In some embodiments, the instructions specify separately administering the CD4+ T cells and CD8+ T cells to the subject. In other embodiments, the instructions specify administering the CD4+ T cells and the CD8+ T cells to the subject at a desired ratio.

In some embodiments of any of the methods described herein, the method is performed in less than 21 days, inclusive.

DETAILED DESCRIPTION

Figure 1:
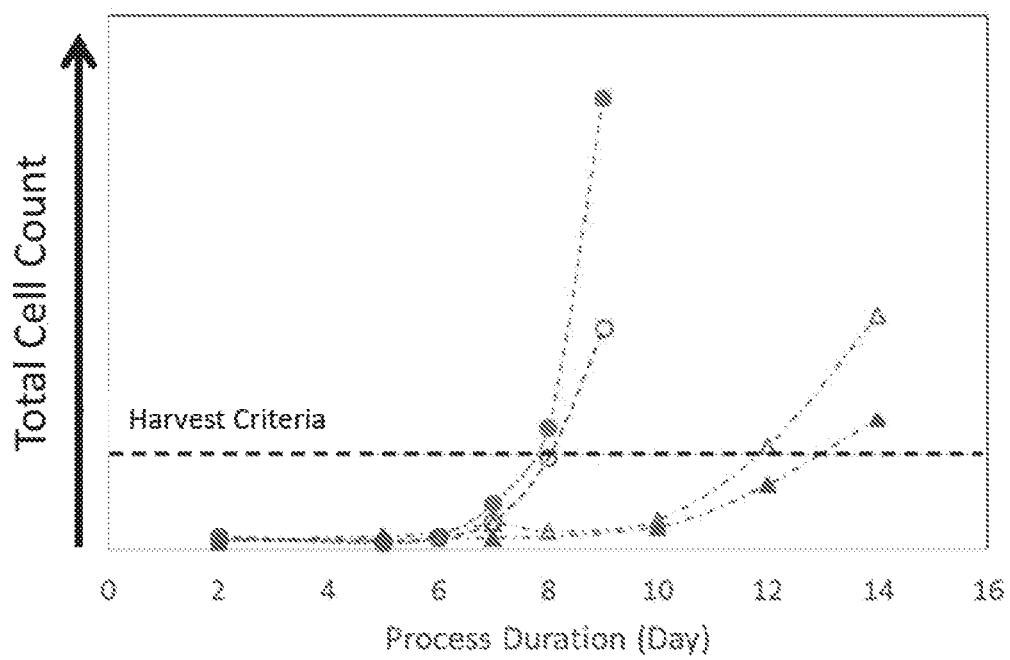
FIG. 1 shows a graph displaying the total cell counts of CD4+(closed symbols) and CD8+(open symbols) cell compositions obtained from the same leukapheresis sample measured at different time points during the stimulation, transduction, and expansion of cells during the alternative (triangles) and exemplary (circles) processes for generating anti-CD19 chimeric antigen receptor (CAR) expressing cells described in Example 1. The dashed horizontal line indicates the threshold cell count required to meet the criteria for harvest.

Provided herein are methods for generating or producing compositions of engineered cells, such as engineered CD4+ and/or CD8+ T cells, that express a recombinant receptor. In particular embodiments, the methods are used in connection with a process that includes incubating cells under stimulating conditions; genetically engineering cells, e.g., by introducing a polynucleotide encoding a recombinant receptor, and/or cultivating the engineered cells under conditions that promote cell proliferation and/or expansion. In some embodiments, the cells are a composition of cells enriched for CD4+ T cells (herein after also referred to as a composition of enriched CD4+ T cells). In some embodiments, the cells are a composition of cells enriched for CD8+ T cells (herein after also referred to as a composition of enriched CD8+ T cells). In some embodiments, the methods are carried out for generating or producing two or separate compositions of engineered T cells, in which each are engineered with the same recombinant receptor from cells from the same biological sample (e.g. from the same subject), such as by separately incubating, engineering, and cultivating separate compositions of CD4+ T cells and CD8+ T cells.

Different processes are available for generating genetically engineered T cell populations, including for generating engineered T cells that express a chimeric antigen receptor. However, in some embodiments, some of these processes may require a long or a relatively long amount of time to generate the engineered cells. In some embodiments, some of the existing processes may vary in the amount of time required to generate engineered T cells from samples obtained from different subjects. For example, in some embodiments, the same process may require 5, 6, 7, or more days longer to generate engineered cells for one subject than for another subject. In certain embodiments, some of processes may vary in their ability to successfully generate engineered cells suitable for therapy from across different subjects. In particular embodiments, the variability and/or the lack of predictability of some processes may present problems for clinicians, for example such as difficulty in determining if a cell therapy may be produced for a given subject, or for example, difficulty in planning or coordinating the administration of a cell therapy when the timing of its availability is not known.

The provided embodiments address one or more of these issues. In particular embodiments, the provided methods generate engineered T cells suitable for therapy, e.g., autologous cell therapy, in a short or relatively short amount of time as compared to some existing processes. Furthermore, in some embodiments, the provided methods result in a more consistent, and less variable, process in terms of the amount of time required for producing engineered cells from samples collected from among different subjects. In particular embodiments, the provided methods are able to successfully generate engineered T cells suitable for cell therapy from a high proportion of subjects. Thus, in certain embodiments, the methods described herein provide a relatively fast and efficient means for generating engineered T cells for therapies. These features may allow for more potential subjects to be treated with T cell therapies, such as autologous T cell therapies, and may ameliorate some of the difficulties associated with planning and coordinating cell therapy for a subject.

In some embodiments, the provided processes shorten duration of expansion and/or are able to generate product within a narrower window of duration as compared to other products, across a wider range of starting samples (including those in which harvest thresholds may not otherwise be reached), and in some aspects can reduce failures due to poor cell expansion.

In certain embodiments, the provided methods are used in connection with a process of generating engineered CD4+ T cells that express a recombinant receptor, e.g., a chimeric antigen receptor. In particular embodiments, the CD4+ T cells are incubated and/or cultivated in the presence of recombinant IL-2. Generally, alternative processes for generating engineered CD4+ T cells do not involve or require the addition of recombinant IL-2 with CD4+ T cells because, in some embodiments, cultured CD4+ T cells are generally understood to produce and/or secrete IL-2. However, without wishing to be bound by theory, some embodiments contemplate that CD4+ T cells derived from some patients, such as diseased subjects and/or subjects whose T cells contain one or more features associated with unhealthy cells, do not produce or secrete IL-2 in sufficient amounts. In certain embodiments, such CD4+ T cells will fail to grow, proliferate, and/or expand without supplementation of recombinant IL-2. Thus, in certain embodiments, by inclusion of recombinant IL-2 into the process for culturing and engineering CD4+ T cells, the provided methods expand the pool of subjects that may provide CD4+ T cells that may be engineered, and thus expands the pool of subjects that may be treated with an autologous cell therapy containing engineered CD4+ T cells.

In certain embodiments, cells are incubated under stimulating conditions with a stimulatory reagent, e.g., an anti-CD3 and anti-CD28 antibody conjugated bead, prior to genetically engineering, e.g., transducing or transfecting, the cells. In some embodiments, the stimulatory reagent is separated or removed from the cells prior to the start of the cultivation step and within 7 days or earlier, e.g., at or at about 4 days or 5 days, after the start or initiation of the incubation. Particular embodiments contemplate that when the stimulatory reagent is removed or separated from the cells at an earlier point in time during the process, then the cells have improved survival and will undergo more robust proliferation and/or expansion during the cultivation step than cells that are cultivated in alternative processes that either do not separate or remove the stimulatory reagent or do so at a later point in time during the process. In such embodiments, the cultivated cells achieve a target or threshold cell count, density, and/or expansion faster than cells that are cultivated in the alternative processes. Thus, in some embodiments, removing or separating the stimulatory reagent from the cells within 7 days or earlier from the start or initiation of the incubation allows for the process of generating or producing engineered cells to be completed in a shorter amount of time than the alternative processes.

In some embodiments, the methods provided herein are used in connection with a process that generates genetically engineered T cells over a short duration of time. In certain embodiments, the short duration of the process may increase the rate, instances, and/or probability of generating a composition of engineered T cells that can be administered to a subject for cell therapy. In some embodiments, manufacturing protocols for therapeutic cell compositions may require that the cell compositions are produced and released for infusion, e.g., verified and/or determined to be suitable for administration to a subject, within a certain amount of time. In some aspects, the short duration of the provided process could be expected to reduce or eliminate process failures that would occur from cell compositions that fail to expand within the required amount of time.

In particular embodiments, the methods provided herein are used in connection with cultivating engineered cells under conditions that promote proliferation and/or expansion. In some embodiments, the cultivation is performed in a setting that allows for constant mixing and/or perfusion of the cultivated cells, such as in or in connection with a bioreactor. In some embodiments, the at least a portion of the cultivation is performed with constant mixing and with a slow, constant perfusion to replace used media with fresh media. In certain embodiments, the cells are initially cultivated under static conditions, e.g., no perfusion or mixing, and are then cultivated with constant mixture and perfusion when the cultivated cells reach a predetermined cell count or density, and/or once the cells have been initially cultivated for a predetermined about of time. In some such embodiments, the cultivated cells achieve a target or threshold cell count, density, and/or expansion faster than cells that are cultivated in the alternative processes. Thus, in some embodiments, cultivation with constant mixture and/or perfusion allows for the process of generating or producing engineered cells to be completed in a shorter amount of time than an alternative processes where the cells are cultivated under static conditions.

In particular embodiments, the provided methods are used in connection with a process for efficiently producing or generating engineered cells that are suitable for use in a cell therapy. In certain embodiments, the timing, conditions, and reagents used for each step of the process improve the efficiency of each subsequent step and/or the overall process. For example, in some embodiments, cells may be incubated with a reagent, e.g., a stimulatory reagent or a transduction adjuvant, at concentrations that are high enough to achieve a desired effect, e.g., stimulation of the cells or improved transduction efficiency, but at concentrations that are low enough to avoid slowed growth or reduced survival in subsequent processing steps. Further, in some embodiments, the steps of the process are timed to begin or end at specific time points to improve the efficiency of subsequent process steps and/or of whole process. For example, in some embodiments, steps for incubation and engineering (e.g., transducing or transfecting, the cells) are completed earlier in the process than in alternative methods, which, in certain embodiments, improves the survival and/or health, and/or the speed of the proliferation and expansion of the cells during subsequent the cultivation step. Thus, in one aspect, the specific timing, conditions, and reagents of each step influences the cells beyond the individual step and, in certain embodiments, influence the performance of the entire process.

In some embodiments, the methods are used in connection with a process that generates or produces genetically engineered cells that are suitable for cell therapy in a manner that may be faster and more efficient than the alternative processes. In certain embodiments, the methods provided herein have a high rate of success for generating or producing compositions of engineered cells from broader population of subjects than what may be possible from alternative processes. In certain embodiments, the engineered cells produced or generated by the provided methods may have greater health, viability, activation, and may have greater expression of the recombinant receptor than cells produced by alternative methods. Thus, in some aspects, the speed and efficiency of the provided methods for generating engineered cells for cell therapy allow for easier planning and coordination of cell therapy treatments, such as autologous therapy, to a broader population of subjects than what may be possible by some alternative methods.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. PROCESS FOR GENERATING ENGINEERING CELLS

Provided herein are methods for generating an output composition of engineered cells, such as engineered CD4+ T cells and/or engineered CD8+ T cells, that express a recombinant protein, e.g., a recombinant receptor such as a T cell receptor (TCR) or a chimeric antigen receptor (CAR). In some embodiments, the methods provided herein are used in connection with manufacturing, generating, or producing a cell therapy, and may be used in connection with additional processing steps, such as steps for the isolation, separation, selection, activation or stimulation, transduction, washing, suspension, dilution, concentration, and/or formulation of the cells. In some embodiments, the methods of generating or producing engineered cells, e.g., engineered CD4+ T cells and/or engineered CD8+ T cells, include one or more of isolating cells from a subject, preparing, processing, incubating under stimulating conditions, and/or engineering (e.g. transducing) the cells. In some embodiments, the method includes processing steps carried out in an order in which: input cells, e.g. primary cells, are first isolated, such as selected or separated, from a biological sample; input cells are incubated under stimulating conditions, engineered with vector particles, e.g., viral vector particles, to introduce a recombinant polynucleotide into the cells, e.g., by transduction or transfection; cultivating the engineered cells, e.g., transduced cells, such as to expand the cells; and collecting, harvesting, and/or filling a container with all or a portion of the cells for formulating the cells in an output composition. In some embodiments, the cells of the generated output composition are re-introduced into the same subject, before or after cryopreservation. In some embodiments, the output compositions of engineered cells are suitable for use in a therapy, e.g., an autologous cell therapy.

In particular embodiments, the provided methods are used in connection with generating output compositions of cells expressing a recombinant receptor from an initial or input composition of cells. In some embodiments, the composition of cells is a composition of enriched T cells, enriched CD4+ T cells, and/or enriched CD8+ T cells (herein after also referred to as compositions of enriched T cells, compositions of enriched CD4+ T cells, and compositions of enriched CD8+ T cells, respectively). In some embodiments, the provided methods are used in connection with one or more of: activating or stimulating a composition of cells enriched for T cells; genetically engineering a composition of enriched T cells, e.g., to introduce a polynucleotide encoding a recombinant protein by transduction or transfection; and/or cultivating the engineered composition of enriched T cells, e.g., under conditions that promote proliferation and/or expansion. In certain embodiments, the methods may also be used in connection with isolating or selecting cells from a biological sample to generate an input composition of enriched T cells, such as from a biological sample taken, collected, and/or obtained from a subject. In particular embodiments, the provided methods may be used in connection with harvesting, collecting, and/or formulating compositions of enriched cells after the cells have been incubated, activated, stimulated, engineered, transduced, transfected, and/or cultivated.

In some embodiments, the provided methods are used in association with the isolation, separation, selection, activation or stimulation, transduction, washing, suspension, dilution, concentration, and/or formulation of a single composition of enriched T cells. In some embodiments, the composition of enriched T cells is a composition of cells that include enriched CD4+ T cells. In certain embodiments, the composition of enriched CD4+ T cells contains at least 60%, 65%, 70%, 75%, 80%, 85%, 90%, 95%, 98%, 99%, or 99.9% CD4+ T cells. In particular embodiments, the composition of enriched CD4+ T cells contains 100% CD4+ T cells or contains about 100% CD4+ T cells. In certain embodiments, the composition of enriched T cells includes or contains less than 20%, less than 10%, less than 5%, less than 1%, less than 0.1%, or less than 0.01% CD8+ T cells, and/or contains no CD8+ T cells, and/or is free or substantially free of CD8+ T cells. In some embodiments, the populations of cells consist essentially of CD4+ T cells.

In some embodiments, the provided methods are used in connection with generating two or more separate output compositions of enriched T cells. In some embodiments, the provided methods are separately performed on two or more separate compositions of enriched T cells, e.g., one or more separate composition of enriched CD4+ T cells and one or more separate composition of enriched CD8+ T cells. In certain embodiments, the methods may be used in connection with separately activating and/or stimulating two or more compositions of enriched T cells; separately engineering two or more compositions of enriched T cells; and/or separately cultivating two or more compositions of enriched T cells. In certain embodiments, the methods may also be used in connection with isolating or selecting different cells from a biological sample to generate separate input composition of enriched T cells, such as separate compositions of enriched CD4+ T cells and enriched CD8+ T cells. In particular embodiments, the provided methods may be used in connection with separately harvesting, collecting, and/or formulating separate compositions of enriched T cells after the T cells have been incubated, activated, stimulated, engineered, transduced, transfected, and/or cultivated.

In certain embodiments, the methods may be used in connection with separately incubating at least one separate composition of enriched CD4+ T cells and at least one separate composition of enriched CD8+ T cells; separately activating and/or stimulating the at least one separate composition of enriched CD4+ T cells and the at least one separate composition of enriched CD8+ T cells after the incubation; separately engineering, transducing, and/or transfecting the at least one separate composition of enriched CD4+ T cells and the at least one separate composition of enriched CD8+ T cells after the activation and/or stimulation; separately cultivating the at least one separate composition of enriched CD4+ T cells and the at least one separate composition of enriched CD8+ T cells after the engineering, transduction, and/or transfection; separately harvesting and/or collecting the at least one separate composition of enriched CD4+ T cells and the at least one separate composition of enriched CD8+ T cells after the cultivation; separately formulating the at least one separate composition of enriched CD4+ T cells and the at least one separate composition of enriched CD8+ T cells after the harvest and/or collection; and/or separately administering the formulated compositions to a subject in need thereof.

In some embodiments, the two or more separate compositions of enriched T cells include a composition of enriched CD4+ T cells. In certain embodiments, the two or more separate compositions include CD8+ T cells. In some embodiments, the two or more separate compositions include a composition of enriched CD4+ T cells and a composition of enriched CD8+ T cells. In particular embodiments, a separate composition of enriched CD4+ T cells and a separate composition of enriched CD8+ T cells originated, e.g., were initially isolated, selected, and/or enriched, from the same biological sample, such as the same biological sample obtained, collected, and/or taken from a single subject. In some embodiments, the same biological sample is first subjected to selection of CD4+ T cells, where both the negative and positive fractions are retained, and the negative fraction is further subjected to selection of CD8+ T cells. In other embodiments, the same biological sample is first subjected to selection of CD8+ T cells, where both the negative and positive fractions are retained, and the negative fraction is further subjected to selection of CD4+ T cells.

In some embodiments, the composition of enriched T cells is a composition of enriched CD8+ T cells. In certain embodiments, the composition of enriched CD8+ T cells contains at least 60%, 65%, 70%, 75%, 80%, 85%, 90%, 95%, 98%, 99%, or 99.9% CD8+ T cells, or contains or contains about 100% CD8+ T cells. In certain embodiments, the composition of enriched CD8+ T cells includes or contains less than 20%, less than 10%, less than 5%, less than 1%, less than 0.1%, or less than 0.01% CD4+ T cells, and/or contains no CD4+ T cells, and/or is free or substantially free of CD4+ T cells. In some embodiments, the populations of cells consist essentially of CD8+ T cells.

In some embodiments, a composition of enriched CD4+ T cells and/or an engineered composition of enriched CD4+ T cells, is incubated, activated, stimulated, engineered, transduced, transfected, and/or cultivated with and/or in the presence of recombinant IL-2. In particular embodiments, the methods are used in connection with incubating an input composition of enriched CD4+ T cells under stimulating conditions with and/or in the presence of recombinant IL-2. In some embodiments, the methods are used in connection with cultivating an engineered composition of enriched CD4+ T cells under conditions that promote proliferation and/or expansion with and/or in the presence of recombinant IL-2.

In some embodiments, incubating the input compositions of enriched T cells under stimulating conditions is or includes incubating the cells with a stimulatory reagent, e.g., a stimulatory reagent described in Section I-B-1. In certain embodiments, the stimulatory reagent is removed or separated from the cells prior to a cultivation step. In certain embodiments, the stimulatory reagent is removed or separated from the cells after a genetic engineering, e.g., transfection or transduction. In some embodiments, the stimulatory reagent is removed from the cells within a set amount of time from the start or the initiation of the incubation with the stimulatory reagent, e.g., within 7 or fewer days from the start or initiation of the incubation. In particular embodiments, the incubation under stimulating conditions is performed in the presence of one or more antioxidants, e.g., a sulfur containing antioxidant and/or a glutathione precursor.

In particular embodiments, the compositions of enriched T cells, e.g., stimulated compositions of enriched T cells, are engineered in the presence of a polycation, for example to improve the efficiency of transfection or transduction. In certain embodiments, the polycation is present at a low and/or a relatively low amount and/or concentration.

In certain embodiments, at least a portion of the cultivation step is performed with constant mixing and/or perfusion, e.g., with a bioreactor in a closed system. In certain embodiments, the mixing and/or perfusion incorporates a steady and/or gradual replacement of used or old cell media or solution with fresh media or solution. In particular embodiments, the cells are cultivated in the presence of a surfactant and/or an agent that reduces or prevents cell shearing, such as shearing during constant mixing and/or perfusion.

In some embodiments, the provided methods are carried out such that one, more, or all steps in the preparation of cells for clinical use, e.g., in adoptive cell therapy, are carried out without exposing the cells to non-sterile conditions. In some embodiments of such a process, the cells are isolated, separated or selected, transduced, washed, optionally activated or stimulated and formulated, all within a closed system. In some embodiments, the one or more of the steps are carried out apart from the closed system or device. In some such embodiments, the compositions of enriched cells are transferred apart from the closed system or device under sterile conditions, such as by sterile transfer to a separate closed system.

In particular embodiments, the compositions of enriched T cells may be collected, formulated for cryoprotection, cryofrozen, and/or stored below 0° C., below –20° C., or at or below –70 C or –80° C. prior to, during, or after any stage or step of the process for generating output compositions of enriched T cells expressing recombinant receptors. In some embodiments, the cells may be stored for an amount of time under 1, 2, 3, 4, 5, 6, 7, 8, 9, or 10 days, or an amount of time under 1, 2, 3, 4, 5, 6, 7, 8 weeks, or for an amount of time at least 1, 2, 3, 4, 5, 6, 7, or 8 weeks, or for more than 8 weeks. After storage, the compositions of enriched T cells may be thawed and the processing may be resumed from the same point in the process. In some embodiments, input compositions of enriched T cells are cryofrozen and stored prior to further processing, e.g., incubation under stimulating conditions. In particular embodiments, cultivated and/or formulated compositions of enriched T cells are cryofrozen and stored prior to being administered to as subject, e.g., as an autologous cell therapy.

In certain embodiments, separate cell compositions of enriched T cells are combined into a single composition. For example, in some embodiments, a composition of enriched CD4+ T cells is combined with a composition of enriched CD8+ T cells into a single composition of enriched CD4+ and CD8+ T cells. In certain embodiments, the separate compositions originated, e.g., were initially isolated, selected, and/or enriched, from the same biological sample, such as the same biological sample obtained, collected, and/or taken from a single subject. In some embodiments, the separate compositions are separately processed for one or more steps or stages of a process for generating output compositions, e.g., a process in connection with the provided methods. In some embodiments, the separate compositions may be combined into a single composition prior to, during, or subsequent to any step or stage of the process for generating output compositions. Thus in some embodiments, separate input, stimulated, engineered, cultivated, formulated, and/or harvested compositions of enriched T cells from the same biological sample are combined into a single composition and, in certain embodiments, are further processed as a single composition. In certain embodiments, separate output compositions of enriched cells are combined into a single output composition prior to administering the cells to a subject.

In certain embodiments, at any stage or step in the process, a portion of the cells may be sampled or collected, e.g., cells may be taken from the composition of enriched T cells while the composition remains in the closed system, such as during the isolation, incubation, engineering, cultivation, and/or formulation. In certain embodiments, such cells may be analyzed for makers, features, or characteristics including but not limited to viability, apoptosis, activation, stimulation, growth, and/or exhaustion, In some embodiments, the cells are sampled or collected by an automated process while the composition of enriched T cells remains in the closed system. In some embodiments, the analysis of sampled or collected cells is automated. In particular embodiments, the analysis is performed in a closed system under sterile conditions.

In some embodiments, cells or compositions of cells that are produced and/or processed by the provided methods may be compared to cells or compositions of cells processed or produced by an exemplary and/or alternative process. In some embodiments, the alternative and/or exemplary process may differ in one or more specific aspects, but otherwise contains similar or the same features, aspects, steps, stages, reagents, and/or conditions of the embodiment or aspect of the provided methods that be compared. For example, when the provided methods are used in connection with incubating cells in the presence of a reagent, such cells may be compared to cells that are not incubated with the reagent in an exemplary and/or alternative process. In some embodiments, unless otherwise specified, the provided methods and the exemplary and/or alternative process would have been otherwise similar and/or identical, such as with similar or identical steps for isolating, selecting, enriching, activating, stimulating, engineering, transfecting, transducing, cultivating, and/or formulating. In some embodiments, unless otherwise specified, the provided methods and the alternative process isolate, select, and/or enrich cells from the same or similar types of biological samples, and/or process cells and/or input cells of the same cell type.

Also provided are cells and compositions prepared by the methods, including pharmaceutical compositions and formulations, and kits, systems, and devices for carrying out the methods. Also provided are methods for use of the cells and compositions prepared by the methods, including therapeutic methods, such as methods for adoptive cell therapy, and pharmaceutical compositions for administration to subjects.

A. Samples and Cell Preparations

In particular embodiments, the provided methods are used in connection with isolating, selecting, and/or enriching cells from a biological sample to generate one or more input compositions of enriched cells, e.g., T cells. In some embodiments, the provided methods include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the preparation methods include steps for freezing, e.g., cryopreserving, the cells, either before or after isolation, selection and/or enrichment and/or incubation for transduction and engineering, and/or after cultivation and/or harvesting of the engineered cells. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. In some embodiments, the cells are frozen, e.g., cryofrozen or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryofrozen or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and ~5%, between 0.25% and 4%, between 0.5% and 2%, or between 1% and 2% HSA. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to or to about −80° C. at a rate of or of about 1° per minute and stored in the vapor phase of a liquid nitrogen storage tank.

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from 5 minutes to 6 hours or from about 5 minutes to about 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm), such as at an RCF at the sample or wall of the chamber or other container of from 80 g to 100 g or from about 80 g to about 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively. Multiple rounds of the same selection step, e.g., positive or negative selection step, can be performed. In certain embodiments, the positively or negatively selected fraction subjected to the process for selection, such as by repeating a positive or negative selection step. In some embodiments, selection is repeated twice, three times, four times, five times, six times, seven times, eight times, nine times or more than nine times. In certain embodiments, the same selection is performed up to five times. In certain embodiments, the same selection step is performed three times.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In certain embodiments, one or more separation steps are repeated and/or performed more than once. In some embodiments, the positively or negatively selected fraction resulting from a separation step is subjected to the same separation step, such as by repeating the positive or negative selection step. In some embodiments, a single separation step is repeated and/or performed more than once, for example, to increase the yield of positively selected cells, to increase the purity of negatively selected cells, and/or to further remove the positively selected cells from the negatively selected fraction. In certain embodiments, one or more separation steps are performed and/or repeated two times, three times, four times, five times, six times, seven times, eight times, nine times, ten times, or more than ten times. In certain embodiments, the one or more selection steps are performed and/or repeated between one and ten times, between one and five times, or between three and five times. In certain embodiments, one or more selection steps are repeated three times.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, CD3+, CD28+ T cells can be positively selected using CD3/CD28 conjugated magnetic beads (e.g., DYNABEADS® M-450 CD3/CD28 T Cell Expander, and/or ExpACT® beads).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ T cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al., (2012) Blood. 1:72-82; Wang et al. (2012) J Immunother. 35(9):689-701. In some embodiments, combining TCM-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L.

Such selections in some aspects are carried out simultaneously and in other aspects are carried out sequentially, in either order. In some aspects, the same CD4 expression-based selection step used in preparing the CD8+ T cell population or subpopulation, also is used to generate the CD4+ T cell population or sub-population, such that both the positive and negative fractions from the CD4-based separation are retained and used in subsequent steps of the methods, optionally following one or more further positive or negative selection steps. In some embodiments, the selection for the CD4+ T cell population and the selection for the CD8+ T cell population are carried out simultaneously. In some embodiments, the CD4+ T cell population and the selection for the CD8+ T cell population are carried out sequentially, in either order. In some embodiments, methods for selecting cells can include those as described in published U.S. App. No. US20170037369. In some embodiments, the selected CD4+ T cell population and the selected CD8+ T cell population may be combined subsequent to the selecting. In some aspects, the selected CD4+ T cell population and the selected CD8+ T cell population may be combined in a bioreactor bag as described herein. In some embodiments, the selected CD4+ T cell population and the selected CD8+ T cell population are separately processed, whereby the selected CD4+ T cell population is enriched in CD4+ T cells and incubated with a stimulatory reagent (e.g. anti-CD3/anti-CD28 magnetic beads), transduced with a viral vector encoding a recombinant protein (e.g. CAR) and cultivated under conditions to expand T cells and the selected CD8+ T cell population is enriched in CD8+ T cell and incubated with a stimulatory reagent (e.g. anti-CD3/anti-CD28 magnetic beads), transduced with a viral vector encoding a recombinant protein (e.g. CAR), such as the same recombinant protein as for engineering of the CD4+ T cells from the same donor, and cultivated under conditions to expand T cells, such as in accord with the provided methods.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In a particular example, a sample of PBMCs or other white blood cell sample is subjected to selection of CD4+ T cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells may be sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, or CD4+ T cells. In some embodiments, central memory CD4+ T cells are CD62L+ and CD45RO+. In some embodiments, effector CD4+ T cells are CD62L− and CD45RO−.

In one example, to enrich for CD4+ T cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the incubated sample or composition of cells to be separated is incubated with a selection reagent containing small, magnetizable or magnetically responsive material, such as magnetically responsive particles or microparticles, such as paramagnetic beads (e.g., such as Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. Many well-known magnetically responsive materials for use in magnetic separation methods are known, e.g., those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 also may be used.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotech, Auburn, CA). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells.

Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the isolation and/or selection results in one or more input compositions of enriched T cells, e.g., CD3+ T cells, CD4+ T cells, and/or CD8+ T cells. In some embodiments, two or more separate input composition are isolated, selected, enriched, or obtained from a single biological sample. In some embodiments, separate input compositions are isolated, selected, enriched, and/or obtained from separate biological samples collected, taken, and/or obtained from the same subject.

In certain embodiments, the one or more input compositions is or includes a composition of enriched T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD3+ T cells. In particular embodiment, the input composition of enriched T cells consists essentially of CD3+ T cells.

In certain embodiments, the one or more input compositions is or includes a composition of enriched CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the composition of enriched T cells consists essentially of CD4+ T cells.

In certain embodiments, the one or more compositions is or includes a composition of CD8+ T cells that is or includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the composition of enriched T cells consists essentially of CD8+ T cells.

In some embodiments, the one or more input compositions of enriched T cells are frozen, e.g., cryopreserved and/or cryofrozen, after isolation, selection and/or enrichment. In some embodiments, the one or more input compositions of frozen e.g., cryopreserved and/or cryofrozen, prior to any steps of incubating, activating, stimulating, engineering, transducing, transfecting, cultivating, expanding, harvesting, and/or formulating the composition of cells. In particular embodiments, the one or more cryofrozen input compositions are stored, e.g., at or at about −80° C., for between 12 hours and 7 days, between 24 hours and 120 hours, or between 2 days and 5 days. In particular embodiments, the one or more cryofrozen input compositions are stored at or at about −80° C., for an amount of time of less than 10 days, 9 days, 8 days, 7 days, 6 days, or 5 days, 4 days, 3 days, 2 days, or 1 day. In some embodiments, the one or more cryofrozen input compositions are stored at or at about −80° C., for or for about 1 day, 2 days, 3 days, 4 days, 5 days, or 6 days.

B. Activation and Stimulation of Cells

In some embodiments, the provided methods are used in connection with incubating cells under stimulating conditions. In some embodiments, the stimulating conditions include conditions that activate or stimulate, and/or are capable of activing or stimulating a signal in the cell, e.g., a CD4+ T cell or CD8+ T cell, such as a signal generated from a TCR and/or a coreceptor. In some embodiments, the stimulating conditions include one or more steps of culturing, cultivating, incubating, activating, propagating the cells with and/or in the presence of a stimulatory reagent, e.g., a reagent that activates or stimulates, and/or is capable of activing or stimulating a signal in the cell. In some embodiments, the stimulatory reagent stimulates and/or activates a TCR and/or a coreceptor. In particular embodiments, the stimulatory reagent is a reagent described in Section I-B-1.

In certain embodiments, one or more compositions of enriched T cells are incubated under stimulating conditions prior to genetically engineering the cells, e.g., transfecting and/or transducing the cell such as by a technique provided in Section I-C. In particular embodiments, one or more compositions of enriched T cells are incubated under stimulating conditions after the one or more compositions have been isolated, selected, enriched, or obtained from a biological sample. In particular embodiments, the one or more compositions are input compositions. In particular embodiments, the one or more input compositions have been previously cryofrozen and stored, and are thawed prior to the incubation.

In certain embodiments, the one or more compositions of enriched T cells are or include two separate compositions, e.g., separate input compositions, of enriched T cells. In particular embodiments, two separate compositions of enriched T cells, e.g., two separate compositions of enriched T cells selected, isolated, and/or enriched from the same biological sample, are separately incubated under stimulating conditions. In certain embodiments, the two separate compositions include a composition of enriched CD4+ T cells. In particular embodiments, the two separate compositions include a composition of enriched CD8+ T cells. In some embodiments, two separate compositions of enriched CD4+ T cells and enriched CD8+ T cells are separately incubated under stimulating conditions.

In some embodiments, a single composition of enriched T cells is incubated under stimulating conditions. In certain embodiments, the single composition is a composition of enriched CD4+ T cells. In some embodiments, the single composition is a composition of enriched CD4+ and CD8+ T cells that have been combined from separate compositions prior to the incubation.

In some embodiments, the composition of enriched CD4+ T cells that is incubated under stimulating conditions includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the composition of enriched CD4+ T cells that is incubated under stimulating conditions includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells that is incubated under stimulating conditions includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition of enriched CD8+ T cells that is incubated under stimulating conditions includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, separate compositions of enriched CD4+ and CD8+ T cells are combined into a single composition and are incubated under stimulating conditions. In certain embodiments, separate stimulated compositions of enriched CD4+ and enriched CD8+ T cells are combined into a single composition after the incubation has been performed and/or completed. In some embodiments, separate stimulated compositions of stimulated CD4+ and stimulated CD8+ T cells are separately processed after the incubation has been performed and/or completed, whereby the stimulated CD4+ T cell population (e.g. incubated with stimulatory an anti-CD3/anti-CD28 magnetic bead stimulatory reagent) is transduced with a viral vector encoding a recombinant protein (e.g. CAR) and cultivated under conditions to expand T cells and the stimulated CD8+ T cell population (e.g. incubated with stimulatory an anti-CD3/anti-CD28 magnetic bead stimulatory reagent) is transduced with a viral vector encoding a recombinant protein (e.g. CAR), such as the same recombinant protein as for engineering of the CD4+ T cells from the same donor, and cultivated under conditions to expand T cells, such as in accord with the provided methods.

In some embodiments, the incubation under stimulating conditions can include culture, cultivation, stimulation, activation, propagation, including by incubation in the presence of stimulating conditions, for example, conditions designed to induce proliferation, expansion, activation, and/or survival of cells in the population, to mimic antigen exposure, and/or to prime the cells for genetic engineering, such as for the introduction of a recombinant antigen receptor. In particular embodiments, the stimulating conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, the stimulation and/or incubation under stimulating conditions is carried out in accordance with techniques such as those described in U.S. Pat. No. 6,040,177 to Riddell et al., Klebanoff et al. (2012) *J Immunother.* 35(9): 651-660, Terakura et al. (2012) Blood. 1:72-82, and/or Wang et al. (2012) *J Immunother.* 35(9):689-701.

In some embodiments, the cells, e.g., T cells, compositions of cells, and/or cell populations, such as CD4$^+$ and CD8$^+$ T cells or compositions, populations, or subpopulations thereof, are expanded by adding to the culture-initiating composition feeder cells, such as non-dividing peripheral blood mononuclear cells (PBMCs) (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division.

In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. In some embodiments, a temperature shift is effected during culture, such as from 37 degrees Celsius to 35 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, populations of CD4$^+$ and CD8$^+$ that are antigen specific can be obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen. Naive T cells may also be used.

In particular embodiments, the stimulating conditions include incubating, culturing, and/or cultivating the cells with a stimulatory reagent. In particular embodiments, the stimulatory reagent is a reagent described in Section I-B-1. In certain embodiments, the stimulatory reagent contains or includes a bead. An exemplary stimulatory reagent is or includes anti-CD3/anti-CD28 magnetic beads. In certain embodiments, the start and or initiation of the incubation, culturing, and/or cultivating cells under stimulating conditions occurs when the cells come into contact with and/or are incubated with the stimulatory reagent. In particular embodiments, the cells are incubated prior to, during, and/or subsequent to genetically engineering the cells, e.g., introducing a recombinant polynucleotide into the cell such as by transduction or transfection.

In some embodiments, the composition of enriched T cells are incubated at a ratio of stimulatory reagent and/or beads, e.g. anti-CD3/anti-CD28 magnetic beads, to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent and/or beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

In particular embodiments, incubating the cells at a ratio of less than 3:1 or less than 3 stimulatory reagents, e.g. anti-CD3/anti-CD28 magnetic beads. per cell, such as a ratio of 1:1, reduces the amount of cell death that occurs during the incubation, e.g., such as by activation-induced cell death. In some embodiments, the cells are incubated with the stimulatory reagent, e.g. anti-CD3/anti-CD28 magnetic beads, at a ratio of beads to cells of less than 3 (or 3:1 or less than 3 beads per cell). In particular embodiments, incubating the cells at a ratio of less than 3:1 or less than 3 beads per cell, such as a ratio of 1:1, reduces the amount of cell death that occurs during the incubation, e.g., such as by activation-induced cell death.

In particular embodiments, the composition of enriched T cells is incubated with the stimulatory reagent, e.g. anti-CD3/anti-CD28 magnetic beads, at a ratio of less than 3:1 stimulatory reagents and/or beads per cell, such as a ratio of 1:1, and at least 50%, at least 60%, at least 70%, at least 75%, at least 80%, at least 85%, at least 90%, at least 95%, at least 99%, or at least 99.9% of the T cells survive, e.g., are viable and/or do not undergo necrosis, programed cell death, or apoptosis, during or at least 1 day, 2 days, 3 days, 4 days, 5 days, 6 days, 7 days, or more than 7 days after the incubation is complete. In particular embodiments, the composition of enriched T cells is incubated with the stimulatory reagent at a ratio of less than 3:1 stimulatory reagents and/or beads per cell, e.g., a ratio of 1:1, and less than 50%, less than 40%, less than 30%, less than 25%, less than 20%, less than 15%, less than 10%, less than 5%, less than 1%, less than 0.1% or less than 0.01% of the cells undergo activation induced cell death during the incubation.

In certain embodiments, the composition of enriched T cells is incubated with the stimulatory reagent, e.g. anti-CD3/anti-CD28 magnetic beads, at a ratio of less than 3:1 beads per cell, e.g., a ratio of 1:1, and the cells of the composition have at least 10%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-Fold, at least 50-fold, or at least 100-fold greater survival as compared to cells undergoing an exemplary and/or alternative process where the composition of enriched T cells in incubated with the stimulatory reagent at a ratio of 3:1 or greater.

In some embodiments, the composition of enriched T cells incubated with the stimulatory reagent comprises from $1.0 \times 10^5$ cells/mL to $1.0 \times 10^8$ cells/mL or from about $1.0 \times 10^5$ cells/mL to about $1.0 \times 10^8$ cells/mL, such as at least or about at least or about $1.0 \times 10^5$ cells/mL, $5 \times 10^5$ cells/mL, $1 \times 10^6$ cells/mL, $5 \times 10^6$ cells/mL, $1 \times 10^7$ cells/mL, $5 \times 10^7$ cells/mL or $1 \times 10^8$ cells/mL. In some embodiments, the composition of enriched T cells incubated with the stimulatory reagent comprises about $0.5 \times 10^6$ cells/mL, $1 \times 10^6$ cells/mL, $1.5 \times 10^6$ cells/mL, $2 \times 10^6$ cells/mL, $2.5 \times 10^6$ cells/mL, $3 \times 10^6$ cells/mL, $3.5 \times 10^6$ cells/mL, $4 \times 10^6$ cells/mL, $4.5 \times 10^6$ cells/mL, $5 \times 10^6$ cells/mL, $5.5 \times 10^6$ cells/mL, $6 \times 10^6$ cells/mL, $6.5 \times 10^6$ cells/mL, $7 \times 10^6$ cells/mL, $7.5 \times 10^6$ cells/mL, $8 \times 10^6$ cells/mL, $8.5 \times 10^6$ cells/mL, $9 \times 10^6$ cells/mL, $9.5 \times 10^6$ cells/mL, or $10 \times 10^6$ cells/mL, such as about $2.4 \times 10^6$ cells/mL.

In some embodiments, the composition of enriched T cells is incubated with the stimulatory reagent at a temperature from about 25 to about 38° C., such as from about 30 to about 37° C., for example at or about 37° C.±2° C. In some embodiments, the composition of enriched T cells is incubated with the stimulatory reagent at a $CO_2$ level from about 2.5% to about 7.5%, such as from about 4% to about 6%, for example at or about 5%±0.5%. In some embodiments, the composition of enriched T cells is incubated with the stimulatory reagent at a temperature of or about 37° C. and/or at a $CO_2$ level of or about 5%.

In particular embodiments, the stimulating conditions include incubating, culturing, and/or cultivating a composition of enriched T cells with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes IL-2. In some embodiments, the stimulating conditions include incubating composition of enriched T cells, such as enriched CD4+ T cells or enriched CD8+ T cells, in the presence of a stimulatory reagent, e.g. anti-CD3/anti-CD28 magnetic beads, as described and in the presence or one or more recombinant cytokines.

In particular embodiments, the composition of enriched CD4+ T cells are incubated with IL-2, e.g., recombinant IL-2. Without wishing to be bound by theory, particular embodiments contemplate that CD4+ T cells that are obtained from some subjects do not produce, or do not sufficiently produce, IL-2 in amounts that allow for growth, division, and expansion throughout the process for generating a composition of output cells, e.g., engineered cells suitable for use in cell therapy. In some embodiments, incubating a composition of enriched CD4+ T cells under stimulating conditions in the presence of recombinant IL-2 increases the probability or likelihood that the CD4+ T cells of the composition will continue to survive, grow, expand, and/or activate during the incubation step and throughout the process. In some embodiments, incubating the composition of enriched CD4+ T cells in the presence of recombinant IL-2 increases the probability and/or likelihood that an output composition of enriched CD4+ T cells, e.g., engineered CD4+ T cells suitable for cell therapy, will be produced from the composition of enriched CD4+ T cells by at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-fold, at least 50-fold, or at least 100-fold as compared to an alternative and/or exemplary method that does not incubate the composition of enriched CD4+ T cells in the presence of recombinant IL-2.

In certain embodiments, the amount or concentration of the one or more cytokines are measured and/or quantified with International Units (IU). International units may be used to quantify vitamins, hormones, cytokines, vaccines, blood products, and similar biologically active substances. In some embodiments, IU are or include units of measure of the potency of biological preparations by comparison to an international reference standard of a specific weight and strength e.g., WHO 1st International Standard for Human IL-2, 86/504. International Units are the only recognized and standardized method to report biological activity units that are published and are derived from an international collaborative research effort. In particular embodiments, the IU for composition, sample, or source of a cytokine may be obtained through product comparison testing with an analogous WHO standard product. For example, in some embodiments, the IU/mg of a composition, sample, or source of human recombinant IL-2, IL-7, or IL-15 is compared to the WHO standard IL-2 product (NIBSC code: 86/500), the WHO standard IL-17 product (NIBSC code: 90/530) and the WHO standard IL-15 product (NIBSC code: 95/554), respectively.

In some embodiments, the biological activity in IU/mg is equivalent to $(ED_{50} \text{ in ng/ml})^{-1} \times 10^6$. In particular embodiments, the $ED_{50}$ of recombinant human IL-2 or IL-15 is equivalent to the concentration required for the half-maximal stimulation of cell proliferation (XTT cleavage) with CTLL-2 cells. In certain embodiments, the $ED_{50}$ of recombinant human IL-7 is equivalent to the concentration required for the half-maximal stimulation for proliferation of PHA-activated human peripheral blood lymphocytes. Details relating to assays and calculations of IU for IL-2 are discussed in Wadhwa et al., Journal of Immunological Methods (2013), 379 (1-2): 1-7; and Gearing and Thorpe, Journal of Immunological Methods (1988), 114 (1-2): 3-9; details relating to assays and calculations of IU for IL-15 are discussed in Soman et al. Journal of Immunological Methods (2009) 348 (1-2): 83-94; hereby incorporated by reference in their entirety.

In particular embodiments, a composition of enriched CD8+ T cells is incubated under stimulating conditions in the presence of IL-2 and/or IL-15. In certain embodiments, a composition of enriched CD4+ T cells is incubated under stimulating conditions in the presence of IL-2, IL-7, and/or IL-15. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In some aspects, the incubation of the enriched T cell composition also includes the presence of a stimulatory reagent, e.g. anti-CD3/anti-CD28 magnetic beads.

In some embodiments, the cells are incubated with a cytokine, e.g., a recombinant human cytokine, at a concentration of between 1 IU/ml and 1,000 IU/ml, between 10 IU/ml and 50 IU/ml, between 50 IU/ml and 100 IU/ml, between 100 IU/ml and 200 IU/ml, between 100 IU/ml and 500 IU/ml, between 250 IU/ml and 500 IU/ml, or between 500 IU/ml and 1,000 IU/ml.

In some embodiments, a composition of enriched T cells is incubated with IL-2, e.g., human recombinant IL-2, at a concentration between 1 IU/ml and 200 IU/ml, between 10 IU/ml and 200 IU/ml, between 10 IU/ml and 100 IU/ml, between 50 IU/ml and 150 IU/ml, between 80 IU/ml and 120 IU/ml, between 60 IU/ml and 90 IU/ml, or between 70 IU/ml and 90 IU/ml. In particular embodiments, the composition of enriched T cells is incubated with recombinant IL-2 at a concentration at or at about 50 IU/ml, 55 IU/ml, 60 IU/ml, 65 IU/ml, 70 IU/ml, 75 IU/ml, 80 IU/ml, 85 IU/ml, 90 IU/ml, 95 IU/ml, 100 IU/ml, 110 IU/ml, 120 IU/ml, 130 IU/ml, 140 IU/ml, or 150 IU/ml. In some embodiments, the composition of enriched T cells is incubated in the presence of or of about 85 IU/ml recombinant IL-2. In some embodiments, the composition incubated with recombinant IL-2 is enriched for a population of T cells, e.g., CD4+ T cells and/or CD8+ T cells. In some embodiments, the population of T cells is a population of CD4+ T cells. In some embodiments, the composition of enriched T cells is a composition of enriched CD8+ T cells. In particular embodiments, the composition of enriched T cells is enriched for CD8+ T cells, where CD4+ T cells are not enriched for and/or where CD4+ T cells are negatively selected for or depleted from the composition. In some embodiments, the composition of enriched T cells is a composition of enriched CD4+ T cells. In particular embodiments, the composition of enriched T cells is enriched for CD4+ T cells, where CD8+ T cells are not enriched for and/or where CD8+ T cells are negatively selected for or depleted from the composition. In some embodiments, an enriched CD4+ T cell composition incubated with recombinant IL-2 may also be incubated with recombinant IL-7 and/or recombinant IL-15, such as in amounts described. In some embodiments, an enriched CD8+ T cell composition incubated with recombinant IL-2 may also be incubated with recombinant IL-15, such as in amounts described.

In some embodiments, a composition of enriched T cells is incubated with recombinant IL-7, e.g., human recombinant IL-7, at a concentration between 100 IU/ml and 2,000 IU/ml, between 500 IU/ml and 1,000 IU/ml, between 100 IU/ml and 500 IU/ml, between 500 IU/ml and 750 IU/ml, between 750 IU/ml and 1,000 IU/ml, or between 550 IU/ml and 650 IU/ml. In particular embodiments, the composition of enriched T cells is incubated with recombinant IL-7 at a concentration at or at about 50 IU/ml, 100 IU/ml, 150 IU/ml, 200 IU/ml, 250 IU/ml, 300 IU/ml, 350 IU/ml, 400 IU/ml, 450 IU/ml, 500 IU/ml, 550 IU/ml, 600 IU/ml, 650 IU/ml, 700 IU/ml, 750 IU/ml, 800 IU/ml, 750 IU/ml, 750 IU/ml, 750 IU/ml, or 1,000 IU/ml. In particular embodiments, the composition of enriched T cells is incubated in the presence of or of about 600 IU/ml of recombinant IL-7. In some embodiments, the composition incubated with recombinant IL-7 is enriched for a population of T cells, e.g., CD4+ T cells. In some embodiments, an enriched CD4+ T cell composition incubated with recombinant IL-7 may also be incubated with recombinant IL-2 and/or recombinant IL-15, such as in amounts described. In particular embodiments, the composition of enriched T cells is enriched for CD4+ T cells, where CD8+ T cells are not enriched for and/or where CD8+ T cells are negatively selected for or depleted from the composition. In some embodiments, an enriched CD8+ T cell composition is not incubated with recombinant IL-7.

In some embodiments, a composition of enriched T cells is incubated with recombinant IL-15, e.g., human recombinant IL-15, at a concentration between 0.1 IU/ml and 100 IU/ml, between 1 IU/ml and 100 IU/ml, between 1 IU/ml and 50 IU/ml, between 5 IU/ml and 25 IU/ml, between 25 IU/ml and 50 IU/ml, between 5 IU/ml and 15 IU/ml, or between 10 IU/ml and 100 IU/ml. In particular embodiments, the composition of enriched T cells is incubated with recombinant IL-15 at a concentration at or at about 1 IU/ml, 2 IU/ml, 3 IU/ml, 4 IU/ml, 5 IU/ml, 6 IU/ml, 7 IU/ml, 8 IU/ml, 9 IU/ml, 10 IU/ml, 11 IU/ml, 12 IU/ml, 13 IU/ml, 14 IU/ml, 15 IU/ml, 20 IU/ml, 25 IU/ml, 30 IU/ml, 40 IU/ml, or 50 IU/ml. In some embodiments, the composition of enriched T cells is incubated in or in about 10 IU/ml of recombinant IL-15. In some embodiments, the composition incubated with recombinant IL-15 is enriched for a population of T cells, e.g., CD4+ T cells and/or CD8+ T cells. In some embodiments, the population of T cells is a population of CD4+ T cells. In some embodiments, the composition of enriched T cells is a composition of enriched CD8+ T cells. In particular embodiments, the composition of enriched T cells is enriched for CD8+ T cells, where CD4+ T cells are not enriched for and/or where CD4+ T cells are negatively selected for or depleted from the composition. In some embodiments, the composition of enriched T cells is a composition of enriched CD4+ T cells. In particular embodiments, the composition of enriched T cells is enriched for CD4+ T cells, where CD8+ T cells are not enriched for and/or where CD8+ T cells are negatively selected for or depleted from the composition. In some embodiments, an enriched CD4+ T cell composition incubated with recombinant IL-15 may also be incubated with recombinant IL-7 and/or recombinant IL-2, such as in amounts described. In some embodiments, an enriched CD8+ T cell composition incubated with recombinant IL-15 may also be incubated with recombinant IL-2, such as in amounts described.

In particular embodiments, the cells, such as enriched CD4+ T cells and/or enriched CD8+ T cells, are incubated with the stimulatory reagent in the presence of one or more antioxidants. In some embodiments, antioxidants include, but are not limited to, one or more antioxidants comprise a tocopherol, a tocotrienol, alpha-tocopherol, beta-tocopherol, gamma-tocopherol, delta-tocopherol, alpha-tocotrienol, beta-tocotrienol, alpha-tocopherolquinone, Trolox (6-hydroxy-2,5,7,8-tetramethylchroman-2-carboxylic acid), butylated hydroxyanisole (BHA), butylated hydroxytoluene (BHT), a flavonoids, an isoflavone, lycopene, beta-carotene, selenium, ubiquinone, luetin, S-adenosylmethionine, glutathione, taurine, N-acetyl cysteine (NAC), citric acid, L-carnitine, BHT, monothioglycerol, ascorbic acid, propyl gallate, methionine, cysteine, homocysteine, gluthatione, cystamine and cysstathionine, and/or glycine-glycine-histidine. In some aspects, the incubation of the enriched T cell composition, such as enriched CD4+ T cells and/or enriched CD8+ T cells, with an antioxidant also includes the presence of a stimulatory reagent, e.g. anti-CD3/anti-CD28 magnetic beads, and one or more recombinant cytokines, such as described.

In some embodiments, the one or more antioxidants is or includes a sulfur containing oxidant. In certain embodiments, a sulfur containing antioxidant may include thiol-containing antioxidants and/or antioxidants which exhibit one or more sulfur moieties, e.g., within a ring structure. In some embodiments, the sulfur containing antioxidants may include, for example, N-acetylcysteine (NAC) and 2,3-dimercaptopropanol (DMP), L-2-oxo-4-thiazolidinecarboxylate (OTC) and lipoic acid. In particular embodiments, the sulfur containing antioxidant is a glutathione precursor. In some embodiments, the glutathione precursor is a molecule which may be modified in one or more steps within a cell to derived glutathione. In particular embodiments, a glutathione precursor may include, but is not limited to N-acetyl cysteine (NAC), L-2-oxothiazolidine-4-carboxylic acid (Procysteine), lipoic acid, S-allyl cysteine, or methylmethionine sulfonium chloride.

In some embodiments, incubating the cells, such as enriched CD4+ T cells and/or enriched CD8+ T cells, under stimulating conditions includes incubating the cells in the presence of one or more antioxidants. In particular embodiments, the cells are stimulated with the stimulatory reagent in the presence of one or more antioxidants. In some embodiments, the cells are incubated in the presence of between 1 ng/ml and 100 ng/ml, between 10 ng/ml and 1 µg/ml, between 100 ng/ml and 10 µg/ml, between 1 µg/ml and 100 µg/ml, between 10 µg/ml and 1 mg/ml, between 100 µg/ml and 1 mg/ml, between 1 500 µg/ml and 2 mg/ml, 500 µg/ml and 5 mg/ml, between 1 mg/ml and 10 mg/ml, or between 1 mg/ml and 100 mg/ml of the one or more antioxidants. In some embodiments, the cells are incubated in the presence of or of about 1 ng/ml, 10 ng/ml, 100 ng/ml, 1 µg/ml, 10 µg/ml, 100 µg/ml, 0.2 mg/ml, 0.4 mg/ml, 0.6 mg/ml, 0.8 mg/ml, 1 mg/ml, 2 mg/ml, 3 mg/ml, 4 mg/ml, 5 mg/ml, 10 mg/ml, 20 mg/ml, 25 mg/ml, 50 mg/ml, 100 mg/ml, 200 mg/ml, 300 mg/ml, 400 mg/ml, 500 mg/ml of the one or more antioxidant. In some embodiments, the one or more antioxidants is or includes a sulfur containing antioxidant. In particular embodiments, the one or more antioxidants is or includes a glutathione precursor.

In some embodiments, the one or more antioxidants is or includes N-acetyl cysteine (NAC). In some embodiments, incubating the cells, such as enriched CD4+ T cells and/or enriched CD8+ T cells, under stimulating conditions includes incubating the cells in the presence of NAC. In particular embodiments, the cells are stimulated with the stimulatory reagent in the presence of NAC. In some embodiments, the cells are incubated in the presence of between 1 ng/ml and 100 ng/ml, between 10 ng/ml and 1 µg/ml, between 100 ng/ml and 10 µg/ml, between 1 µg/ml and 100 µg/ml, between 10 µg/ml and 1 mg/ml, between 100 µg/ml and 1 mg/ml, between 1-500 µg/ml and 2 mg/ml, 500 µg/ml and 5 mg/ml, between 1 mg/ml and 10 mg/ml, or between 1 mg/ml and 100 mg/ml of NAC. In some embodiments, the cells are incubated in the presence of or of about 1 ng/ml, 10 ng/ml, 100 ng/ml, 1 µg/ml, 10 µg/ml, 100 µg/ml, 0.2 mg/ml, 0.4 mg/ml, 0.6 mg/ml, 0.8 mg/ml, 1 mg/ml, 2 mg/ml, 3 mg/ml, 4 mg/ml, 5 mg/ml, 10 mg/ml, 20 mg/ml, 25 mg/ml, 50 mg/ml, 100 mg/ml, 200 mg/ml, 300 mg/ml, 400 mg/ml, 500 mg/ml of NAC. In some embodiments, the cells are incubated with or with about 0.8 mg/ml.

In particular embodiments, incubating the composition of enriched T cells, such as enriched CD4+ T cells and/or enriched CD8+ T cells, in the presence of one or more antioxidants, e.g., NAC, reduces the activation in the cells as compared to cells that are incubated in alternative and/or exemplary processes without the presence of antioxidants. In certain embodiments, the reduced activation is measured by the expression of one or more activation markers in the cell. In certain embodiments, markers of activation include, but are not limited to, increased intracellular complexity (e.g. as determined by measuring side scatter (SSC), increased cell size (e.g. as determined by measuring cell diameter and/or forward scatter (FSC), increased expression of CD27, and/or decreased expression of CD25. In some embodiments, the cells of the composition have negative, reduced, or low expression and/or degree of markers of activation when examined during or after the incubation, engineering, transduction, transfection, expansion, or formulation, or during or after any stage of the process occurring after the incubation. In some embodiments the cells of the composition have negative, reduced, or low expression and/or degree of markers of activation after the process is completed. In particular embodiments, the cells of the output composition have negative, reduced, or low expression and/or degree of markers of activation.

In some embodiments, flow cytometry is used to determine relative size of cells. In particular embodiments, the FSC and SSC parameters are used to analyze cells and distinguish the cells from one another based off of size and internal complexity. In particular embodiments, a particle or bead of a known size can be measured as a standard to determine the actual size of cells. In some embodiments, flow cytometry is used in combination with a stain, e.g., a labeled antibody, to measure or quantify the expression of a surface protein, such as a marker of activation, e.g., CD25 or CD27.

In some embodiments, the composition of enriched T cells, such as enriched CD4+ T cells and/or enriched CD8+ T cells, is incubated in the presence of one or more antioxidants e.g., NAC, and the cell diameter reduced by at least 0.25 µm, 0.5 µm, 0.75 µm, 1.0 µm, 1.5 µm, 2 µm, 2.5 µm, 3 µm, 3.5 µm, 4 µm, 4.5 µm, 5 µm, or more than 5 µm as compared to cells incubated in an alternative and/or exemplary process where the incubation is not performed in the presence of an antioxidant. In particular embodiments, the composition of enriched T cells is incubated in the presence of one or more antioxidants e.g., NAC, and the cell size, as measured by the FSC is reduced by at least 1%, at least 5%, at least 10%, at least 20%, at least 30%, at least 40%, at least 50%, at least 60%, at least 70%, at least 75%, at least 80%, at least 85%, or at least 90% as compared to cells incubated in an alternative and/or exemplary process where the incubation is not performed in the presence of an antioxidant.

In some embodiments, the composition of enriched T cells, such as enriched CD4+ T cells and/or enriched CD8+ T cells, is incubated in the presence of one or more antioxidants e.g., NAC, and the intracellular complexity, as measured by the SSC, is reduced by at least 1%, at least 5%, at least 10%, at least 20%, at least 30%, at least 40%, at least 50%, at least 60%, at least 70%, at least 75%, at least 80%, at least 85%, or at least 90% as compared to cells incubated in an alternative and/or exemplary process where the incubation is not performed in the presence of an antioxidant.

In particular embodiments, the composition of enriched T cells, such as enriched CD4+ T cells and/or enriched CD8+ T cells, is incubated in the presence of one or more antioxidants e.g., NAC, and the expression of CD27, e.g., as measured by the flow cytometry, is reduced by at least 1%, at least 5%, at least 10%, at least 20%, at least 30%, at least 40%, at least 50%, at least 60%, at least 70%, at least 75%, at least 80%, at least 85%, at least 90%, at least 95%, or at least 99% as compared to cells incubated in an alternative and/or exemplary process where the incubation is not performed in the presence of an antioxidant.

In certain embodiments, the composition of enriched T cells, such as enriched CD4+ T cells and/or enriched CD8+ T cells, is incubated in the presence of one or more antioxidants, e.g., NAC, and the expression of CD25, e.g., as measured by the flow cytometry, is increased by at least 1%, at least 5%, at least 10%, at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, at least 5-fold, at least 10-fold, at least 25-Fold, at least 50-fold, or at least 100-fold as compared to cells incubated in an alternative and/or exemplary process where the incubation is not performed in the presence of an antioxidant.

In particular embodiments, incubating the composition of enriched T cells, such as enriched CD4+ T cells and/or enriched CD8+ T cells, in the presence of one or more antioxidants, e.g., NAC, increases the expansion, e.g., during the incubation or cultivation step or stage as described in Section I-D. In some embodiments, a composition of enriched cells achieves a 2-fold, a 2.5 fold, a 3 fold, a 3.5 fold, a 4 fold, a 4.5 fold a 5 fold, a 6 fold, a 7 fold, an 8 fold, a nine fold, a 10-fold, or greater than a 10 fold expansion within 14 days, 12 days, 10 days, 9 days, 8 days, 7 days, 6 days, 5 days, 4 days, or within 3 days of the start of the cultivation. In some embodiments, the composition of enriched T cells is incubated in the presence of one or more antioxidants and the cells of the compositions undergo at least 10%, at least a 20%, at least a 30%, at least a 40%, at least a 50%, at least a 60%, at least a 70%, at least a 75%, at least an 80%, at least an 85%, at least a 90%, at least a 100%, at least a 150%, at least a 1-fold, at least a 2-fold, at least a 3-fold, at least a 4-fold, at least a 5-fold, at least a 10-fold faster rate of expansion during the cultivation than cultivated cells that were incubated in an alternative and/or exemplary process where the incubation is not performed in the presence of an antioxidant.

In particular embodiments, incubating the composition of enriched cells, such as enriched CD4+ T cells and/or enriched CD8+ T cells, in the presence of one or more antioxidants, e.g., NAC, reduces the amount of cell death, e.g., by apoptosis. In some embodiments, the composition of enriched T cells is incubated in the presence of a one or more antioxidants, e.g., NAC, and at least 50%, at least 60%, at least 70%, at least 75%, at least 80%, at least 85%, at least 90%, at least 95%, at least 99%, or at least 99.9% of the cells survive, e.g., do not undergo apoptosis, during or at least 1 day, 2 days, 3 days, 4 days, 5 days, 6 days, 7 days, or more than 7 days after the incubation is complete. In some embodiments, the composition is incubated in the presence of one or more antioxidants, e.g., NAC, and the cells of the composition have at least 10%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-Fold, at least 50-fold, or at least 100-fold greater survival as compared to cells undergoing an exemplary and/or alternative process where cells are not incubated in the presence or one or more antioxidants.

In particular embodiments, the composition of enriched T cells, such as enriched CD4+ T cells and/or enriched CD8+ T cells, is incubated in the presence of one or more antioxidants e.g., NAC, and caspase expression, e.g., caspase 3 expression, is reduced by at least 1%, at least 5%, at least 10%, at least 20%, at least 30%, at least 40%, at least 50%, at least 60%, at least 70%, at least 75%, at least 80%, at least 85%, at least 90%, at least 95%, or at least 99% as compared to cells incubated in an alternative and/or exemplary process where the incubation is not performed in the presence of an antioxidant.

In some embodiments, the compositions or cells, such as enriched CD4+ T cells and/or enriched CD8+ T cells, are incubated in the presence of stimulating conditions or a stimulatory agent, such as described. Such conditions include those designed to induce proliferation, expansion, activation, and/or survival of cells in the population, to mimic antigen exposure, and/or to prime the cells for genetic engineering, such as for the introduction of a recombinant antigen receptor. Exemplary stimulatory reagents, such as anti-CD3/anti-CD28 magnetic beads, are described below. The incubation with the stimulatory reagent may also be carried out in the presence of one or more stimulatory cytokine, such as in the presence of one or more of recombinant IL-2, recombinant IL-7 and/or recombinant IL-15 and/or in the presence of at least one antioxidant such as NAC, such as described above. In some embodiments, a composition of enriched CD4+ T cells are incubated under stimulatory conditions with a stimulatory agent, recombinant IL-2, recombinant IL-7, recombinant IL-15 and NAC, such as in amounts as described. In some embodiments, a composition of enriched CD8+ T cells are incubated under stimulatory conditions with a stimulatory agent, recombinant IL-2, recombinant IL-15 and NAC, such as in amounts as described.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, at least a portion of the incubation in the presence of one or more stimulating conditions or a stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, about 10 mL to about 200 mL, or about 20 mL to about 125 mL, such as at least or about at least or about 10 mL, 20 mL, 30 mL, 40 mL, 50 mL, 60 mL, 70 mL, 80 mL, 90 mL, 100 mL, 105 mL, 110 mL, 115 mL, 120 mL, 125 mL, 130 mL, 135 mL, 140 mL, 145 mL, 150 mL, 160 mL, 170 mL, 180 mL, 190 mL, or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm), such as at an RCF at the sample or wall of the chamber or other container of from 80 g to 100 g or from about 80 g to about 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours, 18 hours and 30 hours, or 12 hours and 24 hours, such as at least or about at least or about 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the cells are cultured, cultivated, and/or incubated under stimulating conditions prior to and/or during a step for introducing a polynucleotide, e.g., a polynucleotide encoding a recombinant receptor, to the cells, e.g., by transduction and/or transfection, such as described by Section I-C. In certain embodiments the cells are cultured, cultivated, and/or incubated under stimulating conditions for an amount of time between 30 minutes and 2 hours, between 1 hour and 8 hours, between 1 hour and 6 hours, between 6 hours and 12 hours, between 12 hours and 18 hours, between 16 hours and 24 hours, between 12 hours and 36 hours, between 24 hours and 48 hours, between 24 hours and 72 hours, between 42 hours and 54 hours, between 60 hours and 120 hours between 96 hours and 120 hours, between 90 hours and between 1 days and 7 days, between 3 days and 8 days, between 1 day and 3 days, between 4 days and 6 days, or between 4 days and 5 days prior to the genetic engineering. In some embodiments, the cells are incubated for or for about 2 days prior to the engineering.

In certain embodiments, the cells are incubated with and/or in the presence of the stimulatory reagent prior to and/or during genetically engineering the cells. In certain embodiments the cells are incubated with and/or in the presence of the stimulatory reagent for an amount of time between 12 hours and 36 hours, between 24 hours and 48 hours, between 24 hours and 72 hours, between 42 hours and 54 hours, between 60 hours and 120 hours between 96 hours and 120 hours, between 90 hours and between 2 days and 7 days, between 3 days and 8 days, between 1 day and 8 days, between 4 days and 6 days, or between 4 days and 5 days. In particular embodiments, the cells are cultured, cultivated, and/or incubated under stimulating conditions prior to and/or during genetically engineering the cells for an amount of time of less than 10 days, 9 days, 8 days, 7 days, 6 days, or 5 days, 4 days, or for an amount of time less than 168 hours, 162 hours, 156 hours, 144 hours, 138 hours, 132 hours, 120 hours, 114 hours, 108 hours, 102 hours, or 96 hours. In particular embodiments, the cells are incubated with and/or in the presence of the stimulatory reagent for or for about 4 days, 5 days, 6 days, or 7 days. In some embodiments, the cells are incubated with and/or in the presence of the stimulatory reagent for or for about 4 days. In particular embodiments, the cells are incubated with and/or in the presence of the stimulatory reagent for or for about 5 days. In certain embodiments, the cells are incubated with and/or in the presence of the stimulatory reagent for less than 7 days.

In some embodiments, incubating the cells under stimulating conditions includes incubating the cells with a stimulatory reagent that is described in Section I-B-1. In some embodiments, the stimulatory reagent contains or includes a bead, such as a paramagnetic bead, and the cells are incubated with the stimulatory reagent at a ratio of less than 3:1 (beads:cells), such as a ratio of 1:1. In particular embodiments, the cells are incubated with the stimulatory reagent in the presence of one or more cytokines and/or one or more antioxidants. In some embodiments, a composition of enriched CD4+ T cells is incubated with the stimulatory reagent at a ratio of 1:1 (beads:cells) in the presence of recombinant IL-2, IL-7, IL-15, and NAC. In certain embodiments, a composition of enriched CD8+ T cells is incubated with the stimulatory reagent at a ratio of 1:1 (beads:cells) in the presence of recombinant IL-2, IL-15, and NAC. In some embodiments, the stimulatory reagent is removed and/or separated from the cells at, within, or within about 6 days, 5 days, or 4 days from the start or initiation of the incubation, e.g., from the time the stimulatory reagent is added to or contacted with the cells.

I. Stimulatory Reagents

In some embodiments, incubating a composition of enriched cells under stimulating conditions is or includes incubating and/or contacting the composition of enriched cells with a stimulatory reagent that is capable of activating and/or expanding T cells. In some embodiments, the stimulatory reagent is capable of stimulating and/or activating one or more signals in the cells. In some embodiments, the one or more signals are mediated by a receptor. In particular embodiments, the one or more signals are or are associated with a change in signal transduction and/or a level or amount of secondary messengers, e.g., cAMP and/or intracellular calcium, a change in the amount, cellular localization, confirmation, phosphorylation, ubiquitination, and/or truncation of one or more cellular proteins, and/or a change in a cellular activity, e.g., transcription, translation, protein degradation, cellular morphology, activation state, and/or cell division. In particular embodiments, the stimulatory reagent activates and/or is capable of activating one or more intracellular signaling domains of one or more components of a TCR complex and/or one or more intracellular signaling domains of one or more costimulatory molecules.

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, a stimulatory reagent contains one or more agents that are capable of activating and/or expanding cells, e.g., T cells, that are bound to or otherwise attached to a bead, for example to the surface of the bead. In certain embodiments, the bead is a non-cell particle. In particular embodiments, the bead may include a colloidal particle, a microsphere, nanoparticle, a magnetic bead, or the like. In some embodiments the beads are agarose beads. In certain embodiments, the beads are sepharose beads.

In particular embodiments, the stimulatory reagent contains beads that are monodisperse. In certain embodiments, beads that are monodisperse comprise size dispersions having a diameter standard deviation of less than 5% from each other.

In some embodiments, the bead contains one or more agents, such as an agent that is coupled, conjugated, or linked (directly or indirectly) to the surface of the bead. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD1 la (LFA-1), CD62L (L-selectin), CD29/CD49d (VLA-4), Notch ligand (e.g. Delta-like ¼, Jagged ½, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody. In some embodiments, the bead has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the bead has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the bead has a diameter of about 3 μm to about 5 μm. In some embodiments, the bead has a diameter of at least or at least about or about 0.001 µm, 0.01 µm, 0.1 µm, 0.5 µm, 1.0 µm, 1.5 µm, 2.0 µm, 2.5 µm, 3.0 µm, 3.5 µm, 4.0 µm, 4.5 µm, 5.0 µm, 5.5 µm, 6.0 µm, 6.5 µm, 7.0 µm, 7.5 µm, 8.0 µm, 8.5 µm, 9.0 µm, 9.5 µm, 10 µm, 12 µm, 14 µm, 16 µm, 18 µm or 20 µm. In certain embodiments, the bead has a diameter of or about 4.5 µm. In certain embodiments, the bead has a diameter of or about 2.8 µm.

In some embodiments, the beads have a density of greater than 0.001 g/cm$^3$, greater than 0.01 g/cm$^3$, greater than 0.05 g/cm$^3$, greater than 0.1 g/cm$^3$, greater than 0.5 g/cm$^3$, greater than 0.6 g/cm$^3$, greater than 0.7 g/cm$^3$, greater than 0.8 g/cm$^3$, greater than 0.9 g/cm$^3$, greater than 1 g/cm$^3$, greater than 1.1 g/cm$^3$, greater than 1.2 g/cm$^3$, greater than 1.3 g/cm$^3$, greater than 1.4 g/cm$^3$, greater than 1.5 g/cm$^3$, greater than 2 g/cm$^3$, greater than 3 g/cm$^3$, greater than 4 g/cm$^3$, or greater than 5 g/cm$^3$. In some embodiments, the beads have a density of between about 0.001 g/cm$^3$ and about 100 g/cm$^3$, about 0.01 g/cm$^3$ and about 50 g/cm$^3$, about 0.1 g/cm$^3$ and about 10 g/cm$^3$, about 0.1 g/cm$^3$ and about 0.5 g/cm$^3$, about 0.5 g/cm$^3$ and about 1 g/cm$^3$, about 0.5 g/cm$^3$ and about 1.5 g/cm$^3$, about 1 g/cm$^3$ and about 1.5 g/cm$^3$, about 1 g/cm$^3$ and about 2 g/cm$^3$, or about 1 g/cm$^3$ and about 5 g/cm$^3$. In some embodiments, the beads have a density of about 0.5 g/cm$^3$, about 0.5 g/cm$^3$, about 0.6 g/cm$^3$, about 0.7 g/cm$^3$, about 0.8 g/cm$^3$, about 0.9 g/cm$^3$, about 1.0 g/cm$^3$, about 1.1 g/cm$^3$, about 1.2 g/cm$^3$, about 1.3 g/cm$^3$, about 1.4 g/cm$^3$, about 1.5 g/cm$^3$, about 1.6 g/cm$^3$, about 1.7 g/cm$^3$, about 1.8 g/cm$^3$, about 1.9 g/cm$^3$, or about 2.0 g/cm$^3$. In certain embodiments, the beads have a density of about 1.6 g/cm$^3$. In particular embodiments, the beads or particles have a density of about 1.5 g/cm$^3$. In certain embodiments, the particles have a density of about 1.3 g/cm$^3$.

In certain embodiments, a plurality of the beads has a uniform density. In certain embodiments, a uniform density comprises a density standard deviation of less than 10%, less than 5%, or less than 1% of the mean bead density.

In some embodiments, the beads have a surface area of between about 0.001 m$^2$ per each gram of particles (m$^2$/g) to about 1,000 m$^2$/g, about 0.010 m$^2$/g to about 100 m$^2$/g, about 0.1 m$^2$/g to about 10 m$^2$/g, about 0.1 m$^2$/g to about 1 m$^2$/g, about 1 m$^2$/g to about 10 m$^2$/g, about 10 m$^2$/g to about 100 m$^2$/g, about 0.5 m$^2$/g to about 20 m$^2$/g, about 0.5 m$^2$/g to about 5 m$^2$/g, or about 1 m$^2$/g to about 4 m$^2$/g. In some embodiments, the particles or beads have a surface area of about 1 m$^2$/g to about 4 m$^2$/g.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite (Fe3O4), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 µm to about 10 µm. In some embodiments, the bead has a diameter of about 3 µm to about 5 µm. In certain embodiments, the bead has a diameter of about 3.5 µm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite ($Fe_3O_4$) and/or maghemite (γFe$_2$O$_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the stimulatory reagent is or comprises anti-CD3/anti-CD28 magnetic beads, In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 g/cm$^3$ and a surface area of about 1 m$^2$/g to about 4 m$^2$/g. In particular embodiments; the beads are monodisperse superparamagnetic beads that have a diameter of about 4.5 μm and a density of about 1.5 g/cm$^3$. In some embodiments, the beads the beads are monodisperse superparamagnetic beads that have a mean diameter of about 2.8 μm and a density of about 1.3 g/cm$^3$.

In some embodiments, the composition of enriched T cells is incubated with stimulatory reagent a ratio of beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

2. Removal of the Stimulatory Reagent from Cells

In certain embodiments, the stimulatory reagent, e.g. anti-CD3/anti-CD28 magnetic beads, is removed and/or separated from the cells. Without wishing to be bound by theory, particular embodiments contemplate that the binding and/or association between a stimulatory reagent and cells may, in some circumstances, be reduced over time during the incubation. In certain embodiments, one or more agents may be added to reduce the binding and/or association between the stimulatory reagent and the cells. In particular embodiments, a change in cell culture conditions, e.g., media temperature of pH, may reduce the binding and/or association between the stimulatory reagent and the cells. Thus, in some embodiments, the stimulatory reagent may be removed from an incubation, cell culture system, and/or a solution separately from the cells, e.g., without removing the cells from the incubation, cell culture system, and/or a solution as well.

Methods for removing stimulatory reagents (e.g. stimulatory reagents that are or contain particles such as bead particles or magnetizable particles) from cells are known. In some embodiments, the use of competing antibodies, such as non-labeled antibodies, can be used, which, for example, bind to a primary antibody of the stimulatory reagent and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the stimulatory reagent is magnetic, paramagnetic, and/or superparamagnetic, and/or contains a bead that is magnetic, paramagnetic, and/or superparamagnetic, and the stimulatory reagent may be removed from the cells by exposing the cells to a magnetic field. Examples of suitable equipment containing magnets for generating the magnetic field include DynaMag CTS (Thermo Fisher), Magnetic Separator (Takara) and EasySep Magnet (Stem Cell Technologies).

In particular embodiments, the stimulatory reagent is removed or separated from the cells prior to the completion of the provided methods, e.g., prior to harvesting, collecting, and/or formulating engineered cells produced by the methods provided herein. In some embodiments, the stimulatory reagent is removed and/or separated from the cells prior to engineering, e.g., transducing or transfecting, the cells. In particular embodiments, the stimulatory reagent is removed and/or separated from the cells after the step of engineering the cells. In certain embodiments, the stimulatory reagent is removed prior to the cultivation of the cells, e.g., prior to the cultivation of the engineered, e.g., transfected or transduced, cells under conditions to promote proliferation and/or expansion.

In certain embodiments, the stimulatory reagent is separated and/or removed from the cells after an amount of time. In particular embodiments, the amount of time is an amount of time from the start and/or initiation of the incubation under stimulating conditions. In particular embodiments the start of the incubation is considered at or at about the time the cells are contacted with the stimulatory reagent and/or a media or solution containing the stimulatory reagent. In particular embodiments, the stimulatory reagent is removed or separated from the cells within or within about 10 days, 9 days, 8 days, 7 days, 6 days, 5 days, 4 days, 3 days, or 2 days after the start or initiation of the incubation. In particular embodiments, the stimulatory reagent is removed and/or separated from the cells at or at about 9 days, 8 days, 7 days, 6 days, 5 days, 4 days, 3 days, or 2 days after the start or initiation of the incubation. In certain embodiments, the stimulatory reagent is removed and/or separated from the cells at or at about 168 hours, 162 hours, 156 hours, 144 hours, 138 hours, 132 hours, 120 hours, 114 hours, 108 hours, 102 hours, or 96 hours after the start or initiation of the incubation. In particular embodiments, the stimulatory reagent is removed and/or separated from the cells at or at about 5 days after the start and/or initiation of the incubation. In some embodiments, the stimulatory reagent is removed and/or separated from the cells at or at about 4 days after the start and/or initiation of the incubation.

C. Engineering Cells

In some embodiments, the provided methods involve administering to a subject having a disease or condition cells expressing a recombinant antigen receptor. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the methods provided herein are used in association with engineering one or more compositions of enriched T cells. In certain embodiments, the engineering is or includes the introduction of a polynucleotide, e.g., a recombinant polynucleotide encoding a recombinant protein. In particular embodiments, the recombinant proteins are recombinant receptors, such as any described in Section II. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation. In some embodiments, the engineering produces one or more engineered compositions of enriched T cells.

In certain embodiments, one or more compositions of enriched T cells are engineered, e.g., transduced or transfected, prior to cultivating the cells, e.g., under conditions that promote proliferation and/or expansion, such as by a method provided in Section I-D. In particular embodiments, one or more compositions of enriched T cells are engineered after the one or more compositions have been stimulated, activated, and/or incubated under stimulating conditions, such as described in methods provided in Section I.B. In particular embodiments, the one or more compositions are stimulated compositions. In particular embodiments, the one or more stimulated compositions have been previously cryofrozen and stored, and are thawed prior to engineering.

In certain embodiments, the one or more compositions of stimulated T cells are or include two separate stimulated compositions of enriched T cells. In particular embodiments, two separate compositions of enriched T cells, e.g., two separate compositions of enriched T cells that have been selected, isolated, and/or enriched from the same biological sample, are separately engineered. In certain embodiments, the two separate compositions include a composition of enriched CD4+ T cells. In particular embodiments, the two separate compositions include a composition of enriched CD8+ T cells. In some embodiments, two separate compositions of enriched CD4+ T cells and enriched CD8+ T cells, such as following incubation under stimulating conditions as described above, are genetically engineered separately. In some embodiments, a single composition of enriched T cells is genetically engineered. In certain embodiments, the single composition is a composition of enriched CD4+ T cells. In some embodiments, the single composition is a composition of enriched CD4+ and CD8+ T cells that have been combined from separate compositions prior to the engineering.

In some embodiments, the composition of enriched CD4+ T cells, such as stimulated CD4+ T cells, that is engineered, e.g., transduced or transfected, includes at least 60%, at least 65%, at least 70%, at least 75%, at least 80%, at least 85%, at least 90%, at least 95%, at least 98%, at least 99%, at least 99.5%, at least 99.9%, or at or about 100% CD4+ T cells. In certain embodiments, the composition of enriched CD4+ T cells, such as stimulated CD4+ T cells, that is engineered includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells, such as stimulated CD8+ T cells, that is engineered, e.g., transduced or transfected, includes at least 60%, at least 65%, at least 70%, at least 75%, at least 80%, at least 85%, at least 90%, at least 95%, at least 98%, at least 99%, at least 99.5%, at least 99.9%, or at or about 100% CD8+ T cells.

In certain embodiments, the composition of enriched CD8+ T cells that, such as stimulated CD8+ T cells, that is engineered includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, separate compositions of enriched CD4+ and CD8+ T cells are combined into a single composition and are genetically engineered, e.g., transduced or transfected. In certain embodiments, separate engineered compositions of enriched CD4+ and enriched CD8+ T cells are combined into a single composition after the genetic engineering has been performed and/or completed. In particular embodiments, separate compositions of enriched CD4+ and CD8+ T cells, such as separate compositions of stimulated DD4+ and CD8+ T cells are separately engineered and are separately processed for cultivation and/or expansion of T cells after the genetic engineering and been performed and/or completed.

In some embodiments, the introduction of a polynucleotide, e.g., a recombinant polynucleotide encoding a recombinant protein, is carried out by contacting enriched CD4+ or CD8+ T cells, such as stimulated CD4+ or CD8+ T cells, with a viral particles containing the polynucleotide. In some embodiments, contacting can be effected with centrifugation, such as spinoculation (e.g., centrifugal inoculation). In some embodiments, the composition containing cells, viral particles and reagent can be rotated, generally at relatively low force or speed, such as speed lower than that used to pellet the cells, such as from 600 rpm to 1700 rpm or from about 600 rpm to about 1700 rpm (e.g., at or about or at least 600 rpm, 1000 rpm, or 1500 rpm or 1700 rpm). In some embodiments, the rotation is carried at a force, e.g., a relative centrifugal force, of from 100 g to 3200 g or from about 100 g to about 3200 g (e.g., at or about or at least at or about 100 g, 200 g, 300 g, 400 g, 500 g, 1000 g, 1500 g, 2000 g, 2500 g, 3000 g or 3200 g), such as at or about 693 g, as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured). In some embodiments, at least a portion of the contacting, incubating, and/or engineering of the cells, e.g., cells from an stimulated composition of enriched CD4+ T cell or enriched CD8+ T cells, with the virus is performed with a rotation of between about 100 g and 3200 g, 1000 g and 2000 g, 1000 g and 3200 g, 500 g and 1000 g, 400 g and 1200 g, 600 g and 800 g, 600 and 700 g, or 500 g and 700 g. In some embodiments, the rotation is between 600 g and 700 g, e.g., at or about 693 g.

In certain embodiments, at least a portion of the engineering, transduction, and/or transfection is performed with rotation, e.g., spinoculation and/or centrifugation. In some embodiments, the rotation is performed for, for about, or for at least or about 5 minutes, 10 minutes, 15 minutes, 30 minutes, 60 minutes, 90 minutes, 1 hour, 2 hours, 3 hours, 4 hours, 6 hours, 8 hours, 12 hours, 24 hours, 48 hours, 72 hours, 2 days, 3 days, 4 days, 5 days, 6 days, or for at least 7 days. In some embodiments, the rotation is performed for or for about 60 minutes. In certain embodiments, the rotation is performed for about 30 minutes. In some embodiments, the rotation performed for about 30 minutes at between 600 g and 700 g, e.g., at or about 693 g.

In certain embodiments, the number of viable cells to be engineered, transduced, and/or transfected ranges from about $5\times10^6$ cells to about $100\times10^7$ cells, such as from about $10\times10^6$ cells to about $100\times10^6$ cells, from about $100\times10^6$ cells to about $200\times10^6$ cells, from about $200\times10^6$ cells to about $300\times10^6$ cells, from about $300\times10^6$ cells to about $400\times10^6$ cells, from about $400\times10^6$ cells to about $500\times10^6$ cells, or from about $500\times10^6$ cells to about $100\times10^7$ cells. In particular examples, the number of viable cells to be engineered, transduced, and/or transfected is about or less than about $300\times10^6$ cells.

In certain embodiments, at least a portion of the engineering, transduction, and/or transfection is conducted at a volume (e.g., the spinoculation volume) from about 5 mL to about 100 mL, such as from about 10 mL to about 50 mL, from about 15 mL to about 45 mL, from about 20 mL to about 40 mL, from about 25 mL to about 35 mL, or at or at about 30 mL. In certain embodiments, the cell pellet volume after spinoculation ranges from about 1 mL to about 25 mL, such as from about 5 mL to about 20 mL, from about 5 mL to about 15 mL, from about 5 mL to about 10 mL, or at or at about 10 mL.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications. In certain embodiments, the gene transfer is accomplished by first incubating the cells under stimulating conditions, such as by any of the methods described in Section I-B.

In some embodiments, methods for genetic engineering are carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells and composition containing viral vector particles, and optionally air, can be combined or mixed prior to providing the compositions to the cavity. In some embodiments, the composition containing cells and composition containing viral vector particles, and optionally air, are provided separately and combined and mixed in the cavity. In some embodiments, a composition containing cells, a composition containing viral vector particles, and optionally air, can be provided to the internal cavity in any order. In any of such some embodiments, a composition containing cells and viral vector particles is the input composition once combined or mixed together, whether such is combined or mixed inside or outside the centrifugal chamber and/or whether cells and viral vector particles are provided to the centrifugal chamber together or separately, such as simultaneously or sequentially.

In some embodiments, intake of a volume of gas, such as air, occurs prior to the incubating the cells and viral vector particles, such as rotation, in the transduction method. In some embodiments, intake of the volume of gas, such as air, occurs during the incubation of the cells and viral vector particles, such as rotation, in the transduction method.

In some embodiments, the liquid volume of the cells or viral vector particles that make up the transduction composition, and optionally the volume of air, can be a predetermined volume. The volume can be a volume that is programmed into and/or controlled by circuitry associated with the system.

In some embodiments, intake of the transduction composition, and optionally gas, such as air, is controlled manually, semi-automatically and/or automatically until a desired or predetermined volume has been taken into the internal cavity of the chamber. In some embodiments, a sensor associated with the system can detect liquid and/or gas flowing to and from the centrifuge chamber, such as via its color, flow rate and/or density, and can communicate with associated circuitry to stop or continue the intake as necessary until intake of such desired or predetermined volume has been achieved. In some aspects, a sensor that is programmed or able only to detect liquid in the system, but not gas (e.g. air), can be made able to permit passage of gas, such as air, into the system without stopping intake. In some such embodiments, a non-clear piece of tubing can be placed in the line near the sensor while intake of gas, such as air, is desired. In some embodiments, intake of gas, such as air, can be controlled manually.

In aspects of the provided methods, the internal cavity of the centrifuge chamber is subjected to high speed rotation. In some embodiments, rotation is effected prior to, simultaneously, subsequently or intermittently with intake of the liquid input composition, and optionally air. In some embodiments, rotation is effected subsequent to intake of the liquid input composition, and optionally air. In some embodiments, rotation is by centrifugation of the centrifugal chamber at a relative centrifugal force at the inner surface of side wall of the internal cavity and/or at a surface layer of the cells of at or about or at least at or about 800 g, 1000 g, 1100 g, 1500, 1600 g, 1800 g, 2000 g, 2200 g, 2500 g, 3000 g, 3500 g or 4000 g. In some embodiments, rotation is by centrifugation at a force that is greater than or about 1100 g, such as by greater than or about 1200 g, greater than or about 1400 g, greater than or about 1600 g, greater than or about 1800 g, greater than or about 2000 g, greater than or about 2400 g, greater than or about 2800 g, greater than or about 3000 g or greater than or about 3200 g. In some embodiments, rotation is by centrifugation at a force that is or is about 1600 g.

In some embodiments, the method of transduction includes rotation or centrifugation of the transduction composition, and optionally air, in the centrifugal chamber for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes. In some embodiments, the transduction composition, and optionally air, is rotated or centrifuged in the centrifugal chamber for greater than 5 minutes, but for no more than 60 minutes, no more than 45 minutes, no more than 30 minutes or no more than 15 minutes. In particular embodiments, the transduction includes rotation or centrifugation for or for about 60 minutes.

In some embodiments, the method of transduction includes rotation or centrifugation of the transduction composition, and optionally air, in the centrifugal chamber for between or between about 10 minutes and 60 minutes, 15 minutes and 60 minutes, 15 minutes and 45 minutes, 30 minutes and 60 minutes or 45 minutes and 60 minutes, each inclusive, and at a force at the internal surface of the side wall of the internal cavity and/or at a surface layer of the cells of at least or greater than or about 1000 g, 1100 g, 1200 g, 1400 g, 1500 g, 1600 g, 1800 g, 2000 g, 2200 g, 2400 g, 2800 g, 3200 g or 3600 g. In particular embodiments, the method of transduction includes rotation or centrifugation of the transduction composition, e.g., the cells and the viral vector particles, at or at about 1600 g for or for about 60 minutes.

In some embodiments, the gas, such as air, in the cavity of the chamber is expelled from the chamber. In some embodiments, the gas, such as air, is expelled to a container that is operably linked as part of the closed system with the centrifugal chamber. In some embodiments, the container is a free or empty container. In some embodiments, the air, such as gas, in the cavity of the chamber is expelled through a filter that is operably connected to the internal cavity of the chamber via a sterile tubing line. In some embodiments, the air is expelled using manual, semi-automatic or automatic processes. In some embodiments, air is expelled from the chamber prior to, simultaneously, intermittently or subsequently with expressing the output composition containing incubated cells and viral vector particles, such as cells in which transduction has been initiated or cells have been transduced with a viral vector, from the cavity of the chamber.

In some embodiments, the transduction and/or other incubation is performed as or as part of a continuous or semi-continuous process. In some embodiments, a continuous process involves the continuous intake of the cells and viral vector particles, e.g., the transduction composition (either as a single pre-existing composition or by continuously pulling into the same vessel, e.g., cavity, and thereby mixing, its parts), and/or the continuous expression or expulsion of liquid, and optionally expelling of gas (e.g. air), from the vessel, during at least a portion of the incubation, e.g., while centrifuging. In some embodiments, the continuous intake and continuous expression are carried out at least in part simultaneously. In some embodiments, the continuous intake occurs during part of the incubation, e.g., during part of the centrifugation, and the continuous expression occurs during a separate part of the incubation. The two may alternate. Thus, the continuous intake and expression, while carrying out the incubation, can allow for a greater overall volume of sample to be processed, e.g., transduced.

In some embodiments, the incubation is part of a continuous process, the method including, during at least a portion of the incubation, effecting continuous intake of said transduction composition into the cavity during rotation of the chamber and during a portion of the incubation, effecting continuous expression of liquid and, optionally expelling of gas (e.g. air), from the cavity through the at least one opening during rotation of the chamber.

In some embodiments, the semi-continuous incubation is carried out by alternating between effecting intake of the composition into the cavity, incubation, expression of liquid from the cavity and, optionally expelling of gas (e.g. air) from the cavity, such as to an output container, and then intake of a subsequent (e.g., second, third, etc.) composition containing more cells and other reagents for processing, e.g., viral vector particles, and repeating the process. For example, in some embodiments, the incubation is part of a semi-continuous process, the method including, prior to the incubation, effecting intake of the transduction composition into the cavity through said at least one opening, and subsequent to the incubation, effecting expression of fluid from the cavity; effecting intake of another transduction composition comprising cells and the viral vector particles into said internal cavity; and incubating the another transduction composition in said internal cavity under conditions whereby said cells in said another transduction composition are transduced with said vector. The process may be continued in an iterative fashion for a number of additional rounds. In this respect, the semi-continuous or continuous methods may permit production of even greater volume and/or number of cells.

In some embodiments, a portion of the transduction incubation is performed in the centrifugal chamber, which is performed under conditions that include rotation or centrifugation.

In some embodiments, the method includes an incubation in which a further portion of the incubation of the cells and viral vector particles is carried out without rotation or centrifugation, which generally is carried out subsequent to the at least portion of the incubation that includes rotation or centrifugation of the chamber. In certain embodiments, the incubation of the cells and viral vector particles is carried out without rotation or centrifugation for at least 1 hour, 6 hours, 12 hours, 24 hours, 32 hours, 48 hours, 60 hours, 72 hours, 90 hours, 96 hours, 3 days, 4 days, 5 days, or greater than 5 days. In certain embodiments, the incubation is carried out for or for about 72 hours.

In some such embodiments, the further incubation is effected under conditions to result in integration of the viral vector into a host genome of one or more of the cells. It is within the level of a skilled artisan to assess or determine if the incubation has resulted in integration of viral vector particles into a host genome, and hence to empirically determine the conditions for a further incubation. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In some embodiments, the composition containing cells, the vector, e.g., viral particles, and reagent can be rotated, generally at relatively low force or speed, such as speed lower than that used to pellet the cells, such as from 600 rpm to 1700 rpm or from about 600 rpm to about 1700 rpm (e.g. at or about or at least 600 rpm, 1000 rpm, or 1500 rpm or 1700 rpm). In some embodiments, the rotation is carried at a force, e.g., a relative centrifugal force, of from 100 g to 3200 g or from about 100 g to about 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, during at least a part of the genetic engineering, e.g. transduction, and/or subsequent to the genetic engineering the cells are transferred to the bioreactor bag assembly for culture of the genetically engineered cells, such as for cultivation or expansion of the cells, as described above.

In certain embodiments, a composition of enriched T cells in engineered, e.g., transduced or transfected, in the presence of a transduction adjuvant. In some embodiments, a composition of enriched T cells is engineered in the presence of one or more polycations. In some embodiments, a composition of enriched T cells is transduced, e.g., incubated with a viral vector particle, in the presence of one or more transduction adjuvants. In particular embodiments, a composition of enriched T cells is transfected, e.g., incubated with a non-viral vector, in the presence of one or more transduction adjuvants. In certain embodiments, the presence of one or more transduction adjuvants increases the efficiency of gene delivery, such as by increasing the amount, portion, and/or percentage of cells of the composition that are engineered (e.g., transduced or transfected). In certain embodiments, the presence of one or more transduction adjuvants increases the efficiency of transfection. In certain embodiments, the presence of one or more transduction adjuvants increases the efficiency of transduction. In particular embodiments, at least 25%, at least 30%, at least 40%, at least 50%, at least 60%, at least 70% at least 75%, at least 80%, at least 85%, at least 90%, at least 95%, or at least 99% of the cells that are engineered in the presence of a polycation contain or express the recombinant polynucleotide. In some embodiments, at least 10%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-Fold, at least 50-fold, or at least 100-fold more cells of a composition are engineered to contain or express the recombinant transduction adjuvants in the presence of a polycation as compared to an alternative and/or exemplary method of engineering cells without the presence of a transduction adjuvant.

In some embodiments, the composition of enriched cells are engineered in the presence of less than 100 μg/ml, less than 90 μg/ml, less than 80 μg/ml, less than 75 μg/ml, less than 70 μg/ml, less than 60 μg/ml, less than 50 μg/ml, less than 40 μg/ml, less than 30 μg/ml, less than 25 μg/ml, less than 20 μg/ml, or less than μg/ml, less than 10 μg/ml of a transduction adjuvant. In certain embodiments, transduction adjuvants suitable for use with the provided methods include, but are not limited to polycations, fibronectin or fibronectin-derived fragments or variants, RetroNectin, and combinations thereof.

In some embodiments, the cells are engineered in the presence of a cytokine, e.g., a recombinant human cytokine, at a concentration of between 1 IU/ml and 1,000 IU/ml, between 10 IU/ml and 50 IU/ml, between 50 IU/ml and 100 IU/ml, between 100 IU/ml and 200 IU/ml, between 100 IU/ml and 500 IU/ml, between 250 IU/ml and 500 IU/ml, or between 500 IU/ml and 1,000 IU/ml.

In some embodiments, a composition of enriched T cells is engineered in the presence of IL-2, e.g., human recombinant IL-2, at a concentration between 1 IU/ml and 200 IU/ml, between 10 IU/ml and 100 IU/ml, between 50 IU/ml and 150 IU/ml, between 80 IU/ml and 120 IU/ml, between 60 IU/ml and 90 IU/ml, or between 70 IU/ml and 90 IU/ml. In particular embodiments, the composition of enriched T cells is engineered in the presence of recombinant IL-2 at a concentration at or at about 50 IU/ml, 55 IU/ml, 60 IU/ml, 65 IU/ml, 70 IU/ml, 75 IU/ml, 80 IU/ml, 85 IU/ml, 90 IU/ml, 95 IU/ml, 100 IU/ml, 110 IU/ml, 120 IU/ml, 130 IU/ml, 140 IU/ml, or 150 IU/ml. In some embodiments, the composition of enriched T cells is engineered in the presence of or of about 85 IU/ml. In some embodiments, the population of T cells is a population of CD4+ T cells. In particular embodiments, the composition of enriched T cells is enriched for CD4+ T cells, where CD8+ T cells are not enriched for and/or where CD8+ T cells are negatively selected for or depleted from the composition. In particular embodiments, the composition of enriched T cells is a composition of enriched CD8+ T cells. In particular embodiments, the composition of enriched T cells is enriched for CD8+ T cells, where CD4+ T cells are not enriched for and/or where CD4+ T cells are negatively selected for or depleted from the composition.

In some embodiments, a composition of enriched T cells is engineered in the presence of recombinant IL-7, e.g., human recombinant IL-7, at a concentration between 100 IU/ml and 2,000 IU/ml, between 500 IU/ml and 1,000 IU/ml, between 100 IU/ml and 500 IU/ml, between 500 IU/ml and 750 IU/ml, between 750 IU/ml and 1,000 IU/ml, or between 550 IU/ml and 650 IU/ml. In particular embodiments, the composition of enriched T cells is engineered in the presence of IL-7 at a concentration at or at about 50 IU/ml, 100 IU/ml, 150 IU/ml, 200 IU/ml, 250 IU/ml, 300 IU/ml, 350 IU/ml, 400 IU/ml, 450 IU/ml, 500 IU/ml, 550 IU/ml, 600 IU/ml, 650 IU/ml, 700 IU/ml, 750 IU/ml, 800 IU/ml, 750 IU/ml, 750 IU/ml, 750 IU/ml, or 1,000 IU/ml. In particular embodiments, the composition of enriched T cells is engineered in the presence of or of about 600 IU/ml of IL-7. In some embodiments, the composition engineered in the presence of recombinant IL-7 is enriched for a population of T cells, e.g., CD4+ T cells. In particular embodiments, the composition of enriched T cells is enriched for CD4+ T cells, where CD8+ T cells are not enriched for and/or where CD8+ T cells are negatively selected for or depleted from the composition.

In some embodiments, a composition of enriched T cells is engineered in the presence of recombinant IL-15, e.g., human recombinant IL-15, at a concentration between 0.1 IU/ml and 100 IU/ml, between 1 IU/ml and 50 IU/ml, between 5 IU/ml and 25 IU/ml, between 25 IU/ml and 50 IU/ml, between 5 IU/ml and 15 IU/ml, or between 10 IU/ml and 100 IU/ml. In particular embodiments, the composition of enriched T cells is engineered in the presence of IL-15 at a concentration at or at about 1 IU/ml, 2 IU/ml, 3 IU/ml, 4 IU/ml, 5 IU/ml, 6 IU/ml, 7 IU/ml, 8 IU/ml, 9 IU/ml, 10 IU/ml, 11 IU/ml, 12 IU/ml, 13 IU/ml, 14 IU/ml, 15 IU/ml, 20 IU/ml, 25 IU/ml, 30 IU/ml, 40 IU/ml, or 50 IU/ml. In some embodiments, the composition of enriched T cells is engineered in or in about 10 IU/ml of IL-15. In some embodiments, the composition of enriched T cells is incubated in or in about 10 IU/ml of recombinant IL-15. In some embodiments, the composition engineered in the presence of recombinant IL-15 is enriched for a population of T cells, e.g., CD4+ T cells and/or CD8+ T cells. In some embodiments, the composition of enriched T cells is a composition of enriched CD8+ T cells. In particular embodiments, the composition of enriched T cells is enriched for CD8+ T cells, where CD4+ T cells are not enriched for and/or where CD4+ T cells are negatively selected for or depleted from the composition. In some embodiments, the composition of enriched T cells is a composition of enriched CD4+ T cells. In particular embodiments, the composition of enriched T cells is enriched for CD4+ T cells, where CD8+ T cells are not enriched for and/or where CD8+ T cells are negatively selected for or depleted from the composition.

In particular embodiments, a composition of enriched CD8+ T cells is engineered in the presence of IL-2 and/or IL-15. In certain embodiments, a composition of enriched CD4+ T cells is engineered in the presence of IL-2, IL-7, and/or IL-15. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15.

In particular embodiments, the cells are engineered in the presence of one or more antioxidants. In some embodiments, antioxidants include, but are not limited to, one or more antioxidants comprise a tocopherol, a tocotrienol, alpha-tocopherol, beta-tocopherol, gamma-tocopherol, delta-tocopherol, alpha-tocotrienol, beta-tocotrienol, alpha-tocopherolquinone, Trolox (6-hydroxy-2,5,7,8-tetramethylchroman-2-carboxylic acid), butylated hydroxyanisole (BHA), butylated hydroxytoluene (BHT), a flavonoids, an isoflavone, lycopene, beta-carotene, selenium, ubiquinone, luetin, S-adenosylmethionine, glutathione, taurine, N-acetyl cysteine (NAC), citric acid, L-carnitine, BHT, monothioglycerol, ascorbic acid, propyl gallate, methionine, cysteine, homocysteine, gluthatione, cystamine and cysstathionine, and/or glycine-glycine-histidine.

In some embodiments, the one or more antioxidants is or includes a sulfur containing oxidant. In certain embodiments, a sulfur containing antioxidant may include thiol-containing antioxidants and/or antioxidants which exhibit one or more sulfur moieties, e.g., within a ring structure. In some embodiments, the sulfur containing antioxidants may include, for example, N-acetylcysteine (NAC) and 2,3-dimercaptopropanol (DMP), L-2-oxo-4-thiazolidinecarboxylate (OTC) and lipoic acid. In particular embodiments, the sulfur containing antioxidant is a glutathione precursor. In some embodiments, the glutathione precursor is a molecule which may be modified in one or more steps within a cell to derived glutathione. In particular embodiments, a glutathione precursor may include, but is not limited to N-acetyl cysteine (NAC), L-2-oxothiazolidine-4-carboxylic acid (Procysteine), lipoic acid, S-allyl cysteine, or methylmethionine sulfonium chloride.

In some embodiments, the cells are engineered in the presence of one or more antioxidants. In some embodiments, the cells are engineered in the presence of between 1 ng/ml and 100 ng/ml, between 10 ng/ml and 1 µg/ml, between 100 ng/ml and 10 µg/ml, between 1 µg/ml and 100 µg/ml, between 10 µg/ml and 1 mg/ml, between 100 µg/ml and 1 mg/ml, between 1 500 µg/ml and 2 mg/ml, 500 µg/ml and 5 mg/ml, between 1 mg/ml and 10 mg/ml, or between 1 mg/ml and 100 mg/ml of the one or more antioxidants. In some embodiments, the cells are engineered in the presence of or of about 1 ng/ml, 10 ng/ml, 100 ng/ml, 1 µg/ml, 10 µg/ml, 100 µg/ml, 0.2 mg/ml, 0.4 mg/ml, 0.6 mg/ml, 0.8 mg/ml, 1 mg/ml, 2 mg/ml, 3 mg/ml, 4 mg/ml, 5 mg/ml, 10 mg/ml, 20 mg/ml, 25 mg/ml, 50 mg/ml, 100 mg/ml, 200 mg/ml, 300 mg/ml, 400 mg/ml, 500 mg/ml of the one or more antioxidant. In some embodiments, the one or more antioxidants is or includes a sulfur containing antioxidant. In particular embodiments, the one or more antioxidants is or includes a glutathione precursor.

In some embodiments, the cells are engineered in the presence of NAC. In some embodiments, the cells are engineered in the presence of between 1 ng/ml and 100 ng/ml, between 10 ng/ml and 1 µg/ml, between 100 ng/ml and 10 µg/ml, between 1 µg/ml and 100 µg/ml, between 10 µg/ml and 1 mg/ml, between 100 µg/ml and 1 mg/ml, between 1,500 µg/ml and 2 mg/ml, 500 µg/ml and 5 mg/ml, between 1 mg/ml and 10 mg/ml, or between 1 mg/ml and 100 mg/ml of NAC. In some embodiments, the cells are engineered in the presence of or of about 1 ng/ml, 10 ng/ml, 100 ng/ml, 1 µg/ml, 10 µg/ml, 100 µg/ml, 0.2 mg/ml, 0.4 mg/ml, 0.6 mg/ml, 0.8 mg/ml, 1 mg/ml, 2 mg/ml, 3 mg/ml, 4 mg/ml, 5 mg/ml, 10 mg/ml, 20 mg/ml, 25 mg/ml, 50 mg/ml, 100 mg/ml, 200 mg/ml, 300 mg/ml, 400 mg/ml, 500 mg/ml of NAC. In some embodiments, the cells are engineered with or with about 0.8 mg/ml.

In some embodiments, a composition of enriched T cells, such as stimulated T cells, e.g. stimulated CD4+ T cells or stimulated CD8+ T cells, is engineered in the presence of one or more polycations. In some embodiments, a composition of enriched T cells, such as stimulated T cells, e.g. stimulated CD4+ T cells or stimulated CD8+ T cells, is transduced, e.g., incubated with a viral vector particle, in the presence of one or more polycations. In particular embodiments, a composition of enriched T cells, such as stimulated T cells, e.g. stimulated CD4+ T cells or stimulated CD8+ T cells, is transfected, e.g., incubated with a non-viral vector, in the presence of one or more polycations. In certain embodiments, the presence of one or more polycations increases the efficiency of gene delivery, such as by increasing the amount, portion, and/or percentage of cells of the composition that are engineered (e.g., transduced or transfected). In certain embodiments, the presence of one or more polycations increases the efficiency of transfection. In certain embodiments, the presence of one or more polycations increases the efficiency of transduction. In particular embodiments, at least 25%, at least 30%, at least 40%, at least 50%, at least 60%, at least 70% at least 75%, at least 80%, at least 85%, at least 90%, at least 95%, or at least 99% of the cells that are engineered in the presence of a polycation contain or express the recombinant polynucleotide. In some embodiments, at least 10%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-Fold, at least 50-fold, or at least 100-fold more cells of a composition are engineered to contain or express the recombinant polynucleotide in the presence of a polycation as compared to an alternative and/or exemplary method of engineering cells without the presence of a polycation.

In certain embodiments, the composition of enriched cells, e.g., the composition of enriched CD4+ T cells or enriched CD8+ T cells, such as stimulated T cells thereof, is engineered in the presence of a low concentration or amount of a polycation, e.g., relative to an exemplary and/or alternative method of engineering cells in the presence of a polycation. In certain embodiments, the composition of enriched cells, such as stimulated T cells, e.g. stimulated CD4+ T cells or stimulated CD8+ T cells, is engineered in the presence of less than 90%, less than 80%, less than 75%, less than 70%, less than 60%, less than 50%, less than 40%, less than 30%, less than 25%, less than 20%, less than 10%, less than 5%, less than 1%, less than 0.1%, of less than 0.01% of the amount and/or concentration of the polycation of an exemplary and/or alternative process for engineering cells. In some embodiments, the composition of enriched cells, such as stimulated T cells, e.g. stimulated CD4+ T cells or stimulated CD8+ T cells, are engineered in the presence of less than 100 µg/ml, less than 90 µg/ml, less than 80 µg/ml, less than 75 µg/ml, less than 70 µg/ml, less than 60 µg/ml, less than 50 µg/ml, less than 40 µg/ml, less than 30 µg/ml, less than 25 µg/ml, less than 20 µg/ml, or less than 10 µg/ml of the polycation. In particular embodiments, the composition of enriched cells, such as stimulated T cells, e.g. stimulated CD4+ T cells or stimulated CD8+ T cells, is engineered in the presence of or of about 1 µg/ml, 5 µg/ml, 10 µg/ml, 15 µg/ml, 20 µg/ml, 25 µg/ml, 30 µg/ml, 35 µg/ml, 40 µg/ml, 45 µg/ml, or 50 µg/ml, of the polycation.

In particular embodiments, engineering the composition of enriched cells, such as stimulated T cells, e.g. stimulated CD4+ T cells or stimulated CD8+ T cells, in the presence of a polycation reduces the amount of cell death, e.g., by necrosis, programmed cell death, or apoptosis. In some embodiments, the composition of enriched T cells, such as stimulated T cells, e.g. stimulated CD4+ T cells or stimulated CD8+ T cells, is engineered in the presence of a low amount of a polycation, e.g., less than 100 µg/ml, 50 µg/ml, or 10 µg/ml, and at least 50%, at least 60%, at least 70%, at least 75%, at least 80%, at least 85%, at least 90%, at least 95%, at least 99%, or at least 99.9% of the cells survive, e.g., do not undergo necrosis, programmed cell death, or apoptosis, during or at least 1 day, 2 days, 3 days, 4 days, 5 days, 6 days, 7 days, or more than 7 days after the engineering step is complete. In some embodiments, the composition is engineered in the presence of a low concentration or amount of polycation as compared to the alternative and/or exemplary method of engineering cells in the presence of higher amount or concentration of polycation, e.g., more than 50 µg/ml, 100 µg/ml, 500 µg/ml, or 1,000 µg/ml, and the cells of the composition have at least 10%, at least 20%, at least 30%, at least 40%, at least 50%, at least 60%, at least 70%, at least 80%, at least 90%, at least 95%, at least 100%, at least 150%, at least 1-fold, at least 2-fold, at least 3-fold, at least 4-fold, at least 5-fold, at least 10-fold, at least 25-Fold, at least 50-fold, or at least 100-fold greater survival as compared to cells undergoing the exemplary and/or alternative process.

In some embodiments, the polycation is positively-charged. In certain embodiments, the polycation reduces repulsion forces between cells and vectors, e.g., viral or non-viral vectors, and mediates contact and/or binding of the vector to the cell surface. In some embodiments, the polycation is polybrene, DEAE-dextran, protamine sulfate, poly-L-lysine, or cationic liposomes.

In particular embodiments, the polycation is protamine sulfate. In some embodiments, the composition of enriched T cells, such as stimulated T cells, e.g. stimulated CD4+ T cells or stimulated CD8+ T cells, are engineered in the presence of less than or about 500 µg/ml, less than or about 400 µg/ml, less than or about 300 µg/ml, less than or about 200 µg/ml, less than or about 150 µg/ml, less than or about 100 µg/ml, less than or about 90 µg/ml, less than or about 80 µg/ml, less than or about 75 µg/ml, less than or about 70 µg/ml, less than or about 60 µg/ml, less than or about 50 µg/ml, less than or about 40 µg/ml, less than or about 30 µg/ml, less than or about 25 µg/ml, less than or about 20 µg/ml, or less than or about 15 µg/ml, or less than or about 10 µg/ml of protamine sulfate. In particular embodiments, the composition of enriched cells, such as stimulated T cells, e.g. stimulated CD4+ T cells or stimulated CD8+ T cells, is engineered in the presence of or of about 1 µg/ml, 5 µg/ml, 10 µg/ml, 15 µg/ml, 20 µg/ml, 25 µg/ml, 30 µg/ml, 35 µg/ml, 40 µg/ml, 45 µg/ml, 50 µg/ml, 55 µg/ml, 60 µg/ml, 75 µg/ml, 80 µg/ml, 85 µg/ml, 90 µg/ml, 95 µg/ml, 100 µg/ml, 105 µg/ml, 110 µg/ml, 115 µg/ml, 120 µg/ml, 125 µg/ml, 130 µg/ml, 135 µg/ml, 140 µg/ml, 145 µg/ml, or 150 µg/ml of protamine sulfate.

In some embodiments, the engineered composition of enriched CD4+ T cells, such as stimulated T cells, e.g. stimulated CD4+ T cells, includes at least 40, at least 60%, at least 65%, at least 70%, at least 75%, at least 80%, at least 85%, at least 90%, at least 95%, at least 98%, at least 99%, at least 99.5%, at least 99.9%, or at or about 100% CD4+ T cells. In certain embodiments, the composition of enriched CD4+ T cells, such as stimulated T cells, e.g. stimulated CD4+ T cells, that is engineered includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells, such as stimulated T cells, e.g. stimulated CD8+ T cells, that is engineered includes at least 60%, at least 65%, at least 70%, at least 75%, at least 80%, at least 85%, at least 90%, at least 95%, at least 98%, at least 99%, at least 99.5%, at least 99.9%, or at or about 100% CD8+ T cells. In certain embodiments, the composition of enriched CD8+ T cells, such as stimulated T cells, e.g. stimulated CD8+ T cells, that is engineered includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, engineering the cells includes a culturing, contacting, or incubation with the vector, e.g., the viral vector of the non-viral vector. In certain embodiments, the engineering includes culturing, contacting, and/or incubating the cells with the vector is performed for, for about, or for at least 4 hours, 6 hours, 8 hours, 12 hours, 16 hours, 18 hours, 24 hours, 30 hours, 36 hours, 40 hours, 48 hours, 54 hours, 60 hours, 72 hours, 84 hours, 1 day, 2 days, 3 days, 4 days, 5 days, 6 days, or 7 days, or more than 7 days. In particular embodiments, the engineering includes culturing, contacting, and/or incubating the cells with the vector for or for about 24 hours, 36 hours, 48 hours, 60 hours, 72 hours, or 84 hours, or for or for about 2 days, 3 days, 4 days, or 5 days. In some embodiments, the engineering step is performed for or for about 24 hours, 36 hours, 48 hours, 60 hours, 72 hours, or 84 hours. In certain embodiments, the engineering is performed for about 60 hours or about 84 hours, for or for about 72 hours, or for or for about 2 days.

In some embodiments, the engineering is performed at a temperature from about 25 to about 38° C., such as from about 30 to about 37° C., from about 36 to about 38° C., or at or about 37° C.±2° C. In some embodiments, the composition of enriched T cells is engineered at a $CO_2$ level from about 2.5% to about 7.5%, such as from about 4% to about 6%, for example at or about 5%±0.5%. In some embodiments, the composition of enriched T cells is engineered at a temperature of or about 37° C. and/or at a $CO_2$ level of or about 5%.

In some embodiments, the cells, e.g., the CD4+ and/or the CD8+ T cells, are cultivated, after one or more steps are performed for genetic engineering, e.g., transducing or transfection the cells to contain a polynucleotide encoding a recombinant receptor. In some embodiments, the cultivation may include culture, incubation, stimulation, activation, expansion, and/or propagation. In some such embodiments, the further cultivation is effected under conditions to result in integration of the viral vector into a host genome of one or more of the cells. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, the further incubation is carried out at temperatures greater than room temperature, such as greater than or greater than about 25° C., such as generally greater than or greater than about 32° C., 35° C. or 37° C. In some embodiments, the further incubation is effected at a temperature of at or about 37° C.±2° C., such as at a temperature of at or about 37° C.

In some embodiments, the further incubation is performed under conditions for stimulation and/or activation of cells, which conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent (e.g. stimulatory and/or accessory agents), e.g., ligand, which is capable of activating an intracellular signaling domain of a TCR complex. In some aspects, the agent turns on or initiates TCR/CD3 intracellular signaling cascade in a T cell, such as agents suitable to deliver a primary signal, e.g., to initiate activation of an ITAM-induced signal, such as those specific for a TCR component, and/or an agent that promotes a costimulatory signal, such as one specific for a T cell costimulatory receptor, e.g., anti-CD3, anti-CD28, or anti-41-BB, for example, optionally bound to solid support such as a bead, and/or one or more cytokines. Among the stimulating agents are anti-CD3/anti-CD28 beads (e.g., DYNABEADS® M-450 CD3/CD28 T Cell Expander, and/or ExpACT® beads). Optionally, the expansion method may further comprise the step of adding anti-CD3 and/or anti-CD28 antibody to the culture medium. In some embodiments, the stimulating agents include IL-2 and/or IL-15, for example, an IL-2 concentration of at least about 10 units/mL.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2 and/or IL-15, for example, an IL-2 concentration of at least about 10 units/mL, at least about 50 units/mL, at least about 100 units/mL or at least about 200 units/mL.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the further incubation is carried out in the same container or apparatus in which the contacting occurred. In some embodiments, the further incubation is carried out without rotation or centrifugation, which generally is carried out subsequent to the at least portion of the incubation done under rotation, e.g. in connection with centrifugation or spinoculation. In some embodiments, the further incubation is carried out outside of a stationary phase, such as outside of a chromatography matrix, for example, in solution.

In some embodiments, the further incubation is carried out in a different container or apparatus from that in which the contacting occurred, such as by transfer, e.g. automatic transfer, of the cell composition into a different container or apparatus subsequent to contacting with the viral particles and reagent.

In some embodiments, the further culturing or incubation, e.g. to facilitate ex vivo expansion, is carried out of for greater than or greater than about 24 hours, 2 days, 3 days, 4 days, 5 days, 6 days, 7 days, 8 days, 9 days, 10 days, 11 days, 12 days, 13 days or 14 days. In some embodiments, the further culturing or incubation is carried out for no more than 6 days, no more than 5 days, no more than 4 days, no more than 3 days, no more than 2 days or no more than 24 hours.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least or about 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the methods provided herein do not include further culturing or incubation, e.g. do not include ex vivo expansion step, or include a substantially shorter ex vivo expansion step.

In some embodiments, the stimulatory reagent is removed and/or separated from the cells prior to the engineering. In particular embodiments, the stimulatory reagent is removed and/or separated from the cells after the engineering. In certain embodiments, the stimulatory agent is removed and/or separated from the cells subsequent to the engineering and prior to cultivating the engineered cells, e.g., under conditions that promote proliferation and/or expansion. In certain embodiments, the stimulatory reagent is a stimulatory reagent that is described in Section I-B-1. In particular embodiments, the stimulatory reagent is removed and/or separated from the cells as described in Section I-B-2.

1. Vectors and Methods

Also provided are one or more polynucleotides (e.g., nucleic acid molecules) encoding recombinant receptors, vectors for genetically engineering cells to express such receptors in accord with provided methods for producing the engineered cells. In some embodiments, the vector contains the nucleic acid encoding the recombinant receptor. In particular embodiments, the vector is a viral vector a non-viral vector. In some cases, the vector is a viral vector, such as a retroviral vector, e.g., a lentiviral vector or a gammaretroviral vector.

In some cases, the nucleic acid sequence encoding the recombinant receptor, e.g., chimeric antigen receptor (CAR) contains a signal sequence that encodes a signal peptide.

Non-limiting exemplary examples of signal peptides include, for example, the GMCSFR alpha chain signal peptide set forth in SEQ ID NO: 61 and encoded by the nucleotide sequence set forth in SEQ ID NO: 60, the CD8 alpha signal peptide set forth in SEQ ID NO: 59, or the CD33 signal peptide set forth in SEQ ID NO:58.

In some embodiments, the vectors include viral vectors, e.g., retroviral or lentiviral, non-viral vectors or transposons, e.g. Sleeping Beauty transposon system, vectors derived from simian virus 40 (SV40), adenoviruses, adeno-associated virus (AAV), lentiviral vectors or retroviral vectors, such as gamma-retroviral vectors, retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV) or adeno-associated virus (AAV).

In some embodiments, the viral vector or the non-viral DNA contains a nucleic acid that encodes a heterologous recombinant protein. In some embodiments, the heterologous recombinant molecule is or includes a recombinant receptor, e.g., an antigen receptor, SB-transposons, e.g., for gene silencing, capsid-enclosed transposons, homologous double stranded nucleic acid, e.g., for genomic recombination or reporter genes (e.g., fluorescent proteins, such as GFP) or luciferase).

a. Viral Vector Particles

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) Blood. 101: 1637-1644; Verhoeyen et al. (2009) *Methods Mol Biol.* 506: 97-114; and Cavalieri et al. (2003) Blood. 102(2): 497-505.

In some embodiments, the viral vector particles contain a genome derived from a retroviral genome based vector, such as derived from a lentiviral genome based vector. In some aspects of the provided viral vectors, the heterologous nucleic acid encoding a recombinant receptor, such as an antigen receptor, such as a CAR, is contained and/or located between the 5' LTR and 3' LTR sequences of the vector genome.

In some embodiments, the viral vector genome is a lentivirus genome, such as an HIV-1 genome or an SIV genome. For example, lentiviral vectors have been generated by multiply attenuating virulence genes, for example, the genes env, vif, vpu and nef can be deleted, making the vector safer for therapeutic purposes. Lentiviral vectors are known. See Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, the viral genome vector can contain sequences of the 5' and 3' LTRs of a retrovirus, such as a lentivirus. In some aspects, the viral genome construct may contain sequences from the 5' and 3' LTRs of a lentivirus, and in particular can contain the R and U5 sequences from the 5' LTR of a lentivirus and an inactivated or self-inactivating 3' LTR from a lentivirus. The LTR sequences can be LTR sequences from any lentivirus from any species. For example, they may be LTR sequences from HIV, SIV, FIV or BIV. Typically, the LTR sequences are HIV LTR sequences.

In some embodiments, the nucleic acid of a viral vector, such as an HIV viral vector, lacks additional transcriptional units. The vector genome can contain an inactivated or self-inactivating 3' LTR (Zufferey et al. *J Virol* 72: 9873, 1998; Miyoshi et al., *J Virol* 72:8150, 1998). For example, deletion in the U3 region of the 3' LTR of the nucleic acid used to produce the viral vector RNA can be used to generate self-inactivating (SIN) vectors. This deletion can then be transferred to the 5' LTR of the proviral DNA during reverse transcription. A self-inactivating vector generally has a deletion of the enhancer and promoter sequences from the 3' long terminal repeat (LTR), which is copied over into the 5' LTR during vector integration. In some embodiments enough sequence can be eliminated, including the removal of a TATA box, to abolish the transcriptional activity of the LTR. This can prevent production of full-length vector RNA in transduced cells. In some aspects, the U3 element of the 3' LTR contains a deletion of its enhancer sequence, the TATA box, Sp1, and NF-kappa B sites. As a result of the self-inactivating 3' LTR, the provirus that is generated following entry and reverse transcription contains an inactivated 5' LTR. This can improve safety by reducing the risk of mobilization of the vector genome and the influence of the LTR on nearby cellular promoters. The self-inactivating 3' LTR can be constructed by any method known in the art. In some embodiments, this does not affect vector titers or the in vitro or in vivo properties of the vector.

Optionally, the U3 sequence from the lentiviral 5' LTR can be replaced with a promoter sequence in the viral construct, such as a heterologous promoter sequence. This can increase the titer of virus recovered from the packaging cell line. An enhancer sequence can also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the risk of insertional mutagenesis can be minimized by constructing the retroviral vector genome, such as lentiviral vector genome, to be integration defective. A variety of approaches can be pursued to produce a non-integrating vector genome. In some embodiments, a mutation(s) can be engineered into the integrase enzyme component of the pol gene, such that it encodes a protein with an inactive integrase. In some embodiments, the vector genome itself can be modified to prevent integration by, for example, mutating or deleting one or both attachment sites, or making the 3' LTR-proximal polypurine tract (PPT) non-functional through deletion or modification. In some embodiments, non-genetic approaches are available; these include pharmacological agents that inhibit one or more functions of integrase. The approaches are not mutually exclusive; that is, more than one of them can be used at a time. For example, both the integrase and attachment sites can be non-functional, or the integrase and PPT site can be non-functional, or the attachment sites and PPT site can be non-functional, or all of them can be non-functional. Such methods and viral vector genomes are known and available (see Philpott and Thrasher, *Human Gene Therapy* 18:483, 2007; Engelman et al. *J Virol* 69:2729, 1995; Brown et al *J Virol* 73:9011 (1999); WO 2009/076524; McWilliams et al., *J Virol* 77:11150, 2003; Powell and Levin *J Virol* 70:5288, 1996).

In some embodiments, the vector contains sequences for propagation in a host cell, such as a prokaryotic host cell. In some embodiments, the nucleic acid of the viral vector contains one or more origins of replication for propagation in a prokaryotic cell, such as a bacterial cell. In some embodiments, vectors that include a prokaryotic origin of replication also may contain a gene whose expression confers a detectable or selectable marker such as drug resistance.

The viral vector genome is typically constructed in a plasmid form that can be transfected into a packaging or producer cell line. Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g., vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g., HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g., antigen receptor, such as CAR, can be detected.

In some embodiments, the provided methods involve methods of transducing cells by contacting, e.g., incubating, a cell composition comprising a plurality of cells with a viral particle. In some embodiments, the cells to be transfected or transduced are or comprise primary cells obtained from a subject, such as cells enriched and/or selected from a subject.

In some embodiments, the concentration of cells to be transduced of the composition is from $1.0 \times 10^5$ cells/mL to $1.0 \times 10^8$ cells/mL or from about $1.0 \times 10^5$ cells/mL to about $1.0 \times 10^8$ cells/mL, such as at least or about at least or about $1.0 \times 10^5$ cells/mL, $5 \times 10^5$ cells/mL, $1 \times 10^6$ cells/mL, $5 \times 10^6$ cells/mL, $1 \times 10^7$ cells/mL, $5 \times 10^7$ cells/mL or $1 \times 10^8$ cells/mL.

In some embodiments, the viral particles are provided at a certain ratio of copies of the viral vector particles or infectious units (IU) thereof, per total number of cells to be transduced (IU/cell). For example, in some embodiments, the viral particles are present during the contacting at or about or at least at or about 0.5, 1, 2, 3, 4, 5, 10, 15, 20, 30, 40, 50, or 60 IU of the viral vector particles per one of the cells.

In some embodiments, the titer of viral vector particles is between or between about $1\times10^6$ IU/mL and $1\times10^8$ IU/mL, such as between or between about $5\times10^6$ IU/mL and $5\times10^7$ IU/mL, such as at least $6\times10^6$ IU/mL, $7\times10^6$ IU/mL, $8\times10^6$ IU/mL, $9\times10^6$ IU/mL, $1\times10^7$ IU/mL, $2\times10^7$ IU/mL, $3\times10^7$ IU/mL, $4\times10^7$ IU/mL, or $5\times10^7$ IU/mL.

In some embodiments, transduction can be achieved at a multiplicity of infection (MOI) of less than 100, such as generally less than 60, 50, 40, 30, 20, 10, 5 or less.

In some embodiments, the method involves contacting or incubating, the cells with the viral particles. In some embodiments, the contacting is for 30 minutes to 72 hours, such as 30 minute to 48 hours, 30 minutes to 24 hours or 1 hour to 24 hours, such as at least or about at least or about 30 minutes, 1 hour, 2 hours, 6 hours, 12 hours, 24 hours, 36 hours or more.

In some embodiments, contacting is performed in solution. In some embodiments, the cells and viral particles are contacted in a volume of from 0.5 mL to 500 mL or from about 0.5 mL to about 500 mL, such as from or from about 0.5 mL to 200 mL, 0.5 mL to 100 mL, 0.5 mL to 50 mL, 0.5 mL to 10 mL, 0.5 mL to 5 mL, 5 mL to 500 mL, 5 mL to 200 mL, 5 mL to 100 mL, 5 mL to 50 mL, 5 mL to 10 mL, 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL.

In certain embodiments, the input cells are treated, incubated, or contacted with particles that comprise binding molecules that bind to or recognize the recombinant receptor that is encoded by the viral DNA.

In some embodiments, the incubation of the cells with the viral vector particles results in or produces an output composition comprising cells transduced with the viral vector particles.

b. Non-Viral Vectors

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In embodiments, recombinant nucleic acids are transferred into T cells via transposons. Transposons (transposable elements), are mobile segments of DNA that can move from one locus to another within genomes. These elements move via a conservative, "cut-and-paste" mechanism: the transposase catalyzes the excision of the transposon from its original location and promotes its reintegration elsewhere in the genome. Transposase-deficient elements can be mobilized if the transposase is provided by another transposase gene. Thus, transposons can be utilized to incorporate a foreign DNA into a host genome without the use of a viral transduction system. Examples of transposons suitable for use with mammalian cells, e.g., human primary leukocytes, include but are not limited to Sleeping Beauty and Piggybac.

Transposon-based transfection is a two-component system consisting of a transposase and a transposon. In some embodiments, the system comprises a transposon is engineered to comprise a foreign DNA (also referred herein as cargo DNA), e.g., a gene encoding a recombinant receptor, that is flanked by inverted repeat/direct repeat (IR/DR) sequences that are recognized by an accompanying tranposase. In some embodiments, a non-viral plasmid encodes a transposase under the control of a promoter. Transfection of the plasmid into a host cell results in a transitory expression of the transposase, thus for an initial period following transfection, the transposase is expressed at sufficiently levels to integrate the transposon into the genomic DNA. In some embodiments, the transposase itself is not integrated into the genomic DNA, and therefor expression of the transposase decreases over time. In some embodiments, the transposase expression is expressed by the host cell at levels sufficient to integrate a corresponding transposon for less than about 4 hours, less than about 8 hours, less than about 12 hours, less than about 24 hours, less than about 2 days, less than about 3 days, less than about 4 days, less than about 5 days, less than about 6 days, less than about 7 days, less than about 2 weeks, less than about 3 weeks, less than about 4 weeks, less than about weeks, or less than about 8 weeks. In some embodiments, the cargo DNA that is introduced into the host's genome is not subsequently removed from the host's genome, at least because the host dose not express an endogenous transposase capable of excising the cargo DNA.

Sleeping Beauty (SB) is a synthetic member of the Tc/1-mariner superfamily of transposons, reconstructed from dormant elements harbored in the salmonid fish genome. SB transposon-based transfection is a two-component system consisting of a transposase and a transposon containing inverted repeat/direct repeat (IR/DR) sequences that result in precise integration into a TA dinucleotide. The transposon is designed with an expression cassette of interest flanked by IR/DRs. The SB transposase binds specific binding sites that are located on the IR of the Sleeping beauty transposon. The SB transposase mediates integration of the transposon, a mobile element encoding a cargo sequence flanked on both sides by inverted terminal repeats that harbor binding sites for the catalytic enzyme (SB). Stable expression results when SB inserts gene sequences into vertebrate chromosomes at a TA target dinucleotide through a cut-and-paste mechanism. This system has been used to engineer a variety of vertebrate cell types, including primary human peripheral blood leukocytes. In some embodiments, the cells are contacted, incubated, and/or treated with an SB transposon comprising a cargo gene, e.g., a gene encoding a recombinant receptor or a CAR, flanked by SB IR sequences. In particular embodiments, the cells to be transfected are contacted, incubated, and/or treated with a plasmid comprising an SB transposon comprising a cargo gene, e.g., a gene encoding a CAR, flanked by SB IR sequences. In certain embodiments, the plasmid further comprises a gene encoding an SB transposase that is not flanked by SB IR sequences.

PiggyBac (PB) is another transposon system that can be used to integrate cargo DNA into a host's, e.g., a human's, genomic DNA. The PB transposase recognizes PB transposon-specific inverted terminal repeat sequences (ITRs) located on both ends of the transposon and efficiently moves the contents from the original sites and efficiently integrates them into TTAA chromosomal sites. The PB transposon system enables genes of interest between the two ITRs in the PB vector to be mobilized into target genomes. The PB system has been used to engineer a variety of vertebrate cell types, including primary human cells. In some embodiments, the cells to be transfected are contacted, incubated, and/or treated with an PB transposon comprising a cargo gene, e.g., a gene encoding a CAR, flanked by PB IR sequences. In particular embodiments, the cells to be transfected are contacted, incubated, and/or treated with a plasmid comprising a PB transposon comprising a cargo gene, e.g., a gene encoding a CAR, flanked by PB IR sequences. In certain embodiments, the plasmid further comprises a gene encoding an SB transposase that is not flanked by PB IR sequences.

In some embodiments, the various elements of the transposon/transposase the employed in the subject methods, e.g., SB or PB vector(s), may be produced by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources, e.g., a vector comprising the transposase gene. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g., sequences corresponding to the various elements of the subject vectors, as described above is produced. Where desired, the circular molecules so constructed are then amplified in a prokaryotic host, e.g., *E. coli*. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982-83, New England Biolabs, Inc.; Catalog 1982-83, Bethesda Research Laboratories, Inc. An example of how to construct the vectors employed in the subject methods is provided in the Experimental section, infra. The preparation of a representative Sleeping Beauty transposon system is also disclosed in WO 98/40510 and WO 99/25817).

In some embodiments, transduction with transposons is performed with a plasmid that comprises a transposase gene and a plasmid that comprises a transposon that contains a cargo DNA sequence that is flanked by inverted repeat/direct repeat (IR/DR) sequences that are recognized by the transposase. In certain embodiments, the cargo DNA sequence encodes a heterologous protein, e.g., a recombinant T cell receptor or a CAR. In some embodiments, the plasmid comprises transposase and the transposon. In some embodiments, the transposase is under control of a ubiquitous promoter, or any promoter suitable to drive expression of the transposase in the target cell. Ubiquitous promoters include, but are not limited to, EF1a, CMB, SV40, PGK1, Ubc, human β-actin, CAG, TRE, UAS, Ac5, CaMKIIa, and U6. In some embodiments, the cargo DNA comprises a selection cassette allowing for the selection of cells with stable integration of the cargo DNA into the genomic DNA. Suitable selection cassettes include, but are not limited to, selection cassettes encoding a kanamycin resistance gene, spectinomycin resistance gene, streptomycin resistance gene, ampicillin resistance gene, carbenicillin resistance gene, hygromycin resistance gene, bleomycin resistance gene, erythromycin resistance gene, and polymyxin B resistance gene.

In some embodiments, the components for transduction with a transposon, e.g., plasmids comprising an SB transposase and SB transposon, are introduced into the target cell. Any convenient protocol may be employed, where the protocol may provide for in vitro or in vivo introduction of the system components into the target cell, depending on the location of the target cell. For example, where the target cell is an isolated cell, the system may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

In some embodiments, the SB transposon and the SB transposase source are introduced into a target cell of a multicellular organism, e.g., a mammal or a human, under conditions sufficient for excision of the inverted repeat flanked nucleic acid from the vector carrying the transposon and subsequent integration of the excised nucleic acid into the genome of the target cell. Some embodiments further comprise a step of ensuring that the requisite transposase activity is present in the target cell along with the introduced transposon. Depending on the structure of the transposon vector itself, i.e. whether or not the vector includes a region encoding a product having transposase activity, the method may further include introducing a second vector into the target cell which encodes the requisite transposase activity.

In some embodiments, the amount of vector nucleic acid comprising the transposon and the amount of vector nucleic acid encoding the transposase that is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed, e.g., the particular ex vivo administration protocol that is employed.

Once the vector DNA has entered the target cell in combination with the requisite transposase, the nucleic acid region of the vector that is flanked by inverted repeats, i.e.

the vector nucleic acid positioned between the Sleeping Beauty transposase recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell. In particular embodiments, the vector is integrated into the genomes of at least 1%, at least 2%, at least 3%, at least 4%, at least 5%, at least 6% at least 7% at least 8%, at least 9%, at least 10%, at least 15%, or at least 20% of the cells that are transfected with the SB transposon and/or SB transposase. In some embodiments, integration of the nucleic acid into the target cell genome is stable, i.e., the vector nucleic acid remains present in the target cell genome for more than a transient period of time and is passed on a part of the chromosomal genetic material to the progeny of the target cell.

In certain embodiments, the transposons are used to integrate nucleic acids, i.e. polynucleotides, of various sizes into the target cell genome. In some embodiments, the size of DNA that is inserted into a target cell genome using the subject methods ranges from about 0.1 kb to 200 kb, from about 0.5 kb to 100 kb, from about 1.0 kb to about 8.0 kb, from about 1.0 to about 200 kb, from about 1.0 to about 10 kb, from about 10 kb to about 50 kb, from about 50 kb to about 100 kb, or from about 100 kb to about 200 kb. In some embodiments, the size of DNA that is inserted into a target cell genome using the subject methods ranges from about from about 1.0 kb to about 8.0 kb. In some embodiments, the size of DNA that is inserted into a target cell genome using the subject methods ranges from about 1.0 to about 200 kb. In particular embodiments, the size of DNA that is inserted into a target cell genome using the subject methods ranges from about 1.0 kb to about 8.0 kb.

D. Cultivation and/or Expansion of Cells

In some embodiments, the provided methods include one or more steps for cultivating cells, e.g., cultivating cells under conditions that promote proliferation and/or expansion. In some embodiments, cells are cultivated under conditions that promote proliferation and/or expansion subsequent to a step of genetically engineering, e.g., introducing a recombinant polypeptide to the cells by transduction or transfection. In particular embodiments, the cells are cultivated after the cells have been incubated under stimulating conditions and transduced or transfected with a recombinant polynucleotide, e.g., a polynucleotide encoding a recombinant receptor. In some embodiments, the cultivation produces one or more cultivated compositions of enriched T cells.

In certain embodiments, one or more compositions of enriched T cells, including stimulated and transduced T cells, such as separate compositions of such CD4+ and CD8+ T cells, are cultivated, e.g., under conditions that promote proliferation and/or expansion, prior to formulating the cells. In some aspects, the methods of cultivation, such as for promoting proliferation and/or expansion include methods provided herein, such as in Section I-F. In particular embodiments, one or more compositions of enriched T cells are cultivated after the one or more compositions have been engineered, e.g., transduced or transfected. In particular embodiments, the one or more compositions are engineered compositions. In particular embodiments, the one or more engineered compositions have been previously cryofrozen and stored, and are thawed prior to cultivating.

In certain embodiments, the one or more compositions of engineered T cells are or include two separate compositions of enriched T cells. In particular embodiments, two separate compositions of enriched T cells, e.g., two separate compositions of enriched T cells selected, isolated, and/or enriched from the same biological sample, that are introduced with a recombinant receptor (e.g. CAR), are separately cultivated under conditions that promote proliferation and/or expansion of the cells. In some embodiments, the conditions are stimulating conditions. In certain embodiments, the two separate compositions include a composition of enriched CD4+ T cells, such as engineered CD4+ T cells that were introduced with the nucleic acid encoding the recombinant receptor and/or that express the recombinant receptor. In particular embodiments, the two separate compositions include a composition of enriched CD8+ T cells, such as engineered CD8+ T cells that were introduced with the nucleic acid encoding the recombinant receptor and/or that express the recombinant receptor. In some embodiments, two separate compositions of enriched CD4+ T cells and enriched CD8+ T cells, such as engineered CD4+ T cells and engineered CD8+ T cells, are separately cultivated, e.g., under conditions that promote proliferation and/or expansion. In some embodiments, a single composition of enriched T cells is cultivated. In certain embodiments, the single composition is a composition of enriched CD4+ T cells. In some embodiments, the single composition is a composition of enriched CD4+ and CD8+ T cells that have been combined from separate compositions prior to the cultivation.

In some embodiments, the composition of enriched CD4+ T cells, such as engineered CD4+ T cells, that is cultivated, e.g., under conditions that promote proliferation and/or expansion, includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In some embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD4+ T cells that express the recombinant receptor and/or have been transduced or transfected with the recombinant polynucleotide encoding the recombinant receptor. In certain embodiments, the composition of enriched CD4+ T cells that is cultivated includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells, such as engineered CD8+t cells, that is cultivated, e.g., under conditions that promote proliferation and/or expansion, includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In particular embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD8+ T cells that express the recombinant receptor and/or have been transduced or transfected with the recombinant polynucleotide encoding the recombinant receptor. In certain embodiments, the composition of enriched CD8+ T cells that is incubated under stimulating conditions includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, separate compositions of enriched CD4+ and CD8+ T cells, such as separate compositions of engineered CD4+ and engineered CD8+ T cells, are combined into a single composition and are cultivated, e.g., under conditions that promote proliferation and/or expansion. In certain embodiments, separate cultivated compositions of enriched CD4+ and enriched CD8+ T cells are combined into a single composition after the cultivation has been performed and/or completed. In particular embodiments, separate compositions of enriched CD4+ and CD8+ T cells, such as separate compositions of engineered CD4+ and engineered CD8+ T cells, are separately cultivated, e.g., under conditions that promote proliferation and/or expansion.

In some embodiments, the cells, e.g., the engineered cells are cultivated in a volume of media that is, is about, or is at least 100 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL, or 2,400 mL. In some embodiments, the cells are cultivated at an initial volume that is later adjusted to a different volume. In particular embodiments, the volume is later adjusted during the cultivation. In particular embodiments, the volume is increased from the initial volume during the cultivation. In certain embodiments, the volume is increased when the cells achieve a density during the cultivation. In certain embodiment, the initial volume is or is about 500 mL.

In particular embodiments, the volume is increased from the initial volume when the cells achieve a density or concentration during the cultivation. In particular embodiments, the volume is increased when the cells achieve a density and/or concentration of, of about, or of at least $0.1 \times 10^6$ cells/ml, $0.2 \times 10^6$ cells/ml, $0.4 \times 10^6$ cells/ml, $0.6 \times 10^6$ cells/ml, $0.8 \times 10^6$ cells/ml, $1 \times 10^6$ cells/ml, $1.2 \times 10^6$ cells/ml, $1.4 \times 10^6$ cells/ml, $1.6 \times 10^6$ cells/ml, $1.8 \times 10^6$ cells/ml, $2.0 \times 10^6$ cells/ml, $2.5 \times 10^6$ cells/ml, $3.0 \times 10^6$ cells/ml, $3.5 \times 10^6$ cells/ml, $4.0 \times 10^6$ cells/ml, $4.5 \times 10^6$ cells/ml, $5.0 \times 10^6$ cells/ml, $6 \times 10^6$ cells/ml, $8 \times 10^6$ cells/ml, or $10 \times 10^6$ cells/ml. In some embodiments, the volume is increased from the initial volume when the cells achieve a density and/or concentration of, of at least, or of about $0.6 \times 10^6$ cells/ml. In some embodiments, the density and/or concentration is of viable cells in the culture. In particular embodiments, the volume is increased when the cells achieve a density and/or concentration of, of about, or of at least $0.1 \times 10^6$ viable cells/ml, $0.2 \times 10^6$ viable cells/ml, $0.4 \times 10^6$ viable cells/ml, $0.6 \times 10^6$ viable cells/ml, $0.8 \times 10^6$ viable cells/ml, $1 \times 10^6$ viable cells/ml, $1.2 \times 10^6$ viable cells/ml, $1.4 \times 10^6$ viable cells/ml, $1.6 \times 10^6$ viable cells/ml, $1.8 \times 10^6$ viable cells/ml, $2.0 \times 10^6$ viable cells/ml, $2.5 \times 10^6$ viable cells/ml, $3.0 \times 10^6$ viable cells/ml, $3.5 \times 10^6$ viable cells/ml, $4.0 \times 10^6$ viable cells/ml, $4.5 \times 10^6$ viable cells/ml, $5.0 \times 10^6$ viable cells/ml, $6 \times 10^6$ viable cells/ml, $8 \times 10^6$ viable cells/ml, or $10 \times 10^6$ viable cells/ml. In some embodiments, the volume is increased from the initial volume when the viable cells achieve a density and/or concentration of, of at least, or of about $0.6 \times 10^6$ viable cells/ml. In some embodiments, density and/or concentration of the cells or viable cells can be determined or monitored during the cultivation, such as by using methods as described, including optical methods, including digital holography microscopy (DHM) or differential digital holography microscopy (DDHM).

In some embodiments, the cells achieve a density and/or concentration, and the volume is increased by, by about, or by at least 100 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In some embodiments, the volume is increased by 500 mL. In particular embodiments, the volume is increased to a volume of, of about, or of at least 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In certain embodiments, the volume is increased to a volume of 1,000 mL. In certain embodiments, the volume is increase at a rate of, of at least, or of about 5 mL, 10 mL, 20 mL, 25 mL, 30 mL, 40 mL, 50 mL, 60 mL, 70 mL, 75 mL, 80 mL, 90 mL, or 100 mL, every 1, 2, 3, 4, 5, 6, 7, 8, 9, or 10 minutes. In certain embodiments, the rate is or is about 50 mL every 8 minutes.

In some embodiments, a composition of enriched T cells, such as engineered T cells, is cultivated under conditions that promote proliferation and/or expansion. In some embodiments, such conditions may be designed to induce proliferation, expansion, activation, and/or survival of cells in the population. In particular embodiments, the stimulating conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to promote growth, division, and/or expansion of the cells.

In some embodiments, the cultivation is performed under conditions that generally include a temperature suitable for the growth of primary immune cells, such as human T lymphocytes, for example, at least about 25 degrees Celsius, generally at least about 30 degrees, and generally at or about 37 degrees Celsius. In some embodiments, the composition of enriched T cells is incubated at a temperature of 25 to 38° C., such as 30 to 37° C., for example at or about 37° C.±2° C. In some embodiments, the incubation is carried out for a time period until the culture, e.g. cultivation or expansion, results in a desired or threshold density, concentration, number or dose of cells. In some embodiments, the incubation is carried out for a time period until the culture, e.g. cultivation or expansion, results in a desired or threshold density, concentration, number or dose of viable cells. In some embodiments, the incubation is greater than or greater than about or is for about or 24 hours, 48 hours, 72 hours, 96 hours, 5 days, 6 days, 7 days, 8 days, 9 days or more. In some embodiments, density, concentration and/or number or dose of of the cells can be determined or monitored during the cultivation, such as by using methods as described, including optical methods, including digital holography microscopy (DHM) or differential digital holography microscopy (DDHM).

In some embodiments, the stimulatory reagent is removed and/or separated from the cells prior to the cultivation. In certain embodiments, the stimulatory agent is removed and/or separated from the cells subsequent to the engineering and prior to cultivating the engineered cells, e.g., under conditions that promote proliferation and/or expansion. In some embodiments, the stimulatory reagent is a stimulatory reagent that is described herein, e.g., in Section I-B-1. In particular embodiments, the stimulatory reagent is removed and/or separated from the cells as described herein, e.g., in Section I-B-2.

In particular embodiments, a composition of enriched T cells, such as engineered T cells, for example separate compositions of engineered CD4+ T cells and engineered CD8+ T cells, is cultivated in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In particular embodiments, the composition of enriched CD4+ T cells, such as engineered CD4+ T cells, is cultivated with recombinant IL-2. In some embodiments, cultivating a composition of enriched CD4+ T cells, such as engineered CD4+ T cells, in the presence of recombinant IL-2 increases the probability or likelihood that the CD4+ T cells of the composition will continue to survive, grow, expand, and/or activate during the cultivation step and throughout the process. In some embodiments, cultivating the composition of enriched CD4+ T cells, such as engineered CD4+ T cells, in the presence of recombinant IL-2 increases the probability and/or likelihood that an output composition of enriched CD4+ T cells, e.g., engineered CD4+ T cells suitable for cell therapy, will be produced from the composition of enriched CD4+ T cells by at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 30%, at least 40%, at least 50%, at least 60%, at least 70%, at least 80%, at least 90%, at least 95%, at least 100%, or at least 200% CD4+ as compared to an alternative and/or exemplary method that does not cultivate the composition of enriched CD4+ T cells in the presence of recombinant IL-2.

In some embodiments, the cells, such as separate compositions of engineered CD4+ T cells and engineered CD8+ T cells, are cultivated with a cytokine, e.g., a recombinant human cytokine, at a concentration of between 1 IU/ml and 2,000 IU/ml, between 10 IU/ml and 100 IU/ml, between 50 IU/ml and 500 IU/ml, between 100 IU/ml and 200 IU/ml, between 500 IU/ml and 1400 IU/ml, between 250 IU/ml and 500 IU/ml, or between 500 IU/ml and 2,500 IU/ml.

In some embodiments, a composition of enriched of T cells, such as separate compositions of engineered CD4+ T cells and CD8+ T cells, is cultivated with recombinant IL-2, e.g., human recombinant IL-2, at a concentration between 2 IU/ml and 500 IU/ml, between 10 IU/ml and 250 IU/ml, between 100 IU/ml and 500 IU/ml, or between 100 IU/ml and 400 IU/ml. In particular embodiments, the composition of enriched T cells is cultivated with IL-2 at a concentration at or at about 50 IU/ml, 75 IU/ml, 100 IU/ml, 125 IU/ml, 150 IU/ml, 175 IU/ml, 200 IU/ml, 225 IU/ml, 250 IU/ml, 300 IU/ml, or 400 IU/ml. In some embodiments, the composition of enriched T cells is cultivated with recombinant IL-2 at a concentration of 200 IU/ml. In some embodiments, the composition of enriched T cells is a composition of enriched CD4+ T cells, such as a composition of engineered CD4+ T cells. In particular embodiments, the composition of enriched T cells is a composition of enriched CD8+ T cells, such as a composition of engineered CD8+ T cells.

In some embodiments, a composition of enriched T cells, such as separate compositions of engineered CD4+ T cells and CD8+ T cells, is cultivated with IL-7, e.g., human recombinant IL-7, at a concentration between 10 IU/ml and 5,000 IU/ml, between 500 IU/ml and 2,000 IU/ml, between 600 IU/ml and 1,500 IU/ml, between 500 IU/ml and 2,500 IU/ml, between 750 IU/ml and 1,500 IU/ml, or between 1,000 IU/ml and 2,000 IU/ml. In particular embodiments, the composition of enriched T cells is cultivated with IL-7 at a concentration at or at about 100 IU/ml, 200 IU/ml, 300 IU/ml, 400 IU/ml, 500 IU/ml, 600 IU/ml, 700 IU/ml, 800 IU/ml, 900 IU/ml, 1,000 IU/ml, 1,200 IU/ml, 1,400 IU/ml, or 1,600 IU/ml. In some embodiments, the cells are cultivated in the presence of recombinant IL-7 at a concertation of or of about 1,200 IU/ml. In some embodiments, the composition of enriched T cells is a composition of enriched CD4+ T cells, such as engineered CD4+ T cells.

In some embodiments, a composition of enriched T cells, such as separate compositions of engineered CD4+ T cells and CD8+ T cells, is cultivated with IL-15, e.g., human recombinant IL-15, at a concentration between 0.1 IU/ml and 200 IU/ml, between 1 IU/ml and 50 IU/ml, between 5 IU/ml and 25 IU/ml, between 25 IU/ml and 50 IU/ml, between 5 IU/ml and 15 IU/ml, or between 10 IU/ml and 00 IU/ml. In particular embodiments, the composition of enriched T cells is cultivated with IL-15 at a concentration at or at about 1 IU/ml, 2 IU/ml, 3 IU/ml, 4 IU/ml, 5 IU/ml, 6 IU/ml, 7 IU/ml, 8 IU/ml, 9 IU/ml, 10 IU/ml, 11 IU/ml, 12 IU/ml, 13 IU/ml, 14 IU/ml, 15 IU/ml, 20 IU/ml, 25 IU/ml, 30 IU/ml, 40 IU/ml, 50 IU/ml, 100 IU/ml, or 200 IU/ml. In particular embodiments, a composition of enriched T cells is cultivated with recombinant IL-15 at a concentration of 20 IU/ml. In some embodiments, the composition of enriched T cells is a composition of enriched CD4+ T cells, such as engineered CD4+ T cells. In particular embodiments, the composition of enriched T cells is a composition of enriched CD8+ T cells, such as engineered CD8+ T cells.

In particular embodiments, a composition of enriched CD8+ T cells, such as engineered CD8+ T cells, is cultivated in the presence of IL-2 and/or IL-15, such as in amounts as described. In certain embodiments, a composition of enriched CD4+ T cells, such as engineered CD4+ T cells, is cultivated in the presence of IL-2, IL-7, and/or IL-15, such as in amounts as described. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15.

In particular embodiments, the cultivation is performed in a closed system. In certain embodiments, the cultivation is performed in a closed system under sterile conditions. In particular embodiments, the cultivation is performed in the same closed system as one or more steps of the provided systems. In some embodiments the composition of enriched T cells is removed from a closed system and placed in and/or connected to a bioreactor for the cultivation. Examples of suitable bioreactors for the cultivation include, but are not limited to, GE Xuri W25, GE Xuri W5, Sartorius BioSTAT RM 20|50, Finesse SmartRocker Bioreactor Systems, and Pall XRS Bioreactor Systems. In some embodiments, the bioreactor is used to perfuse and/or mix the cells during at least a portion of the cultivation step.

In some embodiments, cells cultivated while enclosed, connected, and/or under control of a bioreactor undergo expansion during the cultivation more rapidly than cells that are cultivated without a bioreactor, e.g., cells that are cultivated under static conditions such as without mixing, rocking, motion, and/or perfusion. In some embodiments, cells cultivated while enclosed, connected, and/or under control of a bioreactor reach or achieve a threshold expansion, cell count, and/or density within 14 days, 10 days, 9 days, 8 days, 7 days, 6 days, 5 days, 4 days, 3 days, 2 days, 60 hours, 48 hours, 36 hours, 24 hours, or 12 hours. In some embodiments, cells cultivated while enclosed, connected, and/or under control of a bioreactor reach or achieve a threshold expansion, cell count, and/or density at least 50%, at least 60%, at least 70%, at least 80%, at least 90%, at least 95%, at least 100%, at least 150%, at least 1-fold, at least 2-fold, at least 3-fold, at least 4-fold, at least 5-fold than cells cultivated in an exemplary and/or alternative process where cells are not cultivated while enclosed, connected, and/or under control of a bioreactor.

In some embodiments, the mixing is or includes rocking and/or motioning. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive.

In some embodiments, the bioreactor maintains the temperature at or near 37° C. and $CO_2$ levels at or near 5% with a steady air flow at, at about, or at least 0.01 L/min, 0.05 L/min, 0.1 L/min, 0.2 L/min, 0.3 L/min, 0.4 L/min, 0.5 L/min, 1.0 L/min, 1.5 L/min, or 2.0 L/min or greater than 2.0 L/min. In certain embodiments, at least a portion of the cultivation is performed with perfusion, such as with a rate of 290 ml/day, 580 ml/day, and/or 1160 ml/day, e.g., depending on the timing in relation to the start of the cultivation and/or density of the cultivated cells. In some embodiments, at least a portion of the cell culture expansion is performed with a rocking motion, such as at an angle of between 5° and 10°, such as 6°, at a constant rocking speed, such as a speed of between 5 and 15 RPM, such as 6 RMP or 10 RPM.

In some embodiments, the at least a portion of the cultivation step is performed under constant perfusion, e.g., a perfusion at a slow steady rate. In some embodiments, the perfusion is or include an outflow of liquid e.g., used media, and an inflow of fresh media. In certain embodiments, the perfusion replaces used media with fresh media. In some embodiments, at least a portion of the cultivation is performed under perfusion at a steady rate of or of about or of at least 100 ml/day, 200 ml/day, 250 ml/day, 275 ml/day, 290 ml/day, 300 ml/day, 350 ml/day, 400 ml/day, 450 ml/day, 500 ml/day, 550 ml/day, 575 ml/day, 580 ml/day, 600 ml/day, 650 ml/day, 700 ml/day, 750 ml/day, 800 ml/day, 850 ml/day, 900 ml/day, 950 ml/day, 1000 ml/day, 1100 ml/day, 1160 ml/day, 1200 ml/day, 1400 ml/day, 1600 ml/day, 1800 ml/day, 2000 ml/day, 2200 ml/day, or 2400 ml/day.

In particular embodiments, cultivation is started under conditions with no perfusion, and perfusion started after a set and/or predetermined amount of time, such as or as about or at least 12 hours, 24 hours, 36 hours, 48 hours, 60 hours, 72 hours, or more than 72 hours after the start or initiation of the cultivation. In particular embodiments, perfusion is started when the density or concentration of the cells reaches a set or predetermined density or concentration. In some embodiments, the perfusion is started when the cultivated cells reach a density or concentration of, of about, or at least $0.1 \times 10^6$ cells/ml, $0.2 \times 10^6$ cells/ml, $0.4 \times 10^6$ cells/ml, $0.6 \times 10^6$ cells/ml, $0.8 \times 10^6$ cells/ml, $1 \times 10^6$ cells/ml, $1.2 \times 10^6$ cells/ml, $1.4 \times 10^6$ cells/ml, $1.6 \times 10^6$ cells/ml, $1.8 \times 10^6$ cells/ml, $2.0 \times 10^6$ cells/ml, $2.5 \times 10^6$ cells/ml, $3.0 \times 10^6$ cells/ml, $3.5 \times 10^6$ cells/ml, $4.0 \times 10^6$ cells/ml, $4.5 \times 10^6$ cells/ml, $5.0 \times 10^6$ cells/ml, $6 \times 10^6$ cells/ml, $8 \times 10^6$ cells/ml, or $10 \times 10^6$ cells/ml. In particular embodiments, perfusion is started when the density or concentration of viable cells reaches a set or predetermined density or concentration. In some embodiments, the perfusion is started when the cultivated viable cells reach a density or concentration of, of about, or at least $0.1 \times 10^6$ viable cells/ml, $0.2 \times 10^6$ viable cells/ml, $0.4 \times 10^6$ viable cells/ml, $0.6 \times 10^6$ viable cells/ml, $0.8 \times 10^6$ viable cells/ml, $1 \times 10^6$ viable cells/ml, $1.2 \times 10^6$ viable cells/ml, $1.4 \times 10^6$ viable cells/ml, $1.6 \times 10^6$ viable cells/ml, $1.8 \times 10^6$ viable cells/ml, $2.0 \times 10^6$ viable cells/ml, $2.5 \times 10^6$ viable cells/ml, $3.0 \times 10^6$ viable cells/ml, $3.5 \times 10^6$ viable cells/ml, $4.0 \times 10^6$ viable cells/ml, $4.5 \times 10^6$ viable cells/ml, $5.0 \times 10^6$ viable cells/ml, $6 \times 10^6$ viable cells/ml, $8 \times 10^6$ viable cells/ml, or $10 \times 10^6$ viable cells/ml.

In particular embodiments, the perfusion is performed at different speeds during the cultivation. For example, in some embodiments, the rate of the perfusion depends on the density and/or concentration of the cultivated cells. In certain embodiments, the rate of perfusion is increased when the cells reach a set or predetermined density or concentration. The perfusion rate may change, e.g., change from one steady perfusion rate to an increased steady perfusion rate, once, twice, three times, four times, five times, more than five times, more than ten times, more than 15 times, more than 20 times, more than 25 times, more than 50 times, or more than 100 times during the cultivation. In some embodiments, the steady perfusion rate increases when the cells reach a set or predetermined cell density or concentration of, of about, or at least $0.6 \times 10^6$ cells/ml, $0.8 \times 10^6$ cells/ml, $1 \times 10^6$ cells/ml, $1.2 \times 10^6$ cells/ml, $1.4 \times 10^6$ cells/ml, $1.6 \times 10^6$ cells/ml, $1.8 \times 10^6$ cells/ml, $2.0 \times 10^6$ cells/ml, $2.5 \times 10^6$ cells/ml, $3.0 \times 10^6$ cells/ml, $3.5 \times 10^6$ cells/ml, $4.0 \times 10^6$ cells/ml, $4.5 \times 10^6$ cells/ml, $5.0 \times 10^6$ cells/ml, $6 \times 10^6$ cells/ml, $8 \times 10^6$ cells/ml, or $10 \times 10^6$ cells/ml. In some embodiments, the steady perfusion rate increases when the cells reach a set or predetermined viable cell density or concentration of, of about, or at least $0.6 \times 10^6$ viable cells/ml, $0.8 \times 10^6$ viable cells/ml, $1 \times 10^6$ viable cells/ml, $1.2 \times 10^6$ viable cells/ml, $1.4 \times 10^6$ viable cells/ml, $1.6 \times 10^6$ viable cells/ml, $1.8 \times 10^6$ viable cells/ml, $2.0 \times 10^6$ viable cells/ml, $2.5 \times 10^6$ viable cells/ml, $3.0 \times 10^6$ viable cells/ml, $3.5 \times 10^6$ viable cells/ml, $4.0 \times 10^6$ viable cells/ml, $4.5 \times 10^6$ viable cells/ml, $5.0 \times 10^6$ viable cells/ml, $6 \times 10^6$ viable cells/ml, $8 \times 10^6$ viable cells/ml, or $10 \times 10^6$ viable cells/ml. In some embodiments, density and/or concentration of the cells or of the viable cells during the cultivation, such as under perfusion, can be determined or monitored, such as by using methods as described, including optical methods, including digital holography microscopy (DHM) or differential digital holography microscopy (DDHM).

In some embodiments, cultivation is started under conditions with no perfusion, and, perfusion is started when the density or concentration of the cells reaches a set or predetermined density or concentration. In some embodiments, the perfusion is started at a rate of, of about, or of at least 100 ml/day, 200 ml/day, 250 ml/day, 275 ml/day, 290 ml/day, 300 ml/day, 350 ml/day, 400 ml/day, 450 ml/day, 500 ml/day, 550 ml/day, 575 ml/day, 580 ml/day, 600 ml/day, 650 ml/day, 700 ml/day, 750 ml/day, 800 ml/day, 850 ml/day, 900 ml/day, 950 ml/day, 1000 ml/day, 1100 ml/day, 1160 ml/day, 1200 ml/day, 1400 ml/day, 1600 ml/day, 1800 ml/day, 2000 ml/day, 2200 ml/day, or 2400 ml/day when the density or concentration of the cells reaches a set or predetermined density or concentration. In some embodiments, the perfusion is started when the cultivated cells or cultivated viable cells reach a density or concentration of, of about, or at least $0.1 \times 10^6$ cells/ml, $0.2 \times 10^6$ cells/ml, $0.4 \times 10^6$ cells/ml, $0.6 \times 10^6$ cells/ml, $0.8 \times 10^6$ cells/ml, $1 \times 10^6$ cells/ml, $1.2 \times 10^6$ cells/ml, $1.4 \times 10^6$ cells/ml, $1.6 \times 10^6$ cells/ml, $1.8 \times 10^6$ cells/ml, $2.0 \times 10^6$ cells/ml, $2.5 \times 10^6$ cells/ml, $3.0 \times 10^6$ cells/ml, $3.5 \times 10^6$ cells/ml, $4.0 \times 10^6$ cells/ml, $4.5 \times 10^6$ cells/ml, $5.0 \times 10^6$ cells/ml, $6 \times 10^6$ cells/ml, $8 \times 10^6$ cells/ml, or $10 \times 10^6$ cells/ml.

In certain embodiments, at least part of the cultivation is performed with perfusion at a certain rate, and the perfusion rate is increased to, to about, or to at least 100 ml/day, 200 ml/day, 250 ml/day, 275 ml/day, 290 ml/day, 300 ml/day, 350 ml/day, 400 ml/day, 450 ml/day, 500 ml/day, 550 ml/day, 575 ml/day, 580 ml/day, 600 ml/day, 650 ml/day, 700 ml/day, 750 ml/day, 800 ml/day, 850 ml/day, 900 ml/day, 950 ml/day, 1000 ml/day, 1100 ml/day, 1160 ml/day, 1200 ml/day, 1400 ml/day, 1600 ml/day, 1800 ml/day, 2000 ml/day, 2200 ml/day, or 2400 ml/day when the density or concentration of the cells reaches a set or predetermined density or concentration. In some embodiments, the perfusion is started when the cultivated cells or cultivated viable cells reach a density or concentration of, of about, or at least $0.1 \times 10^6$ cells/ml, $0.2 \times 10^6$ cells/ml, $0.4 \times 10^6$ cells/ml, $0.6 \times 10^6$ cells/ml, $0.8 \times 10^6$ cells/ml, $1 \times 10^6$ cells/ml, $1.2 \times 10^6$ cells/ml, $1.4 \times 10^6$ cells/ml, $1.6 \times 10^6$ cells/ml, $1.8 \times 10^6$ cells/ml, $2.0 \times 10^6$ cells/ml, $2.5 \times 10^6$ cells/ml, $3.0 \times 10^6$ cells/ml, $3.5 \times 10^6$ cells/ml, $4.0 \times 10^6$ cells/ml, $4.5 \times 10^6$ cells/ml, $5.0 \times 10^6$ cells/ml, $6 \times 10^6$ cells/ml, $8 \times 10^6$ cells/ml, or $10 \times 10^6$ cells/ml. In some embodiments, the perfusion is performed when the cells are cultivated in a volume of, of about, or at least 300 mL, 400 mL, 500 mL, 600 mL, 700 mL, 800 mL, 900 mL, or 1000 mL. In some embodiments, the volume is 1000 mL.

In certain embodiments, cultivation is started under conditions with either no perfusion or perfusion at a certain rate, and the perfusion rate is increased to, to about, or to at 290 ml/day when the density or concentration of the cells reaches a concentration of, of about, or of at least $0.61 \times 10^6$ cells/ml. In certain embodiments, the cells are perfused at a rate of, of about, or at least 290 ml/day when the density or concentration of the cells reaches a concentration of, of about, or of at least $0.61 \times 10^6$ cells/ml when the cells are cultivated at a volume of, of about, or at least 1000 mL. In some embodiments, the perfusion rate is increased to, to about, or to at 580 ml/day when the density or concentration of the cells reaches a concentration of, of about, or of at least $0.81 \times 10^6$ cells/ml. In certain embodiments, the perfusion rate is increased to, to about, or to at 1160 ml/day when the density or concentration of the cells reaches a concentration of, of about, or of at least $1.01 \times 10^6$ cells/ml. In some embodiments, the perfusion rate is increased to, to about, or to at 1160 ml/day when the density or concentration of the cells reaches a concentration of, of about, or of at least $1.2 \times 10^6$ cells/ml.

In aspects of the provided embodiments, the rate of perfusion, including the timing of when it is started or increased as described herein and above, is determined from assessing density and/or concentration of the cells or assessing the density and/or concentration of viable cells during the cultivation. In some embodiments, density and/or concentration of the cells can be determined using methods as described, including optical methods, including digital holography microscopy (DHM) or differential digital holography microscopy (DDHM).

In some embodiments, a composition of enriched cells, such as engineered T cells, e.g. engineered CD4+ T cells or engineered CD8+ T cells, is cultivated in the presence of a surfactant. In particular embodiments, cultivating the cells of the composition reduces the amount of shear stress that may occur during the cultivation, e.g., due to mixing, rocking, motion, and/or perfusion. In particular embodiments, the composition of enriched T cells, such as engineered T cells, e.g. engineered CD4+ T cells or engineered CD8+ T cells, is cultivated with the surfactant and at least 50%, at least 60%, at least 70%, at least 75%, at least 80%, at least 85%, at least 90%, at least 95%, at least 99%, or at least 99.9% of the T cells survive, e.g., are viable and/or do not undergo necrosis, programed cell death, or apoptosis, during or at least 1 day, 2 days, 3 days, 4 days, 5 days, 6 days, 7 days, or more than 7 days after the cultivation is complete. In particular embodiments, the composition of enriched T cells, such as engineered T cells, e.g. engineered CD4+ T cells or engineered CD8+ T cells, is cultivated in the presence of a surfactant and less than 50%, less than 40%, less than 30%, less than 25%, less than 20%, less than 15%, less than 10%, less than 5%, less than 1%, less than 0.1% or less than 0.01% of the cells undergo cell death, e.g., programmed cell death, apoptosis, and/or necrosis, such as due to shearing or shearing-induced stress.

In particular embodiments, a composition of enriched T cells, such as engineered T cells, e.g. engineered CD4+ T cells or engineered CD8+ T cells, is cultivated in the presence of between 0.1 µl/ml and 10.0 µl/ml, between 0.2 µl/ml and 2.5 µl/ml, between 0.5 µl/ml and 5 µl/ml, between 1 µl/ml and 3 µl/ml, or between 2 µl/ml and 4 µl/ml of the surfactant. In some embodiments, the composition of enriched T cells, such as engineered T cells, e.g. engineered CD4+ T cells or engineered CD8+ T cells, is cultivated in the presence of, of about, or at least 0.1 µl/ml, 0.2 µl/ml, 0.4 µl/ml, 0.6 µl/ml, 0.8 µl/ml, 1 µl/ml, 1.5 µl/ml, 2.0 µl/ml, 2.5 µl/ml, 5.0 µl/ml, 10 µl/ml, 25 µl/ml, or 50 µl/ml of the surfactant. In certain embodiments, the composition of enriched T cells is cultivated in the presence of or of about 2 µl/ml of the surfactant.

In some embodiments, a surfactant is or includes an agent that reduces the surface tension of liquids and/or solids. For example, a surfactant includes a fatty alcohol (e.g., steryl alcohol), a polyoxyethylene glycol octylphenol ether (e.g., Triton X-100), or a polyoxyethylene glycol sorbitan alkyl ester (e.g., polysorbate 20, 40, 60). In certain embodiments the surfactant is selected from the group consisting of Polysorbate 80 (PS80), polysorbate 20 (PS20), poloxamer 188 (P188). In an exemplary embodiment, the concentration of the surfactant in chemically defined feed media is about 0.0025% to about 0.25% (v/v) of PS80; about 0.0025% to about 0.25% (v/v) of PS20; or about 0.1% to about 5.0% (w/v) of P188.

In some embodiments, the surfactant is or includes an anionic surfactant, a cationic surfactant, a zwitterionic surfactant, or a nonionic surfactant added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate).

In some embodiments, suitable nonionic surfactants include: glyceryl esters, polyoxyethylene fatty alcohol ethers, polyoxyethylene sorbitan fatty acid esters (polysorbates), polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethyl cellulose, hydroxypropyl cellulose, hydroxypropylmethyl cellulose, noncrystalline cellulose, polysaccharides including starch and starch derivatives such as hydroxyethylstarch (HES), polyvinyl alcohol, and polyvinylpyrrolidone. In certain embodiments, the nonionic surfactant is a polyoxyethylene and polyoxypropylene copolymer and preferably a block copolymer of propylene glycol and ethylene glycol. Such polymers are sold under the tradename POLOXAMER, also sometimes referred to as PLURONIC® F68 or Kolliphor® P188. Among polyoxyethylene fatty acid esters is included those having short alkyl chains. One example of such a surfactant is SOLUTOL® HS 15, polyethylene-660-hydroxystearate.

In some embodiments, suitable cationic surfactants may include, but are not limited to, natural phospholipids, synthetic phospholipids, quaternary ammonium compounds, benzalkonium chloride, cetyltrimethyl ammonium bromide, chitosans, lauryl dimethyl benzyl ammonium chloride, acyl carnitine hydrochlorides, dimethyl dioctadecyl ammomium bromide (DDAB), dioleyoltrimethyl ammonium propane (DOTAP), dimyristoyl trimethyl ammonium propane (DMTAP), dimethyl amino ethane carbamoyl cholesterol (DC-Chol), 1,2-diacylglycero-3-(O-alkyl) phosphocholine, O-alkylphosphatidylcholine, alkyl pyridinium halides, or long-chain alkyl amines such as, for example, n-octylamine and oleylamine.

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semi-synthetic or synthetic.

In certain embodiments, the surfactant is poloxamer, e.g., poloxamer 188. In some embodiments, a composition of enriched T cells is cultivated in the presence of between 0.1 µl/ml and 10.0 µl/ml, between 0.2 µl/ml and 2.5 µl/ml, between 0.5 µl/ml and 5 µl/ml, between 1 µl/ml and 3 µl/ml, or between 2 µl/ml and 4 µl/ml of poloxamer. In some embodiments, the composition of enriched T cells is cultivated in the presence of, of about, or at least 0.1 µl/ml, 0.2 µl/ml, 0.4 µl/ml, 0.6 µl/ml, 0.8 µl/ml, 1 µl/ml, 1.5 µl/ml, 2.0 µl/ml, 2.5 µl/ml, 5.0 µl/ml, 10 µl/ml, 25 µl/ml, or 50 µl/ml of the surfactant. In certain embodiments, the composition of enriched T cells is cultivated in the presence of or of about 2 µl/ml of poloxamer.

In particular embodiments, the cultivation ends, such as by harvesting cells, when cells achieve a threshold amount, concentration, and/or expansion. In particular embodiments, the cultivation ends when the cell achieve or achieve about or at least a 1.5-fold expansion, a 2-fold expansion, a 2.5-fold expansion, a 3-fold expansion, a 3.5-fold expansion, a 4-fold expansion, a 4.5-fold expansion, a 5-fold expansion, a 6-fold expansion, a 7-fold expansion, a 8-fold expansion, a 9-fold expansion, a 10-fold expansion, or greater than a 10-fold expansion, e.g., with respect and/or in relation to the amount of density of the cells at the start or initiation of the cultivation. In some embodiments, the threshold expansion is a 4-fold expansion, e.g., with respect and/or in relation to the amount of density of the cells at the start or initiation of the cultivation.

In some embodiments, the cultivation ends, such as by harvesting cells, when the cells achieve a threshold total amount of cells, e.g., threshold cell count. In some embodiments, the cultivation ends when the cells achieve a threshold total nucleated cell (TNC) count. In some embodiments, the cultivation ends when the cells achieve a threshold viable amount of cells, e.g., threshold viable cell count. In some embodiments, the threshold cell count is or is about or is at least of $50\times10^6$ cells, $100\times10^6$ cells, $200\times10^6$ cells, $300\times10^6$ cells, $400\times10^6$ cells, $600\times10^6$ cells, $800\times10^6$ cells, $1000\times10^6$ cells, $1200\times10^6$ cells, $1400\times10^6$ cells, $1600\times10^6$ cells, $1800\times10^6$ cells, $2000\times10^6$ cells, $2500\times10^6$ cells, $3000\times10^6$ cells, $4000\times10^6$ cells, $5000\times10^6$ cells, $10,000\times10^6$ cells, $12,000\times10^6$ cells, $15,000\times10^6$ cells or $20,000\times10^6$ cells, or any of the foregoing threshold of viable cells. In particular embodiments, the cultivation ends when the cells achieve a threshold cell count. In some embodiments, the cultivation ends at, at about, or within 6 hours, 12 hours, 24 hours, 36 hours, 1 day, 2 days, 3 days, 4 days, 5 days, 6 days, or 7 or more days, after the threshold cell count is achieved. In particular embodiments, the cultivation is ended at or about 1 day after the threshold cell count is achieved. In certain embodiments, the threshold density is, is about, or is at least $0.1\times10^6$ cells/ml, $0.5\times10^6$ cells/ml, $1\times10^6$ cells/ml, $1.2\times10^6$ cells/ml, $1.5\times10^6$ cells/ml, $1.6\times10^6$ cells/ml, $1.8\times10^6$ cells/ml, $2.0\times10^6$ cells/ml, $2.5\times10^6$ cells/ml, $3.0\times10^6$ cells/ml, $3.5\times10^6$ cells/ml, $4.0\times10^6$ cells/ml, $4.5\times10^6$ cells/ml, $5.0\times10^6$ cells/ml, $6\times10^6$ cells/ml, $8\times10^6$ cells/ml, or $10\times10^6$ cells/ml, or any of the foregoing threshold of viable cells. In particular embodiments, the cultivation ends when the cells achieve a threshold density. In some embodiments, the cultivation ends at, at about, or within 6 hours, 12 hours, 24 hours, 36 hours, 1 day, 2 days, 3 days, 4 days, 5 days, 6 days, or 7 or more days, after the threshold density is achieved. In particular embodiments, the cultivation is ended at or about 1 day after the threshold density is achieved.

In some embodiments, the cultivation step is performed for the amount of time required for the cells to achieve a threshold amount, density, and/or expansion. In some embodiments, the cultivation is performed for or for about, or for less than, 6 hours, 12 hours, 18 hours, 24 hours, 36 hours, 48 hours, 60 hours, 72 hours, 2 days, 3 days 4 days, 5 days, 6 days, 7 days, 7 days, 8 days, 9 days, 10 days, 1 week, 2 weeks, 3 weeks, or 4 weeks. In particular embodiments, the mean amount of time required for the cells of a plurality of separate compositions of enriched T cells that were isolated, enriched, and/or selected from different biological samples to achieve the threshold density is, is about, or is less than 6 hours, 12 hours, 18 hours, 24 hours, 36 hours, 48 hours, 60 hours, 72 hours, 2 days, 3 days 4 days, 5 days, 6 days, 7 days, 7 days, 8 days, 9 days, 10 days, 1 week, 2 weeks, 3 weeks, or 4 weeks. In certain embodiments, the mean amount of time required for the cells of a plurality of separate compositions of enriched T cells that were isolated, enriched, and/or selected from different biological samples to achieve the threshold density is, is about, or is less than 6 hours, 12 hours, 18 hours, 24 hours, 36 hours, 48 hours, 60 hours, 72 hours, 2 days, 3 days 4 days, 5 days, 6 days, 7 days, 7 days, 8 days, 9 days, 10 days, 1 week, 2 weeks, 3 weeks, or 4 weeks.

In certain embodiments, the cultivation step is performed for a minimum of 4 days, 5 days, 6 days, 7 days, 7 days, 8 days, 9 days, or 10 days, and/or until 12 hours, 24 hours, 36 hours, 1 day, 2 days, or 3 days after the cells active a threshold cell count (or number) or threshold viable cell count (or number) of or of about $1000 \times 10^6$ cells, $1200 \times 10^6$ cells, $1400 \times 10^6$ cells, $1600 \times 10^6$ cells, $1800 \times 10^6$ cells, $2000 \times 10^6$ cells, $2500 \times 10^6$ cells, $3000 \times 10^6$ cells, $4000 \times 10^6$ cells, or $5000 \times 10^6$ cells. In some embodiments, the cultivation step is performed until 1 day after the cells achieve a threshold cell count of or of about $1200 \times 10^6$ cells and are cultured for a minimum of 10 days, and/or until 1 day after the cells achieve a threshold cell count of or of about $5000 \times 10^6$ cells. In some embodiments, the cultivation step is performed until 1 day after the cells achieve a threshold cell count of or of about $1200 \times 10^6$ cells and are cultured for a minimum of 9 days, and/or until 1 day after the cells achieve a threshold cell count of or of about $5000 \times 10^6$ cells. In some embodiments, the cultivation step is performed until 1 day after the cells achieve a threshold cell count of or of about $1000 \times 10^6$ cells and are cultured for a minimum of 8 days, and/or until 1 day after the cells achieve a threshold cell count of or of about $4000 \times 10^6$ cells. In certain embodiments, the cultivation is an expansion step and is performed for a minimum of 4 days, 5 days, 6 days, 7 days, 7 days, 8 days, 9 days, or 10 days, and/or until 12 hours, 24 hours, 36 hours, 1 day, 2 days, or 3 days after the cells active a threshold cell count (or number) or threshold viable cell count (or number) of or of about $1000 \times 10^6$ cells, $1200 \times 10^6$ cells, $1400 \times 10^6$ cells, $1600 \times 10^6$ cells, $1800 \times 10^6$ cells, $2000 \times 10^6$ cells, $2500 \times 10^6$ cells, $3000 \times 10^6$ cells, $4000 \times 10^6$ cells, or $5000 \times 10^6$ cells. In some embodiments, the expansion step is performed until 1 day after the cells achieve a threshold cell count of or of about $1200 \times 10^6$ cells and are expanded for a minimum of 10 days, and/or until 1 day after the cells achieve a threshold cell count of or of about $5000 \times 10^6$ cells. In some embodiments, the expansion step is performed until 1 day after the cells achieve a threshold cell count of or of about $1200 \times 10^6$ cells and are expanded for a minimum of 9 days, and/or until 1 day after the cells achieve a threshold cell count of or of about $5000 \times 10^6$ cells. In some embodiments, the expansion step is performed until 1 day after the cells achieve a threshold cell count of or of about $1000 \times 10^6$ cells and are expanded for a minimum of 8 days, and/or until 1 day after the cells achieve a threshold cell count of or of about $4000 \times 10^6$ cells. In some embodiments, the expansion step is performed until 1 day after the cells achieve a threshold cell count of or of about $1400 \times 10^6$ cells and are expanded for a minimum of 5 days, and/or until 1 day after the cells achieve a threshold cell count of or of about $4000 \times 10^6$ cells.

In some embodiments, the cultivation is performed for at least a minimum amount of time. In some embodiments, the cultivation is performed for at least 14 days, at least 12 days, at least 10 days, at least 7 days, at least 6 days, at least 5 days, at least 4 days, at least 3 days, at least 2 days, at least 36 hours, at least 24 hours, at least 12 hours, or at least 6 hours, even if the threshold is achieved prior to the minimum amount of time. In some embodiments, increasing the minimum amount of time that the cultivation is performed, may, in some cases, reduce the activation and/or reduce the level or one or more activation markers, in the cultivated cells, formulated cells, and/or cells of the output composition. In some embodiments, the minimum cultivation time counts from a determined point an exemplary process (e.g. a selection step; a thaw step; and/or an activation step) to the day the cells are harvested.

In aspects of the provided embodiments, the density and/or concentration of the cells or of the viable cells during the cultivation is monitored or carried out during the cultivation, such as until a threshold amount, density, and/or expansion is achieved as described. In some embodiments such methods include those as described, including optical methods, including digital holography microscopy (DHM) or differential digital holography microscopy (DDHM).

In certain embodiments, the cultivated cells are output cells. In some embodiments, a composition of enriched T cells, such as engineered T cells, that has been cultivated is an output composition of enriched T cells. In particular embodiments, CD4+ T cells and/or CD8+ T cells that have been cultivated are output CD4+ and/or CD8+ T cells. In particular embodiments, a composition of enriched CD4+ T cells, such as engineered CD4+ T cells, that has been cultivated is an output composition of enriched CD4+ T cells. In some embodiments, a composition of enriched CD8+ T cells, such as engineered CD8+ T cells, that has been cultivated is an output composition of enriched CD8+ T cells.

In some embodiments, the cells are cultivated under conditions that promote proliferation and/or expansion in presence of one or more cytokines. In particular embodiments, at least a portion of the cultivation is performed with constant mixing and/or perfusion, such as mixing or perfusion controlled by a bioreactor. In some embodiments, the cells are cultivated in the presence or one or more cytokines and with a surfactant, e.g., poloxamer, such as poloxamer 188, to reduce shearing and/or shear stress from constant mixing and/or perfusion. In some embodiments, a composition of enriched CD4+ T cells, such as engineered CD4+ T cells, is cultivated in the presence of recombinant IL-2, IL-7, IL-15, and poloxamer, wherein at least a portion of the cultivating is performed with constant mixing and/or perfusion. In certain embodiments, a composition of enriched CD8+ T cells, such as engineered CD8+ T cells, is cultivated in the presence of recombinant IL-2, IL-15, and poloxamer, wherein at least a portion of the cultivating is performed with constant mixing and/or perfusion. In some embodiments, the cultivation is performed until the cells reach as threshold expansion of at least 4-fold e.g., as compared to the start of the cultivation.

Monitoring Cells During Cultivation

In some embodiments, the cells are monitored during the cultivation step. Monitoring may be performed, for example, to ascertain (e.g., measure, quantify) cell morphology, cell viability, cell death, and/or cell concentration (e.g., viable cell concentration). In some embodiments, the monitoring is performed manually, such as by a human operator. In some embodiments, the monitoring is performed by an automated system. The automated system may require minimal or no manual input to monitor the cultivated cells. In some embodiments, the monitoring is performed both manually and by an automated system.

In certain embodiments, the cells are monitored by an automated system requiring no manual input. In some embodiments, the automated system is compatible with a bioreactor, for example a bioreactor as described herein, such that cells undergoing cultivation can be removed from the bioreactor, monitored, and subsequently returned to the bioreactor. In some embodiments, the monitoring and cultivation occur in a closed loop configuration. In some aspects, in a closed loop configuration, the automated system and bioreactor remain sterile. In embodiments, the automated system is sterile. In some embodiments, the automated system is an in-line system.

In some embodiments, the automated system includes the use of optical techniques (e.g., microscopy) for detecting cell morphology, cell viability, cell death, and/or cell concentration (e.g., viable cell concentration). Any optical technique suitable for determining, for example, cell features, viability, and concentration are contemplated herein. Non-limiting examples of useful optical techniques include bright field microscopy, fluorescence microscopy, differential interference contrast (DIC) microscopy, phase contrast microscopy, digital holography microscopy (DHM), differential digital holography microscopy (DDHM), or a combination thereof. Differential digital holography microscopy, DDHM, and differential DHM may be used herein interchangeably. In certain embodiments, the automated system includes a differential digital holography microscope. In certain embodiments, the automated system includes a differential digital holography microscope including illumination means (e.g., laser, led). Descriptions of DDHM methodology and use may be found, for example, in U.S. Pat. No. 7,362,449; EP 1,631,788; U.S. Pat. Nos. 9,904,248; and 9,684,281, which are incorporated herein by reference in their entirety.

DDHM permits label-free, non-destructive imaging of cells, resulting in high-contrast holographic images. The images may undergo object segmentation and further analysis to obtain a plurality of morphological features that quantitatively describe the imaged objects (e.g., cultivated cells, cellular debris). As such, various features (e.g., cell morphology, cell viability, cell concentration) may be directly assessed or calculated from DDHM using, for example, the steps of image acquisition, image processing, image segmentation, and feature extraction. In some embodiments, the automated system includes a digital recording device to record holographic images. In some embodiments, the automated system includes a computer including algorithms for analyzing holographic images. In some embodiments, the automated system includes a monitor and/or computer for displaying the results of the holographic image analysis. In some embodiments, the analysis is automated (i.e., capable of being performed in the absence of user input). An example of a suitable automated system for monitoring cells during the cultivating step includes, but is not limited to, Ovizio iLine F (Ovizio Imaging Systems NV/SA, Brussels, Belgium).

In certain embodiments, the monitoring is performed continuously during the cultivation step. In some embodiments, the monitoring is performed in real-time during the cultivation step. In some embodiments, the monitoring is performed at discrete time points during the cultivation step. In some embodiments, the monitoring is performed at least every 15 minutes for the duration of the cultivating step. In some embodiments, the monitoring is performed at least every 30 minutes for the duration of the cultivating step. In some embodiments, the monitoring is performed at least every 45 minutes for the duration of the cultivating step. In some embodiments, the monitoring is performed at least every hour for the duration of the cultivating step. In some embodiments, the monitoring is performed at least every 2 hours for the duration of the cultivating step. In some embodiments, the monitoring is performed at least every 4 hours for the duration of the cultivating step. In some embodiments, the monitoring is performed at least every 6 hours for the duration of the cultivating step. In some embodiments, the monitoring is performed at least every 8 hours for the duration of the cultivating step. In some embodiments, the monitoring is performed at least every 10 hours for the duration of the cultivating step. In some embodiments, the monitoring is performed at least every 12 hours for the duration of the cultivating step. In some embodiments, the monitoring is performed at least every 14 hours for the duration of the cultivating step. In some embodiments, the monitoring is performed at least every 16 hours for the duration of the cultivating step. In some embodiments, the monitoring is performed at least every 18 hours for the duration of the cultivating step. In some embodiments, the monitoring is performed at least every 20 hours for the duration of the cultivating step. In some embodiments, the monitoring is performed at least every 22 hours for the duration of the cultivating step. In some embodiments, the monitoring is performed at least once a day for the duration of the cultivating step. In some embodiments, the monitoring is performed at least once every second day for the duration of the cultivating step. In some embodiments, the monitoring is performed at least once every third day for the duration of the cultivating step. In some embodiments, the monitoring is performed at least once every fourth day for the duration of the cultivating step. In some embodiments, the monitoring is performed at least once every fifth day for the duration of the cultivating step. In some embodiments, the monitoring is performed at least once every sixth day for the duration of the cultivating step. In some embodiments, the monitoring is performed at least once every seventh day for the duration of the cultivating step. In some embodiments, the monitoring is performed at least once every eighth day for the duration of the cultivating step. In some embodiments, the monitoring is performed at least once every ninth day for the duration of the cultivating step. In some embodiments, the monitoring is performed at least once every tenth day for the duration of the cultivating step. In some embodiments, the monitoring is performed at least once during the cultivating step.

In some embodiments, features of the cells that can be determined by the monitoring, including using optical techniques such as DHM or DDHM, include cell viability, cell concentration, cell number and/or cell density. In some embodiments, cell viability is characterized or determined. In some embodiments, cell concentration, density and/or number is characterized or determined. In some embodiments, viable cell concentration, viable cell number and/or viable cell density is characterized or determined. In some embodiments, the cultivated cells are monitored by the automated system until a threshold of expansion is reached, such as described above. In some embodiments, once a threshold of expansion is reached, the cultivated cells are harvested, such as by automatic or manual methods, for example, by a human operator. The threshold of expansion may depend on the total concentration, density and/or number of cultured cells determined by the automated system. Alternatively, the threshold of expansion may depend on the viable cell concentration, density and/or number.

In some embodiments, the harvested cells are formulated as described, such as in the presence of a pharmaceutically acceptable carrier. In some embodiments, the harvested cells are formulated in the presence of a cryoprotectant.

E. Formulating the Cells

In some embodiments, the provided methods for manufacturing, generating or producing a cell therapy and/or engineered cells may include formulation of cells, such as formulation of genetically engineered cells resulting from the provided processing steps prior to or after the incubating, engineering, and cultivating, and/or one or more other processing steps as described. In some embodiments, the provided methods associated with formulation of cells include processing transduced cells, such as cells transduced and/or expanded using the processing steps described above, in a closed system. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders, or in detection, diagnostic, and prognostic methods.

In some cases, the cells are processed in one or more steps (e.g. carried out in the centrifugal chamber and/or closed system) for manufacturing, generating or producing a cell therapy and/or engineered cells may include formulation of cells, such as formulation of genetically engineered cells resulting from the provided transduction processing steps prior to or after the culturing, e.g. cultivation and expansion, and/or one or more other processing steps as described. In some cases, the cells can be formulated in an amount for dosage administration, such as for a single unit dosage administration or multiple dosage administration. In some embodiments, the provided methods associated with formulation of cells include processing transduced cells, such as cells transduced and/or expanded using the processing steps described above, in a closed system.

In certain embodiments, one or more compositions of enriched T cells, such as engineered and cultivated T cells, e.g. output T cells, are formulated. In particular embodiments, one or more compositions of enriched T cells, such as engineered and cultivated T cells, e.g. output T cells, are formulated after the one or more compositions have been engineered and/or cultivated. In particular embodiments, the one or more compositions are input compositions. In some embodiments, the one or more input compositions have been previously cryofrozen and stored, and are thawed prior to the incubation.

In certain embodiments, the one or more compositions of enriched T cells, such as engineered and cultivated T cells, e.g. output T cells, are or include two separate compositions, e.g., separate engineered and/or cultivated compositions, of enriched T cells. In particular embodiments, two separate compositions of enriched T cells, e.g., two separate compositions of enriched CD4+ T cells and CD8+ T cells selected, isolated, and/or enriched from the same biological sample, separately engineered and separately cultivated, are separately formulated. In certain embodiments, the two separate compositions include a composition of enriched CD4+ T cells, such as a composition of engineered and/or cultivated CD4+ T cells. In particular embodiments, the two separate compositions include a composition of enriched CD8+ T cells, such as a composition of engineered and/or cultivated CD8+ T cells. In some embodiments, two separate compositions of enriched CD4+ T cells and enriched CD8+ T cells, such as separate compositions of engineered and cultivated CD4+ T cells and engineered and cultivated CD8+ T cells, are separately formulated. In some embodiments, a single composition of enriched T cells is formulated. In certain embodiments, the single composition is a composition of enriched CD4+ T cells, such as a composition of engineered and/or cultivated CD4+ T cells. In some embodiments, the single composition is a composition of enriched CD4+ and CD8+ T cells that have been combined from separate compositions prior to the formulation.

In some embodiments, separate compositions of enriched CD4+ and CD8+ T cells, such as separate compositions of engineered and cultivated CD4+ and CD8+ T cells, are combined into a single composition and are formulated. In certain embodiments, separate formulated compositions of enriched CD4+ and enriched CD8+ T cells are combined into a single composition after the formulation has been performed and/or completed. In particular embodiments, separate compositions of enriched CD4+ and CD8+ T cells, such as separate compositions of engineered and cultivated CD4+ and CD8+ T cells, are separately formulated as separate compositions.

In some embodiments, the composition of enriched CD4+ T cells, such as an engineered and cultivated CD4+ T cells, e.g. output CD4+ T cells, that is formulated, includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In some embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD4+ T cells that express a recombinant receptor and/or have been transduced or transfected with the recombinant polynucleotide. In certain embodiments, the composition of enriched CD4+ T cells, such as an engineered and cultivated CD4+ T cells, e.g. output CD4+ T cells, that is formulated includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells, such as an engineered and cultivated CD8+ T cells, e.g. output CD8+ T cells, that is formulated, includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD8+ T cells that express the recombinant receptor and/or have been transduced or transfected with the recombinant polynucleotide. In certain embodiments, the composition of enriched CD8+ T cells, such as an engineered and cultivated CD8+ T cells, e.g. output CD8+ T cells, that is incubated under stimulating conditions includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In certain embodiments, the formulated cells are output cells. In some embodiments, a formulated composition of enriched T cells, such as a formulated composition of engineered and cultivated T cells, is an output composition of enriched T cells. In particular embodiments, the formulated CD4+ T cells and/or formulated CD8+ T cells are the output CD4+ and/or CD8+ T cells. In particular embodiments, a formulated composition of enriched CD4+ T cells is an output composition of enriched CD4+ T cells. In some embodiments, a formulated composition of enriched CD8+ T cells is an output composition of enriched CD8+ T cells.

In some embodiments, cells can be formulated into a container, such as a bag or vial. In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

Particular embodiments contemplate that cells are in a more activated state at early stages during the cultivation than at later stages during the cultivation. Further, in some embodiments, it may be desirable to formulate cells that are in a less activated state than the peak activation that occurs or may occur during the cultivation. In certain embodiments, the cells are cultivated for a minimum duration or amount of time, for example, so that cells are harvested in a less activated state than if they were formulated at an earlier time point during the cultivation, regardless of when the threshold is achieved. In some embodiments, the cells are cultivated between 1 day and 3 days after the threshold cell count, density, and/or expansion has been achieved during the cultivation. In certain embodiments, the cells achieve the threshold cell count, density, and/or expansion and remain cultivated for a minimum time or duration prior to the formulation. In some embodiments, cells that have achieved the threshold are not formulated until they have been cultivated for a minimum duration and/or amount of time, such as a minimum time or duration of between 1 day and 14 days, 2 days and 7 days, or 3 days and 6 days, or a minimum time or duration of the cultivation of or of about 2 days, 3 days, 4 days, 5 days, 6 days, 7 days, or more than 7 days. In some embodiments, the minimum time or duration of the cultivation is between 3 days and 6 days.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryofrozen or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryofrozen or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of enriched T cells, e.g., T cells that have been stimulated, engineered, and/or cultivated, are formulated, cryofrozen, and then stored for an amount of time. In certain embodiments, the formulated, cryofrozen cells are stored until the cells are released for infusion. In particular embodiments, the formulated cryofrozen cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryofrozen and stored for, for about, or for less than 1 days, 2 days, 3 days, 4 days, 5 days, 6 days, or 7 days. In certain embodiments, the cells are thawed and administered to a subject after the storage. In certain embodiments, the cells are stored for or for about 5 days.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from 10 mL to 1000 mL or from about 10 mL to about 1000 mL, such as at least or about at least or about 50 mL, 100 mL, 200 mL, 300 mL, 400 mL, 500 mL, 600 mL, 700 mL, 800 mL, 900 mL or 1000 mL.

In some embodiments, such processing steps for formulating a cell composition is carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as the vials of the biomedical material vessels described herein, that is operably linked as part of a closed system with the centrifugal chamber. In some embodiments, the biomedical material vessels are configured for integration and or operable connection and/or is integrated or operably connected, to a closed system or device that carries out one or more processing steps. In some embodiments, the biomedical material vessel is connected to a system at an output line or output position. In some cases, the closed system is connected to the vial of the biomedical material vessel at the inlet tube. Exemplary close systems for use with the biomedical material vessels described herein include the Sepax® and Sepax® 2 system.

In some embodiments, the closed system, such as associated with a centrifugal chamber or cell processing system, includes a multi-port output kit containing a multi-way tubing manifold associated at each end of a tubing line with a port to which one or a plurality of containers can be connected for expression of the formulated composition. In some aspects, a desired number or plurality of vials, can be sterilely connected to one or more, generally two or more, such as at least 3, 4, 5, 6, 7, 8 or more of the ports of the multi-port output. For example, in some embodiments, one or more containers, e.g., biomedical material vessels, can be attached to the ports, or to fewer than all of the ports. Thus, in some embodiments, the system can effect expression of the output composition into a plurality of vials of the biomedical material vessels.

In some aspects, cells can be expressed to the one or more of the plurality of output containers, e.g., vials of the biomedical material vessels, in an amount for dosage administration, such as for a single unit dosage administration or multiple dosage administration. For example, in some embodiments, the vials of the biomedical material vessels, may each contain the number of cells for administration in a given dose or fraction thereof. Thus, each vial, in some aspects, may contain a single unit dose for administration or may contain a fraction of a desired dose such that more than one of the plurality of vials, such as two of the vials, or 3 of the vials, together constitutes a dose for administration.

Thus, the vials described herein, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags of vials individually comprises a unit dose of the cells. Thus in some embodiments, each of the containers comprises the same or approximately or substantially the same number of cells. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each container, e.g. bag or vial, is 10 mL to 100 mL, such as at least or about at least or about 20 mL, 30 mL, 40 mL, 50 mL, 60 mL, 70 mL, 80 mL, 90 mL or 100 mL. In some embodiments, the cells in the container, e.g. bag or vials, can be cryopreserved. In some embodiments, the container, e.g. vials, can be stored in liquid nitrogen until further use.

In some embodiments, such cells produced by the method, or a composition comprising such cells, are administered to a subject for treating a disease or condition.

F. Exemplary Features of the Process and/or Output Composition

In particular embodiments, the provided methods are used in connection with a process that produces or generates one or more output compositions of enriched T cells from one or more input compositions and/or from a single biological sample. In certain embodiments, the one or more output compositions contain cells that express a recombinant receptor, e.g., a TCR or a CAR. In particular embodiments, the cells of the output compositions are suitable for administration to a subject as a therapy, e.g., an autologous cell therapy. In some embodiments, the one or more output composition is a composition of enriched CD4+ and CD8+ T cells. In certain embodiments, the one or more output compositions include a composition of enriched CD4+ T cells. In particular embodiments, the one or more output compositions include a composition of enriched CD8+ T cells. In some embodiments, the one or more output compositions include an output composition of enriched CD4+ T cells and an output composition of enriched CD8+ T cells.

In some embodiments, the provided methods are used in connection with an entire process for generating or producing output cells and/or output compositions of enriched T cells, such as a process including some or all of the steps of: collecting or obtaining a biological sample; isolating, selecting, or enriching input cells from the biological sample; cryofreezing and storing the input cells; thawing and/or incubating the input cells under stimulating conditions; engineering the stimulated cells to express or contain a recombinant polynucleotide, e.g., a polynucleotide encoding a recombinant receptor such as a CAR; cultivating the engineered cells to a threshold amount, density, or expansion; formulating the cultivated cells in an output composition; and/or cryofreezing and storing the formulated output cells until the cells are released for infusion and/or administration to a subject. In some embodiments, the entire process is performed with a single composition of enriched T cells, e.g., CD4+ T cells or CD4+ and CD8+ T cells. In particular embodiments, the entire process is performed with two or more compositions of enriched T cells, e.g., a composition of enriched CD4+ T cells and a composition of enriched CD8+ T cells. In certain embodiments, the process is performed with two or more input compositions of enriched T cells that are combined prior to and/or during the process to generate or produce a single output composition of enriched T cells.

In some embodiments, at least one separate composition of enriched CD4+ T cells and at least one separate composition of enriched CD8+ T cells are isolated, selected, and/or enriched from the same biological sample (e.g., the same apheresis or leukapheresis product containing autologous PBMCs) that is obtained, collected, and/or taken from the same subject, such as a patient or healthy donor. In one aspect, the same biological sample is first subjected to positive selection of CD4+ T cells, where both the negative and positive fractions are retained, and the negative fraction is further subjected to positive selection of CD8+ T cells. In another aspect, the same biological sample is first subjected to positive selection of CD8+ T cells, where both the negative and positive fractions are retained, and the negative fraction is further subjected to positive selection of CD4+ T cells. In some aspects, a separate composition of enriched CD4+ T cells and a separate composition of enriched CD8+ T cells from the same donor are separately frozen, e.g., cryofrozen or cryopreserved in a cryopreservation media. In some aspects, the separately cryopreserved cell compositions are stored and/or shipped in separate containers. In other aspects, the cryopreserved cell compositions are thawed and optionally washed. In some aspects, two or more separate compositions of enriched T cells, at least one being a composition of enriched CD4+ T cells and at least one being a separate composition of enriched CD8+ T cells from the same donor, are separately activated and/or stimulated by contacting with a stimulatory reagent (e.g., by incubation with CD3/CD28 conjugated magnetic beads for T cell activation), and the volumes of the separate enriched cell compositions after activation/stimulation are optionally adjusted, e.g., reduced, in order to achieve a target volume. In some aspects, the activated/stimulated enriched cell compositions are separately engineered, transduced, and/or transfected, e.g., using the same retroviral vector encoding a recombinant protein (e.g. CAR), to express the same recombinant protein in the separate CD4+ T cell and CD8+ T cell compositions. In some aspects, the volumes of the separate enriched cell compositions after the engineering are optionally adjusted, e.g., reduced, in order to achieve a target volume. In some aspects, the method may comprise removing the stimulatory reagent, e.g., magnetic beads, from the separate compositions. In some aspects, the composition containing the separately engineered CD4+ T cells and the composition containing the separately engineered CD8+ T cells are separately cultivated, e.g., for expansion of the CD4+ or CD8+ T cell population therein. In certain embodiments, the separate cell compositions after cultivation are separately harvested and/or collected and/or separately formulated, e.g., by washing the cell compositions in a formulation buffer. In certain embodiments, at least one separately formulated enriched CD4+ T cell composition and at least one separately formulated enriched CD8+ T cell composition are frozen, e.g., cryofrozen or cryopreserved in a cryopreservation media. In some aspects, the separately cryopreserved formulations may be stored and/or shipped in separate containers. In some aspects, at least one CD4+ T cell formulation and at least one CD8+ T cell formulation originated from the same donor and expressing the same recombination protein (e.g., CAR) are separately administered to a subject in need thereof. In some aspects, the separate administrations are carried out simultaneously, or sequentially, in any order.

In some embodiments, an output composition of enriched CD4+ T cells includes at least 60%, at least 65%, at least 70%, at least 75%, at least 80%, at least 85%, at least 90%, at least 95%, at least 98%, at least 99%, at least 99.5%, at least 99.9%, or at or about 100% CD4+ T cells. In certain embodiments, the output composition includes at least 30%, at least 40%, at least 50%, at least 60%, at least 70%, at least 80%, at least 90%, at least 95%, at least 98%, at least 99%, at least 99.5%, at least 99.9%, or at or about 100% CD4+ T cells that express the recombinant receptor and/or have been transduced or transfected with the recombinant polynucleotide. In certain embodiments, the output composition of enriched CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, an output composition of enriched CD8+ T cells includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In particular embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD8+ T cells that express the recombinant receptor and/or have been transduced or transfected with the recombinant polynucleotide. In certain embodiments, the output composition of enriched CD8+ T cells includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, the process associated with the provided methods is compared to an exemplary and/or alternative process. In particular embodiments, the alternative and/or exemplary process may differ in one or more specific aspects, but otherwise contains similar or the same features, aspects, steps, stages, reagents, and/or conditions of the process associated with the provided methods. In some embodiments, the alternative and/or exemplary process is similar or the same as the process associated with the provided methods, with the exception that: compositions of enriched CD4+ T cells are not incubated and/or cultivated with recombinant IL-2; the cells are incubated with a stimulatory reagent at a ratio of greater than 3 (or 3:1) stimulatory reagent to cells; the stimulatory reagent is not removed or separated from the cells prior to the cultivation and/or within 6, 5, or 4 days from the start of the incubation under stimulating conditions; cells are not incubated in the presence of an antioxidant; cells are not engineered with a low amount or concentration, e.g., between 1 µg/ml and 50 µg/ml, of a polycation; the cells are not cultivated with surfactant; and/or cells are not cultivated under conditions with consistent perfusion and/or mixing.

In certain embodiments, the process is completed within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days. In certain embodiments, the process is completed within 21 days. In some embodiments, the process is deemed completed when the composition is harvested and/or formulated; the composition is ready to be harvested and/or formulated; the composition has reached a target threshold value for harvest; and/or the composition is released and/or ready for post-formulation testing.

In some embodiments, the process is completed within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the start or collection of the biological sample and/or the isolation, selection, stimulation, and/or enrichment of input cells from the biological sample to when the output cells are released for infusion; the output cells are harvested and/or formulated; the output cells are ready to be harvested and/or formulated; the output cells have reached a target threshold value for harvest; and/or the output cells are released and/or ready for post-formulation testing, including the storage times for cryofrozen compositions. In particular embodiments, when the process is performed on more than one composition of enriched T cells obtained from the same biological sample, the process is complete when at least one representative sample of each and every composition from the same biological sample has completed the process. In some embodiments, the process is completed within 21 days as measured from the start or collection of the biological sample and/or the isolation, selection, stimulation, and/or enrichment of input cells from the biological sample to when the output cells are released for infusion.

In some embodiments, the process is completed within a duration and/or amount of time of or of about 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, or less than 9 days, as measured from the start or collection of the biological sample, e.g., an apheresis or leukapheresis sample, to when the output composition is administered or ready to be administered to the subject, the output cells are harvested and/or formulated; the output cells are ready to be harvested and/or formulated; the output cells have reached a target threshold value for harvest; and/or the output composition is released for testing, including the storage times for cryofrozen compositions. In some embodiments, the process is completed within 21 days as measured from the start or collection of the biological sample to when the output cells are ready to be and/or are released for infusion into to a subject.

In certain embodiments, the duration and/or amount of time to complete the process is between 10 days and 35 days, between 12 days and 33 days, between 17 days and 25 days, between, or between 19 days and 23 days, e.g., when storage time is included, for samples obtained from one subject, for samples from a number of subjects, and/or for at least a certain percentage of subjects such as those having a particular indication or disease such as at least 90, 91%, 92%, 93%, 94%, 95 or greater % of such subjects. In certain embodiments, the median amount of time and/or duration to complete the process (such as when measured from taking of the sample from the subject to when the product is ready or released for infusion to the subject) on a plurality of starting compositions from different biological samples is between 15 days and 27 days, between 17 days and 25 days, or between 19 days and 23 days or is or is about 19 days, 20 days, 21 days, 22 days, or 23 days, e.g., when storage time is included. In particular embodiments, the mean amount of time and/or duration to complete the process on a plurality of compositions from different biological samples is between 15 days and 27 days, between 17 days and 25 days, or between 19 days and 23 days or is or is about 19 days, 20 days, 21 days, 22 days, or 23 days, e.g., when transport and/or storage time is included. In particular embodiments, the duration to complete the process on a plurality of compositions from different biological samples is between 15 days and 27 days, between 17 days and 25 days, or between 19 days and 23 days or is or is about 19 days, 20 days, 21 days, 22 days, or 23 days, e.g., when storage time is included. In certain embodiments, the duration of the process, such as across a range of starting compositions, such as from different biological samples and/or subjects with different diseases, is less than or no more than 21 days; in some aspects, such result is achieved with a greater than 85%, 90%, 91%, 92%, 93%, 94%, or 95% rate of success in manufacturing product across such samples or patients.

In some embodiments, the duration and/or amount of time to complete the process is between 7 days and 27 days, between 9 days and 25 days, between 11 days and 18 days, between, or between 11 days and 15 days when the storage time of cryofrozen cells is not included or factor in. In certain embodiments, the median amount of time and/or duration required to complete the process on a plurality of compositions from different biological samples is between 7 days and 27 days, between 9 days and 25 days, between 11 days and 18 days, between, or between 11 days and 15 days, or is or is about 11 days, 12 days, 13 days, 14 days, or 15 days when the storage time of cryofrozen cells is not included or factor in. In particular embodiments, the mean amount of time and/or duration required to complete the process on a plurality of compositions from different biological samples is between 7 days and 27 days, between 9 days and 25 days, between 11 days and 18 days, between, or between 11 days and 15 days, or is or is about 11 days, 12 days, 13 days, 14 days, or 15 days when the storage time of cryofrozen cells is not included or factor in. In some embodiments, the mean amount of time and/or duration required to complete the process on a plurality of compositions from different biological samples is less than 21 days when the storage time of cryofrozen cells is not included.

In particular embodiments, the amount of time to complete the process on at least 10% of a plurality of compositions obtained from different sources, e.g., different biological samples and/or different input compositions of enriched T cells isolated, enriched, and/or selected from different biological samples, is between 7 days and 18 days, between 10 days and 17 days, or between 11 days and 15 days or is or is about 11 days, 12 days, or 13 days when the storage time of cryofrozen cells is not included or factor in. In particular embodiments, the amount of time required to complete the process on at least 50% of a plurality of compositions from different biological sources is between 7 days and 27 days, between 9 days and 25 days, between 11 days and 18 days, between, or between 11 days and 15 days, or is or is about 11 days, 12 days, 13 days, 14 days, or 15 days when the storage time of cryofrozen cells is not included or factor in. In certain embodiments, the amount of time required to complete the process on at least 90% of a plurality of compositions from different sources is between 7 days and 27 days, between 9 days and 25 days, between 11 days and 18 days, between, or between 11 days and 15 days, or is or is about 11 days, 12 days, 13 days, 14 days, or 15 days when the storage time of cryofrozen cells is not included or factor in. In certain embodiments, the amount of time required to complete the process on at least 90% of a plurality of compositions from different sources is less than 21 days when the storage time of cryofrozen cells is not included.

In some embodiments, the duration and/or amount of time during the process that occurs from the start or initiation of the incubation under stimulating conditions to the time at which a threshold amount, density, and/or degree of expansion (such as a particular fold expansion such as four-fold or a particular dose) is achieved during cultivation is between 5 days and 25 days, between 7 days and 18 days, between 8 and 15 days, between 8 and 14 days, or between 8 and 15 days, such as between 8 and 13 days or between 9 days and 13 days. In certain embodiments, the median amount of time and/or duration of the process that occurs from the start or initiation of the incubation to the time at which the threshold is achieved is between 5 days and 25 days, between 7 days and 18 days, or between 9 days and 13 days, or is or is about 8 days, 9 days, 10 days, 11 days, 12 days, or 13 days. In particular embodiments, The mean amount of time and/or duration of the process that occurs from the start or initiation of the incubation to the time at which the threshold is achieved is between 5 days and 25 days, between 7 days and 18 days, between 8 days and 13 days, or between 9 days and 13 days, or is or is about 8 days, 9 days, 10 days, 11 days, 12 days, or 13 days.

In certain embodiments, the duration and/or amount of time during the process that occurs from the start or initiation of the incubation under stimulating conditions to the time at which a the output cells are collected, formulated, and/or cryofrozen is between 5 days and 25 days, between 7 days and 18 days between 8 and 15 days, between 8 and 14 days, or between 8 and 15 days, such as between 8 and 13 days or between 9 days and 13 days. In certain embodiments, the median amount of time and/or duration of the process that occurs from the start or initiation of the incubation to the time at which the threshold is achieved is between 5 days and 25 days, between 7 days and 18 days, or between 9 days and 13 days, or is or is about 8 days, 9 days, 10 days, 11 days, 12 days, or 13 days. In particular embodiments, the mean amount of time and/or duration of the process that occurs from the start or initiation of the incubation to the time at which the threshold is achieved is between 5 days and 25 days, between 7 days and 18 days, between 8 days and 13 days, or between 9 days and 13 days, or is or is about 8 days, 9 days, 10 days, 11 days, 12 days, or 13 days. In some embodiments, the duration and/or amount of time during the process that occurs from the start or initiation of the incubation under stimulating conditions to the time at which a the output cells are collected, formulated, and/or cryofrozen is between 9 days and 15 days for, for about, or for at least 85%, 90%, 95% of subjects.

In some embodiments, the duration and/or amount of time during the process that occurs from the isolation, enrichment, and/or selection of the compositions of enriched CD4+ and CD8+ cells from a biological sample, e.g., apheresis and/or leukapheresis, to the time at which a the output cells are collected, formulated, and/or cryofrozen is between 5 days and 25 days, between 7 days and 18 days, between 8 and 19 days, between 8 and 14 days, or between 10 and 16 days. In certain embodiments, the output cells are collected, formulated, and harvested between 10 and 16 days after the isolation, enrichment, and/or selection for at least 85%, at least 90%, at least 95%, of the subjects.

In some embodiments, the duration and/or amount of time of the process from the start or initiation of the incubation under stimulating conditions to the time at which the threshold amount, density, and/or expansion is achieved during cultivation is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% less time than that of an exemplary and/or alternative process. In particular embodiments, the duration and/or amount of time during the process from the start or initiation of the incubation under stimulating conditions to the time at which the threshold amount, density, and/or expansion is achieved during cultivation is shorter than the duration and/or amount of time of an exemplary and/or alternative process by, by about, or by at least 0.5 days, 1 day, 1.5 days, 2 days, 3 days, 4 days, 5 days, 6 days, 7 days, 8 days, 9 days, 10 days, 11 days, 12 days, 13 days, 14 days, or more than 14 days.

In certain embodiments, the amount of time required for at least 10% of a plurality of compositions from different biological samples to reach the threshold amount, density, and/or expansion from the start or initiation of the incubation under stimulating conditions to the time that the threshold amount, density, and/or expansion is achieved during the cultivation is between 5 days and 20 days, between 7 days and 15 days, or between 9 days and 11 days, or is or is about 7 days, 8 days, 9 days, or 10 days. In particular embodiments, the amount of time required for at least 50% of a plurality of compositions from different biological samples to reach the threshold amount, density, and/or expansion from the start or initiation of the incubation under stimulating conditions is s between 5 days and 25 days, between 7 days and 18 days, or between 9 days and 13 days, or is or is about 7 days, 8 days, 9 days, 10 days, 11 days, 12 days, of 13 days. In some embodiments, the amount of time required for at least 90% of a plurality of compositions from different biological samples to reach the threshold amount, density, and/or expansion from the start or initiation of the incubation under stimulating conditions is s between 5 days and 25 days, between 7 days and 18 days, or between 9 days and 13 days, or is or is about 7 days, 8 days, 9 days, 10 days, 11 days, 12 days, of 13 days.

In some embodiments, the methods provided herein are used in connection with a process that generates genetically engineered T cells over an amount of time that is less than an exemplary alternative process. In some embodiments, the short duration of the process may increase the rate, instances, and/or probability of generating a composition of engineered T cells that can be administered to a subject for cell therapy. In certain embodiments, manufacturing protocols for therapeutic cell compositions may require that the cell compositions are produced and released for infusion within a certain amount of time. Thus, in some embodiments, the shorter duration of the process could be expected to reduce or eliminate process failures that would occur from cell compositions that fail to expand within the required amount of time.

In some embodiments of the provided process herein, the amount of time required for a cell composition to reach a threshold amount, density, and/or expansion from the start or initiation of the incubation under stimulating conditions to the time that the threshold amount, density, and/or expansion is achieved during the cultivation is between about 9 days and about 13 days, or between 9 days and 13 days, or 9 days, while in the alternative process, the corresponding amount of time is between about 12 days and about 23 days, or between 12 days and 23 days, or about 15 days, or 15 days. In some embodiments, the amount of time required for sample collection, isolation of cell compositions, and cryofreezing in both the provided process and the alternative process is between about 1 day and about 2 days, or between 1 day and 2 days. In some embodiments, cryofrozen cell compositions in both the provided process and the alternative process are stored for about 3 days or for 3 days. In some embodiments, the amount of time required from when the threshold amount, density, and/or expansion is achieved or from when the cell compositions are harvested to when the output composition is administered or ready to be administered to the subject in both the provided process and the alternative process is or about 5 days. In some embodiments, the total amount of time required from sample collection to when the output composition is administered or ready to be administered to the subject in the provided process is or about 19 days, while in the alternative process, the corresponding total amount of time is or about 25 days.

In certain embodiments, the total amount of time required for 50% or about 50% of a plurality of cell compositions from sample collection to when the output compositions are administered or ready to be administered to the subject (which would require the cell compositions to reach the threshold amount, density, and/or expansion) in the provided process is or about 19 days, while in the alternative process, the corresponding total amount of time is or about 25 days. In certain embodiments, the total amount of time required for 80% or about 80% of a plurality of cell compositions from sample collection to when the output compositions are administered or ready to be administered to the subject (which would require the cell compositions to reach the threshold amount, density, and/or expansion) in the provided process is or about 21 days, while in the alternative process, the corresponding total amount of time is or about 27 days. In certain embodiments, the total amount of time required for 90% or about 90% of a plurality of cell compositions from sample collection to when the output compositions are administered or ready to be administered to the subject (which would require the cell compositions to reach the threshold amount, density, and/or expansion) in the provided process is or about 21 days, while in the alternative process, the corresponding total amount of time is or about 33 days.

from the start or initiation of the incubation under stimulating conditions to the time that the threshold amount, density, and/or expansion is achieved during the cultivation is In certain embodiments, the provided methods are used in connection with successfully generating or producing output compositions of engineered T cells that are suitable for use in cell therapy. In some embodiments, an output composition is successfully generated if the cells of the composition achieve the threshold cell count, density, and/or expansion during cultivation. In particular embodiments, an output composition is successfully generated if the cells of at least 40%, 50%, 60%, 70%, 80%, 85%, 90%, or 95% of the cells express the recombinant receptor. In particular embodiments, an output composition is successfully produced or generated if the output composition is suitable for therapeutic use, e.g., as an autologous cell therapy. In particular embodiments, an output composition is suitable for therapeutic use if the cells of the output compositions meet one or more criteria. In some embodiments, the cells and/or cell compositions that are suitable for use in cell therapy are sterile (e.g., lack detectable microbial contamination), free of endotoxin, free of replication competent virus, viable, active (e.g., possess cytolytic activity and/or release cytokine in response to a target antigen), and/or contain a high portion of cells that express the recombinant receptor.

In particular embodiments, the provided methods have an at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% probability or likelihood of successfully generating or producing an output composition of enriched T cells from a composition of input cells and/or a biological sample. In certain embodiments, the probability or likelihood is between 85% and 100%, between 90% and 95%, or between 92% and 94%. In certain embodiments, the provided methods successfully generate or produce an output composition of enriched T cells from at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of compositions and/or samples from a plurality of compositions of input cells and/or of a plurality of biological samples. In some embodiments, the provided methods successfully generate or produce an output composition of enriched T cells from between 85% and 100%, between 90% and 95%, or between 92% and 94% of compositions and/or samples from a plurality of compositions of input cells and/or of a plurality of biological samples.

In certain embodiments, the process is completed within 21 days and has a success rate of at least 85%, 90%, 95%, or greater. In some embodiments, the process is considered to be complete when the output cells are administered and/or ready to be administered to the subject. In some embodiments, the process is considered to be complete when the output composition has been harvested and/or is ready to be tested and/or evaluated, e.g., such as for a release assay.

In particular embodiments, the process associated with the provided methods has a probability or likelihood of successfully generating or producing an output composition that is greater than the probability or likelihood for an alternative and/or exemplary process of successfully generating or producing an output composition by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In certain embodiments, the process associated with the provided methods has a probability or likelihood of successfully generating or producing an output composition of enriched CD4+ T cells that is greater than the probability or likelihood for an alternative and/or exemplary process of successfully generating or producing an output composition of enriched CD4+ T cells by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In particular embodiments, the process associated with the provided methods has a probability or likelihood of successfully generating or producing an output composition of enriched CD8+ T cells that is greater than the probability or likelihood for an alternative and/or exemplary process of successfully generating or producing an output composition of enriched CD8+ T cells by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In some embodiments, the one or more output compositions generated or produced in connection with the provided methods contain cells expressing a recombinant receptor, e.g., a TCR or a CAR. In some embodiments, expressing a recombinant receptor may include, but is not limited to, having one or more recombinant receptor proteins localized at the cell membrane and/or cell surface, having a detectable amount of recombinant receptor protein, having a detectable amount of mRNA encoding the recombinant receptor, having or containing a recombinant polynucleotide that encodes the recombinant receptor, and/or having or containing an mRNA or protein that is a surrogate marker for recombinant receptor expression.

In some embodiments, at least 30%, at least 40%, at least 45%, at least 50%, at least 55%, at least 60%, at least 65%, at least 70%, at least 75%, at least 80%, at least 85%, at least 90%, at least 95%, at least 97%, at least 99%, or more than 99% of the cells of the one or more output compositions express the recombinant receptor. In particular embodiments, at least 40%, at least 45%, at least 50%, at least 55%, at least 60%, at least 65%, at least 70%, at least 75%, at least 80%, at least 85%, at least 90%, at least 95%, at least 97%, at least 99%, or more than 99% of the CD4+ T cells of an output composition express the recombinant receptor. In some embodiments, between 30% and 90%, between 40% and 85%, between 50% and 80%, or between 60% and 80% of the CD4+ T cells express the recombinant receptor. In particular embodiments, at least 30%, at least 40%, at least 45%, at least 50%, at least 55%, at least 60%, at least 65%, at least 70%, at least 75%, at least 80%, at least 85%, at least 90%, at least 95%, at least 97%, or at least 99% of the cells of an output composition of enriched CD4+ T cells express the recombinant receptor. In certain embodiments, between 30% and 90%, between 40% and 85%, between 50% and 80%, or between 60% and 80% of the cells of an output composition of enriched CD4+ T cells express the recombinant receptor.

In certain embodiments, at least 30%, at least 40%, at least 45%, at least 50%, at least 55%, at least 60%, at least 65%, at least 70%, at least 75%, at least 80%, at least 85%, at least 90%, at least 95%, at least 97%, at least 99%, or more than 99% of the CD8+ T cells of an output composition express the recombinant receptor. In some embodiments, between 30% and 90%, between 40% and 85%, between 50% and 80%, or between 60% and 80% of the CD8+ T cells express the recombinant receptor. In particular embodiments, at least 30%, at least 40%, at least 45%, at least 50%, at least 55%, at least 60%, at least 65%, at least 70%, at least 75%, at least 80%, at least 85%, at least 90%, at least 95%, at least 97%, or at least 99% of the cells of an output composition of enriched CD8+ T cells express the recombinant receptor. In certain embodiments, between 30% and 90%, between 40% and 85%, between 50% and 80%, or between 60% and 80% of the cells of an output composition of enriched CD8+ T cells express the recombinant receptor.

In some embodiments, the percentage of cells of the output composition that express the recombinant receptor is greater than the percentage of cells expressing the recombinant receptor that were produced or generated by an alternative and/or exemplary process, such as by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In certain embodiments, the percentage of CD4+ T cells of the output composition that express the recombinant receptor is greater than the percentage of CD4+ T cells expressing the recombinant receptor that were produced or generated by an alternative and/or exemplary process, such as by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In some embodiments, the percentage of CD8+ T cells of the output composition that express the recombinant receptor is greater than the percentage of CD8+ T cells expressing the recombinant receptor that were produced or generated by an alternative and/or exemplary process, such as by at least 0.5%, at least 1%, at least 1.5%, at least 2%, at least 2.5%, at least 3%, at least 3.5%, at least 4.0%, at least 4.5%, at least 5%, at least 5.5%, at least 6%, at least 6.5%, at least 7%, at least 7.5%, at least 8%, at least 8.5%, at least 9%, at least 9.5%, or at least 10%, or by more than 10%.

In some embodiments, the one or more output compositions generated or produced by the provided methods contain activated cells, and/or contain cells that have or display one or more markers of activation. In particular embodiments, the cells of the output compositions produced or generated by the provided methods are more activated and/or have or display a greater amount or degree of one or more markers of activation than cells that are generated or produced by an exemplary and/or alternative process. Markers of activation may include any known marker that indicates, is correlated to, and/or is associated with an activation state in an immune cell, such as a T cell. In some embodiments, markers of activation include, but are not limited to, increased intracellular complexity (e.g. as determined by measuring side scatter (SSC), increased cell size (e.g. as determined by measuring cell diameter and/or forward scatter (FSC), increased expression of CD27, and/or decreased expression of CD25.

In some embodiments, the output cells that are generated or produced by the provided methods are larger than the cells generated or produced by the alternative and/or exemplary process. In some embodiments, FSC and/or SSC parameters are measured and compared to a reference and/or a standard to assess the size of the cells, such by flow cytometry. In certain embodiments, the FSC parameter is measured and compared to a reference or standard to assess the size of the cells. In some embodiments, the cell diameter, e.g., the median or mean cell diameter, of the cells of the output composition is at least 0.25 µm, 0.5 µm, 0.75 µm, 1.0 µm, 1.5 µm, 2 µm, 2.5 µm, 3 µm, 3.5 µm, 4 µm, 4.5 µm, 5 µm, or more than 5 µm larger than the diameter of the cells generated or produced by the alternative and/or exemplary process.

In certain embodiments, the output cells are active and expand, and/or are capable of activation and expansion, in vivo, when administered to a subject. In particular embodiments, the output cells display features and/or characteristics that indicate and/or are associated with in vivo efficacy, activity, and/or expansion. For example, in some embodiments, such features or characters may include the expression of a protein, such as a surface protein, that is associated with activation, proliferation, and/or expansion. In some embodiments, such features or characteristic may include production or secretion of factors such as cytokines, e.g., in response to exposure to an antigen.

In certain embodiments, the output cells that are generated or produced by the provided methods have greater expression of CD25 than the cells that are generated or produced by the alternative and/or exemplary process. In some embodiments, the output CD4+ T cells have a greater expression of CD25 than CD4+ T cells that are generated or produced by the alternative and/or exemplary process. In some embodiments, at least 20%, at least 30%, at least 40%, at least 50%, at least 60%, at least 70%, at least 75%, at least 80%, at least 85%, at least 90%, at least 100%, of the cells of the output composition are positive for CD25 staining, e.g., express a detectable amount of CD25. In particular embodiments, the output composition contains a greater portion of cells that are positive for CD25 than a composition of cells produced or generated by the alternative and/or exemplary process. In some embodiments, the cells of the output composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, more CD25, e.g., as indicated by measuring the mean or median expression of CD25 in the cells of the output composition by flow cytometry, as compared to cells produced or generated by the alternative and/or exemplary process.

In some embodiments, the expression of CD27 by the output cells that are generated or produced by the provided methods is reduced compared to CD27 expression in cells that are generated or produced by the alternative and/or exemplary process. In some embodiments, a greater portion of the cells of the output composition are CD27 negative and/or have low or undetectable levels of CD27 than the portion of cells generated or produced by the alternative and/or exemplary process. In some embodiments, the expression of CD27, e.g., the mean or median expression of CD27 as measured by the flow cytometry, by the cells of the output composition is reduced by at least 1%, at least 5%, at least 10%, at least 20%, at least 30%, at least 40%, at least 50%, at least 60%, at least 70%, at least 75%, at least 80%, at least 85%, at least 90%, at least 95%, or at least 99% as compared to cells generated or produced in the alternative and/or exemplary process.

In certain embodiments, the output cells that are generated or produced by the provided methods have greater expression of markers associated with cell division than the cells that are generated or produced by the alternative and/or exemplary process. In some embodiments, the output cells express Ki67. In some embodiments, a greater portion of output CD4+ T cells express Ki67 than the portion of CD4+ T cells that are generated or produced by the alternative and/or exemplary process. In certain embodiments, a greater portion of output CD8+ T cells express Ki67 than the portion of CD8+ T cells that are generated or produced by the alternative and/or exemplary process. In particular embodiments, the output composition contains a greater portion of cells that are positive for Ki67 than a composition of cells produced or generated by the alternative and/or exemplary process. In some embodiments, at least 20%, at least 30%, at least 40%, at least 50%, at least 60%, at least 70%, at least 75%, at least 80%, at least 85%, at least 90%, at least 100%, of the cells of the output composition are positive for Ki67 staining, e.g., express a detectable amount of ki67. In some embodiments, the cells of the output composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, at least 5-fold, more Ki67, e.g., as indicated by measuring the mean or median expression of Ki67 in the cells of the output composition by flow cytometry, as compared to cells produced or generated by the alternative and/or exemplary process.

In some embodiments, the output cells have increased production and/or secretion, and/or are capable of increased production and/or secretion of one or more cytokines, e.g., in response to exposure to an antigen. In some embodiments, the output cells have increased production and/or secretion, and/or are capable of increased production and/or secretion of IFN-gamma as compared to cells that are produced or generated by an alternative and/or exemplary process. In some embodiments, CD8+ T cells of the output composition, e.g., CD8+ T cells that express the recombinant receptor, have increased production and/or secretion, and/or are capable of increased production and/or secretion of IFN-gamma as compared to cells that are produced or generated by an alternative and/or exemplary process. In some embodiments, the production or secretion by the output cells is at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold greater than production or secretion by cells produced by an alternative and/or exemplary process.

In certain embodiments, the output cells have increased production and/or secretion, and/or are capable of increased production and/or secretion of TNF-alpha as compared to cells that are produced or generated by an alternative and/or exemplary process. In some embodiments, CD8+ T cells of the output composition, e.g., CD8+ T cells that express the recombinant receptor, have increased production and/or secretion, and/or are capable of increased production and/or secretion of TNF-alpha as compared to cells that are produced or generated by an alternative and/or exemplary process. In some embodiments, the production or secretion by the output cells is at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold greater than production or secretion by cells produced by an alternative and/or exemplary process.

In certain embodiments, the output cells have decreased production and/or secretion of one or more cytokines, e.g., in response to exposure to an antigen as compared to cells that are produced or generated by an alternative and/or exemplary process. In particular embodiments, the output cells have decreased production and/or secretion of INF-gamma. In certain embodiments, CD4+ T cells of the output composition, e.g., CD4+ T cells that express the recombinant receptor, have decreased production and/or secretion INF-gamma as compared to CD4+ T cells that are produced or generated by an alternative and/or exemplary process. In some embodiments, the production or secretion of INF-gamma by the output cells, e.g. CD4+ T cells that express the recombinant receptor, is reduced by at least 20%, at least 30%, at least 40%, at least 50%, at least 60%, at least 70%, at least 75%, at least 80%, at least 85%, at least 90%, or at least 99% as compared to production or secretion by cells produced by an alternative and/or exemplary process.

In particular embodiments, the output cells have decreased production and/or secretion of IL-2. In some embodiments, CD4+ T cells of the output composition, e.g., CD4+ T cells that express the recombinant receptor, have decreased production and/or secretion IL-2 as compared to CD4+ T cells that are produced or generated by an alternative and/or exemplary process. In some embodiments, the production or secretion of IL-2 by the output cells, e.g. CD4+ T cells that express the recombinant receptor, is reduced by at least 20%, at least 30%, at least 40%, at least 50%, at least 60%, at least 70%, at least 75%, at least 80%, at least 85%, at least 90%, or at least 99% as compared to production or secretion by cells produced by an alternative and/or exemplary process.

In certain embodiments, the output cells have decreased production and/or secretion of GM-CSF. In particular embodiments, CD4+ T cells of the output composition, e.g., CD4+ T cells that express the recombinant receptor, have decreased production and/or secretion GM-CSF as compared to CD4+ T cells that are produced or generated by an alternative and/or exemplary process. In certain embodiments, the production or secretion of GM-CSF by the output cells, e.g. CD4+ T cells that express the recombinant receptor, is reduced by at least 20%, at least 30%, at least 40%, at least 50%, at least 60%, at least 70%, at least 75%, at least 80%, at least 85%, at least 90%, or at least 99% as compared to production or secretion by cells produced by an alternative and/or exemplary process.

In particular embodiments, the output cells have decreased production and/or secretion of M1P1-alpha. In some embodiments, CD4+ T cells of the output composition, e.g., CD4+ T cells that express the recombinant receptor, have decreased production and/or secretion MIP1-alpha as compared to CD4+ T cells that are produced or generated by an alternative and/or exemplary process. In certain embodiments, the production or secretion of MIP1-alpha by the output cells, e.g. CD4+ T cells that express the recombinant receptor, is reduced by at least 20%, at least 30%, at least 40%, at least 50%, at least 60%, at least 70%, at least 75%, at least 80%, at least 85%, at least 90%, or at least 99% as compared to production or secretion by cells produced by an alternative and/or exemplary process.

In particular embodiments, the output cells that are generated or produced by the provided methods have less expression of markers associated with apoptosis, e.g., levels of activated caspases and/or positive staining with Annexin V, than the cells that are generated or produced by the alternative and/or exemplary process.

In some embodiments, the output CD4+ T cells contain fewer Annexin V+ cells than CD4+ T cells that are generated or produced by the alternative and/or exemplary process. In some embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD4+ cells of the output composition are positive for Annexin V staining, e.g., bind and/or are capable of binding Annexin V, such as recombinant and/or labeled Annexin V. In certain embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD4+ cells of the output composition that express the recombinant receptor are positive for Annexin V staining.

In certain embodiments, the output CD8+ T cells contain fewer Annexin V+ cells than CD4+ T cells that are generated or produced by the alternative and/or exemplary process. In particular embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD8+ cells of the output composition are positive for Annexin V staining. In certain embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD8+ cells of the output composition that express the recombinant receptor are positive for Annexin V staining.

In certain embodiments, the output CD4+ T cells contain fewer cells that are positive for an activated caspase, e.g., activated caspase 3, than CD4+ T cells that are generated or produced by the alternative and/or exemplary process. In particular embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD4+ cells of the output composition are positive for an activated caspase, e.g., activated caspase 3. In certain embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD4+ cells of the output composition that express the recombinant receptor are positive for an activated caspase, e.g., activated caspase 3.

In some embodiments, the output CD8+ T cells contain fewer cells that are positive for an activated caspase, e.g., activated caspase 3, than CD4+ T cells that are generated or produced by the alternative and/or exemplary process. In certain embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD8+ cells of the output composition are positive for an activated caspase, e.g., activated caspase 3. In certain embodiments, less than 25%, less than 20%, less than 18%, less than 16%, less than 15%, less than 14%, less than 13%, less than 12%, less than 11%, less than 10%, less than 8%, less than 6%, less than 5%, less than 3%, less than 1%, or less than 0.1% of the CD8+ cells of the output composition that express the recombinant receptor are positive for an activated caspase, e.g., activated caspase 3.

In certain embodiments, the cells of the output composition are administered to a subject. In some embodiments, the cells of the output composition are administered to treat a disease or condition. In some embodiments, the disease or condition is cancer. In some embodiments, the cells the output compositions are administered to the subject, and the subject experiences a reduction in cancer cells and/or tumor volume. In some embodiments, the subject has, has about, or has at least a 25%, 50%, 60%, 70%, 75%, 80%, 85%, 90%, 95%, 97%, 98%, 99%, 100% reduction of the amount of cancer cells and/or tumor reduction following administration of the cells of the output composition, e.g., as compared to the amount of cancer cells and/or the tumor volume in the subject prior to the administration. In some embodiments, administration of cells of the output composition results in an increased reduction of tumor volume and/or the amount of cancer cells in the subject as compared to the reduction of tumor volume and/or the amount of cancer cells in the subject following administration of output cells produced by an exemplary alternative process In particular embodiments, administration of cells of the output composition results in an increase in the reduction of tumor volume and/or the amount of cancer cells in the subject of, of about, or of at least 5%, 10%, 20%, 30%, 40%, 50%, 60%, 70%, 80%, 90%, 100%, 125%, 150%, 1-fold, 2-fold, 3-fold, 4-fold, of 5-fold, as compared to the reduction of tumor volume and/or the amount of cancer cells in the subject following administration of output cells produced by an exemplary alternative process.

In particular embodiments, cells of the output composition, e.g., a portion and/or a dose of cells of the output composition, are administered to a subject. In some embodiments, the subject that is administered cells of the output composition has a probability and/or a likelihood of achieving and/or experiencing a complete response (CR). In certain embodiments, the likelihood and/or probability of achieving and/or experiencing CR is at least 10%, at least 15%, at least 20%, at least 25%, at least 30%, at least 35%, at least 40%, at least 45%, at least 50%, at least 55%, at least 60%, at least 70%, at least 80%, at least 90%, or at least 95%. In certain embodiments, the probability and/or likelihood of achieving and/or experiencing CR is at least 25%. In particular embodiments, the probability and/or likelihood of achieving CR is at least 50%.

In certain embodiments, the subject that is administered cells of the output composition has a probability and/or a likelihood of achieving and/or experiencing ORR. In certain embodiments, the likelihood and/or probability of achieving and/or experiencing ORR is at least at least 40%, at least 45%, at least 50%, at least 55%, at least 60%, at least 70%, at least 80%, at least 90%, or at least 95%. In certain embodiments, the probability and/or likelihood of achieving and/or experiencing ORR is at least 80%. In particular embodiments, the probability and/or likelihood of achieving ORR is at least 90%. In certain embodiments, the probability and/or likelihood of achieving ORR is or is about 100%.

In some embodiments, the efficacy of the output cells, e.g., the probability that a subject will achieve and/or experience CR or ORR following administration of cells of the output composition, is greater than that of a therapeutic cell composition containing cells expressing a recombinant receptor that are produced by an alternative process. In certain embodiments, there is an at least 5%, 10%, 15%, 20%, 25%, 30%, 40%, 50%, 60%, 70%, 80%, 90%, 100%, 125%, 150%, 1-fold, 2-fold, 5-fold, 10-fold, 50-fold, or 100-fold greater probability of achieving CR or ORR following administration of the output cells as compared to administration of the cells of the therapeutic cell composition that are produced by the alternative process.

In some embodiments, the output cells produced by the methods provided herein have a high and/or a relatively high degree of safety. In some embodiments, cells of the output composition, e.g., a portion and/or a dose of cells of the output composition, are administered to a subject. In some embodiments, the subject that is administered cells of the output composition has a risk, probability, and/or a likelihood of experiencing a toxicity, e.g., CRS or neurotoxicity, that is less than 80%, 75%, 70%, 60%, 50%, 40%, 30%, 25%, 20%, 15%, 10%, or 5%. In some embodiments, the toxicity is any grade of neurotoxicity or CRS. In certain embodiments, the subject administered cells of the output composition has a risk, probability, and/or likelihood of less than 80% for experiencing any grade of CRS or neurotoxicity. In particular embodiments, the subject administered cells of the output composition has a risk, probability, and/or likelihood of less than 80% for experiencing any grade of CRS or neurotoxicity.

In some embodiments, cells of the output composition, e.g., a portion and/or a dose of cells of the output composition, are safer than the cells of an output composition produced by an alternative process. In some embodiments, the incidence or probability of experience any grade, grade 3 or higher, prolonged grade 3 or higher, grade 4 or higher, or grade 5 neurotoxicity is less than 10%, 20%, 30%, 40%, 50%, 60%, 70%, 80%, 90%, 95%, or less than 95% of the incidence and/or probability following administration of output cells produced by an alternative process.

In certain embodiments, the provided methods are used in connection with a process that generates one or more output compositions of enriched T cells that are engineered to express a recombinant receptor with a success rate of at least 85% (e.g., successfully generates compositions of output cells from at least 85% of a plurality of different biological samples and/or compositions of input cells), such as a success rate of between 92% and 94%. In some embodiments, the process includes the steps for incubating cells under stimulating conditions; engineering the stimulated cells to express or contain a recombinant polynucleotide, e.g., a polynucleotide encoding a recombinant receptor such as a CAR; and cultivating the engineered cells to a threshold amount, density, or expansion. In some embodiments, the duration and/or amount of time these required to complete these steps is between 8 and 15 days or between 9-13 days. In certain embodiments, the process includes steps for collecting or obtaining a biological sample; isolating, selecting, or enriching input cells from the biological sample; cryofreezing and storing the input cells; thawing and/or incubating the input cells under stimulating conditions; engineering the stimulated cells to express or contain a recombinant polynucleotide, e.g., a polynucleotide encoding a recombinant receptor such as a CAR; cultivating the engineered cells to a threshold amount, density, or expansion; formulating the cultivated cells in an output composition; and cryofreezing and storing the formulated output cells until the cells are released for infusion and/or administration to a subject. In some embodiments, the process is completed within 19-23 days from obtaining or collection the biological sample.

In some embodiments, the provided methods are used in connection with a process that generates one or more compositions of enriched T cells, such as from a single source, e.g., a biological sample and/or input compositions isolated, selected, or enriched from a biological sample. In particular embodiments, the one or more compositions of enriched T cells is or includes a composition of enriched CD4+ T cells that contain at least 80% CD4+ T cells and at least 50% CD4+ T cells that express the recombinant receptor. In some embodiments, embodiments, the one or more compositions of enriched T cells includes a composition of enriched CD4+ T and a composition of enriched CD8+ T cells that contain at least 80% CD8+ T cells and at least 50% CD8+ T cells that express the recombinant receptor.

II. RECOMBINANT PROTEINS

In some embodiments, the cells that are treated, processed, engineered, and/or produced by the methods provided herein contain or express, or are engineered to contain or express, a recombinant protein, such as a recombinant receptor, e.g., a chimeric antigen receptor (CAR), or a T cell receptor (TCR). In certain embodiments, the methods provided herein produce and/or a capable of producing cells, or populations or compositions containing and/or enriched for cells, that are engineered to express or contain a recombinant protein. In some embodiments, CD4+ T cells, or populations or compositions of CD4+ T cells, are treated, processed, engineered, and/or produced In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors A. Chimeric Antigen Receptors In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat.

Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen is or includes $\alpha v \beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen or antigen binding domain is CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method, or other known schemes. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the antibodies included in the provided CARs are antibody fragments. An "antibody fragment" or "antigen-binding fragment" refers to a molecule other than an intact antibody that comprises a portion of an intact antibody that binds the antigen to which the intact antibody binds.

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32 . . . 34 | H26--H35B | H30--H35B |
| CDR-H1 (Chothia Numbering) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

1 - Kabat et al. (1991), "Sequences of Proteins of Immunological Interest," 5th Ed. Public Health Service, National Institutes of Health, Bethesda, MD
2 - Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antigen-binding domain in the provided CARs is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). In some embodiments, the FMC63 antibody comprises CDRH1 and H2 set forth in SEQ ID NOS: 38 and 39, respectively, and CDRH3 set forth in SEQ ID NO: 40 or 54 and CDRL1 set forth in SEQ ID NO: 35 and CDR L2 set forth in SEQ ID NO: 36 or 55 and CDR L3 set forth in SEQ ID NO: 37 or 34. In some embodiments, the FMC63 antibody comprises the heavy chain variable region ($V_H$) comprising the amino acid sequence of SEQ ID NO: 41 and the light chain variable region ($V_L$) comprising the amino acid sequence of SEQ ID NO: 42.

In some embodiments, the scFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chains are connected by a linker. In some embodiments, the linker is set forth in SEQ ID NO:56. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). In some embodiments, the SJ25C1 antibody comprises CDRH1, H2 and H3 set forth in SEQ ID NOS: 47-49, respectively, and CDRL1, L2 and L3 sequences set forth in SEQ ID NOS: 44-46, respectively. In some embodiments, the SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51.

In some embodiments, the scFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen or antigen binding domain is BCMA. In some embodiments, the scFv contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the antigen or antigen binding domain is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312.

In some embodiments, the antigen is CD20. In some embodiments, the scFv contains a VH and a VL derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a VH and a VL derived from an antibody or an antibody fragment specific to CD22. In some embodiments, the antibody or antibody fragment that binds CD22 is an antibody that is or is derived from m971, such as is m971 scFv.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) *Clin. Cancer Res.,* 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5. In some embodiments, the spacer has the sequence set forth in SEQ ID NOS: 25-33. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 25-33.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD3 transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or 17 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

For example, in some embodiments, the CAR contains an antibody, e.g., an antibody fragment, such as an scFv, specific to an antigen including any as described, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, such as an scFv, specific to an antigen including any as described, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in 7 or 16) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered to express the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

B. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ T cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPredl (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPredl (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wiilfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from 10 to 45 amino acids or from about 10 to about 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO:28). In some embodiments, the linker has the sequence GSADD-AKKDAAKKDGKS (SEQ ID NO:29)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as a and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

III. METHODS OF ADMINISTRATION

In some embodiments, output compositions of enriched T cells, such as separated compositions of CD4+ and CD8 output compositions, produced by the provided methods, such as provided in Section I, are administered as a cell therapy, e.g., an adoptive cell therapy. In particular embodiments, one or more cell compositions, e.g., output cell compositions described herein are administered as a cell therapy. In some embodiments, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In certain embodiments, the methods provided herein produce a single output composition of enriched T cells from input cells isolated, selected and/or enriched from a single biological sample that is administered as a cell therapy. In particular embodiments, the single output composition is a composition of enriched CD4+ T cells. In certain embodiments, the single output composition is a composition of enriched CD4+ and CD8+ T cells. In some embodiments, the methods provided herein produce two or more output compositions from a single source, e.g., a biological sample and/or input compositions isolated, selected, or enriched from a biological sample, that are administered to a subject. In some embodiments, the two or more output compositions are administered to the subject separately. In certain embodiments, the two or more output compositions are combined into a single composition and administered to the subject. In certain embodiments, the two or more output compositions include an output composition of enriched CD4+ T cells and an output composition of enriched CD8+ T cells.

In some embodiments, an output composition of enriched CD4+ T cells that is administered to a subject includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the output composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD4+ T cells that express the recombinant receptor and/or have been transduced or transfected with the recombinant polynucleotide. In certain embodiments, the output composition of enriched CD4+ T cells that is administered to the subject includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, an output composition of enriched CD8+ T cells that is administered to a subject includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In particular embodiments, the composition includes at least 30%, at least 40%, at least 50%, at least 60%, at least 70%, at least 80%, at least 90%, at least 95%, at least 98%, at least 99%, at least 99.5%, at least 99.9%, or at or at about 100% CD8+ T cells that express the recombinant receptor and/or have been transduced or transfected with the recombinant polynucleotide. In certain embodiments, the output composition of enriched CD8+ T cells that is administered to the subject includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from among αvβ6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-AI), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30. In some embodiments, the antigen is a pathogen-specific antigen. In some embodiments, the antigen is a viral antigen (such as a viral antigen from HIV, HCV, HBV, etc.), bacterial antigens, and/or parasitic antigens.

In some embodiments, the disease or condition is a B cell malignancy. In some embodiments, the B cell malignancy is a leukemia or a lymphoma. In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the antigen is a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells, e.g., engineered cells generated by a method provided herein, such as described in Section I, can be administered by any suitable means. In particular embodiments, cells from two or more separate output compositions, e.g., compositions of enriched T cells produced by the methods provided herein, such as described in Section-I, are combined into a single composition of cells to be administered. In certain embodiments, the cells from separate output compositions are each administered separately to the subject. In certain embodiments, CD4+ T cells are administered separately from CD8+ T cells.

In some embodiments the cells may be administered by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about 2×10$^5$ of the cells/kg and at or about 2×10$^6$ of the cells/kg, such as between at or about 4×10$^5$ of the cells/kg and at or about 1×10$^6$ of the cells/kg or between at or about 6×10$^5$ of the cells/kg and at or about 8×10$^5$ of the cells/kg. In some embodiments, the dose of cells comprises no more than 2×10$^5$ of the cells (e.g. antigen-expressing, such as CAR-expressing cells) per kilogram body weight of the subject (cells/kg), such as no more than at or about 3×10$^5$ cells/kg, no more than at or about 4×10$^5$ cells/kg, no more than at or about 5×10$^5$ cells/kg, no more than at or about 6×10$^5$ cells/kg, no more than at or about 7×10$^5$ cells/kg, no more than at or about 8×10$^5$ cells/kg, no more than at or about 9×10$^5$ cells/kg, no more than at or about 1×10$^6$ cells/kg, or no more than at or about 2×10$^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, for example, where the subject is a human, the dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values. In some embodiments, where the subject is a human, the dose includes between about $1\times10^6$ and $3\times10^8$ total recombinant receptor (e.g., CAR)-expressing cells, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from $1\times10^5$ to $5\times10^8$ or from about $1\times10^5$ to about $5\times10^8$ total recombinant receptor-expressing T cells or total T cells, from $1\times10^5$ to $1\times10^8$ or from about $1\times10^5$ to about $1\times10^8$ total recombinant receptor-expressing T cells or total T cells, from $5\times10^5$ to $1\times10^7$ or from about $5\times10^5$ to about $1\times10^7$ total recombinant receptor-expressing T cells or total T cells, or from $1\times10^6$ to $1\times10^7$ or from about $1\times10^6$ to about $1\times10^7$ total recombinant receptor-expressing T cells or total T cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $1\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$ or $1\times10^8$ total such cells, or the range between any two of the foregoing values. In some embodiments, the patient is administered multiple doses, and each of the doses or the total dose can be within any of the foregoing values. In some embodiments, the dose of cells comprises the administration of from $1\times10^7$ to $0.75\times10^8$ or from about $1\times10^7$ to about $0.75\times10^8$ total recombinant receptor-expressing CD8+ T cells, from $1\times10^7$ to $2.5\times10^7$ or from about $1\times10^7$ to about $2.5\times10^7$ total recombinant receptor-expressing CD8+ T cells, from $1\times10^7$ to $0.75\times10^8$ or from about $1\times10^7$ to about $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$ or $1\times10^8$ total recombinant receptor-expressing CD8+ T cells.

In some embodiments, for example, where the subject is human, the CD4+ T cells of the dose, including in a dose including CD4+ and CD8+ T cells, includes between about $1\times10^6$ and $1\times10^8$ total recombinant receptor (e.g., CAR)-expressing CD4+ cells, e.g., in the range of about $5\times10^6$ to $1\times10^8$ such cells, such cells $1\times10^7$, $2.5\times10^7$, $5\times10^7$, $7.5\times10^7$ or $1\times10^8$ total such cells, or the range between any two of the foregoing values. In some embodiments, the patient is administered multiple doses, and each of the doses or the total dose can be within any of the foregoing values. In some embodiments, the dose of cells comprises the administration of from $1\times10^7$ to $0.75\times10^8$ or from about $1\times10^7$ to about $0.75\times10^8$ total recombinant receptor-expressing CD4+ T cells, from $1\times10^7$ to $2.5\times10^7$ or from about $1\times10^7$ to about $2.5\times10^7$ total recombinant receptor-expressing CD4+ T cells, from $1\times10^7$ to $0.75\times10^8$ or from about $1\times10^7$ to about $0.75\times10^8$ total recombinant receptor-expressing CD4+ T cells, each inclusive. In some embodiments, the dose of cells comprises the administration of or about $1\times10^7$, $2.5\times10^7$, $5\times10^7$ $7.5\times10^7$ or $1\times10^8$ total recombinant receptor-expressing CD4+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some embodiments, the cell compositions are separate output compositions produced by the provided methods, such as described in Section I. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ T cells expressing a recombinant receptor to CD8+ T cells expressing a recombinant receptor and/or of CD4+ T cells to CD8+ T cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+: CAR+CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ T cells and/or a desired dose of CD8+ T cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ T cells, and/or is based on a desired fixed or minimum dose of CD4$^+$ and/or CD8$^+$ T cells.

In some embodiments, the cells are administered at or within a tolerated range of a desired output ratio of multiple cell populations or sub-types, such as CD4+ and CD8+ T cells or sub-types. In some aspects, the desired ratio can be a specific ratio or can be a range of ratios. for example, in some embodiments, the desired ratio (e.g., ratio of CD4$^+$ to CD8$^+$ T cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges. In certain embodiments, the compositions of enriched CD4+ T cells and enriched CD8+ T cells are combined at the desired ratio and administered to the subject as a single cell composition. In particular embodiment, the compositions of enriched CD4+ T cells and enriched CD8+ T cells are administered as separate compositions at the desired ratio.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more of the steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

A. Response, Activity, and Survival

In some embodiments, cells, e.g., output cells, produced by the methods provided herein, e.g., such as described in Section-I, are administered to a subject, and the subject is monitored for response, survival, and/or signs or symptoms of toxicity.

In some embodiments, at least 35%, at least 40% or at least 50% of subjects treated with compositions of cells, e.g., therapeutic cell compositions containing CAR+CD4+ and CD8+ T cells, produce remission (CR); and/or at least 50%, at least 60% or at least 70% of the subjects treated according to the method achieve objective response rate (ORR). In some embodiments, at least or about at least 50% of subjects, at least or about at least 60% of the subjects, at least or about at least 70% of the subjects, at least or about at least 80% of the subjects or at least or about at least 90% of the subjects treated according to the method achieve CR and/or achieve an objective response (OR). In some embodiments, criteria assessed for effective treatment includes overall response rate (ORR), complete response (CR), duration of response (DOR) progression-free survival (PFS), and/or overall survival (OS).

In some embodiments, at least 40% or at least 50% of subjects treated according to the methods provided herein achieve complete remission (CR), exhibit progression-free survival (PFS) and/or overall survival (OS) of greater than at or about 3 months, 6 months or 12 months; on average, subjects treated according to the method exhibit a median PFS or OS of greater than at or about 6 months, 12 months, or 18 months; and/or the subject exhibits PFS or OS following therapy for at least at or about 6, 12, 18 or more months.

In some aspects, response rates in subjects, such as subjects with NHL, are based on the Lugano criteria. (Cheson et al., (2014) JCO 32(27):3059-3067; Johnson et al., (2015) Radiology 2:323-338; Cheson, B. D. (2015) Chin Clin Oncol 4(1):5). In some aspects, response assessment utilizes any of clinical, hematologic, and/or molecular methods. In some aspects, response assessed using the Lugano criteria involves the use of positron emission tomography (PET)-computed tomography (CT) and/or CT as appropriate. PET-CT evaluations may further comprise the use of fluorodeoxyglucose (FDG) for FDG-avid lymphomas. In some aspects, where PET-CT will be used to assess response in FDG-avid histologies, a 5-point scale may be used. In some respects, the 5-point scale comprises the following criteria: 1, no uptake above background; 2, uptake≤mediastinum; 3, uptake>mediastinum but≤liver; 4, uptake moderately>liver; 5, uptake markedly higher than liver and/or new lesions; X, new areas of uptake unlikely to be related to lymphoma.

In some aspects, a complete response as described using the Lugano criteria involves a complete metabolic response and a complete radiologic response at various measureable sites. In some aspects, these sites include lymph nodes and extralymphatic sites, wherein a CR is described as a score of 1, 2, or 3 with or without a residual mass on the 5-point scale, when PET-CT is used. In some aspects, in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake. In some aspects, response is assessed in the lymph nodes using CT, wherein a CR is described as no extralymphatic sites of disease and target nodes/nodal masses must regress to ≤1.5 cm in longest transverse diameter of a lesion (LDi). Further sites of assessment include the bone marrow wherein PET-CT-based assessment should indicate a lack of evidence of FDG-avid disease in marrow and a CT-based assessment should indicate a normal morphology, which if indeterminate should be IHC negative. Further sites may include assessment of organ enlargement, which should regress to normal. In some aspects, nonmeasured lesions and new lesions are assessed, which in the case of CR should be absent (Cheson et al., (2014) JCO 32(27): 3059-3067; Johnson et al., (2015) Radiology 2:323-338; Cheson, B. D. (2015) Chin Clin Oncol 4(1):5).

In some aspects, a partial response (PR; also known in some cases as partial remission) as described using the Lugano criteria involves a partial metabolic and/or radiological response at various measureable sites. In some aspects, these sites include lymph nodes and extralymphatic sites, wherein a PR is described as a score of 4 or 5 with reduced uptake compared with baseline and residual mass (es) of any size, when PET-CT is used. At interim, such findings can indicate responding disease. At the end of treatment, such findings can indicate residual disease. In some aspects, response is assessed in the lymph nodes using CT, wherein a PR is described as ≥50% decrease in SPD of up to 6 target measureable nodes and extranodal sites. If a lesion is too small to measure on CT, 5 mm×5 mm is assigned as the default value; if the lesion is no longer visible, the value is 0 mm×0 mm; for a node >5 mm×5 mm, but smaller than normal, actual measurements are used for calculation. Further sites of assessment include the bone marrow wherein PET-CT-based assessment should indicate residual uptake higher than uptake in normal marrow but reduced compared with baseline (diffuse uptake compatible with reactive changes from chemotherapy allowed). In some aspects, if there are persistent focal changes in the marrow in the context of a nodal response, consideration should be given to further evaluation with MRI or biopsy, or an interval scan. In some aspects, further sites may include assessment of organ enlargement, where the spleen must have regressed by >50% in length beyond normal. In some aspects, nonmeasured lesions and new lesions are assessed, which in the case of PR should be absent/normal, regressed, but no increase. No response/stable disease (SD) or progressive disease (PD) can also be measured using PET-CT and/or CT based assessments. (Cheson et al., (2014) JCO 32(27):3059-3067; Johnson et al., (2015) Radiology 2:323-338; Cheson, B. D. (2015) Chin Clin Oncol 4(1):5).

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months or greater than 6 months.

In some aspects, the RECIST criteria is used to determine objective tumor response; in some aspects, in solid tumors. (Eisenhauer et al., European Journal of Cancer 45 (2009) 228-247.) In some aspects, the RECIST criteria is used to determine objective tumor response for target lesions. In some respects, a complete response as determined using RECIST criteria is described as the disappearance of all target lesions and any pathological lymph nodes (whether target or non-target) must have reduction in short axis to <10 mm. In other aspects, a partial response as determined using RECIST criteria is described as at least a 30% decrease in the sum of diameters of target lesions, taking as reference the baseline sum diameters. In other aspects, progressive disease (PD) is described as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (in some aspects the appearance of one or more new lesions is also considered progression). In other aspects, stable disease (SD) is described as neither sufficient shrinkage to qualify for PR nor sufficient increase to qualify for PD, taking as reference the smallest sum diameters while on study.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow.

In some aspects, response rates in subjects, such as subjects with CLL, are based on the International Workshop on Chronic Lymphocytic Leukemia (IWCLL) response criteria (Hallek, et al., Blood 2008, Jun. 15; 111(12): 5446-5456). In some aspects, these criteria are described as follows: complete remission (CR; also known in some cases as complete response), which in some aspects requires the absence of peripheral blood clonal lymphocytes by immunophenotyping, absence of lymphadenopathy, absence of hepatomegaly or splenomegaly, absence of constitutional symptoms and satisfactory blood counts; complete remission with incomplete marrow recovery (CRi), which in some aspects is described as CR above, but without normal blood counts; partial remission (PR; also known in some cases as partial response), which in some aspects is described as ≥50% fall in lymphocyte count, ≥50% reduction in lymphadenopathy or ≥50% reduction in liver or spleen, together with improvement in peripheral blood counts; progressive disease (PD), which in some aspects is described as ≥50% rise in lymphocyte count to >5×10$^9$/L, ≥50% increase in lymphadenopathy, ≥50% increase in liver or spleen size, Richter's transformation, or new cytopenias due to CLL; and stable disease, which in some aspects is described as not meeting criteria for CR, CRi, PR or PD.

In some embodiments, the subjects exhibits a CR or OR if, within 1 month of the administration of the dose of cells, lymph nodes in the subject are less than at or about 20 mm in size, less than at or about 10 mm in size or less than at or about 10 mm in size.

In some embodiments, an index clone of the CLL is not detected in the bone marrow of the subject (or in the bone marrow of greater than 50%, 60%, 70%, 80%, 90% or more of the subjects treated according to the methods. In some embodiments, an index clone of the CLL is assessed by IgH deep sequencing. In some embodiments, the index clone is not detected at a time that is at or about or at least at or about 1, 2, 3, 4, 5, 6, 12, 18 or 24 months following the administration of the cells.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject has leukemia. The extent of disease burden can be determined by assessment of residual leukemia in blood or bone marrow.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD−, such that, in some cases, no leukemia cells are able to be detected in the subject using PCR or flow cytometry techniques.

In some embodiments, an index clone of the leukemia, e.g. CLL, is not detected in the bone marrow of the subject (or in the bone marrow of greater than 50%, 60%, 70%, 80%, 90% or more of the subjects treated according to the methods. In some embodiments, an index clone of the leukemia, e.g. CLL, is assessed by IGH deep sequencing. In some embodiments, the index clone is not detected at a time that is at or about or at least at or about 1, 2, 3, 4, 5, 6, 12, 18 or 24 months following the administration of the cells.

In some aspects MRD is detected by flow cytometry. Flow cytometry can be used to monitor bone marrow and peripheral blood samples for cancer cells. In particular aspects, flow cytometry is used to detect or monitor the presence of cancer cells in bone marrow. In some aspects, multiparameter immunological detection by flow cytometry is used to detect cancer cells (see for example, Coustan-Smith et al., (1998) Lancet 351:550-554). In some aspects, multiparameter immunological detection by mass cytometry is used to detect cancer cells. In some examples, 1, 2, 3, 4, 5, 6, 7, 8, 9, 10, 11, 12, 13, 14, 15, 20, 25, 30, 35, 40, 45 or 50 parameters can be used to detect cancer cells. The antigens used for detection are selected based on the cancer being detected (Foon and Todd (1986) Blood 68:1-31).

In some embodiments, administering a dose or composition of cells produced by the methods provided herein reduces the burden of the disease or condition, e.g., number of tumor cells, size of tumor, duration of patient survival or event-free survival, to a greater degree and/or for a greater period of time as compared to the reduction that would be observed with a comparable method using cells generated by an alternative process. In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, the event-free survival rate or overall survival rate of the subject is improved by administering cells produced from the provided methods, e.g., the methods described in Section-I, as compared with cell generated by alternative methods. For example, in some embodiments, event-free survival rate or probability for subjects treated by the methods at 6 months following the dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the cells produced by the provided methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods, for example, methods in which the subject receives a cell therapy containing cells produced by alternative methods. For example, in some embodiments, the probability of relapse at 6 months following the first dose is less than about 80%, less than about 70%, less than about 60%, less than about 50%, less than about 40%, less than about 30%, less than about 20%, or less than about 10%.

B. Toxicity

In certain embodiments, cells, e.g., output cells, produced by the methods provided herein, e.g., such as described in Section-I, are administered to a subject, and the subject is monitored for signs or symptoms of toxicity.

In certain embodiments, the a dose or composition of cells, e.g., output cells produced by the provided methods result in a lower rate and/or lower degree of toxicity, toxic outcome or symptom, toxicity-promoting profile, factor, or property, such as a symptom or outcome associated with or indicative of cytokine release syndrome (CRS) or neurotoxicity, for example, compared to administration of an alternative cell therapy, such as an CAR+ T cell composition produced by an alternative process.

In some embodiments, administering cells produced by the provided methods do not result in a high rate or likelihood of toxicity or toxic outcomes, or reduces the rate or likelihood of toxicity or toxic outcomes, such as neurotoxicity (NT), cytokine release syndrome (CRS), such as compared to certain other cell therapies and/or cells produced by alternative methods. In some embodiments, the administering the cells, e.g., output cells, produced by the provided methods result in, or do not increase the risk of, severe NT (sNT), severe CRS (sCRS), macrophage activation syndrome, tumor lysis syndrome, fever of at least at or about 38 degrees Celsius for three or more days and a plasma level of CRP of at least at or about 20 mg/dL. In some embodiments, greater than or greater than about 30%, 35%, 40%, 50%, 55%, 60% or more of the subjects treated according to the provided methods do not exhibit any grade of CRS or any grade of neurotoxcity. In some embodiments, no more than 50% of subjects treated (e.g. at least 60%, at least 70%, at least 80%, at least 90% or more of the subjects treated) exhibit a cytokine release syndrome (CRS) higher than grade 2 and/or a neurotoxicity higher than grade 2. In some embodiments, at least 50% of subjects treated according to the method (e.g. at least 60%, at least 70%, at least 80%, at least 90% or more of the subjects treated) do not exhibit a severe toxic outcome (e.g. severe CRS or severe neurotoxicity), such as do notexhibit grade 3 or higher neurotoxicity and/or does not exhibit severe CRS, or does not do so within a certain period of time following the treatment, such as within a week, two weeks, or one month of the administration of the cells. In some embodiments, parameters assessed to determine certain toxicities include adverse events (AEs), dose-limiting toxicities (DLTs), CRS and NT.

Administration of adoptive T cell therapy, such as treatment with T cells expressing chimeric antigen receptors, can induce toxic effects or outcomes such as cytokine release syndrome and neurotoxicity. In some examples, such effects or outcomes parallel high levels of circulating cytokines, which may underlie the observed toxicity.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

CRS may be treated using anti-inflammatory therapy such as an anti-IL-6 therapy, e.g., anti-IL-6 antibody, e.g., tocilizumab, or antibiotics or other agents as described. Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

CRS criteria that appear to correlate with the onset of CRS to predict which patients are more likely to be at risk for developing sCRS have been developed (see Davila et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 2 below.

TABLE 2

Exemplary Grading Criteria for CRS

| Grade | Description of Symptoms |
|---|---|
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention: Oxygen requirement <40%, or Hypotension responsive to fluids or low dose of a single vasopressor, or Grade 2 organ toxicity (by CTCAE v4.0) |
| 3<br>Severe | Require and respond to aggressive intervention: Oxygen requirement ≥40%, or Hypotension requiring high dose of a single vasopressor (e.g., norepinephrine ≥20 µg/kg/min, dopamine ≥10 µg/kg/min, phenylephrine ≥200 µg/kg/min, or epinephrine ≥10 µg/kg/min), or Hypotension requiring multiple vasopressors (e.g., vasopressin + one of the above agents, or combination vasopressors equivalent to ≥20 µg/kg/min norepinephrine), or Grade 3 organ toxicity or Grade 4 transaminitis (by CTCAE v4.0) |
| 4<br>Life-threatening | Life-threatening: Requirement for ventilator support, or Grade 4 organ toxicity (excluding transaminitis) |
| 5<br>Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as set forth in Table 2.

In some embodiments, outcomes associated with severe CRS or grade 3 CRS or greater, such as grade 4 or greater, include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures). In some embodiments, severe CRS includes CRS that requires management or care in the intensive care unit (ICU).

In some embodiments, the CRS, such as severe CRS, encompasses a combination of (1) persistent fever (fever of at least 38 degrees Celsius for at least three days) and (2) a serum level of CRP of at least at or about 20 mg/dL. In some embodiments, the CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

The method of measuring or detecting the various outcomes may be specified.

In some aspects, the toxic outcome is or is associated with neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli Nature Reviews Neurology 6, 657-666 (December 2010); National Cancer Institute—Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 3.

TABLE 3

Exemplary Grading Criteria for neurotoxicity

| Grade | Description of Symptoms |
| --- | --- |
| 1<br>Asymptomatic or Mild | Mild or asymptomatic symptoms |
| 2<br>Moderate | Presence of symptoms that limit instrumental activities of daily living (ADL), such as preparing meals, shopping for groceries or clothes, using the telephone, managing money |
| 3<br>Severe | Presence of symptoms that limit self-care ADL, such as bathing, dressing and undressing, feeding self, using the toilet, taking medications |
| 4<br>Life-threatening | Symptoms that are life-threatening, requiring urgent intervention |
| 5<br>Fatal | Death |

In some embodiments, the methods reduce symptoms associated with CRS or neurotoxicity compared to other methods. In some aspects, the provided methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 2. In some embodiments, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysesthesia, neuralgia or paresthesia.

In some embodiments, the administering cells produced by the provided methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, one or more interventions or agents for treating the toxicity, such as a toxicity-targeting therapies, is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

IV. ARTICLES OF MANUFACTURE

Also provided are articles of manufacture and kits containing engineered cells expressing a recombinant receptor produced by the methods provided herein, such as the methods described in Section I and/or the output compositions of cells described in Section I-F, and optionally instructions for use, for example, instructions for administering the engineered cells to a subject, such as by methods described in Section III.

In some embodiments, provided herein are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods for administrating the cells that are provided herein. In some embodiments, the instructions specify particular instructions for administration of the cells for cell therapy, e.g., doses, timing, selection and/or identification of subjects for administration and conditions for administration. In some embodiments, the articles of manufacture and/or kits further comprise an agent for lymphodepleting therapy, and optionally further includes instructions for administering the lymphodepleting therapy. In some embodiments, the instructions can be included as a label or package insert accompanying the compositions for administration.

In some embodiments, the article of manufacture may have a container, optionally a vial, containing a composition of enriched CD4+ T cells expressing a recombinant receptor. In some embodiments, the article of manufacture or kit comprises optionally comprises a second container, optionally a second vial, containing a composition of enriched CD8+ T cells expressing a recombinant receptor. In some embodiments, a cryoprotectant is included with the cells. In some aspects the container is a vial or a bag. In some embodiments, the container contains a composition of enriched CD4+ and CD8+ T cells.

In some embodiments, the composition of enriched CD4+ T cells within the container includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the composition of the container includes at least 30%, at least 40%, at least 50%, at least 60%, at least 70%, at least 80%, at least 90%, at least 95%, at least 98%, at least 99%, at least 99.5%, at least 99.9%, or at or at about 100% CD4+ T cells that express the recombinant receptor and/or have been transduced or transfected with the recombinant polynucleotide. In certain embodiments, the composition of enriched CD4+ T cells within the container includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells.

In some embodiments, the composition of enriched CD8+ T cells within the container includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In particular embodiments, the composition with the container at least 30%, at least 40%, at least 50%, at least 60%, at least 70%, at least 80%, at least 90%, at least 95%, at least 98%, at least 99%, at least 99.5%, at least 99.9%, or at or at about 100% CD8+ T cells that express the recombinant receptor and/or have been transduced or transfected with the recombinant polynucleotide. In certain embodiments, the output composition of enriched CD8+ T cells that is administered to the subject includes less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free or substantially free of CD4+ T cells.

In some embodiments, the instructions specify the dose of cells to be administered. For example, in some embodiments, the dose specified in the instructions include a total recombinant receptor (e.g., CAR)-expressing cells between about $1\times10^6$ and $3\times10^8$, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values.

In some embodiments, the container such as the vial comprises greater than or greater than about $10\times10^6$ T cells or recombinant receptor-expressing T cells, greater than or greater than about $15\times10^6$ T cells or recombinant receptor-expressing T cells, greater than or greater than about $25\times10^6$ T cells or recombinant receptor-expressing T cell. In some aspects, the vial comprises between about 10 million cells per ml and about 70 million cells per ml, between about 10 million cells per ml and about 50 million cells per ml, between about 10 million cells per ml and about 25 million cells per ml, between about 10 million cells per ml and about 15 million cells per ml, 15 million cells per ml and about 70 million cells per ml, between about 15 million cells per ml and about 50 million cells per ml, between about 15 million cells per ml and about 25 million cells per ml, between about 25 million cells per ml and about 70 million cells per ml, between about 25 million cells per ml and about 50 million cells per ml, and between about 50 million cells per ml and about 70 million cells per ml.

In some embodiments, the plurality of vials or plurality of cells or unit dose of cells specified for administration, collectively, comprises a dose of cells comprising from $1\times10^5$ to $5\times10^8$ or from about $1\times10^5$ to about $5\times10^8$ total recombinant receptor-expressing T cells or total T cells, from $1\times10^5$ to $1\times10^8$ or from about $1\times10^5$ to about $1\times10^8$ total recombinant receptor-expressing T cells or total T cells, from $5\times10^5$ to $1\times10^7$ or from about $5\times10^5$ to about $1\times10^7$ total recombinant receptor-expressing T cells or total T cells, or from $1\times10^6$ to $1\times10^7$ or from about $1\times10^6$ to about $1\times10^7$ total recombinant receptor-expressing T cells or total T cells, each inclusive. In some aspects, the article comprises one or more unit dose of the CD4+ and CD8+ T cells or of the CD4+ receptor+ T cells and CD8+ receptor+ T cells, wherein the unit dose comprises between at or about $1\times10^7$ and at or about $2\times10^8$ recombinant receptor-expressing T cells, between at or about $5\times10^7$ and at or about $1.5\times10^8$ recombinant receptor-expressing T cells, at or about $5\times10^7$ recombinant receptor-expressing T cells, at or about $1\times10^8$ recombinant receptor-expressing T cells, or at or about $1.5\times10^8$ recombinant receptor-expressing T cells, optionally wherein the information in the article specifies administration of one or of a plurality of unit doses and/or a volume corresponding to such one or plurality of unit doses. In some cases, the article comprises one or more unit doses of the CD8+ T cells, wherein the dose comprises between at or about $5\times10^6$ and at or about $1\times10^8$ recombinant receptor-expressing CD8+ T cells, the dose comprises between at or about $1\times10^7$ and at or about $0.75\times10^8$ recombinant receptor-expressing CD8+ T cells, the dose comprises at or about 2.5×10⁷ recombinant receptor-expressing CD8+ T cells, or the dose comprises at or about 5×10⁷ recombinant receptor-expressing CD8+ T cells, or the dose comprises at or about 0.75×10⁸ recombinant receptor-expressing CD8+ T cells, optionally wherein the information in the article specifies administration of one or of a plurality of unit doses and/or a volume corresponding to such one or plurality of unit doses. In some embodiments, the cells in the article, collectively, comprise a dose of cells comprising no more than 1×10⁸ total recombinant receptor-expressing T cells or total T cells, no more than 1×10⁷ total recombinant receptor-expressing T cells or total T cells, no more than 0.5×10⁷ total recombinant receptor-expressing T cells or total T cells, no more than 1×10⁶ total recombinant receptor-expressing T cells or total T cells, no more than 0.5×10⁶ total recombinant receptor-expressing T cells or total T cells.

In some embodiments, the instructions can specify dosage regimen and timing of the administration. For example, in some embodiments, the instructions can specify administering to the subject multiple doses, e.g., two or more doses, of the cells. In some embodiments, the instructions specify the timing of the multiple doses, e.g., the second dose being administered approximately 4, 5, 6, 7, 8, 9, 10, 11, 12, 13, 14, 15, 16, 17, 18, 19, 20 or 21 days after the first dose; and/or the dosage amount in each dose.

In some embodiments, the article of manufacture or kit comprises a composition of enriched CD4+ T cells expressing a recombinant receptor, and instructions for administering, to a subject having a disease or condition, all or a portion of the composition of enriched CD4+ T cells and further administering CD8+ T cells expressing a recombinant receptor. In some embodiments, the instructions specify administering the CD4+ T cells prior to administering the CD8+ T cells. In some cases, the instructions specify administering the CD8+ T cells prior to administering the CD4+ T cells. In some embodiments, the article of manufacture or kit comprises a plurality of CD8+ T cells expressing a recombinant receptor, and instructions for administering, to a subject having a disease or condition, all or a portion of the plurality of CD8+ T cells and CD4+ T cells expressing a recombinant receptor. In some embodiments, the instructions specify dosage regimen and timing of the administration of the cells.

In some aspects, the instructions specify administering all or a portion of the CD4+ T cells and the all or a portion of the CD8+ T cells 0 to 12 hours apart, 0 to 6 hours apart or 0 to 2 hours apart. In some cases, the instructions specify administering the CD4+ T cells and the CD8+ T cells no more than 2 hours, no more than 1 hour, no more than 30 minutes, no more than 15 minutes, no more than 10 minutes or no more than 5 minutes apart.

In some embodiments, the instructions specify the dose or number of cells or cell type(s) and/or a ratio of cell types, e.g., individual populations or sub-types, such as the CD4+ to CD8+ ratio. In some embodiments, the populations or sub-types of cells, such as CD8⁺ and CD4⁺ T cells. For example, in some embodiments, the instructions specify that the cells are administered at or within a tolerated range of an output ratio of multiple cell populations or sub-types, such as CD4+ and CD8+ T cells or sub-types, of between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In certain embodiments, the instructions specify that the compositions of enriched CD4+ T cells and enriched CD8+ T cells are combined at the desired ratio and administered to the subject as a single cell composition. In particular embodiments, the instructions specify the compositions of enriched CD4+ T cells and enriched CD8+ T cells are administered as separate compositions at the desired ratio. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

V. DEFINITIONS

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

VI. EXEMPLARY EMBODIMENTS

Among the provided embodiments are:
1. A method for producing a composition of engineered cells, the method comprising:
(a) incubating, under stimulating conditions, an input composition comprising T cells enriched for CD4+ primary human T cells, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines, wherein at least one cytokine is or comprises recombinant human IL-2, thereby generating a stimulated composition; and (b) introducing a recombinant receptor into the stimulated composition, thereby generating an engineered composition comprising engineered T cells.

2. The method of embodiment 1, wherein:
the input composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or
the input composition consists essentially of CD4+ primary human T cells.

3. The method of embodiment 1 or embodiment 2, wherein the concentration of recombinant IL-2 is from 10 IU/mL to 200 IU/mL or from about 10 IU/mL to about 200 IU/mL.

4. The method of any of embodiments 1-3, wherein the one or more cytokines further comprises IL-7 and/or IL-15, optionally wherein the concentration of IL-7 is from 100 IU/mL to 1000 IU/mL or from about 100 IU/mL to about 1000 IU/mL and/or the concentration of IL-15 is from 1 IU/mL to 50 IU/mL or from about 1 IU/mL to about 50 IU/mL.

5. The method of any of embodiments 1-4, wherein the incubating is carried out in the presence of one or more antioxidants.

6. A method for producing a composition of engineered cells, the method comprising:
(a) incubating an input composition comprising T cells enriched for one or both of CD4+ and CD8+ primary human T cells, thereby generating a stimulated composition, wherein the incubating is carried out:
(1) under one or more stimulating conditions, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines; and/or
(2) in the presence of one or more antioxidant; and
(b) introducing a recombinant receptor into the stimulated composition, thereby generating an engineered composition comprising engineered T cells.

7. The method of embodiment 6, wherein:
the input composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells; and/or the input composition consists essentially of CD4+ and/or CD8+ primary human T cells.

8. The method of embodiment 6 or embodiment 7, wherein the one or more cytokines are selected from recombinant IL-2, recombinant IL-7 and/or recombinant IL-15.

9. The method of embodiment 8, wherein:
the concentration of recombinant IL-2 is from 10 IU/mL to 200 IU/mL or from about 10 IU/mL to about 200 IU/mL;
the concentration of recombinant IL-7 is from 100 IU/mL to 1000 IU/mL or from about 100 IU/mL to about 1000 IU/mL; and/or the concentration of recombinant IL-15 is from 1 IU/mL to 25 IU/mL or from about 1 IU/mL to about 25 IU/mL.

10. The method of embodiment 6, wherein:
the input composition comprises greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or
the input composition consists essentially of CD4+ primary human T cells.

11. The method of embodiment 6 or embodiment 10, wherein the one or more cytokines are selected from recombinant IL-2, recombinant IL-7 and recombinant IL-15.

12. The method of embodiment 6, wherein:
the input composition comprises greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells; and/or
the input composition consists essentially of CD8+ primary human T cells.

13. The method of embodiment 6 or embodiment 12, wherein the one or more cytokines are selected from recombinant IL-2 and recombinant IL-15.

14. The method of any of embodiments 1-13, wherein the stimulatory reagent comprises a primary agent that specifically binds to a member of a TCR complex, optionally that specifically binds to CD3.

15. The method of embodiment 14, wherein the stimulatory reagent further comprises a secondary agent that specifically binds to a T cell costimulatory molecule, optionally wherein the costimulatory molecule is selected from CD28, CD137 (4-1-BB), OX40, or ICOS.

16. The method of embodiment 14 or embodiment 15, wherein the primary and/or secondary agents comprise an antibody, optionally wherein the stimulatory reagent comprises incubation with an anti-CD3 antibody and an anti-CD28 antibody, or an antigen-binding fragment thereof.

17. The method of any of embodiments 14-16, wherein the primary agent and/or secondary agent are present on the surface of a solid support.

18. The method of embodiment 17, wherein the solid support is or comprises a bead.

19. The method of embodiment 18, wherein the bead comprises a diameter of greater than or greater than about 3.5 µm but no more than about 9 µm or no more than about 8 µm or no more than about 7 µm or no more than about 6 µm or no more than about 5 µm.

20. The method of embodiment 18 or embodiment 19, wherein the bead comprises a diameter of or about 4.5 µm.

21. The method of any of embodiments 18-20, wherein the bead is inert.

22. The method of any of embodiments 18-21, wherein the bead is or comprises a polystyrene surface.

23. The method of any of embodiments 18-22, wherein the bead is magnetic or superparamagnetic.

24. The method of any of embodiments 18-23, wherein the ratio of beads to cells is less than 3:1.

25. The method of any of embodiments 18-24, wherein the ratio of beads to cells is from 2:1 to 0.5:1 or from about 2:1 to about 0.5:1.

26. The method of any of embodiments 18-25, wherein the ratio of beads to cells is at or at about 1:1.

27. The method of any of embodiments 5-26, wherein the one or more antioxidant comprises a sulfur containing antioxidant.

28. The method of any of embodiments 5-27, wherein the one or more antioxidants comprise a glutathione precursor.

29. The method of any of embodiments 5-28, wherein the one or more antioxidants comprise N-acetyl cysteine (NAC), optionally wherein the NAC is at a concentration of from 0.2 mg/mL to 2.0 mg/mL or from about 0.2 mg/mL to about 2.0 mg/mL.

30. The method of any of embodiments 1-29, wherein the introducing comprises transducing cells of the stimulated composition with a viral vector comprising a polynucleotide encoding the recombinant receptor.

31. The method of embodiment 30, wherein the viral vector is a retroviral vector.

32. The method of embodiment 30 or embodiment 31, wherein the viral vector is a lentiviral vector or gammaretroviral vector.

33. The method of any of embodiments 30-32, wherein the introducing is carried out in the presence of a transduction adjuvant.

34. The method of embodiment 33, wherein the transduction adjuvant is or comprises protamine sulfate, optionally from 1 µg/ml to 50 µg/ml or from about 1 µg/ml to about 50 µg/ml protamine sulfate; a fibronectin-derived transduction adjuvant; and/or RetroNectin.

35. The method of any of embodiments 1-34, wherein the introducing comprises transfecting the cells of the stimulated composition with a vector comprising a polynucleotide encoding the recombinant receptor.

36. The method of embodiment 35, wherein the vector is a transposon, optionally a Sleeping Beauty (SB) transposon or a Piggybac transposon.

37. The method of any of embodiments 1-36, further comprising cultivating the engineered composition under conditions to promote proliferation or expansion of the engineered cells, thereby producing an output composition comprising the engineered T cells.

38. The method of embodiment 37, wherein the cultivating is carried out in the presence of one or more cytokines, wherein at least one cytokine is or comprises recombinant human IL-2.

39. The method of embodiment 37 or embodiment 38, wherein the stimulatory reagent is removed from the engineered composition prior to the cultivating.

40. The method of embodiment 39, wherein the stimulatory agent is removed within or less than 7 days after initiation of the incubating.

41. The method of embodiment 39 or embodiment 40, wherein the stimulatory reagent is removed from 3 days to 6 days or from about 3 days to about 6 days after the initiation of the incubating.

42. The method of any of embodiments 37-41, wherein the stimulatory reagent is removed at or at about 4 days after the initiation of the incubating.

43. The method of any of embodiments 39-42, wherein removing the beads comprises exposing cells of the engineered composition to a magnetic field.

44. A method for producing a composition of engineered cells, the method comprising cultivating, in the presence of one or more cytokines, an engineered cell composition comprising CD4+ primary human T cells comprising cells engineered with a recombinant receptor, wherein at least one cytokine is or comprises recombinant human IL-2;
wherein the method results in the proliferation or expansion of cells in the composition to produce an output composition comprising engineered CD4+ cells.

45. The method of embodiment 44, wherein the proliferation or expansion results in, in about, or in at least a 2-fold, 3-fold, 4-fold, 5-fold, or greater than a 5-fold increase in the number of CD4+ T cells engineered with a recombinant receptor.

46. The method of embodiment 44 or 45, wherein:
the engineered cell composition comprises greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells or CD4+ recombinant receptor-expressing cells; and/or
the engineered cell composition consists essentially of CD4+ primary human T cells.

47. The method of any of embodiments 44-46, wherein the concentration of recombinant IL-2 is from 50 IU/mL to 500 IU/ml or from about 50 IU/mL to about 500 IU/ml.

48. The method of any of embodiments 38-47, wherein the one or more cytokines further comprises IL-7 and/or IL-15, optionally wherein the concentration of IL-7 is from 500 IU/mL to 2000 IU/mL or from about 500 IU/mL to about 2000 IU/mL and/or the concentration of IL-15 is from 5 IU/mL to 50 IU/mL or from about 5 IU/mL to about 50 IU/mL.

49. The method of any of embodiments 44-48, wherein the engineered cell composition is produced by a method comprising:
(a) incubating, under stimulating conditions, an input composition comprising primary T cells enriched for CD4+ primary human T cells, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines, wherein at least one cytokine is or comprises recombinant human IL-2, thereby generating a stimulated composition; and
(b) introducing a recombinant receptor into the stimulated composition, thereby generating an engineered composition comprising engineered T cells.

50. The method of embodiment 49, wherein:
the input composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or
the input composition consists essentially of CD4+ primary human T cells.

51. The method of embodiment 49 or embodiment 50, wherein the one or more cytokines further comprises IL-7 and/or IL-15.

52. The method of any of embodiments 37-51, wherein the cultivating is carried out in the presence of a surfactant.

53. The method of any of embodiments 37-52, wherein at least a portion of the cultivating is performed with continual mixing and/or perfusion.

54. A method for producing a composition of engineered cells, the method comprising cultivating, in the presence of one or more cytokines, an engineered cell composition comprising one or both of CD4+ and CD8+ primary human T cells comprising cells engineered with a recombinant receptor, wherein the cultivating is carried out in the presence of a surfactant and/or at least a portion of the cultivating is performed with continual mixing and/or perfusion; wherein the method results in the proliferation or expansion of cells in the composition to produce an output composition comprising engineered CD4+ and/or CD8+ T cells.

55. The method of embodiment 48, wherein:
the engineered cell composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells or CD4+ and/or CD8+ recombinant receptor-expressing primary T cells; and/or
the engineered cell composition consists essentially of CD4+ and/or CD8+ primary human T cells.

56. The method of embodiment 48, wherein the proliferation or expansion results in, in about, or in at least a 2-fold, 3-fold, 4-fold, 5-fold, or greater than a 5-fold increase in the number of CD4+ and/or CD8+ T cells engineered with a recombinant receptor.

57. The method of embodiment 55, wherein the one or more cytokines are selected from recombinant IL-2, recombinant IL-7 and/or recombinant IL-15.

58. The method of embodiment 56 or embodiment 57, wherein:
the concentration of recombinant IL-2 is from 50 IU/mL to 500 IU/mL or from about 50 IU/mL to about 500 IU/mL;
the concentration of recombinant IL-7 is from 500 IU/mL to 2000 IU/mL or from about 500 IU/mL to about 2000 IU/mL; and/or
the concentration of recombinant IL-15 is from 5 IU/mL to 50 IU/mL or from about 5 IU/mL to about 50 IU/mL.

59. The method of embodiment 54, wherein:
the engineered cell composition comprises greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells or CD4+ and recombinant receptor-expressing primary human T cells; and/or
the engineered cell composition consists essentially of CD4+ primary human T cells.

60 The method of embodiment 59, wherein the proliferation or expansion results in, in about, or in at least a 2-fold, 3-fold, 4-fold, 5-fold, or greater than a 5-fold increase in the number of CD8+ T cells engineered with a recombinant receptor.

61. The method of embodiment 54 or embodiment 55, wherein the one or more cytokines are selected from recombinant IL-2, recombinant IL-7 and recombinant IL-15.

62. The method of embodiment 54, wherein:
the engineered cell composition comprises greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells or CD8+ and recombinant receptor-expressing primary human T cells; and/or
the engineered cell composition consists essentially of CD8+ primary human T cells.

63. The method of embodiment 54 or embodiment 62, wherein the one or more cytokines are selected from recombinant IL-2 and recombinant IL-15.

64. The method of any of embodiments 52-63, wherein the surfactant comprises a poloxamer, optionally wherein the poloxamer is present at a concentration of from 0.5 μL/mL to 5 μL/mL or from about 0.5 μL/mL to about 5 μL/mL.

65. The method of embodiment 64, wherein the poloxamer is Poloxamer 188.

66. The method of any of embodiments 54-65, wherein the engineered cell composition is produced by a method comprising:
(a) incubating, under stimulating conditions, an input composition comprising primary T cells enriched for one or both of CD4+ and CD8+ primary human T cells, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines, thereby generating a stimulated composition; and
(b) introducing a recombinant receptor into the stimulated composition, thereby generating an engineered composition comprising engineered T cells.

67. The method of embodiment 66, wherein:
the input composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells; and/or
the input composition consists essentially of CD4+ and/or CD8+ primary human T cells.

68. The method of embodiment 66 or embodiment 67, wherein the one or more cytokines are selected from recombinant IL-2, recombinant IL-7 and/or recombinant IL-15.

69. The method of embodiment 66, wherein:
the input composition comprises greater than about 70%, greater than or greater than about 75%, greater than or greater than about 80%, greater than or greater than about 85%, greater than or greater than about 90%, greater than or greater than about 95% or greater than or greater than about 98% CD4+ primary human T cells; and/or
the input composition consists essentially of CD4+ primary human T cells.

70. The method of embodiment 66 or embodiment 69, wherein the one or more cytokines are selected from recombinant IL-2, recombinant IL-7 and recombinant IL-15.

71. The method of embodiment 66, wherein:
the input composition comprises greater than about 70%, greater than or greater than about 75%, greater than or greater than about 80%, greater than or greater than about 85%, greater than or greater than about 90%, greater than or greater than about 95% or greater than or greater than about 98% CD8+ primary human T cells; and/or the input composition consists essentially of CD8+ primary human T cells.

72. The method of embodiment 66 or embodiment 71, wherein the one or more cytokines are selected from recombinant IL-2 and recombinant IL-15.

73. The method of any of embodiments 49-53 and 66-72, wherein the stimulatory reagent comprises a primary agent that specifically binds to a member of a TCR complex, optionally that specifically binds to CD3.

74. The method of embodiment 73, wherein the stimulatory reagent further comprises a secondary agent that specifically binds to a T cell costimulatory molecule, optionally wherein the costimulatory molecule is selected from CD28, CD137 (4-1-BB), OX40, or ICOS.

75. The method of embodiment 73 or embodiment 74, wherein the primary and/or secondary agents comprise an antibody, optionally wherein the stimulatory reagent comprises incubation with an anti-CD3 antibody and an anti-CD28 antibody, or an antigen-binding fragment thereof.

76. The method of any of embodiments 73-75, wherein the primary agent and/or secondary agent are present on the surface of a solid support.

77. The method of embodiment 76, wherein the solid support is or comprises a bead.

78. The method of embodiment 77, wherein the bead comprises a diameter of greater than or greater than about 3.5 μm but no more than about 9 μm or no more than about 8 μm or no more than about 7 μm or no more than about 6 μm or no more than about 5 μm.

79. The method of embodiment 77 or embodiment 78, wherein the bead comprises a diameter of or about 4.5 μm.

80. The method of any of embodiments 77-79, wherein the bead is inert.

81. The method of any of embodiments 77-80, wherein the bead is or comprises a polystyrene surface.

82. The method of any of embodiments 77-81, wherein the bead is magnetic or superparamagnetic.

83. The method of any of embodiments 77-82, wherein the ratio of beads to cells is less than 3:1.

84. The method of any of embodiments 77-83, wherein the ratio of beads to cells is from 2:1 to 0.5:1 or from about 2:1 to about 0.5:1.

85. The method of any of embodiments 77-84, wherein the ratio of beads to cells is at or at about 1:1.

86. The method of any of embodiments 49-53 and 66-85, wherein the incubating is carried out in the presence of one or more antioxidant.

87. The method of embodiment 86, wherein the one or more antioxidant comprises a sulfur containing antioxidant.

88. The method of embodiment 86 or embodiment 87, wherein the one or more antioxidants comprise a glutathione precursor.

89. The method of any of embodiments 86-88, wherein the one or more antioxidants comprise N-acetyl cysteine (NAC), optionally wherein the NAC is at a concentration of from 0.2 mg/mL to 2.0 mg/mL or from about 0.2 mg/mL to about 2.0 mg/mL.

90. The method of any of embodiments 49-53 and 66-89, wherein the introducing comprises transducing cells of the stimulated composition with a viral vector comprising a polynucleotide encoding the recombinant receptor.

91. The method of embodiment 90, wherein the viral vector is a retroviral vector.

92. The method of embodiment 90 or embodiment 91, wherein the viral vector is a lentiviral vector or gammaretroviral vector.

93. The method of any of embodiments 49-53 and 66-92, wherein the introducing is carried out in the presence of a transduction adjuvant.

94. The method of embodiment 93, wherein the transduction adjuvant is or comprises protamine sulfate, optionally from 1 μg/ml to 50 μg/ml or from about 1 μg/ml to about 50 μg/ml protamine sulfate; a fibronectin-derived transduction adjuvant; and/or RetroNectin.

95. The method of any of embodiments 49-53 and 66-89, wherein the introducing comprises transfecting the cells of the stimulated composition with a vector comprising a polynucleotide encoding the recombinant receptor.

96. The method of embodiment 95, wherein the vector is a transposon, optionally a Sleeping Beauty (SB) transposon or a Piggybac transposon.

97. The method of any of embodiments 44-69, wherein the engineered cell composition does not comprise a stimulatory reagent and/or the stimulatory reagent has been substantially removed from the composition prior to the cultivating, said stimulatory reagent comprising a reagent capable of activating one or more intracellular signaling domains of one or more components of a TCR complex and/or one or more intracellular signaling domains of one or more costimulatory molecules.

98. The method of any of embodiments 37-97, wherein the cultivating is performed at least until the output composition comprises a threshold number of T cells.

99. The method of embodiment 98, wherein the cultivating is continued for at least one day after the threshold number of T cells is reached.

100. The method of embodiment 98 or embodiment 99, wherein the threshold number is at least 2-fold, at least 3-fold, at least 4-fold, at least 5-fold or more greater than the number of the engineered cell composition prior to the cultivation.

101. The method of any of embodiments 37-100, wherein the cultivating is performed for 2 days to 10 days inclusive, and/or the cultivating is performed for at least 10 days.

102. The method of any of embodiments 37-101, wherein subsequent to the cultivating, collecting cells of the output composition.

103. The method of embodiment 102, wherein the amount of time between initiation of the incubating and collecting cells of the output composition is from 7 days to 15 days or from about 7 days to about 15 days.

104. The method of embodiment 102 or embodiment 102, wherein the amount of time between initiation of the incubating and the collecting cells of the output composition is from 9 days to 13 days or from about 9 days to about 13 days.

105. The method of any of embodiments 102-104, wherein the amount of time between initiation of the incubation and collecting cells of the output composition is from 8 days to 13 days or from about 8 days to about 13 days.

106. The method of any of embodiments 37-105, further comprising formulating cells of the output composition for cryopreservation and/or administration to a subject, optionally in the presence of a pharmaceutically acceptable excipient.

107. The method of embodiment 106, wherein the cells of the output composition are formulated in the presence of a cryoprotectant.

108. The method of embodiment 107, wherein the cryoprotectant comprises DMSO.

109. The method of any of embodiments 106-108, wherein the cells of the output composition are formulated in a container, optionally a vial or a bag.

110. The method of any of embodiments 1-43 and 49-53 and 66-89, further comprising isolating the CD4+ and/or the CD8+ T cells from a biological sample prior to the incubating.

111. The method of embodiment 110, wherein the isolating comprises, selecting cells based on surface expression of CD4 and/or CD8, optionally by positive or negative selection.

112. The method of embodiment 110 or embodiment 111, wherein the isolating comprises carrying out immunoaffinity-based selection.

113. The method of any of embodiments 110-112, wherein the biological sample comprises primary T cells obtained from a subject.

114. The method of embodiment 113, wherein the subject is a human subject.

115. The method of any of embodiments 110-112, wherein the biological sample is or comprises a whole blood sample, a buffy coat sample, a peripheral blood mononuclear cell (PBMC) sample, an unfractionated T cell sample, a lymphocyte sample, a white blood cell sample, an apheresis product, or a leukapheresis product.

116. The method of any of embodiments 1-115, wherein the recombinant receptor is capable of binding to a target antigen that is associated with, specific to, and/or expressed on a cell or tissue of a disease, disorder or condition.

117. The method of embodiment 116, wherein the disease, disorder or condition is an infectious disease or disorder, an autoimmune disease, an inflammatory disease, or a tumor or a cancer.

118. The method of embodiment 116 or 117, wherein the target antigen is a tumor antigen.

119. The method of any of embodiments 116-118, wherein the target antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, G Protein Coupled Receptor 5D (GPCR5D), Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, tEGFR, VEGF receptors, VEGF-R2, Wilms Tumor 1 (WT-1), a pathogen-specific antigen and an antigen associated with a universal tag.

120. The method of any of embodiments 1-119, wherein the recombinant receptor is or comprises a functional non-TCR antigen receptor or a TCR or antigen-binding fragment thereof.

121. The method of any of embodiments 1-120, wherein the recombinant receptor is a chimeric antigen receptor (CAR).

122. The method of any of embodiments 1-121, wherein the recombinant receptor is an anti-CD19 CAR.

123. The method of embodiment 121, wherein the chimeric antigen receptor comprises an extracellular domain comprising an antigen-binding domain.

124. The method of embodiment 123, wherein the antigen-binding domain is or comprises an antibody or an antibody fragment thereof, which optionally is a single chain fragment.

125. The method of embodiment 124, wherein the fragment comprises antibody variable regions joined by a flexible linker.

126. The method of embodiment 124 or embodiment 125, wherein the fragment comprises an scFv.

127. The method of any of embodiments 123-126, wherein the chimeric antigen receptor further comprises a spacer and/or a hinge region.

128. The method of any of embodiments 123-127, wherein the chimeric antigen receptor comprises an intracellular signaling region.

129. The method of embodiment 128, wherein the intracellular signaling region comprises an intracellular signaling domain.

130. The method of embodiment 129, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

131. The method of embodiment 130, wherein the intracellular signaling domain is or comprises an intracellular signaling domain of a CD3 chain, optionally a CD3-zeta (CD3) chain, or a signaling portion thereof.

132. The method of any of embodiments 128-131, wherein the chimeric antigen receptor further comprises a transmembrane domain disposed between the extracellular domain and the intracellular signaling region.

133. The method of any of embodiments 128-132, wherein the intracellular signaling region further comprises a costimulatory signaling region.

134. The method of embodiment 133, wherein the costimulatory signaling region comprises an intracellular signaling domain of a T cell costimulatory molecule or a signaling portion thereof.

135. The method of embodiment 133 or embodiment 134, wherein the costimulatory signaling region comprises an intracellular signaling domain of a CD28, a 4-1BB or an ICOS or a signaling portion thereof.

136. The method of any of embodiments 133-135, wherein the costimulatory signaling region is between the transmembrane domain and the intracellular signaling region.

137. The method of any of embodiments 98-101, wherein the output composition comprising the threshold number or greater number of cells is produced among greater than or greater than about 85%, greater than or greater than about 90% or greater than or greater than about 95% of the iterations of the method.

138. A composition comprising engineered cells produced by a method of any of embodiments 1-137.

139. The composition of embodiment 138, further comprising a pharmaceutically acceptable carrier.

140. The composition of embodiment 138 or embodiment 139, comprising a cryoprotectant, optionally DMSO.

141. An article of manufacture, comprising the composition of any of embodiments 138-140, and instructions for administering the output composition to a subject.

142. The article of manufacture of embodiment 141, wherein the subject has a disease or condition, optionally wherein the recombinant receptor specifically recognizes or specifically bind to an antigen associated with, or expressed or present on cells of, the disease or condition.

143. The article of manufacture of embodiment 141 or 142, wherein the output composition is a composition of engineered CD4+ T cells.

144. The article of manufacture of embodiment 141 or 142, wherein the output composition is a engineered composition of CD8+ T cells.

145. An article of manufacture comprising a composition of engineered CD4+ T cells produced by the method of any of embodiments 1-11, 13-60, 63-70, or 72-137, a composition of engineered CD8+ T cells produced by the method of any of embodiments 6-8, 11-43, 54-58, 60-68, or 70-137, and instructions for administering the engineered CD4+ T cells and the engineered CD8+ T cells to a subject.

146. The article of manufacture of embodiment 145, wherein the instructions specify separately administering the CD4+ T cells and CD8+ T cells to the subject.

147. The article of manufacture of embodiment 145 or 146, wherein the instructions specify administering the CD4+ T cells and the CD8+ T cells to the subject at a desired ratio.

148. The method of any of embodiments 1-137, wherein the method is performed in less than 21 days, inclusive.

VII. EXAMPLES

The following examples are included for illustrative purposes only and are not intended to limit the scope of the invention.

Example 1: Processes for Generating Therapeutic Compositions of CD4+ and CD8+ Cells Expressing an Anti-CD19 CAR Engineered CD4+ T cells and engineered CD8+ T cells each expressing the same anti-CD19 chimeric antigen receptor (CAR) were produced by a process involving subjecting enriched CD4+ and enriched CD8+ cell populations, separately, to process steps. CD4+ and CD8+ cells were separately selected from human peripheral blood mononuclear cells (PBMCs) that had been obtained by leukapheresis, generating separate enriched CD4+ and enriched CD8+ cell compositions, which then were cryofrozen. The CD4+ and CD8+ compositions were subsequently thawed and separately underwent steps for stimulation, transduction, and expansion.

The thawed CD4+ and CD8+ cells were separately stimulated in the presence of paramagnetic polystyrene-coated beads coupled to anti-CD3 and anti-CD28 antibodies at a 1:1 bead to cell ratio. The stimulation was carried out in media containing human recombinant IL-2, human recombinant IL-15, and N-Acetyl Cysteine (NAC). The CD4+ cell media also included human recombinant IL-7.

Following the introduction of the beads, CD4+ and CD8+ cells were separately transduced with a lentiviral vector encoding the same anti-CD19 CAR. The CAR contained an anti-CD19 scFv derived from a murine antibody, an immunoglobulin spacer, a transmembrane domain derived from CD28, a costimulatory region derived from 4-1BB, and a CD3-zeta intracellular signaling domain. The vector also encoded a truncated EGFR (EGFRt) that served as a surrogate marker for CAR expression that was connected to the CAR construct by a T2A sequence. The cells were transduced in the presence of 10 μg/ml protamine sulfate.

After transduction, the beads were removed from the cell compositions by exposure to a magnetic field. The CD4+ and CD8+ cell compositions were then separately cultivated for expansion with continual mixing and oxygen transfer by a bioreactor (Xuri W25 Bioreactor). Poloxamer was added to the media. Both cell compositions were cultivated in the presence of IL-2 and IL-15. The CD4+ cell media also included IL-7. The CD4+ and CD8+ cells were each cultivated, prior to harvest, to 4-fold expansion. One day after reaching the threshold, cells from each composition were separately harvested, formulated, and cryofrozen. The exemplary process is summarized in Table E1.

TABLE E1

Summary of the exemplary process for generating CD4+ and CD8+ CAR-T cells

| Stage | CD4+ cells | CD8+ cells |
| --- | --- | --- |
| Stimulation (day 1-2) | anti-CD3/CD28 antibody conjugated beads 1:1 bead to cell ratio media: IL-2, IL-7, IL-15, and NAC | anti-CD3/CD28 antibody conjugated beads 1:1 bead to cell ratio media: IL-2, IL-15, and NAC |
| Transduction (day 2-5) | transduction adjuvant (e.g. 10 μg/ml protamine sulfate) | transduction adjuvant (e.g. 10 μg/ml protamine sulfate) |
| Bead removal (day 5*) | magnetic bead removal | magnetic bead removal |
| Expansion (day 5* - Harvest) | rocking motion bioreactor and/or continuous mixing media: IL-2, IL-7, IL15, and poloxamer | rocking motion bioreactor and/or continuous mixing media: IL-2, IL15, and poloxamer |

*Approximate

The exemplary process summarized in Table E1 was compared to an exemplary alternative process. The alternative process differed in that: NAC was not added to the media during stimulation; CD4+ cell media did not contain IL-2; cells were stimulated at a bead to cell ratio of 3:1; cells were transduced with a higher concentration of protamine sulfate; bead removal occurred at about day 7; and expansion was performed at a static setting, i.e., without continual mixing or perfusion (e.g., semi-continuous and/or stepwise perfusion), and without poloxamer.

Example 2: Assessment of Process Duration for Generating Therapeutic Compositions of CD4+ and CD8+ CAR-T Cells Various attributes of the exemplary and alternative processes described in Example 1 were assessed. In one experiment, process runs were performed for the exemplary and alternative processes with separate CD4+ and CD8+ cell compositions obtained from the same DLBCL human leukapheresis sample. Total cell counts were measured at different time points during the stimulation, transduction, and expansion phases of each process. As shown in FIG. 1, the CD4+ and CD8+ cell compositions subjected to the exemplary process expanded more quickly and reached an exemplary a degree of expansion (4-fold expansion), which in this study was designated to reach prior to harvesting, in a shorter amount of time than observed with the alternative process.

Durations of the expansion phase (ran until 4-fold expansion in this study) of the exemplary process in Example 1 and the alternative process were assessed from a number of process runs of separate CD4+ and CD8+ cell compositions obtained from leukapheresis samples collected from subjects with DLBCL. The duration of this phase of the exemplary process was assessed based on a set of exemplary runs with separate CD4+ and CD8+ cell compositions obtained from leukapheresis samples collected from healthy subjects and subjects with DLBCL. Duration was measured as the length of time between the start of stimulation to harvest (which in this exemplary study occurred one day after reaching a four-fold expansion). In this study, runs of the exemplary process were observed to have a shorter duration from start of expansion to 4-fold expansion or harvest, with a narrower distribution (such as between 9 and 13 days in one study) among different runs for this duration, as compared to the alternative process duration.

Durations of exemplary manufacturing protocols utilizing the exemplary and alternative processes (exemplary and alternative manufacturing protocols, respectively) were modeled. In general, the modeling results were consistent with the interpretation that the exemplary process is capable of achieving comparatively shorter protocol durations, with less variability, than other manufacturing protocols.

Example 3: Assessment of Processes for Generating Therapeutic Compositions of CD4+ and CD8+ CAR-T Cells An exemplary set of CD4+ and CD8+ cell compositions obtained from samples (including those that in an alternative process, exhibited an expansion phase (expansion to harvest (4-fold expansion)) duration of greater than 17 days and those that exhibited an expansion phase duration of equal to or less than 17 days were processed using the exemplary process. Total cell counts were measured at different time points during the stimulation, transduction, and expansion phases until the harvest threshold was achieved.

CD4+ and CD8+ cell compositions having expanded 4-fold were generated with the exemplary process, from samples from both types of compositions (those observe to expand to 4-fold in less than 17 days, or greater and those observed to do so in greater than 17 days, in the other process), with a low range of variability in duration.

Example 4: Generation of Therapeutic Compositions of CD4+ and CD8+ CAR-T Cells from a Biological Sample Obtained from a Subject with Chronic Lymphocytic Leukemia Separate compositions of CD4+ and CD8+ T cells that were selected from isolated PBMCs from a human leukapheresis sample obtained from a subject with chronic lymphocytic leukemia (CCL) were incubated, transduced, and cultivated by the exemplary process described in Example I. Separate compositions of engineered CD4+ T cells and engineered CD8+ T cells, each expressing the same anti-CD19 CAR, were generated.

Example 5: Continuous in-Line Imaging for Determination of Cell Viability During Cultivation Various optical parameters of T cells in the process of engineering for expression of a recombinant receptor, were obtained using in-line differential digital holography microscopy (DHM). Differential DHM permits label-free imaging of cells, with high-contrast images for object segmentation, and obtaining a plurality of optical or morphological features that quantitatively describe the imaged objects, for example, for determining cell counts and viability.

Primary T cells from healthy human donors were engineered to express an anti-CD19 chimeric antigen receptor (CAR) using an exemplary engineering process, generally as described in Examples 1 above. Two experiments were performed: Experiment 1 with two experimental runs of with CD4+ cells from two different healthy donors (Donor 1 or Donor 2), and Experiment 2 with an experimental run, each of CD4+ cells and CD8+ cells from a third donor (Donor 3). The cells were cultivated for expansion by transfer to a bioreactor (e.g., a rocking motion bioreactor). The cultivation included media replacement with semi-continuous perfusion and continual mixing.

Holographic images and optical parameters of the cells were captured continuously for up to approximately 120 hours of culture using an in-line differential DHM imaging system ("continuous"), for example an Ovizio iLine F (Ovizio Imaging Systems NV/SA, Brussels, Belgium). The in-line differential DHM system contained a disposable tubing system connected to the bioreactor such that a sample can flow from the bioreactor, through the tubing system, where an imaging system captures holographic images and optical parameters of the cells traveling through, and returns the sample to the bioreactor. Cell viability and viable cell count (VCC) were determined from images. Viability of the engineered cells were also compared to results by manual sampling ("manual") and cell counting using an automated cell counter, sampled at various time points for up to approximately 120 hours of culture. The two methods were compared based on time course analysis and linear regression.

Figure 2A:
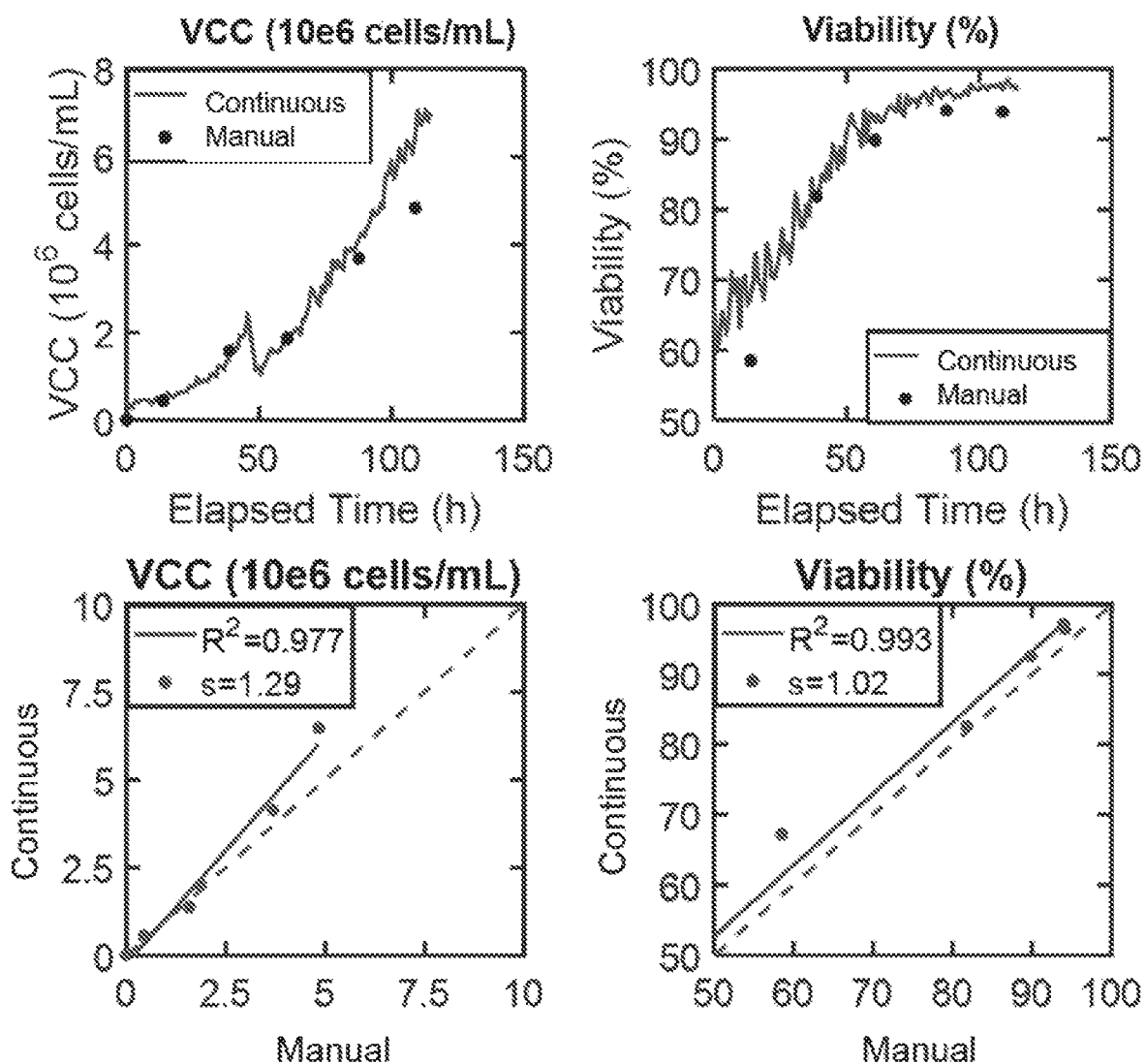
FIGS. 2A-2D depict viable cell count (VCC; ×10$^6$ cells/mL) and cell viability (%), assessed using continuous monitoring by differential DHM ("continuous", line) or manual sampling ("manual", dots, in CD4+ cells from Experiment 1 Donor 1 (FIG. 2A), Experiment 1 Donor 2 (FIG. 2B) or Experiment 2 Donor 3 (FIG. 2C), or CD8+ cells from Experiment 2 Donor 3 (FIG. 2D). Top panels depict the measurements for each, bottom panels depict linear regression analysis and the $R^2$ and slope (s), for comparing the continuous monitoring and manual sampling.
Figure 2B:
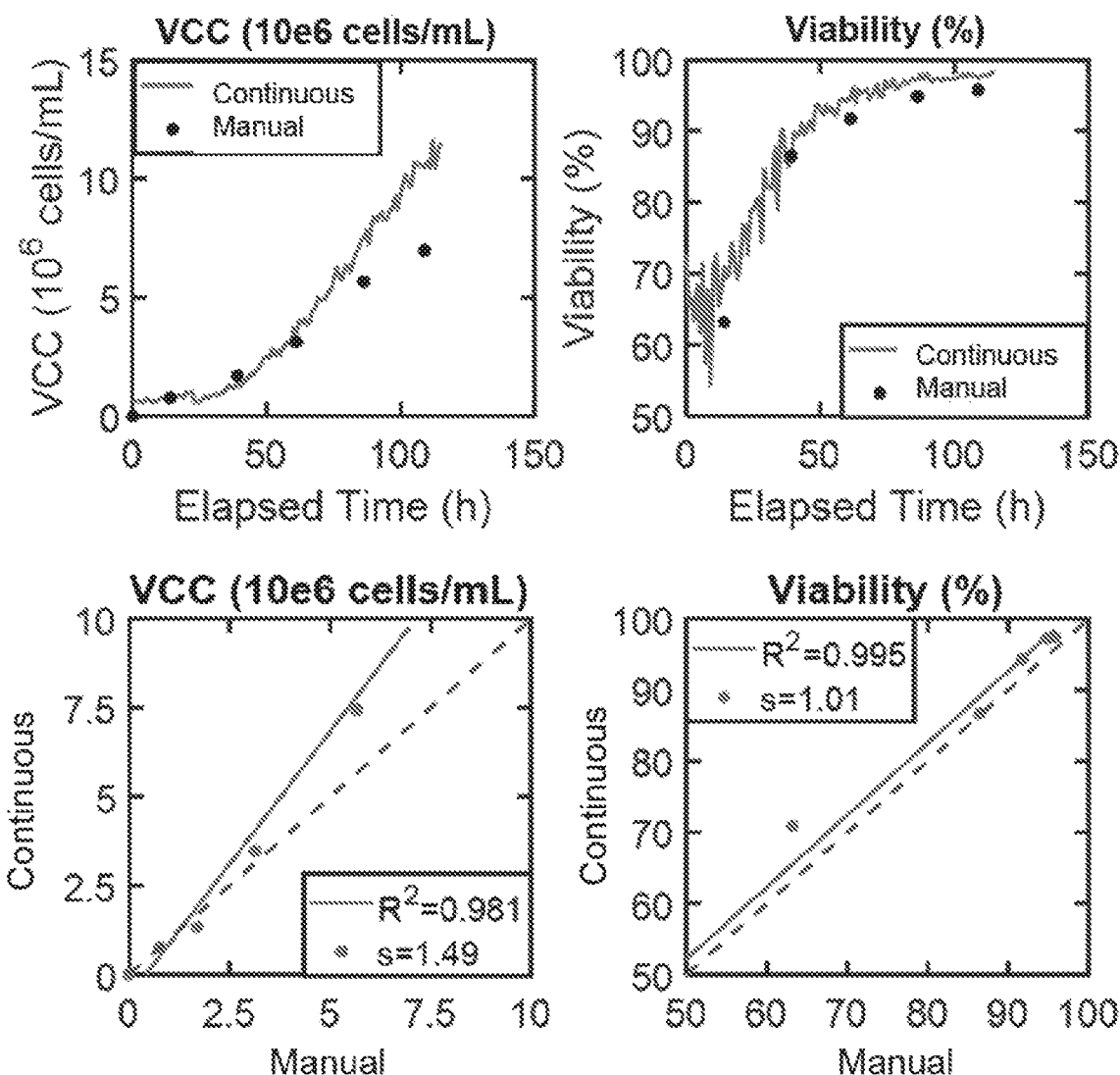
Figure 2C:
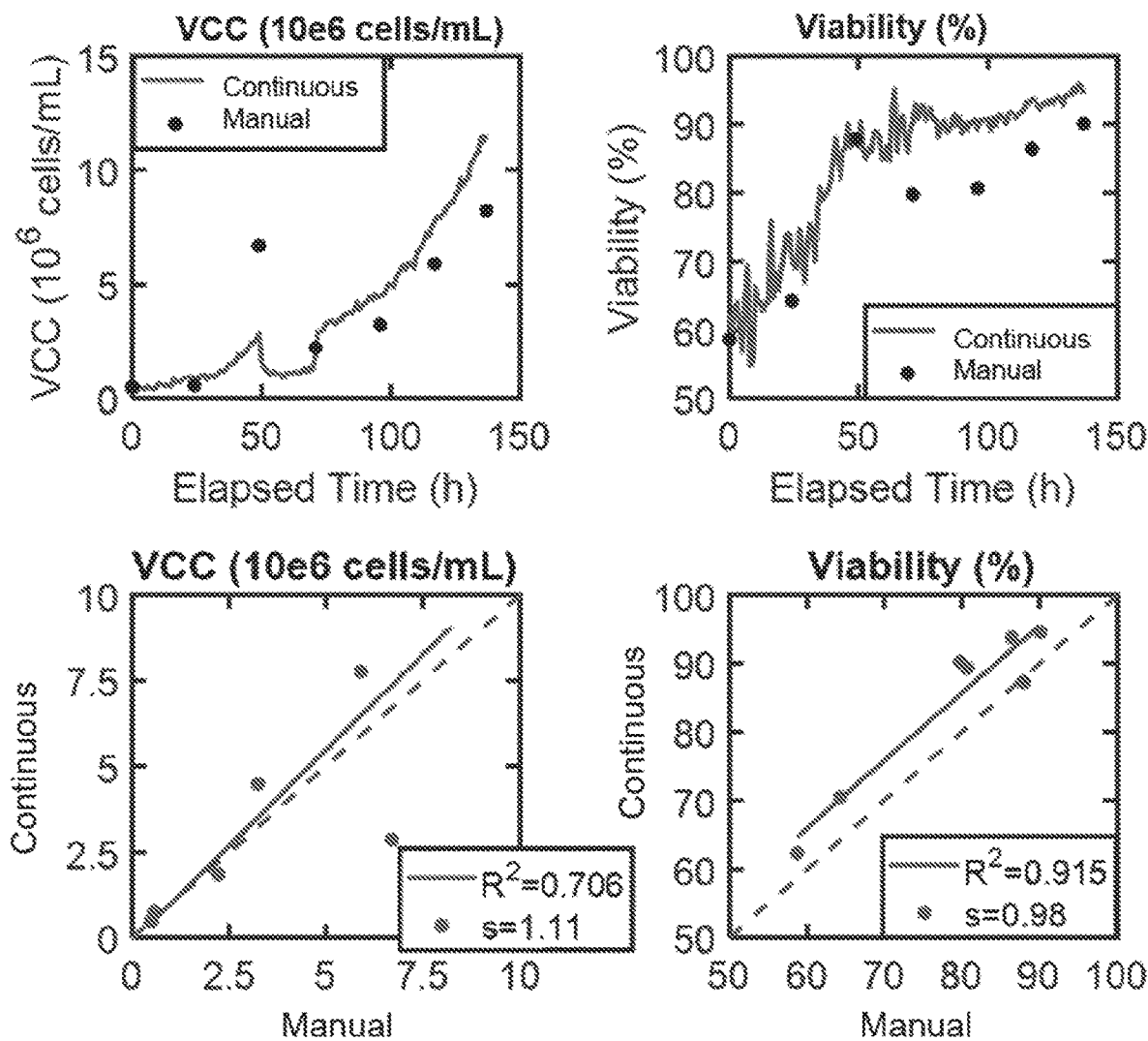
Figure 2D:
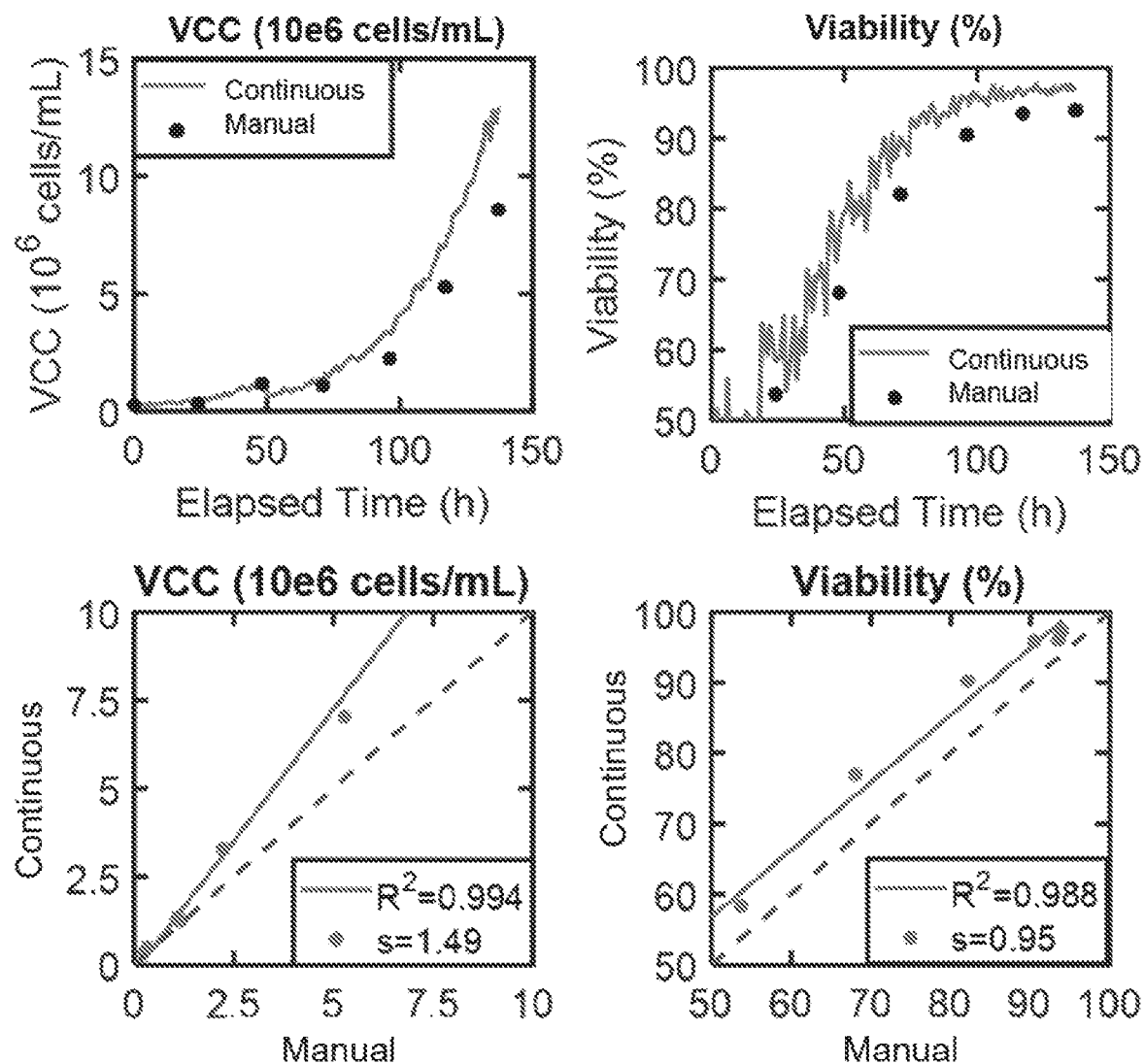

FIGS. 2A-2D show the comparison of viable cell count (VCC) and viability, assessed using continuous monitoring by differential DHM or manual sampling, in CD4+ cells from Experiment 1 Donor 1 (FIG. 2A), Experiment 1 Donor 2 (FIG. 2B) or Experiment 2 Donor 3 (FIG. 2C), or CD8+ cells from Experiment 2 Donor 3 (FIG. 2D). The R2 and slope of the comparison is shown in Table E2 below.

TABLE E2

$R^2$ and slope of comparison between sampling methods.

| Experiment | $R^2$ | | slope | |
| --- | --- | --- | --- | --- |
| | VCC | Viability | VCC | Viability |
| Experiment 1, Donor 1, CD4+ | 0.98 | 0.99 | 1.29 | 1.02 |
| Experiment 1, Donor 2, CD4+ | 0.98 | 1.00 | 1.49 | 1.01 |
| Experiment 2, Donor 3, CD4+ | 0.71 | 0.92 | 1.11 | 0.98 |
| Experiment 2, Donor 3, CD8+ | 0.99 | 0.99 | 1.49 | 0.95 |

The results showed that the VCC and viability as continuous monitoring and manual sampling were highly correlated, for CD4+ and CD8+ cells and cells from different donors. The results were consistent with the utility of the continuous monitoring by differential DHM during cultivation for expansion of the cells in the cell engineering process.

Example 6: Comparison of Manual and Automated Expansion Using Continuous in-Line Imaging A fully automated, operator-free cell expansion method with continuous monitoring of the cells by in-line imaging and automated perfusion, was compared to a manual expansion method.

Primary T cells from a healthy human donor were activated and transduced with a vector to express an exemplary chimeric antigen receptor (CAR), using an exemplary engineering process. After transduction, cells were pooled and inoculated for two different cultures, one automated expansion based on continuous in-line imaging using differential DHM, and one manual expansion method.

In the automated expansion culture, cells were cultivated in a rocking motion bioreactor, with media replacement with perfusion and continual mixing. Cell viability and viable cell count (VCC) were monitored using an automated differential DHM imaging system, generally as described in Example 5 above. The initial VCC at the time of inoculation was similar for both cultures ($0.12 \times 10^6$ cells/mL for automated culture, $0.14 \times 10^6$ cells/mL for manual culture). Perfusion in the automated expansion was based on a four-hour rolling average of VCC calculated by a software algorithm, where a VCC average greater than the target VCC was required for progression of the method. The target VCC was at $0.6 \times 10^6$ cells/mL, $1 \times 10^6$ cells/mL and $4 \times 10^6$ cells/mL for 3 perfusion steps. No additional operator intervention occurred after inoculation. In the manual expansion culture, perfusion was performed based on manual sampling and assessment of VCC, with a particular volume of media added after a threshold VCC was reached. Cells were also assessed for cell surface expression of markers by flow cytometry.

Figure 3:
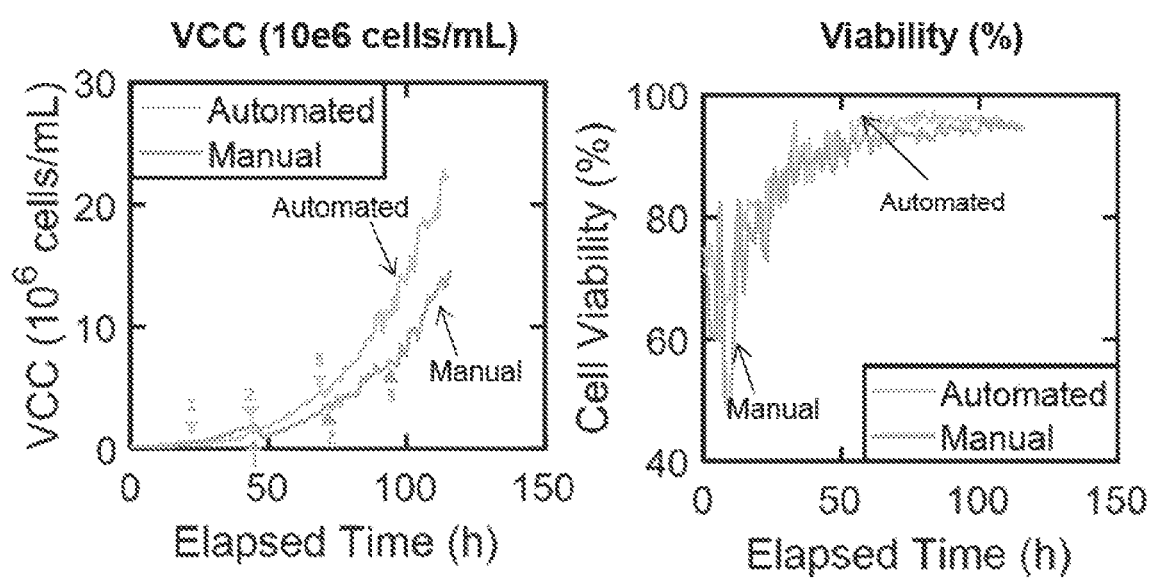
FIG. 3 depicts viable cell count (VCC; ×10$^6$ cells/mL) and cell viability (%), assessed using continuous monitoring by differential DHM, in an automated expansion process compared to a manual expansion process.

As shown in FIG. 3, higher T cell growth was observed with the automated expansion system. Cell viability as assessed by continuous differential DHM imaging, and cell phenotypes, as assessed by flow cytometry, were similar between the automated vs. manual expansion processes.

The results were consistent with the utility of the continuous DHM imaging and automated expansion process, for cultivation and monitoring of cells during a T cell engineering process, without the need for a human operator. In some aspects, such method can be used to determine the growth kinetics of the primary T cells, and determine the time for harvesting the cells for engineering of administration.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2-CH3 spacer Homo sapiens |
| 5 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC EVSGFSPPNILLMWLEDQREVNTSGFAPARPPPQPGSTTFWAWSVLRVP APPSPQPATYTCVVSHEDSRTLLNASRSLEVSYVTDH | IgD-hinge-Fc Homo sapiens |
| 6 | LEGGGEGRGSLLTCGDVEENPGPR | T2A artificial |
| 7 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR artificial |

-continued

| SEQ ID NO. | SEQUENCE | DESCRIPTION |
|---|---|---|
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKPFWVLVVVGGV LACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 14 | RVKFSRSAEPPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 15 | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 16 | RKVCNGIGIGEFKDSLSINATNIKHFKNCTSISGDLHILPVAFRGDSFT HTPPLDPQELDILKTVKEITGFLLIQAWPENRTDLHAFENLEIIRGRTK QHGQFSLAVVSLNITSLGLRSLKEISDGDVIISGNKNLCYANTINWKKL FGTSGQKTKIISNRGENSCKATGQVCHALCSPEGCWGPEPRDCVSCRNV SRGRECVDKCNLLEGEPREFVENSECIQCHPECLPQAMNITCTGRGPDN CIQCAHYIDGPHCVKTCPAGVMGENNTLVWKYADAGHVCHLCHPNCTYG CTGPGLEGCPTNGPKIPSIATGMVGALLLLLVVALGIGLFM | tEGFR artificial |
| 17 | EGRGSLLTCGDVEENPGP | T2A artificial |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | PGGG-(SGGGG)5-P- wherein P is proline, G is glycine and S is serine | Exemplary linker |
| 23 | GSADDAKKDAAKKDGKS | Exemplary Linker |
| 24 | GSTSGSGKPGSGEGSTKG | Exemplary Linker |
| 25 | Glu Val Val Val Lys Tyr Gly Pro Pro Cys Pro Pro Cys Pro | Exemplary IgG Hinge |

-continued

| SEQUENCES | | |
|---|---|---|
| SEQ ID NO. | SEQUENCE | DESCRIPTION |
| 26 | X1PPX2P<br>X1 is glycine, cysteine or arginine<br>X2 is cysteine or threonine | Exemplary IgG Hinge |
| 27 | Glu Pro Lys Ser Cys Asp Lys Thr His Thr Cys Pro Pro Cys Pro | Exemplary IgG Hinge |
| 28 | Glu Arg Lys Cys Cys Val Glu Cys Pro Pro Cys Pro | Exemplary IgG Hinge |
| 29 | ELKTPLGDTHTCPRCPEPKSCDTPPPCPRCPEPKSCDTPPPCPRCPEPK<br>SCDTPPPCPRCP | Exemplary IgG Hinge |
| 30 | Glu Ser Lys Tyr Gly Pro Pro Cys Pro Ser Cys Pro | Exemplary IgG Hinge |
| 31 | Glu Ser Lys Tyr Gly Pro Pro Cys Pro Pro Cys Pro | Exemplary IgG Hinge |
| 32 | Tyr Gly Pro Pro Cys Pro Pro Cys Pro | Exemplary IgG Hinge |
| 33 | Lys Tyr Gly Pro Pro Cys Pro Pro Cys Pro | Exemplary IgG Hinge |
| 34 | QQGNTLPYT | CDR L3 |
| 35 | RASQDISKYLN | CDR L1 |
| 36 | SRLHSGV | CDR L2 |
| 37 | GNTLPYTFG | CDR L3 |
| 38 | DYGVS | CDR H1 |
| 39 | VIWGSETTYYNSALKS | CDR H2 |
| 40 | YAMDYWG | CDR H3 |
| 41 | EVKLQESGPGLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHYYYGGSYAMD<br>YWGQGTSVTVSS | VH |
| 42 | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEIT | VL |
| 43 | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEITG<br>STSGSGKPGSGEGSTKGEVKLQESGPGLVAPSQSLSVTCTVSGVSLPDYGVSWI<br>RQPPRKGLEWLGVIWGSETTYYNSALKSRLTIIKDNSKSQVFLKMNSLQTDDTA<br>IYYCAKHYYYGGSYAMDYWGQGTSVTVSS | scFv |
| 44 | KASQNVGTNVA | CDR L1 |
| 45 | SATYRNS | CDR L2 |
| 46 | QQYNRYPYT | CDR L3 |
| 47 | SYWMN | CDR H1 |
| 48 | QIYPGDGDTNYNGKFKG | CDR H2 |
| 49 | KTISSVVDFYFDY | CDR H3 |
| 50 | EVKLQQSGAELVRPGSSVKISCKASGYAFSSYWMNWVKQRPGQGLEWIGQIYPG<br>DGDTNYNGKFKGQATLTADKSSSTAYMQLSGLTSEDSAVYFCARKTISSVVDFY<br>FDYWGQGTTVTVSS | VH |

| SEQ ID NO. | SEQUENCE | DESCRIPTION |
|---|---|---|
| 51 | DIELTQSPKFMSTSVGDRVSVTCKASQNVGTNVAWYQQKPGQSPKPLIYSATYR NSGVPDRFTGSGSGTDFTLTITNVQSKDLADYFCQQYNRYPYTSGGGTKLEIKR | VL |
| 52 | GGGGSGGGGSGGGGS | Linker |
| 53 | EVKLQQSGAELVRPGSSVKISCKASGYAFSSYWMNWVKQRPGQGLEWIGQIYPG DGDTNYNGKFKGQATLTADKSSSTAYMQLSGLTSEDSAVYFCARKTISSVVDFY FDYWGQGTTVTVSSGGGGSGGGGSGGGGSDIELTQSPKFMSTSVGDRVSVTCKA SQNVGTNVAWYQQKPGQSPKPLIYSATYRNSGVPDRFTGSGSGTDFTLTITNVQ SKDLADYFCQQYNRYPYTSGGGTKLEIKR | scFv |
| 54 | HYYYGGSYAMDY | CDR H3 |
| 55 | HTSRLHS | CDR L2 |
| 56 | GSTSGSGKPGSGEGSTKG | Linker |
| 57 | gacatccagatgacccagaccacctccagcctgagcgccagcctgggcgaccgg gtgaccatcagctgccgggccagccaggacatcagcaagtacctgaactggtat cagcagaagcccgacggcaccgtcaagctgctgatctaccacaccagccggctg cacagcggcgtgcccagccggtttagcggcagcggctccggcaccgactacagc ctgaccatctccaacctggaacaggaagatatcgccacctacttttgccagcag ggcaacacactgcccta cacccttt ggcggcggaacaaagctggaaatcaccggc agcacctccggcagcggcaagcctggcagcggcgagggcagcaccaagggcgag gtgaagctgcaggaaagcggccctggcctggtgccccagccagagcctgagc gtgacctgcaccgtgagcggcgtgagcctgcccgactacggcgtgagctggatc cggcagccccccaggaagggcctggaatggctgggcgtgatctggggcagcgag accacctactacaacagcgccctgaagagccggctgaccatcatcaaggacaac agcaagagccaggtgttcctgaagatgaacagcctgcagaccgacgacaccgcc atctactactgcgccaagcactactactacggcggcagctacgccatggactac tggggccagggcaccagcgtgaccgtgagcagc | Sequence encoding scFv |
| 58 | MPLLLLLPLLWAGALA | CD33 signal peptide |
| 59 | MALPVTALLLPLALLLHA | CD8 alpha signal peptide |
| 60 | atgcttctcctggtgacaagccttctgctctgtgagttaccacacccagcattc ctcctgatccca | GMCSFR alpha chain signal sequence |
| 61 | MLLLVTSLLLCELPHPAFLLIP | GMCS FR alpha chain signal sequence |

What is claimed:

1. A method for producing a composition of engineered cells, the method comprising:
    (a) incubating an input composition comprising T cells enriched for one or both of CD4+ and CD8+ primary human T cells, thereby generating a stimulated composition, wherein:
        the primary human T cells are from a human subject having a disease or condition; and
        the incubating is carried out under one or more stimulating conditions, the stimulating conditions comprising the presence of (i) an anti-CD3 antibody or antibody fragment thereof and an anti-CD28 antibody or antibody fragment thereof, and (ii) recombinant IL-2 and recombinant IL-15, wherein the concentration of recombinant IL-2 is from about 10 IU/mL to about 200 IU/mL and the concentration of recombinant IL-15 is from about 1 IU/mL to about 25 IU/mL;
    (b) introducing a recombinant receptor into cells of the stimulated composition, thereby generating an engineered composition comprising engineered T cells, wherein the recombinant receptor is capable of binding to a target antigen that is expressed on a cell of the disease or condition; and
    (c) cultivating the engineered composition under conditions to promote expansion of the engineered T cells, thereby producing an output composition comprising the engineered T cells that is suitable for an autologous cell therapy to treat the disease or condition of the subject, wherein:
        (i) the cultivating is carried out in the presence of:
            (1) recombinant IL-2 and recombinant IL-15, wherein the concentration of recombinant IL-2 is from about 50 IU/mL to about 500 IU/mL and the concentration of recombinant IL-15 is from about 5 IU/mL to about 50 IU/mL; and
            (2) a surfactant, wherein the surfactant is a poloxamer added during the cultivating step;
        (ii) at least a portion of the cultivating is performed with perfusion; and
        (iii) the cultivating is performed for 2 days to 8 days, inclusive, wherein the cultivating is performed at least until the output composition comprises 4-fold or greater viable T cells compared to the composition prior to the cultivating; and
    (d) collecting cells of the output composition after at most 8 days of the cultivating.

2. The method of claim 1, wherein the incubating is further carried out in the presence of recombinant IL-7.

3. The method of claim 2, wherein:
    the concentration of recombinant IL-7 is from about 100 IU/mL to about 1000 IU/mL.

4. The method of claim 1, wherein the input composition comprises about $200 \times 10^6$ cells to about $300 \times 10^6$ cells.

5. The method of claim 1, wherein the input composition comprises greater than about 70% primary human T cells.

6. The method of claim 1, wherein the input composition comprises greater than about 90% primary human T cells.

7. The method of claim 1, wherein the incubating is carried out in the presence of one or more antioxidants.

8. The method of claim 7, wherein the one or more antioxidants comprise a glutathione precursor.

9. The method of claim 7, wherein the one or more antioxidants comprise N-acetylcysteine (NAC), 2,3-dimercaptopropanol (DMP), L-2-oxo-4-thiazolidinecarboxylate (OTC), lipoic acid, S-allyl cysteine, or methylmethionine sulfonium chloride.

10. The method of claim 7, wherein the one or more antioxidants comprise N-acetyl cysteine (NAC).

11. The method of claim 10, wherein the concentration of NAC is from 0.2 mg/mL to 2.0 mg/mL.

12. The method of claim 1, wherein the anti-CD3 antibody or antibody fragment thereof and the anti-CD28 antibody or antibody fragment thereof are present on the surface of a bead.

13. The method of claim 12, wherein the ratio of beads to cells is from 2:1 to 0.5:1 or from about 2:1 to about 0.5:1.

14. The method of claim 1, wherein the introducing comprises transducing cells of the stimulated composition with a viral vector comprising a polynucleotide encoding the recombinant receptor.

15. The method of claim 14, wherein the viral vector is a retroviral vector.

16. The method of claim 1, wherein the recombinant receptor is a T-cell receptor (TCR) or antigen-binding fragment thereof.

17. The method of claim 1, wherein the recombinant receptor is a chimeric antigen receptor (CAR).

18. The method of claim 1, wherein the recombinant receptor is an anti-CD19 CAR.

19. The method of claim 1, wherein the introducing is carried out in the presence of a transduction adjuvant.

20. The method of claim 19, wherein the transduction adjuvant is protamine sulfate.

21. The method of claim 20, wherein the concentration of protamine sulfate is from 1 µg/mL to 50 µg/mL.

22. The method of claim 1, wherein the cultivating is further carried out in the presence of recombinant IL-7.

23. The method of claim 22, wherein:
    the concentration of recombinant IL-7 during the cultivating is from about 500 IU/mL to about 2000 IU/mL.

24. The method of claim 1, wherein the concentration of the poloxamer is from 0.5 µL/mL to 5 µL/mL.

25. The method of claim 1, wherein the anti-CD3 antibody or antibody fragment thereof and the anti-CD28 antibody or antibody fragment thereof are removed from the engineered composition prior to the cultivating.

26. The method of claim 25, wherein the anti-CD3 antibody or antibody fragment thereof and the anti-CD28 antibody or antibody fragment thereof are removed from 3 days to 6 days after the initiation of the incubating.

27. The method of claim 1, wherein the output composition comprises at least $1200 \times 10^6$ viable T cells.

28. The method of claim 1, wherein the amount of time between the initiation of the incubating and the collecting is from 9 days to 13 days or from about 9 days to about 13 days.

29. The method of claim 1, wherein the method is performed in less than 21 days, inclusive.

30. The method of claim 1, further comprising formulating cells of the output composition for cryopreservation or administration to the human subject.

31. The method of claim 1, wherein for a plurality of input compositions from different biological samples from a plurality of different human subjects having the disease or condition, output compositions are each produced in less than 21 days after the incubating of the plurality of input compositions for greater than 85% of the plurality of input compositions.

32. The method of claim 1, wherein the disease or condition is a cancer.

33. The method of claim 1, wherein during at least a portion of the cultivating, the cells are monitored for cell viability, concentration, density, number, or a combination of any of the foregoing.

34. The method of claim 33, wherein the monitoring is carried out by differential digital holography microscopy (DDHM).

35. The method of claim 1, wherein the input composition is a first input composition enriched in CD8+ primary human T cells, and the method further comprises:
  (a) separately incubating, under stimulating conditions, a second input composition comprising T cells enriched for CD4+ primary human T cells, wherein:
    the T cells enriched for CD4+ primary human T cells are isolated from the same biological sample from the human subject as the T cells enriched for CD8+ primary human T cells; and
    the stimulating conditions comprise the presence of (i) a stimulatory reagent capable of activating one or more intracellular signaling domains of one or more components of a TCR complex and/or one or more intracellular signaling domains of one or more costimulatory molecules and (ii) one or more cytokines, thereby generating a second stimulated composition; and
  (b) introducing a recombinant receptor into the second stimulated composition, thereby generating a second engineered composition comprising engineered T cells.

36. The method of claim 35, wherein the recombinant receptor that is introduced into the second stimulated composition is the same recombinant receptor that is introduced into the first stimulated composition.

37. The method of claim 35, wherein the one or more cytokines present during the stimulating of the second input composition comprise recombinant IL-2, recombinant IL-7, and recombinant IL-15.

38. The method of claim 1, wherein the cultivating is initiated under conditions with no perfusion, and the perfusion is initiated when the concentration of the cells increases to reach a predetermined concentration.

39. The method of claim 38, wherein the predetermined concentration is, is about, or is at least $0.1 \times 10^6$ cells/mL.

40. The method of claim 38, wherein the perfusion rate is increased when the concentration of the cells increases to reach a second predetermined cell concentration.

41. The method of claim 40, wherein the second predetermined concentration is, is about, or is at least $0.6 \times 10^6$ cells/mL.

* * * * *

SEQUENCE LISTING

<160> NUMBER OF SEQ ID NOS: 61

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge) (aa)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge) (nt)

<400> SEQUENCE: 2
gaatctaagt acggaccgcc ctgcccccct tgccct                36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255
```

```
Cys Val Val Ser His Glu Asp Ser Arg Thr Leu Leu Asn Ala Ser Arg
            260                 265                 270

Ser Leu Glu Val Ser Tyr Val Thr Asp His
            275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
```

-continued

```
                245                 250                 255
Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355

<210> SEQ ID NO 8
<211> LENGTH: 27
<212> TYPE: PRT
<213> ORGANISM: Homo sapiens
<220> FEATURE:
<223> OTHER INFORMATION: CD28 (amino acids 153-179 of Accession No.
      P10747)

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28 (amino acids 114-179 of Accession No.
      P10747)

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1               5                   10                  15
```

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 11
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT

```
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60
```

```
Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

```
Glu Gly Arg Gly Ser Leu Leu Thr Cys Gly Asp Val Glu Glu Asn Pro
 1               5                  10                  15

Gly Pro
```

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

```
Gly Ser Gly Ala Thr Asn Phe Ser Leu Leu Lys Gln Ala Gly Asp Val
 1               5                  10                  15
```

```
Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 10
<212> TYPE: PRT
<213> ORGANISM: Artificial Sequence
<220> FEATURE:
<223> OTHER INFORMATION: Exemplary linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Exemplary Linker

<400> SEQUENCE: 23

Gly Ser Ala Asp Asp Ala Lys Lys Asp Ala Ala Lys Lys Asp Gly Lys
```

```
1               5                   10                  15
Ser

<210> SEQ ID NO 24
<211> LENGTH: 18
<212> TYPE: PRT
<213> ORGANISM: Artificial Sequence
<220> FEATURE:
<223> OTHER INFORMATION: Exemplary Linker

<400> SEQUENCE: 24

Gly Ser Thr Ser Gly Ser Gly Lys Pro Gly Ser Gly Glu Gly Ser Thr
1               5                   10                  15

Lys Gly

<210> SEQ ID NO 25
<211> LENGTH: 14
<212> TYPE: PRT
<213> ORGANISM: Artificial Sequence
<220> FEATURE:
<223> OTHER INFORMATION: Exemplary IgG Hinge

<400> SEQUENCE: 25

Glu Val Val Val Lys Tyr Gly Pro Pro Cys Pro Pro Cys Pro
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Exemplary IgG Hinge
<220> FEATURE:
<221> NAME/KEY: VARIANT
<222> LOCATION: (1)...(1)
<223> OTHER INFORMATION: Xaa is glycine, cysteine, or arginine
<220> FEATURE:
<221> NAME/KEY: VARIANT
<222> LOCATION: (4)...(4)
<223> OTHER INFORMATION: Xaa is cysteine or threonine

<400> SEQUENCE: 26

Xaa Pro Pro Xaa Pro
1               5

<210> SEQ ID NO 27
<211> LENGTH: 15
<212> TYPE: PRT
<213> ORGANISM: Artificial Sequence
<220> FEATURE:
<223> OTHER INFORMATION: Exemplary IgG Hinge

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 28

Glu Arg Lys Cys Cys Val Glu Cys Pro Pro Cys Pro
1               5                   10
```

```
<210> SEQ ID NO 29
<211> LENGTH: 61
<212> TYPE: PRT
<213> ORGANISM: Artificial Sequence
<220> FEATURE:
<223> OTHER INFORMATION: Exemplary IgG Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro
    50                  55                  60

<210> SEQ ID NO 30
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 30

Glu Ser Lys Tyr Gly Pro Pro Cys Pro Ser Cys Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 31

Glu Ser Lys Tyr Gly Pro Pro Cys Pro Pro Cys Pro
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Exemplary IgG Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Exemplary IgG Hinge

<400> SEQUENCE: 33

Lys Tyr Gly Pro Pro Cys Pro Pro Cys Pro
1               5                   10

<210> SEQ ID NO 34
<211> LENGTH: 9
<212> TYPE: PRT
<213> ORGANISM: Artificial Sequence
```

```
<220> FEATURE:
<223> OTHER INFORMATION: CDR L3

<400> SEQUENCE: 34

Gln Gln Gly Asn Thr Leu Pro Tyr Thr
1               5

<210> SEQ ID NO 35
<211> LENGTH: 11
<212> TYPE: PRT
<213> ORGANISM: Artificial Sequence
<220> FEATURE:
<223> OTHER INFORMATION: CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: CDR L3

<400> SEQUENCE: 37

Gly Asn Thr Leu Pro Tyr Thr Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence
<220> FEATURE:
<223> OTHER INFORMATION: CDR H2

<400> SEQUENCE: 39

Val Ile Trp Gly Ser Glu Thr Thr Tyr Tyr Asn Ser Ala Leu Lys Ser
1               5                   10                  15

<210> SEQ ID NO 40
<211> LENGTH: 7
<212> TYPE: PRT
<213> ORGANISM: Artificial Sequence
<220> FEATURE:
```

<223> OTHER INFORMATION: CDR H3

<400> SEQUENCE: 40

Tyr Ala Met Asp Tyr Trp Gly
1               5

<210> SEQ ID NO 41
<211> LENGTH: 120
<212> TYPE: PRT
<213> ORGANISM: Artificial Sequence
<220> FEATURE:
<223> OTHER INFORMATION: VH

<400> SEQUENCE: 41

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: VL

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 43
<211> LENGTH: 245
<212> TYPE: PRT
<213> ORGANISM: Artificial Sequence
<220> FEATURE:
<223> OTHER INFORMATION: scFv

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 44
<211> LENGTH: 11
<212> TYPE: PRT
<213> ORGANISM: Artificial Sequence
<220> FEATURE:
<223> OTHER INFORMATION: CDR L1

<400> SEQUENCE: 44

Lys Ala Ser Gln Asn Val Gly Thr Asn Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: CDR L2

<400> SEQUENCE: 45

Ser Ala Thr Tyr Arg Asn Ser
1               5

<210> SEQ ID NO 46

```
<211> LENGTH: 9
<212> TYPE: PRT
<213> ORGANISM: Artificial Sequence
<220> FEATURE:
<223> OTHER INFORMATION: CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95
```

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120

<210> SEQ ID NO 51
<211> LENGTH: 108
<212> TYPE: PRT
<213> ORGANISM: Artificial Sequence
<220> FEATURE:
<223> OTHER INFORMATION: VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 245
<212> TYPE: PRT
<213> ORGANISM: Artificial Sequence
<220> FEATURE:
<223> OTHER INFORMATION: scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

```
Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Ser Gly
        115                 120                 125

Gly Gly Gly Ser Gly Gly Gly Ser Asp Ile Glu Leu Thr Gln Ser
    130                 135                 140

Pro Lys Phe Met Ser Thr Ser Val Gly Asp Arg Val Ser Val Thr Cys
145             150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225             230                 235                 240

Leu Glu Ile Lys Arg
            245

<210> SEQ ID NO 54
<211> LENGTH: 12
<212> TYPE: PRT
<213> ORGANISM: Artificial Sequence
<220> FEATURE:
<223> OTHER INFORMATION: CDR H3

<400> SEQUENCE: 54

His Tyr Tyr Tyr Gly Gly Ser Tyr Ala Met Asp Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: CDR L2

<400> SEQUENCE: 55

His Thr Ser Arg Leu His Ser
1               5

<210> SEQ ID NO 56
<211> LENGTH: 18
<212> TYPE: PRT
<213> ORGANISM: Artificial Sequence
<220> FEATURE:
<223> OTHER INFORMATION: Linker

<400> SEQUENCE: 56

Gly Ser Thr Ser Gly Ser Gly Lys Pro Gly Ser Gly Glu Gly Ser Thr
1               5                   10                  15

Lys Gly

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv
```

<400> SEQUENCE: 57

```
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt ttgccagcag ggcaacacac tgccctacac ctttggcggc   300
ggaacaaagc tggaaatcac cggcagcacc tccggcagcg gcaagcctgg cagcggcgag   360
ggcagcacca agggcgaggt gaagctgcag gaaagcggcc ctggcctggt ggcccccagc   420
cagagcctga gcgtgacctg caccgtgagc ggcgtgagcc tgcccgacta cggcgtgagc   480
tggatccggc agccccccag gaagggcctg aatggctggg gcgtgatctg gggcagcgag   540
accacctact acaacagcgc cctgaagagc cggctgacca tcatcaagga caacagcaag   600
agccaggtgt tcctgaagat gaacagcctg cagaccgacg acaccgccat ctactactgc   660
gccaagcact actactacgg cggcagctac gccatggact actggggcca gggcaccagc   720
gtgaccgtga gcagc                                                    735
```

<210> SEQ ID NO 58
<211> LENGTH: 16
<212> TYPE: PRT
<213> ORGANISM: Homo sapiens
<220> FEATURE:
<223> OTHER INFORMATION: CD33 signal peptide

<400> SEQUENCE: 58

```
Met Pro Leu Leu Leu Leu Leu Pro Leu Leu Trp Ala Gly Ala Leu Ala
1               5                   10                  15
```

<210> SEQ ID NO 59
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 59

```
Met Ala Leu Pro Val Thr Ala Leu Leu Leu Pro Leu Ala Leu Leu Leu
1               5                   10                  15

His Ala
```

<210> SEQ ID NO 60
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 60

```
atgcttctcc tggtgacaag ccttctgctc tgtgagttac cacacccagc attcctcctg    60
atccca                                                               66
```

<210> SEQ ID NO 61
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 61

```
Met Leu Leu Leu Val Thr Ser Leu Leu Leu Cys Glu Leu Pro His Pro
1               5                   10                  15

Ala Phe Leu Leu Ile Pro
            20
```